US012673112B2

(12) United States Patent
Schwartz-Mittleman et al.

(10) Patent No.: US 12,673,112 B2
(45) Date of Patent: Jul. 7, 2026

(54) CCR8 ANTIBODIES, ANTIBODY CONJUGATES, AND USES THEREOF

(71) Applicants: Takeda Pharmaceutical Company Limited, Osaka (JP); Memorial Sloan-Kettering Cancer Center, New York, NY (US)

(72) Inventors: Adrian Schwartz-Mittleman, Cambridge, MA (US); Cierra Casson, Cambridge, MA (US); Sarah Hesse, Cambridge, MA (US); Natalie Roy D'Amore, Cambridge, MA (US); Cory Ahonen, Lebanon, NH (US); George Plitas, Manhattan, NY (US); Alexander Rudensky, Manhattan, NY (US)

(73) Assignees: Takeda Pharmaceutical Company Limited, Osaka (JP); Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 19/412,448

(22) Filed: Dec. 8, 2025

(65) Prior Publication Data

US 2026/0158163 A1 Jun. 11, 2026

Related U.S. Application Data

(60) Provisional application No. 63/880,813, filed on Sep. 12, 2025, provisional application No. 63/729,786, filed on Dec. 9, 2024.

(51) Int. Cl.

| | |
|---|---|
| ***A61K 47/68*** | (2017.01) |
| ***A61P 35/00*** | (2006.01) |
| ***C07K 16/28*** | (2006.01) |

(52) U.S. Cl.
CPC ...... *A61K 47/6849* (2017.08); *A61K 47/6803* (2017.08); *A61P 35/00* (2018.01);
(Continued)

(58) Field of Classification Search
CPC .................................................. A61K 47/6849
See application file for complete search history.

(56) References Cited

U.S. PATENT DOCUMENTS

| | | | |
|---|---|---|---|
| 10,087,259 | B1 | 10/2018 | Rudensky et al. |
| 10,836,796 | B2 | 11/2020 | Zhao et al. |

(Continued)

FOREIGN PATENT DOCUMENTS

| | | | |
|---|---|---|---|
| AU | 2020-263959 | A1 | 11/2021 |
| CN | 110835371 | A | 2/2020 |

(Continued)

OTHER PUBLICATIONS

Proceedings of the American Association for Cancer Research Annual Meeting 2024; Part 1 (Regular Abstracts); Apr. 5-10, 2024; San Diego, CA. Philadelphia (PA): AACR; Cancer Res 2024;84(6_ Suppl):Abstract nr 718 (Year: 2024).*

(Continued)

*Primary Examiner* — Karl J Puttlitz
(74) *Attorney, Agent, or Firm* — Wolf, Greenfield & Sacks, P.C.

(57) ABSTRACT

Disclosed herein are antibodies that bind to CCR8 (e.g., human CCR8) and anti-CCR8 antibody drug conjugates (ADC).

20 Claims, 21 Drawing Sheets

Specification includes a Sequence Listing.

(52) U.S. Cl.
CPC ...... *C07K 16/2866* (2013.01); *C07K 2317/33* (2013.01); *C07K 2317/77* (2013.01); *C07K 2317/92* (2013.01)

(56) References Cited

U.S. PATENT DOCUMENTS

| | | | | |
|---|---|---|---|---|
| 12,235,270 | B2 | 2/2025 | Rudensky et al. | |
| 2010/0196265 | A1 | 8/2010 | Adams et al. | |
| 2011/0256157 | A1 | 10/2011 | Howard et al. | |
| 2013/0266514 | A1 | 10/2013 | Nitsch et al. | |
| 2019/0092875 | A1 | 3/2019 | Rudensky et al. | |
| 2020/0339699 | A1 | 10/2020 | Li et al. | |
| 2021/0364520 | A1* | 11/2021 | Rudensky | G01N 33/57505 |
| 2023/0057350 | A1 | 2/2023 | Zhao et al. | |
| 2025/0019449 | A1 | 1/2025 | Rudensky et al. | |

FOREIGN PATENT DOCUMENTS

| | | | | |
|---|---|---|---|---|
| EP | 1479771 | A2 | 11/2004 | |
| WO | WO 2007/044756 | A2 | 4/2007 | |
| WO | WO 2016/142049 | A1 | 9/2016 | |
| WO | WO 2017/149077 | A1 | 9/2017 | |
| WO | WO 2018/181425 | A1 | 10/2018 | |
| WO | WO 2019/133961 | A1 | 7/2019 | |
| WO | WO 2019/149269 | A1 | 8/2019 | |
| WO | WO-2021142002 | A1 * | 7/2021 | A61K 39/39541 |
| WO | WO2021/178749 | A2 | 9/2021 | |
| WO | WO 2021/163064 | A9 | 4/2023 | |
| WO | WO 2023/116880 | A1 | 6/2023 | |
| WO | WO 2024/076514 | A1 | 4/2024 | |

OTHER PUBLICATIONS

International Search Report, Application No. PCT/US21/21008, 7 pages, Oct. 14, 2021.

Written Opinion, Application No. PCT/US21/21008, 14 pages, Oct. 14, 2021.

Lutz et al., Total Synthesis of α- and β-Amanitin. Angew Chem Int Ed Engl. Jul. 6, 2020;59(28):11390-11393. doi: 10.1002/anie.201914935. Epub Apr. 28, 2020.

Villarreal et al., Targeting CCR8 Induces Protective Antitumor Immunity and Enhances Vaccine-Induced Responses in Colon Cancer. Cancer Res. Sep. 15, 2018;78(18):5340-5348. doi: 10.1158/0008-5472.CAN-18-1119. Epub Jul. 19, 2018.

Invitation to Pay Additional Fees for Application No. PCT/US2025/058532, mailed Apr. 16, 2026.

Xi et al., Antibody-drug conjugates for targeted cancer therapy: Recent advances in potential payloads. Eur J Med Chem. Oct. 5, 2024:276:116709. doi: 10.1016/j.ejmech.2024.116709. Epub Jul. 25, 2024.

Xu et al., Diversity in the CDR3 Region of VH Is Sufficient for Most Antibody Specificities. IMMUNITY. Jul. 2000;13(1):37-45. doi: 10.1016/s1074-7613(00)00006-6.

* cited by examiner

CCR8 ANTIBODIES, ANTIBODY CONJUGATES, AND USES THEREOF

RELATED APPLICATIONS

This Application claims the benefit under 35 U.S.C. § 119(e) of U.S. Provisional Application No. 63/729,786, filed on Dec. 9, 2024, and U.S. Provisional Application No. 63/880,813, filed on Sep. 12, 2025, the entire contents of each of which are incorporated herein by reference.

REFERENCE TO AN ELECTRONIC SEQUENCE LISTING

The contents of the electronic sequence listing (T083370058US02-SEQ-ACZ.xml; Size: 142,558 bytes; and Date of Creation: Dec. 8, 2025) are herein incorporated by reference in their entirety.

BACKGROUND

C-C motif chemokine receptor 8 (CCR8) is expressed primarily on a subset of T cells, T regulatory cells (Tregs). These CCR8+ Tregs are potent drivers of immunosuppression. Tumor resident Tregs predominantly express CCR8, and high expression of CCR8+ Tregs in cancer patients is associated with a poor prognosis.

SUMMARY

Provided herein, in some aspects, are antibodies that bind to C-C motif chemokine receptor 8 (CCR8). In some embodiments, antibodies described herein bind to CCR8 with high binding affinity and specificity. In some embodiments, antibodies described herein bind to CCR8 but do not bind (e.g., show no detectable binding) to other C-C motif chemokine receptors (e.g., CCR5). Compositions comprising anti-CCR8 antibodies are described herein. Anti-CCR8 antibodies are useful for binding to CCR8, for example, in bioassays, diagnostic, or therapeutic methods. An antibody provided in the present disclosure may be produced using recombinant technology.

Further provided herein, in some aspects, are antibody-drug conjugates (ADCs) comprising an anti-CCR8 antibody of the present disclosure, or an antigen fragment thereof, conjugated (e.g., covalently linked) to a compound. In some embodiments, in an ADC described herein, an anti-CCR8 antibody is conjugated (e.g., covalently linked) to a compound via a linker. In some embodiments, the compound conjugated to the anti-CCR8 antibody is an amatoxin. In some embodiments, the amatoxin is amanitin. Compositions comprising the ADC are also provided. In some embodiments the ADCs described herein have antitumor properties. Methods of using the ADCs provided herein to treat cancer are also described.

The disclosure in some aspects provides an antibody that binds to CCR8 wherein the antibody comprises: a heavy chain variable domain (VH) comprising a heavy chain complementary determining region 1 (CDR-H1) comprising the amino acid sequence $FX_{24}FNAYAMN$ (SEQ ID NO: 127), wherein $X_{24}$ is T, Q, S, or N; a heavy chain complementary determining region 2 (CDR-H2) comprising the amino acid sequence $RIRSKSNNYATYYAX_{25}SVKX_{26}$ (SEQ ID NO: 128), wherein $X_{25}$ is D, A, G, E, or V, and $X_{26}$ is D, P, or E; a heavy chain complementary determining region 3 (CDR-H3) comprising the amino acid sequence $VRQSYGNSNYAMDX_{27}$ (SEQ ID NO: 129), wherein $X_{27}$ is Y, H, W, or F; and a light chain variable domain (VL) comprising a light chain complementary determining region 1 (CDR-L1) comprising the amino acid sequence $X_{28}SKX_{29}LX_{30}HSNGNTYLY$ (SEQ ID NO: 130), wherein $X_{28}$ is S or T, $X_{29}$ is S, R, T, or K, and $X_{30}$ is L, Q, I, or N; a light chain complementary determining region 2 (CDR-L2) comprising the amino acid sequence $X_{31}X_{32}SNLAS$ (SEQ ID NO: 131), wherein $X_{31}$ is R or K, and $X_{32}$ is M, V, K, R, or A; a light chain complementary determining region 3 (CDR-L3) comprising the amino acid sequence $MQHX_{33}EYPFT$ (SEQ ID NO: 132), wherein $X_{33}$ is L, F, I, W, or Y; wherein if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L; and wherein if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, the CDR-H1 comprises the amino acid sequence $FX_{24}FNAYAMN$ (SEQ ID NO: 127), wherein $X_{24}$ is T, Q, or S; the CDR-H2 comprises the amino acid sequence $RIRSKSNNYATYYAX_{25}SVKX_{26}$ (SEQ ID NO: 128), wherein $X_{25}$ is D, A, or G, and $X_{26}$ is D or P; the CDR-H3 comprises the amino acid sequence $VRQSYGNSNYAMDX_{27}$ (SEQ ID NO: 129), wherein $X_{27}$ is Y or H; and the CDR-L1 comprises the amino acid sequence $RX_{28}SKX_{29}LX_{30}HSNGNTYLY$ (SEQ ID NO: 130), wherein $X_{28}$ is S or T, $X_{29}$ is S or R, and $X_{30}$ is L or Q; the CDR-L2 comprises the amino acid sequence $X_{31}X_{32}SNLAS$ (SEQ ID NO: 131), wherein $X_{31}$ is R or K, and $X_{32}$ is M, V, or K; the CDR-L3 comprises the amino acid sequence $MQHX_{33}EYPFT$ (SEQ ID NO: 132), wherein $X_{33}$ is L or F; wherein if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L; and wherein if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, the CDR-H1 comprises the amino acid sequence $FX_{24}FNAYAMN$ (SEQ ID NO: 127), wherein $X_{24}$ is Q, or S; the CDR-H2 comprises the amino acid sequence $RIRSKSNNYATYYAX_{25}SVKX_{26}$ (SEQ ID NO: 128), wherein $X_{25}$ is D, A, or G, and $X_{26}$ is D or P; the CDR-H3 comprises the amino acid sequence $VRQSYGNSNYAMDX_{27}$ (SEQ ID NO: 129), wherein $X_{27}$ is Y or H; and the CDR-L1 comprises the amino acid sequence $RX_{28}SKX_{29}LX_{30}HSNGNTYLY$ (SEQ ID NO: 130), wherein $X_{28}$ is S or T, $X_{29}$ is S or R, and $X_{30}$ is L or Q; the CDR-L2 comprises the amino acid sequence $X_{31}X_{32}SNLAS$ (SEQ ID NO: 131), wherein $X_{31}$ is R or K, and $X_{32}$ is M, V, or K; the CDR-L3 comprises the amino acid sequence $MQHX_{33}EYPFT$ (SEQ ID NO: 132), wherein $X_{33}$ is L or F.

In some embodiments, the CDR-H1 comprises the amino acid sequence $FX_{24}FNAYAMN$ (SEQ ID NO: 127), wherein $X_{24}$ is T, Q, or S; the CDR-H2 comprises the amino acid sequence $RIRSKSNNYATYYAX_{25}SVKX_{26}$ (SEQ ID NO: 128), wherein $X_{25}$ is D, A, or G, and $X_{26}$ is D or P; the CDR-H3 comprises the amino acid sequence VRQSYGNSNYAMDH (SEQ ID NO: 90); and the CDR-L1 comprises the amino acid sequence $RX_{28}SKX_{29}LX_{30}HSNGNTYLY$ (SEQ ID NO: 130), wherein $X_{28}$ is S or T, $X_{29}$ is S or R, and $X_{30}$ is L or Q; the CDR-L2 comprises the amino acid sequence $X_{31}X_{32}SNLAS$ (SEQ ID NO: 131), wherein $X_{31}$ is R or K, and $X_{32}$ is M, V, or K; the CDR-L3 comprises the amino acid sequence $MQHX_{33}EYPFT$ (SEQ ID NO: 132), wherein $X_{33}$ is L or F.

In some embodiments, the CDR-H1 comprises the amino acid sequence FQFNAYAMN (SEQ ID NO: 88); the CDR-H2 comprises the amino acid sequence RIRSKSNNYATYY- ADSVK$X_{26}$ (SEQ ID NO: 139), wherein $X_{26}$ is D or P; the CDR-H3 comprises the amino acid sequence VRQSYG-NSNYAMDH (SEQ ID NO: 90); and the CDR-L1 comprises the amino acid sequence RSSKSL$X_{30}$HSNGNTYLY (SEQ ID NO: 140), wherein $X_{30}$ is L or Q; the CDR-L2 comprises the amino acid sequence RVSNLAS (SEQ ID NO: 92); the CDR-L3 comprises the amino acid sequence MQHFEYPFT (SEQ ID NO: 96).

In some embodiments, the CDR-H1 comprises the amino acid sequence SEQ ID NO: 88, the CDR-H2 comprises the amino acid sequence SEQ ID NO: 26, the CDR-H3 comprises the amino acid sequence SEQ ID NO: 90; and the CDR-L1 comprises the amino acid sequence SEQ ID NO: 28, the CDR-L2 comprises the amino acid sequence SEQ ID NO: 92, the CDR-L3 comprises the amino acid sequence SEQ ID NO: 96. In some embodiments the VH comprises the amino acid sequence SEQ ID NO: 99, and the VL comprises the amino acid sequence SEQ ID NO: 100.

In some embodiments, the CDR-H1 comprises the amino acid sequence SEQ ID NO: 88, the CDR-H2 comprises the amino acid sequence SEQ ID NO:89, the CDR-H3 comprises the amino acid sequence SEQ ID NO: 90; and the CDR-L1 comprises the amino acid sequence SEQ ID NO: 102, the CDR-L2 comprises the amino acid sequence SEQ ID NO: 92, the CDR-L3 comprises the amino acid sequence SEQ ID NO: 96. In some embodiments, the VH comprises the amino acid sequence SEQ ID NO: 93, and the VL comprises the amino acid sequence SEQ ID NO: 103.

In some embodiments, the CDR-H1 comprises the amino acid sequence SEQ ID NO: 88, the CDR-H2 comprises the amino acid sequence SEQ ID NO: 89, the CDR-H3 comprises the amino acid sequence SEQ ID NO: 90; and the CDR-L1 comprises the amino acid sequence SEQ ID NO: 91, the CDR-L2 comprises the amino acid sequence SEQ ID NO: 92, the CDR-L3 comprises the amino acid sequence SEQ ID NO: 30. In some embodiments, the VH comprises the amino acid sequence SEQ ID NO: 93, and the VL comprises the amino acid sequence SEQ ID NO: 94.

In some embodiments the CDR-H1 comprises the amino acid sequence SEQ ID NO: 88, the CDR-H2 comprises the amino acid sequence SEQ ID NO: 89, the CDR-H3 comprises the amino acid sequence SEQ ID NO: 90; and the CDR-L1 comprises the amino acid sequence SEQ ID NO: 91, the CDR-L2 comprises the amino acid sequence SEQ ID NO: 95, the CDR-L3 comprises the amino acid sequence SEQ ID NO: 96. In some embodiments, the VH comprises the amino acid sequence SEQ ID NO: 93, and the VL comprises the amino acid sequence SEQ ID NO: 97.

In some embodiments, the CDR-H1 comprises the amino acid sequence SEQ ID NO: 88, the CDR-H2 comprises the amino acid sequence SEQ ID NO: 26, the CDR-H3 comprises the amino acid sequence SEQ ID NO: 27; and the CDR-L1 comprises the amino acid sequence SEQ ID NO: 91, the CDR-L2 comprises the amino acid sequence SEQ ID NO: 95, the CDR-L3 comprises the amino acid sequence SEQ ID NO: 96. In some embodiments, the VH comprises the amino acid sequence SEQ ID NO: 98, and the VL comprises the amino acid sequence SEQ ID NO: 97.

In some embodiments, the CDR-H1 comprises the amino acid sequence SEQ ID NO: 88, the CDR-H2 comprises the amino acid sequence SEQ ID NO: 89, the CDR-H3 comprises the amino acid sequence SEQ ID NO: 90; and the CDR-L1 comprises the amino acid sequence SEQ ID NO: 28, the CDR-L2 comprises the amino acid sequence SEQ ID NO: 95, the CDR-L3 comprises the amino acid sequence SEQ ID NO: 96. In some embodiments, the VH comprises the amino acid sequence SEQ ID NO: 93, and the VL comprises the amino acid sequence SEQ ID NO: 101.

In some embodiments, the CDR-H1 comprises the amino acid sequence SEQ ID NO: 88, the CDR-H2 comprises the amino acid sequence SEQ ID NO: 104, the CDR-H3 comprises the amino acid sequence SEQ ID NO: 27; and the CDR-L1 comprises the amino acid sequence SEQ ID NO: 28, the CDR-L2 comprises the amino acid sequence SEQ ID NO: 105, the CDR-L3 comprises the amino acid sequence SEQ ID NO: 96. In some embodiments, the VH comprises the amino acid sequence SEQ ID NO: 106, and the VL comprises the amino acid sequence SEQ ID NO: 107.

In some embodiments, the CDR-H1 comprises the amino acid sequence SEQ ID NO: 88, the CDR-H2 comprises the amino acid sequence SEQ ID NO: 104, the CDR-H3 comprises the amino acid sequence SEQ ID NO: 27; and the CDR-L1 comprises the amino acid sequence SEQ ID NO: 91, the CDR-L2 comprises the amino acid sequence SEQ ID NO: 92, the CDR-L3 comprises the amino acid sequence SEQ ID NO: 30. In some embodiments, the VH comprises the amino acid sequence SEQ ID NO: 106, and the VL comprises the amino acid sequence SEQ ID NO: 94.

In some embodiments, the CDR-H1 comprises the amino acid sequence SEQ ID NO: 88, the CDR-H2 comprises the amino acid sequence SEQ ID NO: 104, the CDR-H3 comprises the amino acid sequence SEQ ID NO: 27; and the CDR-L1 comprises the amino acid sequence SEQ ID NO: 102, the CDR-L2 comprises the amino acid sequence SEQ ID NO: 92, the CDR-L3 comprises the amino acid sequence SEQ ID NO: 30. In some embodiments, the VH comprises the amino acid sequence SEQ ID NO: 106, and the VL comprises the amino acid sequence SEQ ID NO: 108.

In some embodiments, the CDR-H1 comprises the amino acid sequence SEQ ID NO: 109, the CDR-H2 comprises the amino acid sequence SEQ ID NO: 104, the CDR-H3 comprises the amino acid sequence SEQ ID NO: 27; and the CDR-L1 comprises the amino acid sequence SEQ ID NO: 110, the CDR-L2 comprises the amino acid sequence SEQ ID NO: 92, the CDR-L3 comprises the amino acid sequence SEQ ID NO: 96. In some embodiments, the VH comprises the amino acid sequence SEQ ID NO: 111, and the VL comprises the amino acid sequence SEQ ID NO: 112.

In some embodiments, the CDR-H1 comprises the amino acid sequence SEQ ID NO: 25, the CDR-H2 comprises the amino acid sequence SEQ ID NO: 113, the CDR-H3 comprises the amino acid sequence SEQ ID NO: 90; and the CDR-L1 comprises the amino acid sequence SEQ ID NO: 91, the CDR-L2 comprises the amino acid sequence SEQ ID NO: 92, the CDR-L3 comprises the amino acid sequence SEQ ID NO: 30. In some embodiments, the VH comprises the amino acid sequence SEQ ID NO: 114, and the VL comprises the amino acid sequence SEQ ID NO: 94.

The disclosure in some aspects provides an antibody that binds to CCR8 wherein the antibody comprises: a heavy chain variable domain (VH) comprising a heavy chain complementary determining region 1 (CDR-H1) comprising the amino acid sequence YSISSGYYWG (SEQ ID NO: 9); a heavy chain complementary determining region 2 (CDR-H2) comprising the amino acid sequence SIYHSGN-TYYRPSLKS (SEQ ID NO: 10); a heavy chain complementary determining region 3 (CDR-H3) comprising the amino acid sequence ARGKGGSWTAFGP (SEQ ID NO: 11); and a light chain variable domain (VL) comprising a light chain complementary determining region 1 (CDR-L1) comprising the amino acid sequence RASQS$X_6$SS$X_7$$X_8$N (SEQ ID NO: 119), wherein $X_6$ is I, P, or L, $X_7$ is F, L, I, W, or Y, and $X_8$ is L, A, I, or V; a light chain complementary determining region 2 (CDR-L2) comprising the amino acid sequence $AX_9X_{10}SLQS$ (SEQ ID NO: 120), wherein $X_9$ is A, I, L, or V, and $X_{10}$ is S, E, T, or D; a light chain complementary determining region 3 (CDR-L3) comprising the amino acid sequence $QQGX_{11}STPPT$ (SEQ ID NO: 121), wherein $X_{11}$ is H, I, or L; wherein if $X_6$ is I, $X_7$ is not F, $X_8$ is not L, $X_9$ is not A, $X_{10}$ is not S, and $X_{11}$ is not H.

In some embodiments, the CDR-H1 comprises the amino acid sequence YSISSGYYWG (SEQ ID NO: 9); the CDR-H2 comprises the amino acid sequence SIYHSGN-TYYRPSLKS (SEQ ID NO: 10); the CDR-H3 comprises the amino acid sequence ARGKGGSWTAFGP (SEQ ID NO: 11); and the CDR-L1 comprises the amino acid sequence $RASQSX_6SSX_7X_8N$ (SEQ ID NO: 119), wherein $X_6$ is I or P, $X_7$ is F or L, and $X_8$ is L or A; the CDR-L2 comprises the amino acid sequence $AX_9X_{10}SLQS$ (SEQ ID NO: 120), wherein $X_9$ is A or I, and $X_{10}$ is S or E; the CDR-L3 comprises the amino acid sequence $QQGX_{11}STPPT$ (SEQ ID NO: 121), wherein $X_{11}$ is H or I; wherein if $X_6$ is I, $X_7$ is not F, $X_8$ is not L, $X_9$ is not A, $X_{10}$ is not S, and $X_{11}$ is not H.

In some embodiments, the CDR-H1 comprises the amino acid sequence SEQ ID NO: 9, the CDR-H2 comprises the amino acid sequence SEQ ID NO: 10, the CDR-H3 comprises the amino acid sequence SEQ ID NO: 11; and the CDR-L1 comprises the amino acid sequence SEQ ID NO: 47, the CDR-L2 comprises the amino acid sequence SEQ ID NO: 5, the CDR-L3 comprises the amino acid sequence SEQ ID NO: 13. In some embodiments, the VH comprises the amino acid sequence SEQ ID NO: 14, and the VL comprises the amino acid sequence SEQ ID NO: 48.

In some embodiments, the CDR-H1 comprises the amino acid sequence SEQ ID NO: 9, the CDR-H2 comprises the amino acid sequence SEQ ID NO: 10, the CDR-H3 comprises the amino acid sequence SEQ ID NO: 11; and the CDR-L1 comprises the amino acid sequence SEQ ID NO: 49, the CDR-L2 comprises the amino acid sequence SEQ ID NO: 5, the CDR-L3 comprises the amino acid sequence SEQ ID NO: 13. In some embodiments, the VH comprises the amino acid sequence SEQ ID NO: 14, and the VL comprises the amino acid sequence SEQ ID NO: 50.

In some embodiments, the CDR-H1 comprises the amino acid sequence SEQ ID NO: 9, the CDR-H2 comprises the amino acid sequence SEQ ID NO: 10, the CDR-H3 comprises the amino acid sequence SEQ ID NO: 11; and the CDR-L1 comprises the amino acid sequence SEQ ID NO: 12, the CDR-L2 comprises the amino acid sequence SEQ ID NO: 51, the CDR-L3 comprises the amino acid sequence SEQ ID NO: 13. In some embodiments, the VH comprises the amino acid sequence SEQ ID NO: 14, and the VL comprises the amino acid sequence SEQ ID NO: 52.

In some embodiments, the CDR-H1 comprises the amino acid sequence SEQ ID NO: 9, the CDR-H2 comprises the amino acid sequence SEQ ID NO: 10, the CDR-H3 comprises the amino acid sequence SEQ ID NO: 11; and the CDR-L1 comprises the amino acid sequence SEQ ID NO: 53, the CDR-L2 comprises the amino acid sequence SEQ ID NO: 54, the CDR-L3 comprises the amino acid sequence SEQ ID NO: 55. In some embodiments, the VH comprises the amino acid sequence SEQ ID NO: 14, and the VL comprises the amino acid sequence SEQ ID NO: 56.

The disclosure in some aspects provides an antibody that binds to CCR8 wherein the antibody comprises: a heavy chain variable domain (VH) comprising a heavy chain complementary determining region 1 (CDR-H1) comprising the amino acid sequence $GSISX_{12}SSX_{13}AWX_{14}$ (SEQ ID NO: 122), wherein $X_{12}$ is S, Q, T, or N, $X_{13}$ is Y, N, I, L, W, F, or Q, and $X_{14}$ is G, L, S, T, or I; a heavy chain complementary determining region 2 (CDR-H2) comprising the amino acid sequence SIYYTGSTYYNPSLKS (SEQ ID NO: 17); a heavy chain complementary determining region 3 (CDR-H3) comprising the amino acid sequence $X_{15}RGHRRDYIAFDI$ (SEQ ID NO: 123), wherein $X_{15}$ is L, V, I, or A; and a light chain variable domain (VL) comprising a light chain complementary determining region 1 (CDR-L1) comprising the amino acid sequence $RAX_{16}QSIX_{17}X_{18}X_{19}LN$ (SEQ ID NO: 124), wherein $X_{16}$ is S, D, T, or E, $X_{17}$ is S, L, T, or I, $X_{18}$ is S, D, E, or T, and $X_{19}$ is Y, L, I, W, or F; a light chain complementary determining region 2 (CDR-L2) comprising the amino acid sequence $X_{20}ASSLX_{21}X_{22}$ (SEQ ID NO: 125), wherein $X_{20}$ is A, D, E, or V, $X_{21}$ is Q, D, F, Y, W, E, or N, and $X_{22}$ is S, E, T, or D; a light chain complementary determining region 3 (CDR-L3) comprising the amino acid sequence $QQSHNLPX_{23}$ (SEQ ID NO: 126), wherein $X_{23}$ is T or S; wherein if $X_{12}$ is S, $X_{13}$ is not Y, $X_{14}$ is not G, $X_{15}$ is not L, $X_{16}$ is not S, $X_{17}$ is not S, $X_{18}$ is not S, $X_{19}$ is not Y, $X_{20}$ is not A, $X_{21}$ is not Q, $X_{22}$ is not S, and $X_{23}$ is not T; and wherein if $X_{12}$ is S, $X_{13}$ is not Y, $X_{14}$ is not G, $X_{15}$ is not V, $X_{16}$ is not S, $X_{17}$ is not S, $X_{18}$ is not S, $X_{19}$ is not Y, $X_{20}$ is not A, $X_{21}$ is not Q, $X_{22}$ is not S, and $X_{23}$ is not T.

In some embodiments, the CDR-H1 comprises the amino acid sequence $GSISX_{12}SSX_{13}AWX_{14}$ (SEQ ID NO: 122), wherein $X_{12}$ is S or Q, $X_{13}$ is Y, N, or I, and $X_{14}$ is G, L, or S; the CDR-H2 comprises the amino acid sequence SIYYTGSTYYNPSLKS (SEQ ID NO: 17); the CDR-H3 comprises the amino acid sequence $X_{15}RGHRRDYIAFDI$ (SEQ ID NO: 123), wherein $X_{15}$ is L or V; and the CDR-L1 comprises the amino acid sequence $RAX_{16}QSIX_{17}X_{18}X_{19}LN$ (SEQ ID NO: 124), wherein $X_{16}$ is S or D, $X_{17}$ is S or L, $X_{18}$ is S, D or E, and $X_{19}$ is Y or L; the CDR-L2 comprises the amino acid sequence $X_{20}ASSLX_{21}X_{22}$ (SEQ ID NO: 125), wherein $X_{20}$ is A or D, $X_{21}$ is Q, D, F, or Y, and $X_{22}$ is S or E; the CDR-L3 comprises the amino acid sequence $QQSHNLPX_{23}$ (SEQ ID NO: 126), wherein $X_{23}$ is T or S; wherein if $X_{12}$ is S, $X_{13}$ is not Y, $X_{14}$ is not G, $X_{15}$ is not L, $X_{16}$ is not S, $X_{17}$ is not S, $X_{18}$ is not S, $X_{19}$ is not Y, $X_{20}$ is not A, $X_{21}$ is not Q, $X_{22}$ is not S, and $X_{23}$ is not T; and wherein $X_{12}$ is S, $X_{13}$ is not Y, $X_{14}$ is not G, $X_{15}$ is not V, $X_{16}$ is not S, $X_{17}$ is not S, $X_{18}$ is not S, $X_{19}$ is not Y, $X_{20}$ is not A, $X_{21}$ is not Q, $X_{22}$ is not S, and $X_{23}$ is not T.

In some embodiments, the CDR-H1 comprises the amino acid sequence SEQ ID NO: 57, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 19, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 58, and the VL comprises the amino acid sequence SEQ ID NO: 22.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 59, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 21, and the VL comprises the amino acid sequence SEQ ID NO: 60.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 61, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 21, and the VL comprises the amino acid sequence SEQ ID NO: 62.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 19, the CDR-L2 comprises the amino acid sequence SEQ ID NO: 63, the CDR-H3 comprises the amino acid sequence SEQ ID NO: 20. In some embodiments, the VH comprises the amino acid sequence SEQ ID NO: 21, and the VL comprises the amino acid sequence SEQ ID NO: 64.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 19, the CDR-L2 comprises the amino acid sequence SEQ ID NO: 65, the CDR-L3 comprises the amino acid sequence SEQ ID NO: 20. In some embodiments, the VH comprises the amino acid sequence SEQ ID NO: 21, and the VL comprises the amino acid sequence SEQ ID NO: 66.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 19, the CDR-L2 comprises the amino acid sequence SEQ ID NO: 67, the CDR-L3 comprises the amino acid sequence SEQ ID NO: 20. In some embodiments, the VH comprises the amino acid sequence SEQ ID NO: 21, and the VL comprises the amino acid sequence SEQ ID NO: 68.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 19, the CDR-L2 comprises the amino acid sequence SEQ ID NO: 5, the CDR-L3 comprises the amino acid sequence SEQ ID NO: 69. In some embodiments, the VH comprises the amino acid sequence SEQ ID NO: 21, and the VL comprises the amino acid sequence SEQ ID NO: 70.

In some embodiments, the CDR-H1 comprises the amino acid sequence SEQ ID NO: 71, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 19, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 72, and the VL comprises the amino acid sequence SEQ ID NO: 22.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 18; and the CDR-L1 comprises the amino acid sequence SEQ ID NO: 73, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 21, and the VL comprises the amino acid sequence SEQ ID NO: 74.

In some embodiments, the CDR-H1 comprises the amino acid sequence SEQ ID NO: 75, the CDR-H2 comprises the amino acid sequence SEQ ID NO: 17, the CDR-H3 comprises the amino acid sequence SEQ ID NO: 23; and the CDR-L1 comprises the amino acid sequence SEQ ID NO: 19, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 76, and the VL comprises the amino acid sequence SEQ ID NO: 22.

In some embodiments, the CDR-H1 comprises the amino acid sequence SEQ ID NO: 77, the CDR-H2 comprises the amino acid sequence SEQ ID NO: 17, the CDR-H3 comprises the amino acid sequence SEQ ID NO: 23; and the CDR-L1 comprises the amino acid sequence SEQ ID NO: 19, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 78, and the VL comprises the amino acid sequence SEQ ID NO: 22.

In some embodiments, the CDR-H1 comprises the amino acid sequence SEQ ID NO: 79, the CDR-H2 comprises the amino acid sequence SEQ ID NO: 17, the CDR-H3 comprises the amino acid sequence SEQ ID NO: 23; and the CDR-L1 comprises the amino acid sequence SEQ ID NO: 19, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 80, and the VL comprises the amino acid sequence SEQ ID NO: 22.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 23; and the CDR-L1 comprises the amino acid sequence SEQ ID NO: 81, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 24, and the VL comprises the amino acid sequence SEQ ID NO: 82.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 23; and the CDR-L1 comprises the amino acid sequence SEQ ID NO: 49, the CDR-L2 comprises the amino acid sequence SEQ ID NO: 5, the CDR-L3 comprises the amino acid sequence SEQ ID NO: 20. In some embodiments, the VH comprises the amino acid sequence SEQ ID NO: 24, and the VL comprises the amino acid sequence SEQ ID NO: 83.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 23; and the CDR-L1 comprises the amino acid sequence SEQ ID NO: 19, the CDR-L2 comprises the amino acid sequence SEQ ID NO: 84, the CDR-L3 comprises the amino acid sequence SEQ ID NO: 20. In some embodiments, the VH comprises the amino acid sequence SEQ ID NO: 24, and the VL comprises the amino acid sequence SEQ ID NO: 85.

In some embodiments, the CDR-H1 comprises the amino acid sequence SEQ ID NO: 16, the CDR-H2 comprises the amino acid sequence SEQ ID NO: 17, the CDR-H3 comprises the amino acid sequence SEQ ID NO: 23; and the CDR-L1 comprises the amino acid sequence SEQ ID NO:

19, the CDR-L2 comprises the amino acid sequence SEQ ID NO: 86, the CDR-L3 comprises the amino acid sequence SEQ ID NO: 20. In some embodiments, the VH comprises the amino acid sequence SEQ ID NO: 24, and the VL comprises the amino acid sequence SEQ ID NO: 87.

The disclosure, in some aspects provide an antibody that binds to CCR8 wherein the antibody comprises: a heavy chain variable domain (VH) comprising a heavy chain complementary determining region 1 (CDR-H1) comprising the amino acid sequence FTFSS$X_1$GMH (SEQ ID NO: 115), wherein $X_1$ is Y, H, W, or F; a heavy chain complementary determining region 2 (CDR-H2) comprising the amino acid sequence VISYDGSNKYYAFSVKG (SEQ ID NO: 2); a heavy chain complementary determining region 3 (CDR-H3) comprising the amino acid sequence ARVRRIAGRAGYGMDV (SEQ ID NO: 3); and a light chain variable domain (VL) comprising a light chain complementary determining region 1 (CDR-L1) comprising the amino acid sequence RASQSI$X_2$SYLN (SEQ ID NO: 116), wherein $X_2$ is N, V, Q, or A; a light chain complementary determining region 2 (CDR-L2) comprising the amino acid sequence $X_3$AS$X_4$LQS (SEQ ID NO: 117), wherein $X_3$ is A, S, N, T, or V, and $X_4$ is S, I, T, or L; a light chain complementary determining region 3 (CDR-L3) comprising the amino acid sequence QESYSTPI$X_5$ (SEQ ID NO: 118), wherein $X_5$ is T, F, S, W, or Y; wherein if $X_1$ is Y, $X_2$ is not N, $X_3$ is not A, $X_4$ is not S, and $X_5$ is not T.

In some embodiments, the CDR-H1 comprises the amino acid sequence FTFSS$X_1$GMH (SEQ ID NO: 115), wherein $X_1$ is Y or H; the CDR-H2 comprises the amino acid sequence VISYDGSNKYYAFSVKG (SEQ ID NO: 2); the CDR-H3 comprises the amino acid sequence ARVRRIAGRAGYGMDV (SEQ ID NO: 3); and the CDR-L1 comprises the amino acid sequence RASQSI$X_2$SYLN (SEQ ID NO: 116), wherein $X_2$ is N or V; the CDR-L2 comprises the amino acid sequence $X_3$AS$X_4$LQS (SEQ ID NO: 117), wherein $X_3$ is A or S, and $X_4$ is S or I; and the CDR-L3 comprises the amino acid sequence QESYSTPI$X_5$ (SEQ ID NO: 118), wherein $X_5$ is T or F; wherein if $X_1$ is Y, $X_2$ is not N, $X_3$ is not A, $X_4$ is not S, and $X_5$ is not T.

In some embodiments, the CDR-H1 comprises the amino acid sequence SEQ ID NO: 39, the CDR-H2 comprises the amino acid sequence SEQ ID NO: 2, the CDR-H3 comprises the amino acid sequence SEQ ID NO: 3; and the CDR-L1 comprises the amino acid sequence SEQ ID NO: 4, the CDR-L2 comprises the amino acid sequence SEQ ID NO: 40, the CDR-L3 comprises the amino acid sequence SEQ ID NO: 41. In some embodiments, the VH comprises the amino acid sequence SEQ ID NO: 42, and the VL comprises the amino acid sequence SEQ ID NO: 43.

In some embodiments, the CDR-H1 comprises the amino acid sequence SEQ ID NO: 39, the CDR-H2 comprises the amino acid sequence SEQ ID NO: 2, the CDR-H3 comprises the amino acid sequence SEQ ID NO: 3; and the CDR-L1 comprises the amino acid sequence SEQ ID NO: 44, the CDR-L2 comprises the amino acid sequence SEQ ID NO: 45, the CDR-L3 comprises the amino acid sequence SEQ ID NO: 6. In some embodiments, the VH comprises the amino acid sequence SEQ ID NO: 42, and the VL comprises the amino acid sequence SEQ ID NO: 46.

In some embodiments, the antibody is selected from the group consisting of a full-length IgG, a Fab fragment, a F(ab') fragment, a F(ab')2 fragment, an scFv, and Fv. In some embodiments the antibody is a full-length IgG. In some embodiments, the full-length IgG comprises a heavy chain constant region of isotype IgG1, IgG2, IgG3, or IgG4. In some embodiments, the heavy chain constant region is of IgG1 isotype. In some embodiments, the constant region comprises the amino acid sequence SEQ ID NO: 133. In some embodiments, the heavy chain constant region comprises an L235A (EU numbering) and a G237A (EU numbering) mutation relative to the heavy chain constant region as set forth in SEQ ID NO: 133. In some embodiments, the heavy chain constant region further comprises a D265C (EU numbering) mutation relative to the heavy chain constant region as set forth in SEQ ID NO: 133. In some embodiments, the heavy chain constant region comprises the amino acid sequence SEQ ID NO: 134.

In some embodiments, the antibody comprises a light chain constant region comprising the amino acid sequence SEQ ID NO: 135.

In some embodiments, the antibody is a Fab. In some embodiments, the antibody is a humanized antibody. In some embodiments, the antibody is a human antibody.

In some embodiments, the disclosure provides a pharmaceutical composition comprising the antibody and a pharmaceutically acceptable excipient.

In some embodiments, the disclosure provides a method comprising contacting a biological sample with the antibody. In some embodiments, the method is an in vitro method.

In some embodiments, a nucleic acid sequence encodes the antibody. In some embodiments, a vector comprises the nucleic acid sequence that encodes the antibody.

In some embodiments, the disclosure provides a cell comprising the antibody, the nucleic acid sequence that encodes the antibody, or the vector that comprises the nucleic acid sequence that encodes the antibody.

In some embodiments, the disclosure provides a method of producing an antibody, the method comprising culturing a cell comprising the nucleic acid or the vector under conditions that allow the antibody to express. In some embodiments, the cell is a CHO cell. In some embodiments, the method further comprises isolating the antibody.

The disclosure in some aspects provide an antibody-drug conjugate (ADC) having the structure of Formula (A):

(A)

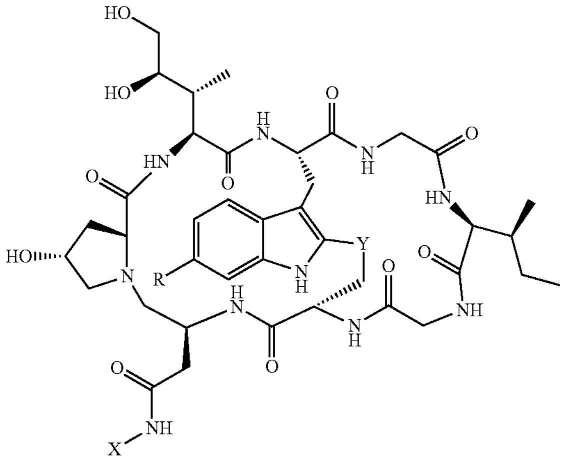

or a pharmaceutically acceptable salt, solvate, hydrate, tautomer, stereoisomer, diastereomer, or enantiomer thereof, wherein: R is H —OH, or —O-L-Z-Ab; Y is —S—, —S(=O)—, or —$SO_2$—; X is H or -L-Z-Ab, wherein: L is a linker; Ab is an antibody of any one of claims A1-E12, or an antigen binding fragment thereof; and Z is a chemical moiety formed by a coupling reaction between a first reactive substituent previously bound to L and a second reactive substituent previously present within the antibody, or antigen-binding fragment thereof; provided that: if X is H then R is —O-L-Z-Ab, and if X is -L-Z-Ab then R is H or —OH.

In some embodiments, the antibody-drug conjugate (ADC) has the structure of Formula (A-I):

(A-I)

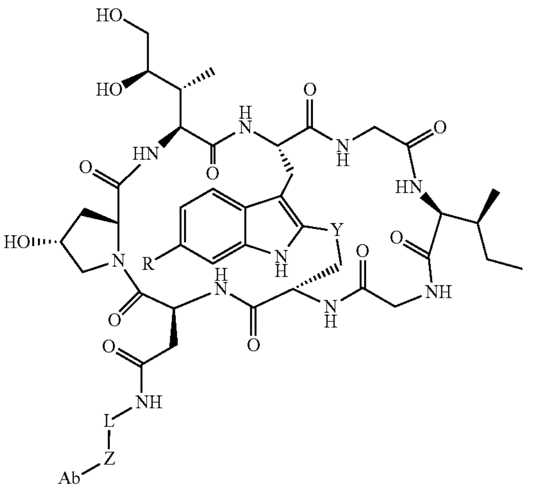

or a pharmaceutically acceptable salt, solvate, hydrate, tautomer, stereoisomer, diastereomer, or enantiomer thereof, wherein R is H or OH. In some embodiments, L is of the formula: $-Q^{L1}-Q^{1}-Q^{L2}-$, wherein: each of $Q^{L1}$ and $Q^{L2}$ is optionally substituted alkylene; and $Q^1$ is a peptide. In some embodiments, $Q^{L1}$ comprises an arylene group. In some embodiments, $Q^{L1}$ is phenylene, benzylene, or phenylethylene. In some embodiments, $Q^{L1}$ is benzyl. In some embodiments, $Q^1$ is a dipeptide. In some embodiments, $Q^1$ is a dipeptide comprising at least one of an alanine and a valine residue. In some embodiments, $Q^1$ is an Ala-Val dipeptide. In some embodiments, $Q^{L2}$ is an alkanoylene group. In some embodiments, $Q^{L2}$ is a propanoylene group. In some embodiments, L is of the formula:

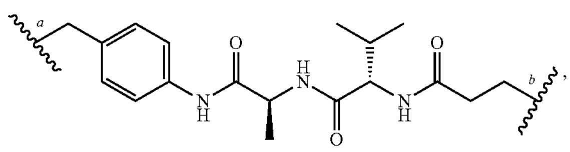

wherein a is the portion of L bonded to the amide moiety linked to L in Formula (A) or Formula (A-I) and b is the portion of L bonded to Z. In some embodiments, the -L-first reactive substituent is of the formula:

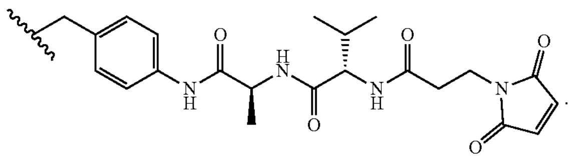 [SMILES: *Cc1ccc(NC(=O)[C@H](C)NC(=O)[C@@H](NC(=O)CCN2C(=O)C=CC2=O)C(C)C)cc1]

In some embodiments, the ADC is of the Formula (A-I-a):

(A-I-a)

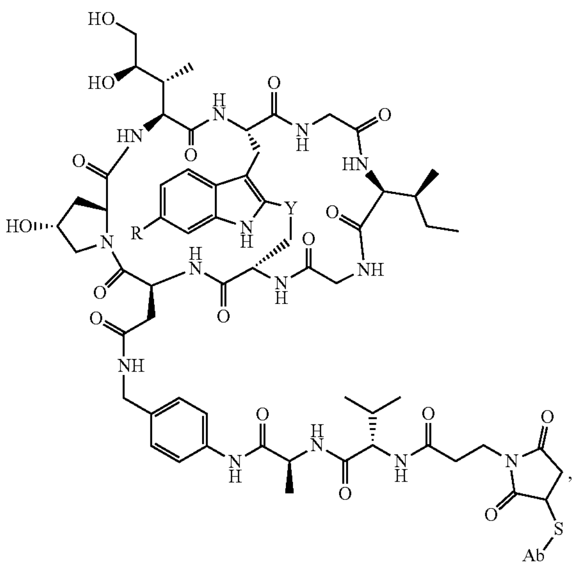

or a pharmaceutically acceptable salt, solvate, hydrate, tautomer, stereoisomer, diastereomer, or enantiomer thereof, wherein R is H or OH. In some embodiments, R is —OH.

In some embodiments, the ADC is of the Formula (A-I-b):

(A-I-b)

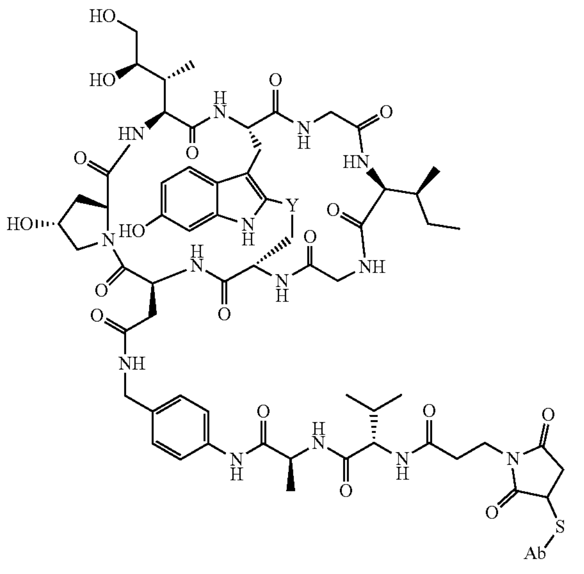

or a pharmaceutically acceptable salt, solvate, hydrate, tautomer, stereoisomer, diastereomer, or enantiomer thereof.

In some embodiments, the ADC is of the Formula (A-I-c):

(A-I-c)

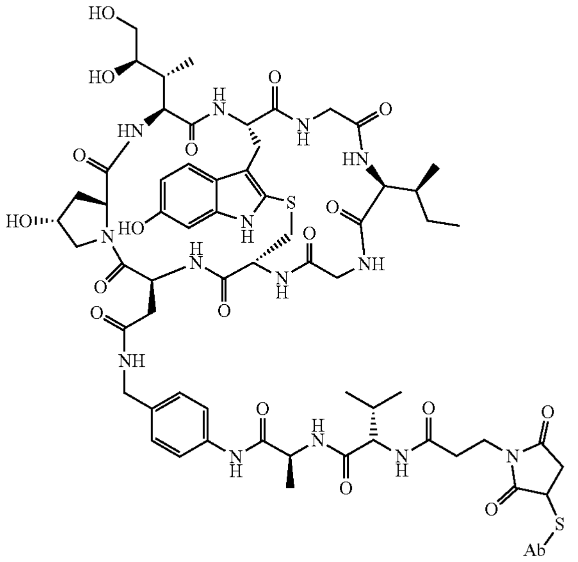

or a pharmaceutically acceptable salt, solvate, hydrate, tautomer, stereoisomer, diastereomer, or enantiomer thereof. In some embodiments, R is —H.

In some embodiments, the ADC is of the Formula (A-I-d):

(A-I-d)

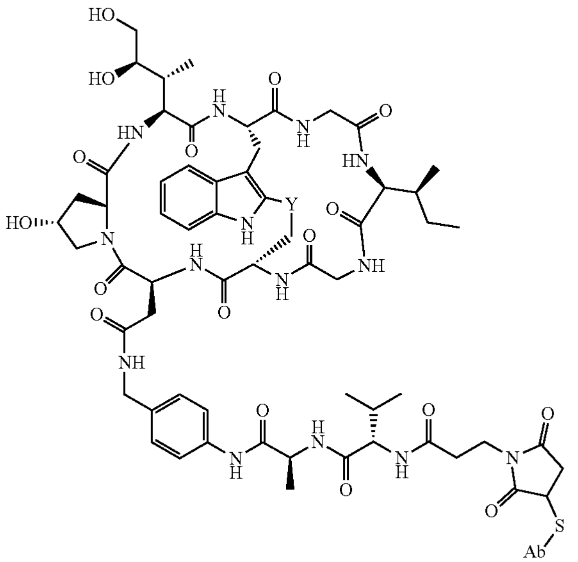

or a pharmaceutically acceptable salt, solvate, hydrate, tautomer, stereoisomer, diastereomer, or enantiomer thereof.

In some embodiments, the ADC is of the Formula (A-I-e):

(A-I-e)

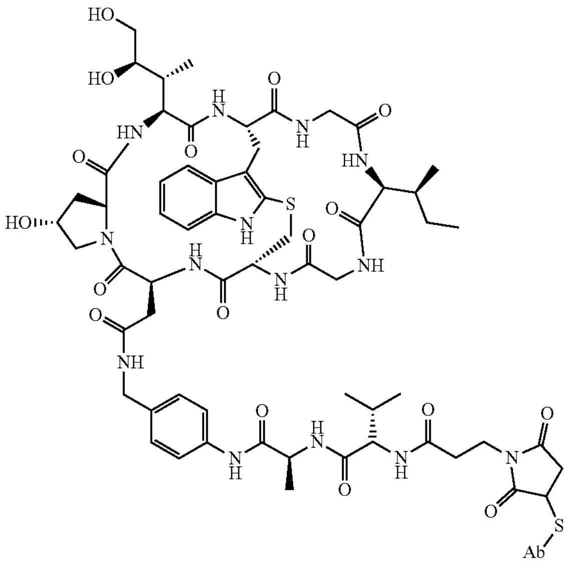

or a pharmaceutically acceptable salt, solvate, hydrate, tautomer, stereoisomer, diastereomer, or enantiomer thereof.

In some embodiments, the ADC is of the Formula (A-II):

(A-II)

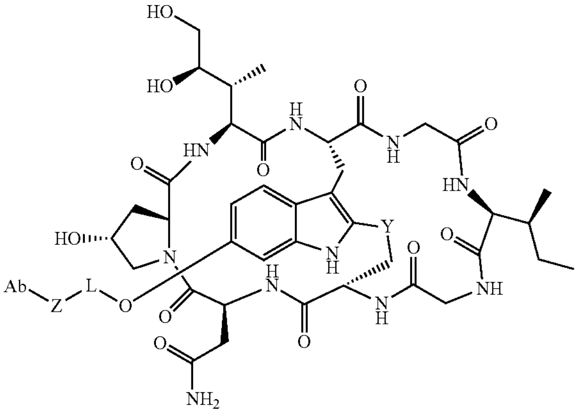

or a pharmaceutically acceptable salt, solvate, hydrate, tautomer, stereoisomer, diastereomer, or enantiomer thereof. In some embodiments, L is $-(CH_2)_n-$, where n is 2, 3, 4, 5, 6, 7, 8, 9, or 10.

In some embodiments, the ADC is of the Formula (A-II-a):

(A-II-a)

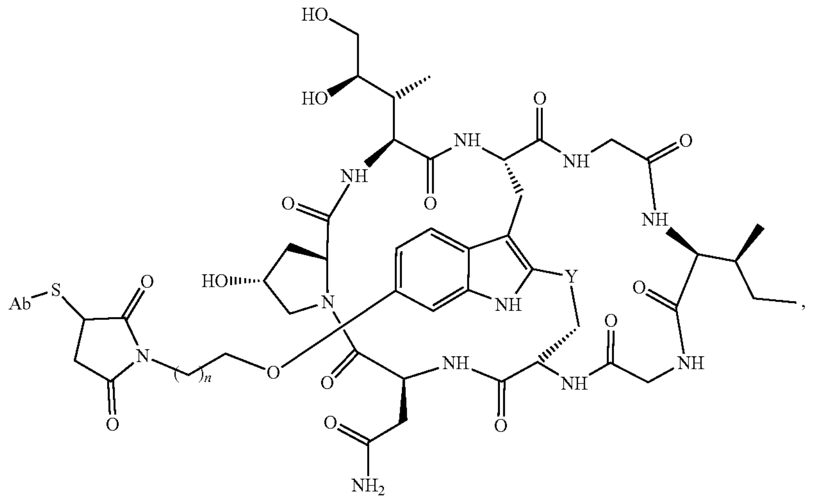

or a pharmaceutically acceptable salt, solvate, hydrate, tautomer, stereoisomer, diastereomer, or enantiomer thereof, wherein n is 2, 3, 4, 5, 6, 7, 8, 9, or 10. In some embodiments, the reactive substituent previously bound to L comprises an olefin. In some embodiments, the reactive substituent previously bound to L comprises an olefin disposed within a ring. In some embodiments, the reactive substituent previously bound to L comprises an olefin disposed within a heterocyclic ring. In some embodiments, the reactive substituent previously bound to L comprises an olefin disposed within a heterocyclic ring comprising an imide. In some embodiments, the reactive substituent previously bound to L comprises a maleimide. In some embodiments, the reactive substituent previously bound to L comprises 1H-pyrrol-1-yl-2,5-dione. In some embodiments, the reactive substituent previously present within the antibody is a thiol.

In some embodiments, Z comprises a sulfide bond. In some embodiments, Z comprises a pyrrolidine-1-yl-2,5-dione moiety. In some embodiments, Z is of the formula:

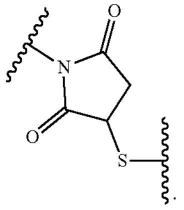 [SMILES: *SC1CC(=O)N(*)C1=O]

In some embodiments, Y is —S—. In some embodiments, Y is —S(═O)—. In some embodiments, Y is —$SO_2$—.

In some embodiments, the ADC is of Formula (A-II-b):

(A-II-b)

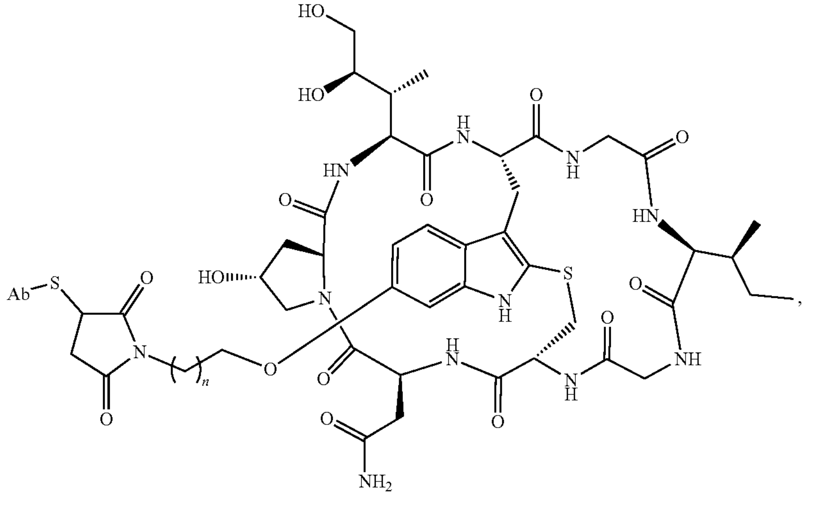

or a pharmaceutically acceptable salt, solvate, hydrate, tautomer, stereoisomer, diastereomer, or enantiomer thereof, wherein n is 1, 2, 3, 4, 5, 6, 7, 8, 9, or 10. In some embodiments, n is 5. In some embodiments the ADC antibody is any CCR8 antibody described herein.

In some embodiments, the ADC is of Formula (A-I-c) and the antibody comprises a heavy chain comprising the amino acid sequence of SEQ ID NO: 145 and a light chain comprising the amino acid sequence of SEQ ID NO: 146.

In some embodiments, the ADC is of Formula (A-I-e) and the antibody comprises a heavy chain comprising the amino acid sequence of SEQ ID NO: 145 and a light chain comprising the amino acid sequence of SEQ ID NO: 146.

In some embodiments, the ADC is of Formula (A-II-b) and the antibody comprises a heavy chain comprising the amino acid sequence of SEQ ID NO: 145 and a light chain comprising the amino acid sequence of SEQ ID NO: 146.

In some embodiments, the ADC is of Formula (A-I-c) and the antibody comprises a heavy chain comprising the amino acid sequence of SEQ ID NO: 147 and a light chain comprising the amino acid sequence of SEQ ID NO: 148.

In some embodiments, the ADC is of Formula (A-I-e) and the antibody comprises a heavy chain comprising the amino acid sequence of SEQ ID NO: 147 and a light chain comprising the amino acid sequence of SEQ ID NO: 148.

In some embodiments, the ADC is of Formula (A-II-b) and the antibody comprises a heavy chain comprising the amino acid sequence of SEQ ID NO: 147 and a light chain comprising the amino acid sequence of SEQ ID NO: 148.

In some embodiments, the ADC is in the form of a pharmaceutically acceptable salt.

The disclosure, in some aspects provide an antibody-drug conjugate (ADC) having the structure of Formula (A-I-c):

(A-I-c)

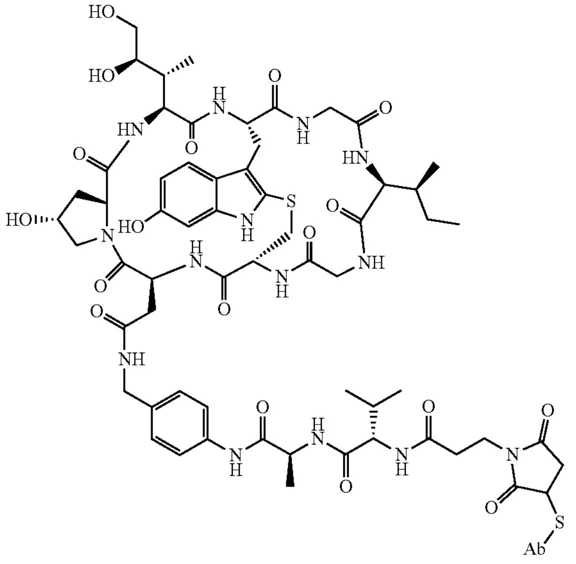

or a pharmaceutically acceptable salt, solvate, hydrate, tautomer, stereoisomer, diastereomer, or enantiomer thereof; wherein the antibody comprises a heavy chain comprising the amino acid sequence of SEQ ID NO: 145 and a light chain comprising the amino acid sequence of SEQ ID NO: 146. In some embodiments, the ADC is a pharmaceutically acceptable salt thereof.

The disclosure, in some aspects provide an antibody-drug conjugate (ADC) having the structure of Formula (A-I-c):

(A-I-c)

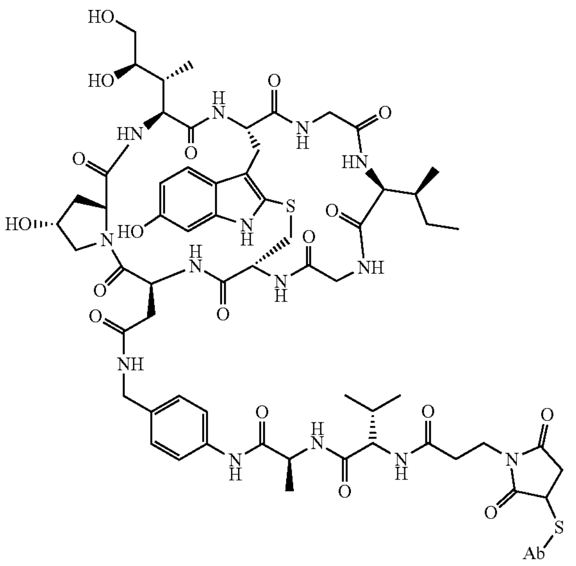

or a pharmaceutically acceptable salt, solvate, hydrate, tautomer, stereoisomer, diastereomer, or enantiomer thereof; wherein the antibody comprises a heavy chain comprising the amino acid sequence of SEQ ID NO: 147 and a light chain comprising the amino acid sequence of SEQ ID NO: 148. In some embodiments, the ADC is in the form of a pharmaceutically acceptable salt.

The disclosure in some aspects provide an antibody-drug conjugate (ADC) having the structure of Formula (A-I-e):

(A-I-e)

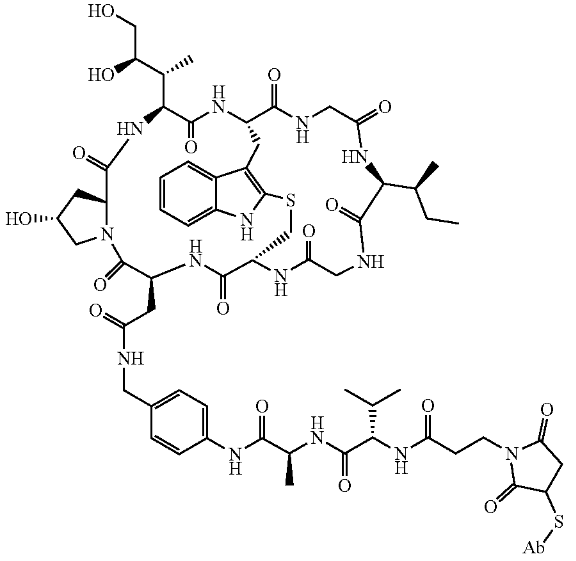

or a pharmaceutically acceptable salt, solvate, hydrate, tautomer, stereoisomer, diastereomer, or enantiomer thereof; wherein the antibody comprises a heavy chain comprising the amino acid sequence of SEQ ID NO: 145 and a light chain comprising the amino acid sequence of SEQ ID NO: 146. In some embodiments, the ADC is in the form of a pharmaceutically acceptable salt.

The disclosure in some aspects provide an antibody-drug conjugate (ADC) having the structure of Formula (A-I-e):

(A-I-e)

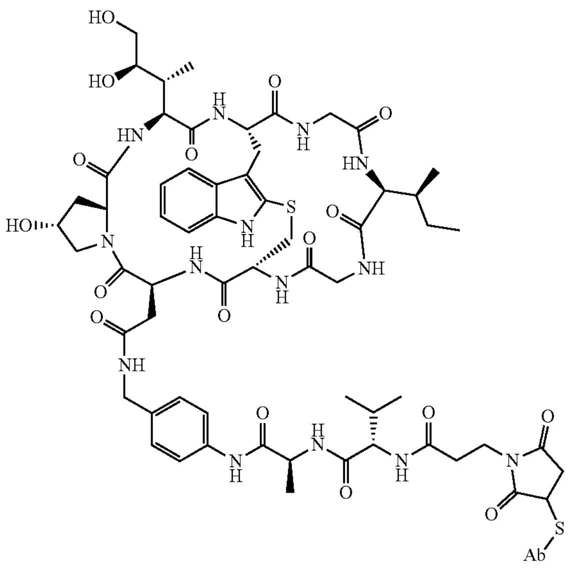

or a pharmaceutically acceptable salt, solvate, hydrate, tautomer, stereoisomer, diastereomer, or enantiomer thereof; wherein the antibody comprises a heavy chain comprising the amino acid sequence of SEQ ID NO: 147 and a light chain comprising the amino acid sequence of SEQ ID NO: 148. In some embodiments, the ADC is in the form of a pharmaceutically acceptable salt.

The disclosure in some aspects provide an antibody-drug conjugate (ADC) having the structure of Formula (A-II-b):

(A-II-b)

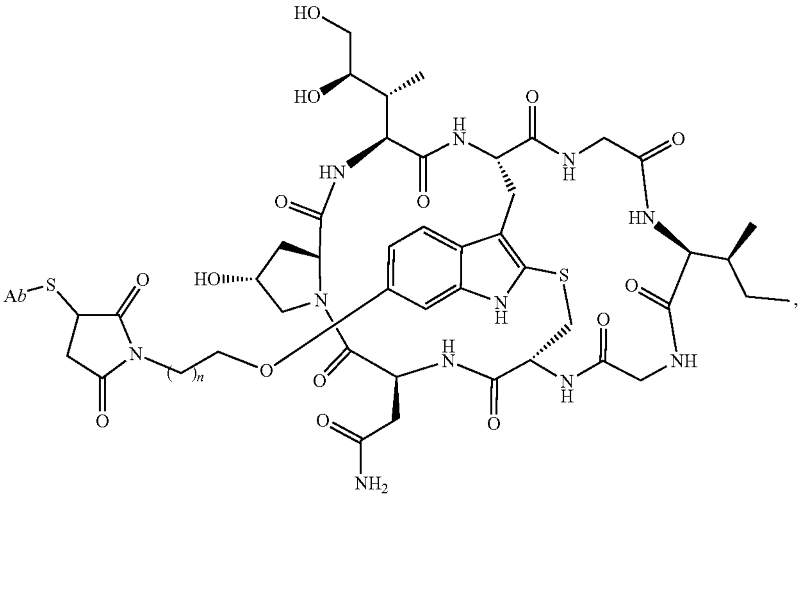
, or a pharmaceutically acceptable salt, solvate, hydrate, tautomer, stereoisomer, diastereomer, or enantiomer thereof; wherein the antibody comprises a heavy chain comprising the amino acid sequence of SEQ ID NO: 145 and a light chain comprising the amino acid sequence of SEQ ID NO: 146. In some embodiments, the ADC is in the form of a pharmaceutically acceptable salt.

The disclosure in some aspects provide an antibody-drug conjugate (ADC) having the structure of Formula (A-II-b):

(A-II-b)

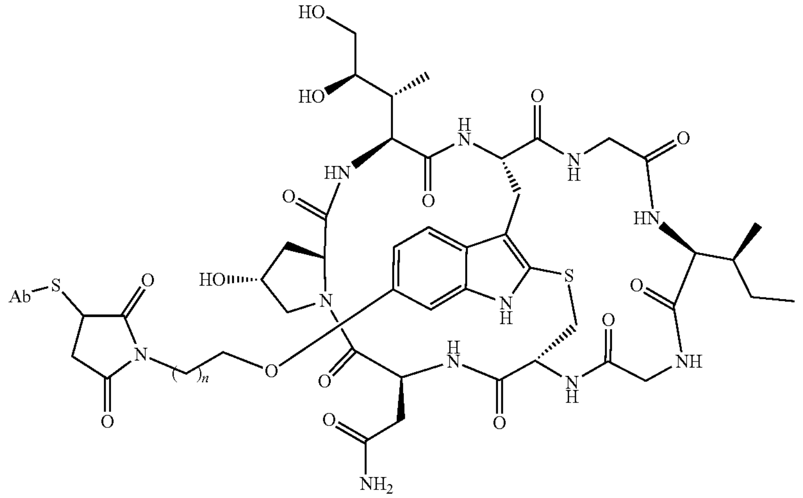

or a pharmaceutically acceptable salt, solvate, hydrate, tautomer, stereoisomer, diastereomer, or enantiomer thereof; wherein the antibody comprises a heavy chain comprising the amino acid sequence of SEQ ID NO: 147 and a light chain comprising the amino acid sequence of SEQ ID NO: 148. In some embodiments, the ADC is in the form of a pharmaceutically acceptable salt.

In some embodiments, the disclosure provides a pharmaceutical composition comprising the ADC, or a pharmaceutically acceptable salt, solvate, hydrate, tautomer, stereoisomer, diastereomer, or enantiomer thereof, and a pharmaceutically acceptable excipient.

In some embodiments, the disclosure provides a method comprising administering to a subject the ADC, or a pharmaceutically acceptable salt, solvate, hydrate, tautomer, stereoisomer, diastereomer, or enantiomer thereof, or the pharmaceutical composition.

In some embodiments, the subject has cancer. In some embodiments, the cancer is a solid tumor. In some embodiments, the cancer is microsatellite stable colorectal cancer, non-small cell lung cancer, triple negative breast cancer, or renal cell carcinoma. In some embodiments, the subject has an underlying condition that increases the risk of developing cancer. In some embodiments, the subject is further administered an additional therapeutic for treatment of cancer. In some embodiments, the additional therapeutic comprises chemotherapy, radiation therapy, targeted therapy, immunotherapy, hormonal therapy, targeted therapies, hyperthermia, or photodynamic therapy.

In some embodiments, the disclosure provides a method of treating cancer in a subject. In some embodiments, the subject has non-small cell lung cancer (NSCLC). In some embodiments, the amount of ADC administered is a therapeutically effective amount. In some embodiments, the subject is human.

BRIEF DESCRIPTION OF DRAWINGS

FIG. 2A shows the image overlay of anti-CCR8 antibody Parent 5. FIG. 2B shows the image overlay of anti-CCR8 antibody A5.1. FIG. 2C shows the image overlay of anti-CCR8 antibody A5.2. FIG. 2D shows the image overlay of anti-CCR8 antibody A5.3. FIG. 2E shows the image overlay of anti-CCR8 antibody A5.4. FIG. 2F shows the image overlay of anti-CCR8 antibody A5.5. FIG. 2G shows the image overlay or anti-CCR8 antibody A5.6.

FIG. 4A shows the cytotoxicity of two anti-CCR8 at 48 hours under developability stressing conditions. FIG. 4B shows the cytotoxicity of two anti-CCR8 at 96 hours under developability stressing conditions.

FIG. 5A shows flow cytometry results of the effect of each ADC on the depletion of Tregs in vitro. FIG. 5B shows the results of the effect of each ADC on the killing of CCR8+ Tregs in vitro. FIG. 5C shows a graph of the antitumor activity of each ADC in vivo.

FIG. 6A is a graph of the antitumor activity of the ADC. FIG. 6B shows the Treg profile of a tumor post treatment. FIG. 6C shows the CD8+ T cell profile of a tumor post treatment.

FIG. 8A shows quantification of T cell populations in non-small cell lung cancer (NSCLC) cancer dispersed tumor cells (DTCs) as a percentage of CD45+ cells versus concentration of a CCR8-ADC (nM). FIG. 8B shows quantification of T cell populations in matched NSCLC cancer PBMCs as a percentage of CD45+ cells versus concentration of a CCR8-ADC (nM). FIG. 8C shows quantification of T cell populations of non-cancer PBMCs as a percentage of CD45+ cells versus concentration of a CCR8-ADC (nM). In FIGS. 8A-8C, average vehicle control (PBS) values are shown with a dotted line and the histograms show the frequency distribution (normalized to mode) versus mean fluorescence intensity for the human CCR8 antibody (CCR8 Expression) on the samples prior to incubation with a CCDR-ADC.

FIG. 9A shows quantification of M2 macrophages as a percentage of CD45+ cells in the tumor of MC38 tumor-bearing huCCR88-KI mice 14 days post-treatment with either vehicle control (PBS) (Veh.), CCR8 mAb (CCR8 Ab #1) mIgG2a (CCR8 mAb), or CCR8-ADC. FIG. 9B shows the M1 to M2 ratio in the tumor of MC38 tumor-bearing huCCR88-KI mice 14 days post-treatment with either vehicle control (PBS) (Veh.), CCR8 mAb (CCR8 Ab #1) mIgG2a (CCR8 mAb), or CCR8-ADC.

FIG. 11A shows average tumor volume over 21 days of MC38 tumor-bearing huCCR8-KI mice treated with either vehicle control (PBS), isotype monoclonal antibody mIgG2a, CCR8 mAb (CCR8 Ab #2) mIgG2a, CCR8 mAb (CCR8 Ab #3) mIgG2a, or CCR8-ADC. FIG. 11B shows average tumor volume over 21 days of MC38 tumor-bearing huCCR8-KI mice treated with either vehicle control (PBS), a CCR8 monoclonal antibody (CCR8 Ab #1) mIgG2a, or CCR8-ADC.

DETAILED DESCRIPTION

Figure 1A:
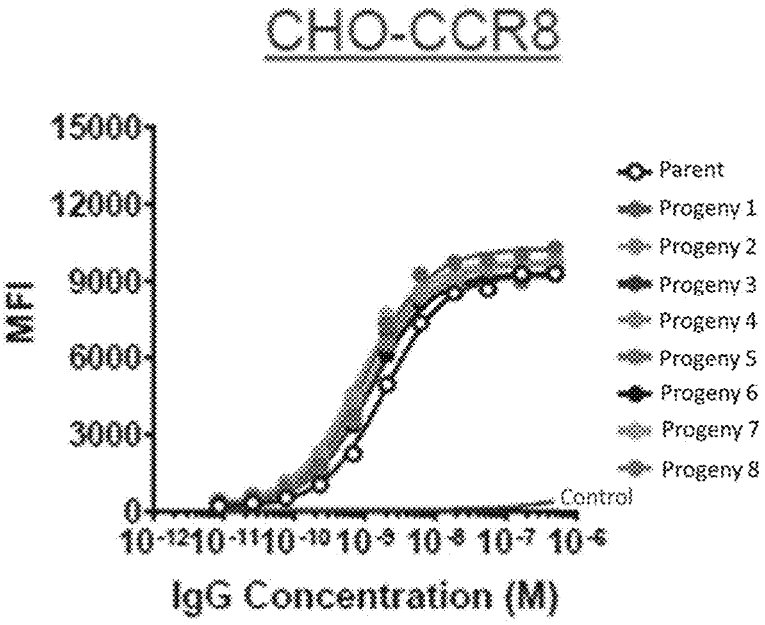
FIGS. 1A-1D show that progenies of affinity maturation of a parental clone have improved binding affinity to CCR8. In an IgG format, affinity matured progeny have improved binding affinity to CCR8 (FIG. 1A) and decreased off target binding to CCR5 (FIG. 1B) in comparison to the parent antibody. Non-specific binding to CHO cells transduced with an empty vector (EV) is shown in FIG. 1C. In a Fab format, affinity matured progeny are shown to have improved binding affinity to CCR8 (FIG. 1D).
Figure 1B:
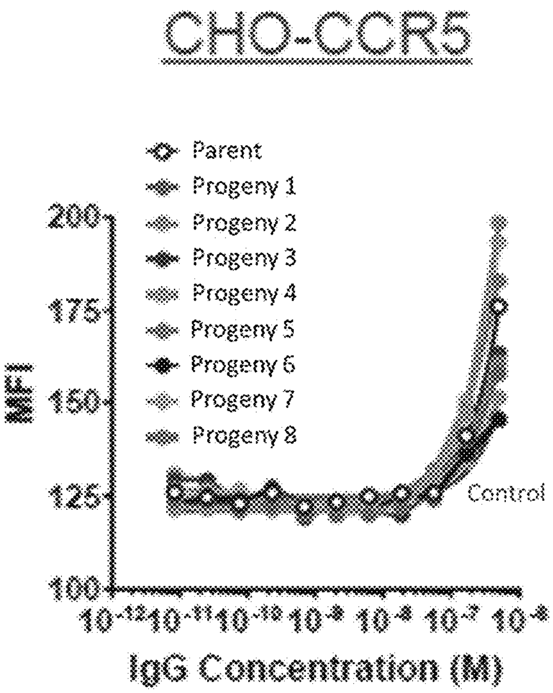
Figure 1C:
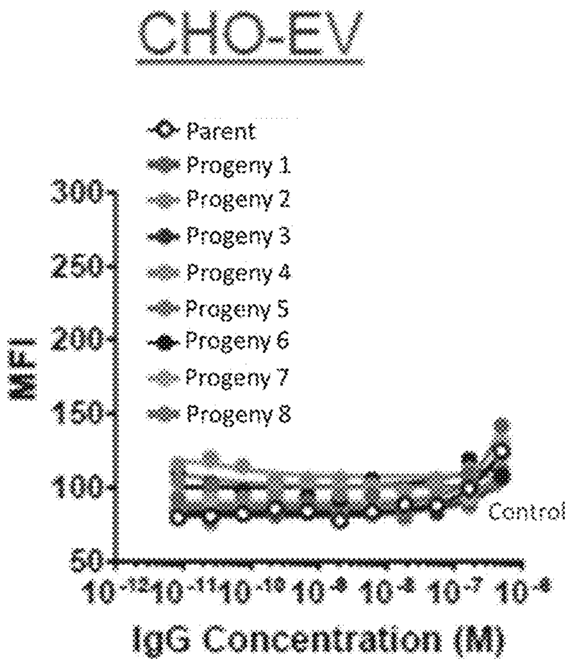
Figure 1D:
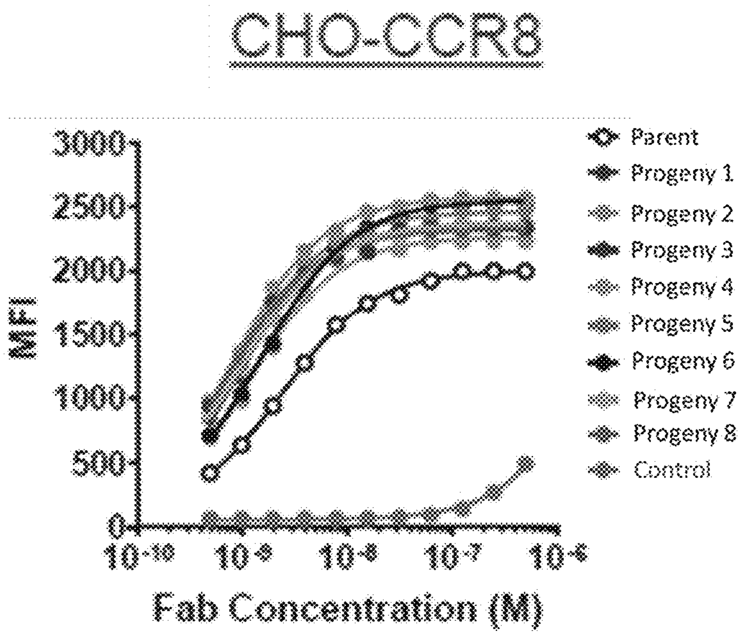

Provided herein, in some aspects, are antibodies that bind to C-C motif chemokine receptor 8 (CCR8). In some embodiments, antibodies described herein bind to CCR8 with high binding affinity and specificity. In some embodiments, antibodies described herein bind to CCR8 with high affinity but have low or substantially no binding affinity to other C-C motif chemokine receptors (e.g., CCR5). In some embodiments, antibodies described herein bind to CCR8 but do not bind (e.g., show no detectable binding) to other C-C motif chemokine receptors (e.g., CCR5). An antibody provided in the present disclosure may be produced using a known method in the art, e.g., recombinant technology.

Further provided herein, in some aspects, are antibody-drug conjugates (ADCs) comprising an anti-CCR8 antibody of the present disclosure, or an antigen fragment thereof, conjugated (e.g., covalently linked) to a compound. In some embodiments, in an ADC described herein, an anti-CCR8 antibody is conjugated (e.g., covalently linked) to a compound via a linker. In some embodiments, the compound conjugated to the anti-CCR8 antibody is amatoxin. In some embodiments, the amatoxin is amanitin. Compositions comprising the ADC are also provided. In some embodiments the ADCs described herein have antitumor properties. Methods of using the ADCs provided herein to treat cancer are also described.

Further aspects of the disclosure, including a description of defined terms, are provided below.

Definitions

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

CDR: As used herein, the term "CDR" refers to the complementarity determining region within antibody variable sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, A1-lazikani et al (1997) J. Molec. Biol. 273:927-948; and Almagro, J. Mol. Recognit. 17:132-143 (2004). As used herein, a CDR may refer to the CDR defined by any method known in the art. Two antibodies having the same CDR means that the two antibodies have the same amino acid sequence of that CDR as determined by the same method, for example, the IMGT definition.

There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designate the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs.

Conservative amino acid substitution: As used herein, a "conservative amino acid substitution" refers to an amino acid substitution that does not alter the relative charge or size characteristics of the protein in which the amino acid substitution is made (i.e., an amino acid replacement in a protein that changes a given amino acid to a different amino acid with similar biochemical properties). Variants can be prepared according to methods for altering polypeptide sequence known to one of ordinary skill in the art such as are found in references which compile such methods, e.g., Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids may include substitutions made amongst amino acids within the following groups: (a) M, I, L, V; (b) F, Y, W; (c) K, R, H; (d) A, G; (e) S, T; (f) Q, N; and (g) E, D. In some embodiments, the term "substitution" is contemplated to include one or more amino acid mutations.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human CCR8 and non-human primate CCR8) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

Effective amount/Therapeutically effective amount: As used in herein, the term "effective amount" means the amount of a drug or agent (e.g., an antibody) that elicits a biological or pharmaceutical response of a tissue, system, animal, or human, for example, which is sought by a researcher or clinician. As will be appreciated by those of ordinary skill in this art, the effective amount of a particular agent may vary depending on such factors as the desired biological endpoint, the pharmacokinetics of the agent, the condition being treated, the mode of administration, and the age and health of the subject. In addition, the term "therapeutically effective amount" refers to an amount that causes an improved treatment, cure, prevention, or alleviation of a disease, disorder, or side effect, or reduces the rate of progression of the disease or condition, compared to a corresponding subject who did not receive the amount. The term "therapeutically effective amount" encompasses an amount that improves overall therapy, reduces or avoids symptoms or causes of the condition, or enhances the therapeutic efficacy of another therapeutic agent.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In some embodiments, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a chicken, have been grafted onto human framework sequences.

Humanized antibody: The term "humanized antibody" refers to antibodies which comprise heavy and light chain variable region sequences from a non-human species (e.g., a chicken) but in which at least a portion of the VH and/or VL sequence has been altered to be more "human-like", i.e., more similar to human germline variable sequences. One type of humanized antibody is a CDR-grafted antibody, in which human CDR sequences are introduced into nonhuman VH and VL sequences to replace the corresponding nonhuman CDR sequences.

Isolated antibody: An "isolated antibody", as used herein, is intended to refer to an antibody that is substantially free of other antibodies having different antigenic specificities. Moreover, an isolated antibody may be substantially free of other cellular material and/or chemicals.

Recombinant antibody: The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V, and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al. (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others. In some embodiments, an antibody specifically binds to a target if the antibody has a KD for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to CCR8 but does not specifically bind to CCR5.

Vector: As used herein, "vector" refers to a nucleic acid delivery vehicle into which polynucleotides can be inserted. When the vector can express the protein encoded by the inserted polynucleotide, the vector is called an expression vector. The vector can be introduced into the host cell through transformation, transduction or transfection, so that the genetic material elements it carries can be expressed in the host cell. Vectors are well known to those skilled in the art, including but not limited to: plasmids; phagemids; artificial chromosomes, such as yeast artificial chromosomes (YAC), bacterial artificial chromosomes (BAC) or artificial chromosomes (PAC) derived from P1; bacteriophages such as lambda Bacteriophage or M13 phage and animal virus etc. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papillary viruses. Polyoma vacuole virus (such as SV40). A vector can contain a variety of elements that control expression, including but not limited to promoter sequences, transcription initiation sequences, enhancer sequences, selection elements, and reporter genes. In addition, the vector may also contain an origin of replication site.

Subject: A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the subject is a mammal. A non-human animal may be a transgenic animal.

Biological sample: The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

Administration: The terms "administer," "administering," or "administration," refers to implanting, absorbing, ingesting, injecting, inhaling, or otherwise introducing a compound, or a pharmaceutical composition thereof.

Treatment: The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

Condition: The terms "condition," "disease," and "disorder" are used interchangeably.

Chemical terms: Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry,* $7^{th}$ Edition, John Wiley & Sons, Inc., New York, 2013; Richard C. Larock, *Comprehensive Organic Transformations*, John Wiley & Sons, Inc., New York, 2018; and Carruthers, Some Modern Methods of Organic Synthesis, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972).

Unless otherwise provided, formulae and structures depicted herein include compounds that do not include isotopically enriched atoms, and also include compounds that include isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

Bond: In a formula, the bond 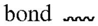 is a single bond, the dashed line - - - is a single bond or absent, and the bond  or  is a single or double bond.

Isotope: The term "isotope" refers to a variant of a particular chemical element such that, while all isotopes of a given element share the same number of protons in each atom of the element, those isotopes differ in the number of neutrons. The term "radioactivity" or "radioactive decay" refers to the process by which a nucleus of an unstable isotope (e.g., $^{18}F$, $^{2}H$) loses energy by emitting particles or rays (e.g., alpha particles, beta particles, and gamma rays) of ionizing radiation. Such an unstable isotope or a material including the unstable isotope is referred to as "radioactive." The Curie (Ci) is a non-SI (non-International System of Units) unit of radioactivity and is defined as $1\ Ci=3.7\times10^{10}$ decays per second. The term "specific activity" refers to the unit radioactivity of a material. In some embodiments, the term "specific activity" refers to the radioactivity of a material per micromole (μmol) of the material. Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

Aliphatic: The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

Range of values: When a range of values ("range") is listed, it encompasses each value and sub-range within the range. A range is inclusive of the values at the two ends of the range unless otherwise provided. For example, "$C_{1-6}$ alkyl" encompasses, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Alkyl: "Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-4}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In some embodiments, the alkyl group is an unsubstituted $C_{1-12}$ alkyl (such as unsubstituted $C_{1-6}$ alkyl, e.g., $-CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In some embodiments, the alkyl group is a substituted $C_{1-12}$ alkyl (such as substituted $C_{1-6}$ alkyl, e.g., $-CH_2F$, $-CHF_2$, $-CF_3$, $-CH_2CH_2F$, $-CH_2CHF_2$, $-CH_2CF_3$, or benzyl (Bn)).

Haloalkyl: "Haloalkyl" is an alkyl group is substituted with one or more halogens.

Perhaloalkyl: In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-4}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include $-CF_3$, $-CF_2CF_3$, $-CF_2CF_2CF_3$, $-CCl_3$, $-CFCl_2$, $-CF_2Cl$, and the like.

Heteroalkyl: The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In certain embodiments, a heteroalkyl group refers to a saturated group having from 1 to 12 carbon atoms and 1 or more heteroatoms within the parent chain ("hetero$C_{1-12}$ alkyl"). In some embodiments, a heteroalkyl group is a saturated group having 1 to 11 carbon atoms and 1 or more heteroatoms within the parent chain ("hetero$C_{1-11}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and lor 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-12}$ alkyl. In certain embodiments, the heteroalkyl group is a substituted hetero$C_{1-12}$ alkyl.

Alkenyl: The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("CI alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C═C double bond for which the stereochemistry is not specified (e.g., $-CH{=}CHCH_3$ or

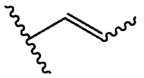

may be in the (E)- or (Z)-configuration.

Heteroalkenyl: The term "heteroalkenyl" refers to an alkenyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkenyl group refers to a group having from 1 to 20 carbon atoms, at least one double bond, and 1 or more heteroatoms within the parent chain ("hetero$C_{1-20}$ alkenyl"). In certain embodiments, a heteroalkenyl group refers to a group having from 1 to 12 carbon atoms, at least one double bond, and 1 or more heteroatoms within the parent chain ("hetero$C_{1-12}$ alkenyl"). In certain embodiments, a heteroalkenyl group refers to a group having from 1 to 11 carbon atoms, at least one double bond, and 1 or more heteroatoms within the parent chain ("hetero$C_{1-11}$ alkenyl"). In certain embodiments, a heteroalkenyl group refers to a group having from 1 to 10 carbon atoms, at least one double bond, and 1 or more heteroatoms within the parent chain ("hetero$C_{1-10}$ alkenyl"). In some embodiments, a heteroalkenyl group has 1 to 9 carbon atoms at least one double bond, and 1 or more heteroatoms within the parent chain ("hetero$C_{1-9}$ alkenyl"). In some embodiments, a heteroalkenyl group has 1 to 8 carbon atoms, at least one double bond, and 1 or more heteroatoms within the parent chain ("hetero$C_{1-8}$ alkenyl"). In some embodiments, a heteroalkenyl group has 1 to 7 carbon atoms, at least one double bond, and 1 or more heteroatoms within the parent chain ("hetero$C_{1-7}$ alkenyl"). In some embodiments, a heteroalkenyl group has 1 to 6 carbon atoms, at least one double bond, and 1 or more heteroatoms within the parent chain ("hetero$C_{1-6}$ alkenyl"). In some embodiments, a heteroalkenyl group has 1 to 5 carbon atoms, at least one double bond, and 1 or 2 heteroatoms within the parent chain ("hetero$C_{1-5}$ alkenyl"). In some embodiments, a heteroalkenyl group has 1 to 4 carbon atoms, at least one double bond, and 1 or 2 heteroatoms within the parent chain ("hetero$C_{1-4}$ alkenyl"). In some embodiments, a heteroalkenyl group has 1 to 3 carbon atoms, at least one double bond, and 1 heteroatom within the parent chain ("hetero$C_{1-3}$ alkenyl"). In some embodiments, a heteroalkenyl group has 1 to 2 carbon atoms, at least one double bond, and 1 heteroatom within the parent chain ("hetero$C_{1-2}$ alkenyl"). In some embodiments, a heteroalkenyl group has 1 to 6 carbon atoms, at least one double bond, and 1 or 2 heteroatoms within the parent chain ("hetero$C_{1-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{1-20}$ alkenyl. In certain embodiments, the heteroalkenyl group is a substituted hetero$C_{1-20}$ alkenyl.

Alkynyl: The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("$C_{1-20}$ alkynyl"). In some embodiments, an alkynyl group has 1 to 10 carbon atoms ("$C_{1-10}$ alkynyl"). In some embodiments, an alkynyl group has 1 to 9 carbon atoms ("$C_{1-9}$ alkynyl"). In some embodiments, an alkynyl group has 1 to 8 carbon atoms ("$C_{1-8}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in 1-butynyl). Examples of $C_{1-4}$ alkynyl groups include, without limitation, methylidynyl ($C_1$), ethynyl ($C_2$), 1-propynyl ($C_3$), 2-propynyl ($C_3$), 1-butynyl ($C_4$), 2-butynyl ($C_4$), and the like. Examples of $C_{1-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

Heteroalkynyl: The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 1 to 20 carbon atoms, at least one triple bond, and 1 or more heteroatoms within the parent chain ("hetero$C_{1-20}$ alkynyl"). In certain embodiments, a heteroalkynyl group refers to a group having from 1 to 10 carbon atoms, at least one triple bond, and 1 or more heteroatoms within the parent chain ("hetero$C_{1-10}$ alkynyl"). In some embodiments, a heteroalkynyl group has 1 to 9 carbon atoms, at least one triple bond, and 1 or more heteroatoms within the parent chain ("hetero$C_{1-9}$ alkynyl"). In some embodiments, a heteroalkynyl group has 1 to 8 carbon atoms, at least one triple bond, and 1 or more heteroatoms within the parent chain ("hetero$C_{1-8}$ alkynyl"). In some embodiments, a heteroalkynyl group has 1 to 7 carbon atoms, at least one triple bond, and 1 or more heteroatoms within the parent chain ("hetero$C_{1-7}$ alkynyl"). In some embodiments, a heteroalkynyl group has 1 to 6 carbon atoms, at least one triple bond, and 1 or more heteroatoms within the parent chain ("hetero$C_{1-6}$ alkynyl"). In some embodiments, a heteroalkynyl group has 1 to 5 carbon atoms, at least one triple bond, and 1 or 2 heteroatoms within the parent chain ("hetero$C_{1-5}$ alkynyl"). In some embodiments, a heteroalkynyl group has 1 to 4 carbon atoms, at least one triple bond, and lor 2 heteroatoms within the parent chain ("hetero$C_{1-4}$ alkynyl"). In some embodiments, a heteroalkynyl group has 1 to 3 carbon atoms, at least one triple bond, and 1 heteroatom within the parent chain ("hetero$C_{1-3}$ alkynyl"). In some embodiments, a heteroalkynyl group has 1 to 2 carbon atoms, at least one triple bond, and 1 heteroatom within the parent chain ("hetero$C_{1-2}$ alkynyl"). In some embodiments, a heteroalkynyl group has 1 to 6 carbon atoms, at least one triple bond, and 1 or 2 heteroatoms within the parent chain ("hetero$C_{1-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{1-20}$ alkynyl. In certain embodiments, the heteroalkynyl group is a substituted hetero$C_{1-20}$ alkynyl.

Carbocyclyl: The term "carbocyclyl," "carbocyclic," or "cycloalkyl" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 14 ring carbon atoms ("$C_{3-14}$ carbocyclyl"). In some embodiments, a carbocyclyl group has 3 to 13 ring carbon atoms ("$C_{3-13}$ carbocyclyl"). In some embodiments, a carbocyclyl group has 3 to 12 ring carbon atoms ("$C_{3-12}$ carbocyclyl"). In some embodiments, a carbocyclyl group has 3 to 11 ring carbon atoms ("$C_{3-11}$ carbocyclyl"). In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. Exemplary $C_{3-8}$ carbocyclyl groups include the aforementioned $C_{3-10}$ carbocyclyl groups as well as cycloundecyl ($C_{11}$), spiro[5.5] undecanyl ($C_{11}$), cyclododecyl ($C_{12}$), cyclododecenyl ($C_{12}$), cyclotridecane ($C_{13}$), cyclotetradecane ($C_{14}$), and the like. As the foregoing examples illustrate, in some embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In some embodiments, the carbocyclyl group is an unsubstituted $C_{3-14}$ carbocyclyl. In some embodiments, the carbocyclyl group is a substituted $C_{3-14}$ carbocyclyl. In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl (C) and cyclohexyl (C). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In some embodiments, the cycloalkyl group is an unsubstituted $C_{3-14}$ cycloalkyl. In some embodiments, the cycloalkyl group is a substituted $C_{3-14}$ cycloalkyl. In some embodiments, the carbocyclyl includes 0, 1, or 2 C═C double bonds in the carbocyclic ring system, as valency permits.

Heterocyclyl: The term "heterocyclyl," "heterocyclic," or "heterocycloalkyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In some embodiments, the heterocyclyl group is an unsubstituted 3-14 membered heterocyclyl. In some embodiments, the heterocyclyl group is a substituted 3-14 membered heterocyclyl. In some embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits. In some embodiments, the heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, the heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, the heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary heterocyclyl groups: Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzo-thienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3, 2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Aryl: The term "aryl" refers to a radical of a monocyclic or polycyclic (e.g., bicyclic or tricyclic) 4n+2 aromatic ring system (e.g., having 6, 10, or 14 pi-electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In some embodiments, the aryl group is an unsubstituted $C_{6-14}$ aryl. In some embodiments, the aryl group is a substituted $C_{6-14}$ aryl.

Aralkyl: "Aralkyl" is a subset of "alkyl" and refers to an alkyl group substituted by an aryl group, wherein the point of attachment is on the alkyl moiety.

Heteroaryl: The term "heteroaryl" refers to a radical of a 5-14 membered monocyclic or polycyclic (e.g., bicyclic, tricyclic) 4n+2 aromatic ring system (e.g., having 6, 10, or 14 pi-electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In some embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In some embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur. In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In some embodiments, the heteroaryl group is an unsubstituted 5-14 membered heteroaryl. In some embodiments, the heteroaryl group is a substituted 5-14 membered heteroaryl.

Exemplary heteroaryl groups: Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

Partially unsaturated: "Partially unsaturated" refers to a group that includes at least one double or triple bond. The term "partially unsaturated" encompasses rings having multiple sites of unsaturation, but does not include aromatic groups (e.g., aryl or heteroaryl groups) as herein defined.

Saturated: The term "saturated" or "fully saturated" refers to a moiety that does not contain a double or triple bond, e.g., the moiety only contains single bonds.

-ene: Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

Optionally substituted: A group is optionally substituted unless expressly provided otherwise. The term "optionally substituted" refers to being substituted or unsubstituted. In some embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which is substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In some embodiments, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. The present disclosure is not limited in any manner by the exemplary substituents described herein.

Exemplary carbon atom substituents: Exemplary carbon atom substituents include halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3^+X^-$, $—N(OR^{cc})R^{bb}$, —SH, $—SR^{aa}—$, $—SSR^{cc}$, $—C(=O)R^{aa}$, $—CO_2H$, —CHO, $—C(OR^{cc})_2$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—NR^{bb}CO_2R^{aa}$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$, $—OC(=NR^{bb})N(R^{bb})_2$, $—NR^{bb}C(=NR^{bb})N(R^{bb})_2$, $—C(=O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(=O)R^{aa}$, $—OS(=O)R^{aa}$, $—Si(R^{aa})_3$, $—OSi(R^{aa})_3—C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)(R^{aa})_2$, $—P(=O)(OR^{cc})_2$, $—OP(=O)(R^{aa})_2$, $—OP(=O)(OR^{cc})_2$, $—P(=O)(N(R^{bb})_2)_2$, $—OP(=O)(N(R^{bb})_2)_2$, $—NR^{bb}P(=O)(R^{aa})_2$, $—NR^{bb}P(=O)(OR^{cc})_2$, $—NR^{bb}P(=O)(N(R^{bb})_2)_2$, $—P(R^{cc})_2$, $—P(OR^{cc})_2$, $—P(R^{cc})_3^+X^-$, $—P(OR^{cc})_3^+X^-$, $—P(R^{cc})_4$, $—P(OR^{cc})_4$, $—OP(R^{cc})_2$, $—OP(R^{cc})_3^+X^-$, $—OP(OR^{cc})_2$, $—OP(OR^{cc})_3^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$; wherein:

each instance of $R^{aa}$ is, independently, selected from $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3^+X^-$, $—N(OR^{ee})R^{ff}$, —SH, $—SR^{ee}$, $—SSR^{ee}$, $—C(=O)R^{ee}$, $—CO_2H$, $—CO_2R^{ee}$, $—OC(=O)R^{ee}$, $—OCO_2R^{ee}$, $—C(=O)N(R^{ff})_2$, $—OC(=O)N(R^{ff})_2$, $—NR^{ff}C(=O)R^{ee}$, $—NR^{ff}CO_2R^{ee}$, $—NR^{ff}C(=O)N(R^{ff})_2$, $—C(=NR^{ff})OR^{ee}$, $—OC(=NR^{ff})R^{ee}$, $—OC(=NR^{ff})OR^{ee}$, $—C(=NR^{ff})N(R^{ff})_2$, $—OC(=NR^{ff})N(R^{ff})_2$, $—NR^{ff}C(=NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(=O)R^{ee}$, $—Si(R^{ee})_3$, $—OSi(R^{ee})_3$, $—C(=S)N(R^{ff})_2$, $—C(=O)SR^{ee}$, $—C(=S)SR^{ee}$, $—SC(=S)SR^{ee}$, —P(═O)(OR$^{ee}$)$_2$, —P(═O)(R$^{ee}$)$_2$, —OP(═O)(R$^{ee}$)$_2$, —OP(═O)(OR$^{ee}$)$_2$, $C_{1-10}$ alkyl, $C_{1-10}$ perhaloalkyl, $C_{1-10}$ alkenyl, $C_{1-10}$ alkynyl, hetero$C_{1-10}$alkyl, hetero$C_{1-10}$alkenyl, hetero$C_{1-10}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents are joined to form ═O or ═S;

each instance of R$^{ee}$ is, independently, selected from $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, 3-10 membered heterocyclyl, $C_{6-10}$ aryl, and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{gg}$ is, independently, halogen, —CN, —$NO_2$, —$N_3$, —$SO_2H$, —$SO_3H$, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(═O)($C_{1-6}$ alkyl), —$CO_2H$, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)O$C_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$ —C(═S)N($C_{1-6}$ alkyl)$_2$, C(═S)NH($C_{1-6}$ alkyl), C(═S)$NH_2$, —C(═O)S($C_{1-6}$ alkyl), —C(═S)S$C_{1-6}$ alkyl, —SC(═S)S$C_{1-6}$ alkyl, —P(═O)(O$C_{1-6}$ alkyl)$_2$, —P(═O)($C_{1-6}$ alkyl)$_2$, —OP(═O)($C_{1-6}$ alkyl)$_2$, —OP(═O)(O$C_{1-6}$ alkyl)$_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal R$^{gg}$ substituents can be joined to form ═O or ═S; and each $X^-$ is independently a counterion.

In some embodiments, each carbon atom substituent is independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, —$NO_2$, —C(═O)R$^{aa}$, —$CO_2$R$^{aa}$, —C(═O)N(R$^{bb}$)$_2$, —OC(═O)R$^{aa}$, —$OCO_2$R$^{aa}$, —OC(═O)N(R$^{bb}$)$_2$, —NR$^{bb}$C(═O)R$^{aa}$, —NR$^{bb}$$CO_2$R$^{aa}$, or —NR$^{bb}$C(═O)N(R$^{bb}$)$_2$. In some embodiments, each carbon atom substituent is independently halogen, substituted (e.g., substituted with one or more halogen) or unsubstituted $C_{1-10}$ alkyl, —OR$^{aa}$, —SR$^{aa}$, —N(R$^{bb}$)$_2$, —CN, —SCN, —$NO_2$, —C(═O)R$^{aa}$, —$CO_2$R$^{aa}$, —C(═O)N(R$^{bb}$)$_2$, —OC(═O)R$^{aa}$, —$OCO_2$R$^{aa}$, —OC(═O)N(R$^{bb}$)$_2$, —NR$^{bb}$C(═O)R$^{aa}$, —NR$^{bb}$$CO_2$R$^{aa}$, or —NR$^{bb}$C(═O)N(R$^{bb}$)$_2$, wherein R$^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts). In some embodiments, each carbon atom substituent is independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, or —$NO_2$. In some embodiments, each carbon atom substituent is independently halogen, substituted (e.g., substituted with one or more halogen moieties) or unsubstituted $C_{1-10}$ alkyl, —OR$^{aa}$, —SR$^{aa}$, —N(R$^{bb}$)$_2$, —CN, —SCN, or —$NO_2$, wherein R$^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts).

In some embodiments, the molecular weight of a carbon atom substituent is lower than 250, lower than 200, lower than 150, lower than 100, or lower than 50 g/mol. In some embodiments, a carbon atom substituent consists of carbon, hydrogen, fluorine, chlorine, bromine, iodine, oxygen, sulfur, nitrogen, and/or silicon atoms. In some embodiments, a carbon atom substituent consists of carbon, hydrogen, fluorine, chlorine, bromine, iodine, oxygen, sulfur, and/or nitrogen atoms. In some embodiments, a carbon atom substituent consists of carbon, hydrogen, fluorine, chlorine, bromine, and/or iodine atoms. In some embodiments, a carbon atom substituent consists of carbon, hydrogen, fluorine, and/or chlorine atoms.

Counterion: A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1- sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

Exemplary nitrogen atom substituents: Nitrogen atoms can be substituted or unsubstituted as valency permits, and include primary, secondary, tertiary, and quaternary nitrogen atoms. Exemplary nitrogen atom substituents include hydrogen, —OH, —$OR^{aa}$, —$N(R^{cc})_2$, —CN, —$C(═O)R^{aa}$, —$C(═O)N(R^{cc})_2$, —$CO_2R^{aa}$, —$SO_2R^{aa}$, —$C(═NR^{bb})R^{aa}$, —$C(═NR^{cc})OR$, —$C(═NR^{cc})N(R^{cc})_2$, —$SO_2N(R^{cc})_2$, —$SO_2R^{cc}$, —$SO_2OR^{cc}$, —$SOR^{aa}$, —$C(═S)N(R^{cc})_2$, —$C(═O)SR^{cc}$, —$C(═S)SR^{cc}$, —$P(═O)(OR^{cc})_2$, —$P(═O)(R^{aa})_2$, —$P(═O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the nitrogen atom substituents are independently substituted (e.g., substituted with one or more halogen) or unsubstituted $C_{1-6}$ alkyl, —$C(═O)R^{aa}$, —$CO_2R^{aa}$, —$C(═O)N(R^{bb})_2$, or a nitrogen protecting group. In certain embodiments, the nitrogen atom substituents are independently substituted (e.g., substituted with one or more halogen) or unsubstituted $C_{1-6}$ alkyl, —$C(═O)R^{aa}$, —$CO_2R^{aa}$, —$C(═O)N(R^{bb})_2$, or a nitrogen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the nitrogen atom substituents are independently substituted (e.g., substituted with one or more halogen) or unsubstituted $C_{1-6}$ alkyl or a nitrogen protecting group.

Nitrogen protecting group: In certain embodiments, the substituent present on a nitrogen atom is a "nitrogen protecting group" (also referred to as an amino protecting group). Nitrogen protecting groups include —OH, —$OR^{aa}$, —$N(R^{cc})_2$, —$C(═O)R^{aa}$, —$C(═O)N(R^{cc})_2$, —$CO_2R^{aa}$, —$SO_2R^{aa}$, —$C(═NR^{cc})R^{aa}$, —$C(═NR^{cc})OR^{aa}$, —$C(═NR^{cc})N(R^{cc})_2$, —$SO_2N(R^{cc})_2$, —$SO_2R^{cc}$, —$SO_2OR^{cc}$, —$SOR^{aa}$, —$C(═S)N(R^{cc})_2$, —$C(═O)SR^{cc}$, —$C(═S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Amide nitrogen protecting groups (e.g., —$C(═O)R^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —$C(═O)OR^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —$S(=O)_2R^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

Exemplary oxygen atom substituents: In certain embodiments, the oxygen atom substituents are independently substituted (e.g., substituted with one or more halogen) or unsubstituted $C_{1-6}$ alkyl, —$C(=O)R^{aa}$, —$CO_2R^{aa}$, —$C(=O)N(R^{bb})_2$, or an oxygen protecting group. In certain embodiments, the oxygen atom substituents are independently substituted (e.g., substituted with one or more halogen) or unsubstituted $C_{1-6}$ alkyl, —$C(=O)R^{aa}$, —$CO_2R^{aa}$, —$C(=O)N(R^{bb})_2$, or an oxygen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

Oxygen protecting group: In certain embodiments, the substituent present on an oxygen atom is an oxygen protecting group (also referred to herein as an "hydroxyl protecting group"). Oxygen protecting groups include —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

Exemplary sulfur atom substituents: In certain embodiments, the sulfur atom substituents are independently substituted (e.g., substituted with one or more halogen) or unsubstituted $C_{1-6}$ alkyl, —C(═O)$R^{aa}$, —$CO_2R^{aa}$, —C(═O)N$(R^{bb})_2$, or a sulfur protecting group. In certain embodiments, the sulfur atom substituents are independently substituted (e.g., substituted with one or more halogen) or unsubstituted $C_{1-6}$ alkyl, —C(═O)$R^{aa}$, —$CO_2R^{aa}$, —C(═O)N$(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

Sulfur protecting group: In certain embodiments, the substituent present on a sulfur atom is a sulfur protecting group (also referred to as a "thiol protecting group"). Sulfur protecting groups include —$R^{aa}$, —N$(R^{bb})_2$, —C(═O)S$R^{aa}$, —C(═O)$R^{aa}$, —$CO_2R^{aa}$, —C(═O)N$(R^{bb})_2$, —C(═N$R^{bb}$)$R^{aa}$, —C(═N$R^{bb}$)O$R^{aa}$, —C(═N$R^{bb}$)N$(R^{bb})_2$, —S(═O)$R^{aa}$, —$SO_2R^{aa}$, —Si$(R^{aa})_3$, —P$(R^{cc})_2$, —P$(R^{cc})_3^+X^-$, —P$(OR^{cc})_2$, —P$(OR^{cc})_3^+X^-$, —P(═O)$(R^{aa})_2$, —P(═O)$(OR^{cc})_2$, and —P(═O)$(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

Molecular weight: The "molecular weight" of —R, wherein —R is any monovalent moiety, is calculated by subtracting the atomic weight of a hydrogen atom from the molecular weight of the molecule R—H. The "molecular weight" of -L-, wherein -L- is any divalent moiety, is calculated by subtracting the combined atomic weight of two hydrogen atoms from the molecular weight of the molecule H-L-H.

Halo: The term "halo" or "halogen" refers to fluorine (fluoro, —F), chlorine (chloro, —Cl), bromine (bromo, —Br), or iodine (iodo, —I).

Hydroxyl: The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON$(R^{bb})_2$, —OC(═O)S$R^{aa}$, —OC(═O)$R^{aa}$, —O$CO_2R^{aa}$, —OC(═O)N$(R^{bb})_2$, —OC(═N$R^{bb}$)$R^{aa}$, —OC(═N$R^{bb}$)O$R^{aa}$, —OC(═N$R^{bb}$)N$(R^{bb})_2$, —OS(═O)$R^{aa}$, —$OSO_2$Ra, —OSi$(R^{aa})_3$, —OP$(R^{cc})_2$, —OP$(R^{cc})_3^+X^-$, —OP$(OR^{cc})_2$, —OP$(OR^{cc})_3^+X^-$, —OP(═O)$(R^{aa})_2$, —OP(═O)$(OR^{cc})_2$, and —OP(═O)$(N(R^{bb}))_2$, wherein $X^-$, $R^{aa}$, $R^{bb}$, and $R^{cc}$ are as defined herein.

Thiol: The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —S$R^{aa}$, —S═S$R^{cc}$, —SC(═S)S$R^{aa}$, —SC(═S)O$R^{aa}$, —SC(═S) N$(R^{bb})_2$, —SC(═O)S$R^{aa}$, —SC(═O)O$R^{aa}$, —SC(═O)N$(R^{bb})_2$, and —SC(═O)$R^{aa}$, wherein $R^{aa}$ and $R^{cc}$ are as defined herein.

Amino: The term "amino" refers to the group —$NH_2$. The term "substituted amino," by extension, refers to a monosubstituted amino, a disubstituted amino, or a trisubstituted amino. In some embodiments, the "substituted amino" is a monosubstituted amino or a disubstituted amino group.

Sulfinyl: The term "sulfinyl" refers to the group —S(═O)$R^{aa}$, wherein $R^{aa}$ is as defined herein.

Acyl: The term "acyl" refers to a group having the general formula —C(═O)$R^{X1}$, —C(═O)O$R^{X1}$, —C(═O)—O—C(═O)$R^{X1}$, —C(═O)S$R^{X1}$, —C(═O)N$(R^{X1})_2$, —C(═S)$R^{X1}$, —C(═S)N$(R^{X1})_2$, and —C(═S)S$(R^{X1})$, —C(═N$R^{X1}$)$R^{X1}$, —C(═N$R^{X1}$)O$R^{X1}$, —C(═N$R^{X1}$)S$R^{X1}$, and —C(═N$R^{X1}$)N$(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di- aliphaticamino, mono- or di- heteroaliphaticamino, mono- or di-alkylamino, mono- or di- heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Carbonyl: The term "carbonyl" refers to a group wherein the carbon directly attached to the parent molecule is $sp^2$ hybridized, and is substituted with an oxygen, nitrogen or sulfur atom, e.g., a group selected from ketones (—C(═O)$R^{aa}$), carboxylic acids (—$CO_2H$), aldehydes (—CHO), esters (—$CO_2R^{aa}$, —C(═O)S$R^{aa}$, —C(═S)S$R^{aa}$), amides (—C(═O)N($R^{bb}$)$_2$, —C(═O)N$R^{bb}SO_2R^{aa}$, —C(═S)N($R^{bb}$)$_2$), and imines (—C(═N$R^{bb}$)$R^{aa}$, —C(═N$R^{bb}$)O$R^{aa}$), —C(═N$R^{bb}$)N($R^{bb}$)$_2$), wherein $R^{aa}$ and $R^{bb}$ are as defined herein.

Oxo: The term "oxo" refers to the group ═O, and the term "thiooxo" refers to the group ═S.

At least one instance: Use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Pharmaceutically acceptable salt: "Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts. It is to be understood that the term "antibody-drug conjugate (ADC) or a pharmaceutically acceptable salt," as used herein, encompasses any one of the ADCs described herein including any associated molecules, e.g., ions, water, solvents, either in vitro or in vivo in a subject.

Solvate: The term "solvate" refers to forms of the compound that are associated with a solvent. This physical association may include hydrogen bonding. Conventional solvents include water, methanol, ethanol, acetic acid, DMSO, THF, diethyl ether, and the like. Suitable solvates include pharmaceutically acceptable solvates and further include both stoichiometric solvates and non-stoichiometric solvates. In certain instances, the solvate will be capable of isolation. "Solvate" encompasses both solution-phase and isolable solvates. Representative solvates include hydrates, ethanolates, and methanolates.

Hydrate: The term "hydrate" refers to a compound that is associated with water. Hydrates include stoichiometric hydrates and non-stoichiometric hydrates. The number of the water molecules contained in a stoichiometric hydrate of a compound is in a definite ratio to the number of the compound molecules in the hydrate. Therefore, a stoichiometric hydrate of a compound may be represented, for example, by the general formula $R \cdot x\ H_2O$, wherein R is the compound and wherein x is a number greater than 0. A given compound may form more than one type of stoichiometric hydrate, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

Tautomers: The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro- forms of phenylnitromethane, that are likewise formed by treatment with acid or base. Tautomeric forms may be relevant to the attainment of the optimal chemical reactivity and biological activity of a compound of interest.

Isomer: "Isomers" are compounds that have the same molecular formula but differ in the nature or sequence of bonding of their atoms or the arrangement of their atoms in space are termed "isomers".

Stereoisomer: Isomers that differ in the arrangement of their atoms in space are termed "stereoisomers".

Diastereomer: Stereoisomers that are not mirror images of one another are termed "diastereomers."

Enantiomer: Diastereomers that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

These and other exemplary substituents are described in more detail in the Detailed Description, Examples, and Claims. The present disclosure is not limited in any manner by the above exemplary listing of substituents.

Anti-CCR8 Antibodies

As used herein, the term "antibody" refers to an isolated or recombinant binding agent that comprises the necessary variable region sequences to specifically bind an antigenic epitope. Therefore, an "antibody" as used herein is any form of antibody or fragment thereof that exhibits the desired biological activity, e.g., binding the specific target antigen. Thus, it is used in the broadest sense and specifically covers monoclonal antibodies (including full-length monoclonal antibodies), polyclonal antibodies, human antibodies, humanized antibodies, chimeric antibodies, single domain antibodies, diabodies, multispecific antibodies (e.g., bispecific antibodies), and antibody fragments including but not limited to scFv, Fab, and (Fab')2, so long as they exhibit the desired biological activity (e.g., binding to CCR8).

In some embodiments, an antibody is a polypeptide that includes at least one immunoglobulin variable domain or at least one antigenic determinant, e.g., paratope that specifically binds to an antigen. In some embodiments, an antibody is a full-length antibody. In some embodiments, an antibody is a humanized antibody. In some embodiments, an antibody is a Fab fragment, a F(ab') fragment, a $F(ab')_2$ fragment, a Fv fragment or a scFv fragment. In some embodiments the antibody is a Fab. In some embodiments, an antibody is a diabody. In some embodiments, an antibody comprises a framework having a human germline sequence. In some embodiments, an antibody is a full length IgG. In some embodiments the full length IgG is IgG1, IgG2, IgG3, or IgG4. In another embodiment, an antibody comprises a heavy chain constant domain that is IgG, IgG1, IgG2, IgG2A, IgG2B, IgG2C, IgG3, IgG4, IgA1, IgA2, IgD, IgM, or IgE. In some embodiments, an antibody comprises a heavy (H) chain variable region (abbreviated herein as VH), and/or a light (L) chain variable region (abbreviated herein as VL).

In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha ($\alpha$), delta ($\Delta$), epsilon ($\varepsilon$), gamma ($\gamma$) or mu ($\mu$) heavy chain. In some embodiments, the heavy chain of an antibody described herein can comprise a human alpha ($\alpha$), delta ($\Delta$), epsilon ($\varepsilon$), gamma ($\gamma$) or mu ($\mu$) heavy chain. In a particular embodiment, an antibody described herein comprises a human gamma 1 CH1, CH2, and/or CH3 domain. In some embodiments, the amino acid sequence of the VH domain comprises the amino acid sequence of a human gamma ($\gamma$) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, the VL domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecules are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecules are a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

Provided herein, in some aspects, are antibodies that bind to CCR8 (e.g., human CCR8). CCR8, also previously called CY6, CKR-L1 or TER1, is a G protein-coupled 7-transmembrane CC chemokine receptor protein expressed in the thymus, spleen, and other regions. A gene encoding this protein resides on human chromosome 3p21. Tumor-infiltrating Treg cells and tumor-infiltrating macrophage cells have been found to specifically express CCR8. CCR8 inhibitory agents (e.g., antibodies) can decrease the cell counts of tumor-infiltrating Treg cells and tumor-infiltrating macrophage cells, and can inhibits tumor growth.

Human CCR8 has a UniProt Accession No. of P51685 (SEQ ID NO: 136). *Macaca fascicularis* (cynomolgus) CCR8 has a UniProt Accession No. of G7NYJ2 (SEQ ID NO: 137). *Macaca mulatta* CCR8 has a UniProt Accession No. of 097665 (SEQ ID NO: 138).

Human CCR8 Amino Acid Sequence (UniProt Accession No. P51685; SEQ ID NO: 136)

MDYTLDLSVTTVTDYYYPDIFSSPCDAELI-
QTNGKLLLAVFYCLLFVFSLLGNSLVILV
LVVCKKLRSITDVYLLNLALSDLL-
FVFSFPFQTYYLLDQWVFGTVMC-
KVVSGFYYIGF YSSMFFITLMSVDRY-
LAVVHAVYALKVRTIRMGTTLCLAVWLTAIMATI-
PLLVFYQV
ASEDGVLQCYSFYNQQTLKWKIFTNFKM-
NILGLLIPFTIFMFCYIKILHQLKRCQNHNK
TKAIRLVLIVVIASLLFWVPFNVVLFLT-
SLHSMHILDGCSISQQLTYATHVTEIISFTHCC
VNPVIYAFVGEKFKKHLSEIFQKSCSQIFNYL-
GRQMPRESCEKSSSCQQHSSRSSSVDYI L

*Macaca fascicularis* (Cynomolgus) CCR8 Amino Acid Sequence (UniProt Accession No. G7NYJ2; SEQ ID NO: 137)

MDYTLDPSMTTMTDYYYPDSLSSPCDGELI-QRNDKLLLAVFYCLLFVFSLLGNSLVIL VLVVCKKLRNITDIYLLNLALSDLL-FVFSFPFQTYYQLDQWVFGTVMCKVVSGFYYIG FYSSMFFITLMSVDRYLAVVHAVYAI-KVRTIRMGTTLSLVVWLTAIMATIPLLVFYQV ASEDGVLQCYSFYNQQTLKWKIFTNFEMNILGL-LIPFTIFMFCYIKILHQLKRCQNHNK TKAIR-LVLIVVIASLLFWVPFNVVLFLTSLHSMHILDGC-SISQQLNYATHVTEIISFTHCC VNPVIYAFVGEKFKKHLSEIFQKSCSHIFIYL-GRQMPRESCEKSSSCQQHSFRSSSIDYIL

*Macaca mulatta* CCR8 Amino Acid Sequence (UniProt Accession No. 097665; SEQ ID NO: 138)

MDYTLDPSMTTMTDYYYPDSLSSPCDGELI-QRNDKLLLAVFYCLLFVFSLLGNSLVIL VLVVCKKLRNITDIYLLNLALSDLL-FVFSFPFQTYYQLDQWVFGTVMCKVVSGFYYIG FYSSMFFITLMSVDRYLAVVHAVYAI-KVRTIRMGTTTLSLLVWLTAIMATIPLLVFYQ VASEDGVLQCYSFYNQQTLKWKIFTNFEM-NILGLLIPFTIFMFCYIKILHQLKRCQNHN KTKAIRLVLIVVIASLLFWVPFNVVLFLT-SLHSMHILDGCSISQQLNYATHVTEIISFTHC CVNPVIYAFVGEKFKKHLSEIFQKSCSHIFIYL-GRQMPRESCEKSSSCQQHSFRSSSIDYI L

In some embodiments, antibodies provided herein bind to CCR8 (e.g., human CCR8) with high affinity and specificity. In some embodiments, an antibody described herein specifically binds to any extracellular epitope of CCR8 or an epitope that becomes exposed to an antibody. In some embodiments, an antibody provided herein binds specifically to CCR8 from human, non-human primates, mouse, and/or rat. In some embodiments, an antibody provided herein binds to human CCR8. In some embodiments, an antibody described herein binds to an amino acid segment of a human or non-human primate CCR8, as provided in SEQ ID NOs: 136-138.

In some embodiments, an antibody described herein specifically binds CCR8 (e.g., a human or non-human primate CCR8) with binding affinity (e.g., as indicated by Kd) of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody described herein binds to CCR8 with a Kd of sub-nanomolar range. In some embodiments, an antibody described herein selectively binds to CCR8 but does not bind to other chemokine receptors (e.g., CCR5). In some embodiments, an antibody described herein binds to human CCR8 and cynomolgus CCR8 (e.g., with a Kd of $10^{-7}$ M, $10^{-8}$ M, $10^{-9}$ M, $10^{-10}$ M, $10^{-11}$ M, $10^{-12}$ M, $10^{-13}$ M, or less), but does not bind to mouse CCR8. The affinity and binding kinetics of antibodies described herein can be tested using any suitable method including but not limited to biosensor technology (e.g., OCTET or BIACORE).

In some embodiments, an antibody of the present disclosure comprises a heavy chain variable region (VH) comprising a heavy chain complementary determining region 1 (CDR-H1), a heavy chain complementary determining region 2 (CDR-H2), a heavy chain complementary determining region 3 (CDR-H3), and/or a light chain variable domain (VL) comprising a light chain complementary determining region 1 (CDR-L1), a light chain complementary determining region 1 (CDR-L2), and a light chain complementary determining region 1 (CDR-L3). In some embodiments, an antibody of the present disclosure is affinity matured, e.g., by introducing amino acid variations into one or more CDRs of a parental antibody (e.g., those disclosed in WO2021178749). In some embodiments, an affinity matured antibody has enhanced binding activity (e.g., affinity and/or specificity) to CCR8 relative to the parental antibody, as disclosed in WO2021178749 and incorporated by reference herein.

In some embodiments, an antibody described herein comprises a CDR-H1, a CDR-H2, and a CDR-H3 that, collectively, contain no more than 10 amino acid variations (e.g., no more than 10, 9, 8, 7, 6, 5, 4, 3, 2, or 1 amino acid variation) as compared with the CDR-H1, CDR-H2, and CDR-H3 of any one of the antibodies of Table 1. In some embodiments, an antibody described herein comprises a CDR-L1, a CDR-L2, and a CDR-L3 that, collectively, contain no more than 10 amino acid variations (e.g., no more than 10, 9, 8, 7, 6, 5, 4, 3, 2, or 1 amino acid variation) as compared with the CDR-L1, CDR-L2, and CDR-L3 of any one of the antibodies of Table 1. In some embodiments, an antibody described herein comprises a CDR-H1, a CDR-H2, a CDR-H3, a CDR-L1, a CDR-L2, and a CDR-L3 that, collectively, contain no more than 10 amino acid variations (e.g., no more than 10, 9, 8, 7, 6, 5, 4, 3, 2, or 1 amino acid variation) as compared with the CDR-H1, CDR-H2, CDR-H3, CDR-L1, CDR-L2, and CDR-L3 of any one of the antibodies of Table 1.

In some embodiments, an antibody described herein comprises a CDR-H1, a CDR-H2, and a CDR-H3 that, collectively, have at least 90% (e.g., at least 90%, at least 95%, or at least 97%) sequence identity to the CDR-H1, CDR-H2, and CDR-H3 of any one of the antibodies of Table 1. In some embodiments, an antibody described herein comprises a CDR-L1, a CDR-L2, and a CDR-L3 that, collectively, have at least 90% % (e.g., at least 90%, at least 95%, or at least 97%) sequence identity to the CDR-L1, CDR-L2, and CDR-L3 of any one of the antibodies of Table 1. In some embodiments, an antibody described herein comprises a CDR-H1, a CDR-H2, a CDR-H3, a CDR-L1, a CDR-L2, and a CDR-L3 that, collectively, have at least 90% (e.g., at least 90%, at least 95%, or at least 97%) sequence identity to the CDR-H1, CDR-H2, CDR-H3, CDR-L1, CDR-L2, and CDR-L3 of any one of the antibodies of Table 1.

In some embodiments, an antibody described herein comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH of any one of the antibodies of Table 1. Alternatively, or in addition, an antibody described herein comprises a VL containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VL of any one of the antibodies of Table 1.

In some embodiments, an antibody described herein comprises a VH comprising an amino acid sequence that is at least 80% (e.g., at least 80%, at least 85%, at least 90%, at least 95%, at least 99%) identical to the VH of any one of the antibodies of Table 1. Alternatively, or in addition, an antibody described herein comprises a VL comprising an amino acid sequence that is at least 80% (e.g., at least 80%, at least 85%, at least 90%, at least 95%, at least 99%) identical to the VL of any one of the antibodies of Table 1.

In some embodiments, an antibody described herein comprises a heavy chain comprising an amino acid sequence that is at least 80% (e.g., at least 80%, at least 85%, at least 90%, at least 95%, at least 99%) identical to the heavy chain of any one of the antibodies of Table 2. Alternatively, or in addition, an antibody described herein comprises a light chain comprising an amino acid sequence that is at least 80%

(e.g., at least 80%, at least 85%, at least 90%, at least 95%, at least 99%) identical to the light chain of any one of the antibodies of Table 2.

In some embodiments, any of the amino acid variations in the antibody sequences (e.g., CDRs, VH, and/or VL) provided herein may be conservative substitutions (e.g., as described above). In some embodiments, binding to CCR8 of the antibodies containing amino acid variations is maintained (e.g., substantially maintained, for example, at least 50%, at least 60%, at least 70%, at least 80%, at least 90%, at least 95% of the binding of the original antibody from which it is derived). Any method can be used to ascertain whether binding to CCR8 is maintained, for example, using binding assays and conditions known in the art.

In some embodiments, an antibody described herein binds to CCR8 and comprises a VH comprising a CDR-H1 comprising the amino acid sequence of $FX_{24}FNAYAMN$ (SEQ ID NO: 127), wherein $X_{24}$ is T, Q, S, or N; a CDR-H2 comprising the amino acid sequence of $RIRSKSNNYATYYAX_{25}SVKX_{26}$ (SEQ ID NO: 128), wherein $X_{25}$ is D, A, G, E, or V, and $X_{26}$ is D, P, or E; a CDR-H3 comprising the amino acid sequence of $VRQSYGNSNYAMDX_{27}$ (SEQ ID NO: 129), wherein $X_{27}$ is Y, H, W, or F; and/or a VL comprising a CDR-L1 comprising the amino acid sequence of $RX_{28}SKX_{29}LX_{30}HSNGNTYLY$ (SEQ ID NO: 130), wherein $X_{28}$ is S or T, $X_{29}$ is S, R, T, or K, $X_{30}$ is L, Q, I, or N; a CDR-L2 comprising the amino acid sequence of $X_{31}X_{32}SNLAS$ (SEQ ID NO: 131), wherein $X_{31}$ is R or K, and $X_{32}$ is M, V, K, R, or A; and a CDR-L3 comprising the amino acid sequence of $MQHX_{33}EYPFT$ (SEQ ID NO: 132), wherein $X_{33}$ is L, F, I, W, or Y; wherein, if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L, and/or if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, an antibody described herein binds to CCR8 and comprises a VH comprising a CDR-H1 comprising the amino acid sequence of $FX_{24}FNAYAMN$ (SEQ ID NO: 127), wherein $X_{24}$ is T, Q, or S; a CDR-H2 comprising the amino acid sequence of $RIRSKSNNYATYYAX_{25}SVKX_{26}$ (SEQ ID NO: 128), wherein $X_{25}$ is D, A, or G, and $X_{26}$ is D or P; a CDR-H3 comprising the amino acid sequence of $VRQSYGNSNYAMDX_{27}$ (SEQ ID NO: 129), wherein $X_{27}$ is Y or H; and/or a VL comprising a CDR-L1 comprising the amino acid sequence of $RX_{28}SKX_{29}LX_{30}HSNGNTYLY$ (SEQ ID NO: 130), wherein $X_{28}$ is S or T, $X_{29}$ is S or R, and $X_{30}$ is L or Q; a CDR-L2 comprising the amino acid sequence of $X_{31}X_{32}SNLAS$ (SEQ ID NO: 131), wherein $X_{31}$ is R or K, and $X_{32}$ is M, V, or K; and a CDR-L3 comprising the amino acid sequence of $MQHX_{33}EYPFT$ (SEQ ID NO: 132), wherein $X_{33}$ is L or F; wherein if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L, and/or if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, an antibody described herein binds to CCR8 and comprises a VH comprising a CDR-H1 comprising the amino acid sequence of $FX_{24}FNAYAMN$ (SEQ ID NO: 127), wherein $X_{24}$ is Q, or S; a CDR-H2 comprising the amino acid sequence of $RIRSKSNNYATYYAX_{25}SVKX_{26}$ (SEQ ID NO: 128), wherein $X_{25}$ is D, A, or G, and $X_{26}$ is D or P; a CDR-H3 comprising the amino acid sequence of $VRQSYGNSNYAMDX_{27}$ (SEQ ID NO: 129), wherein $X_{27}$ is Y or H; and/or a VL comprising a CDR-L1 comprising the amino acid sequence of $RX_{28}SKX_{29}LX_{30}HSNGNTYLY$ (SEQ ID NO: 130), wherein $X_{28}$ is S or T, $X_{29}$ is S or R, and $X_{30}$ is L or Q; a CDR-L2 comprising the amino acid sequence of $X_{31}X_{32}SNLAS$ (SEQ ID NO: 131), wherein $X_{31}$ is R or K, and $X_{32}$ is M, V, or K; and a CDR-L3 comprising the amino acid sequence of $MQHX_{33}EYPFT$ (SEQ ID NO: 132), wherein $X_{33}$ is L or F.

In some embodiments, an antibody described herein binds to CCR8 and comprises a VH comprising a CDR-H1 comprising the amino acid sequence of $FX_{24}FNAYAMN$ (SEQ ID NO: 127), wherein $X_{24}$ is T, Q, or S; a CDR-H2 comprising the amino acid sequence of $RIRSKSNNYATYYAX_{25}SVKX_{26}$ (SEQ ID NO: 128), wherein $X_{25}$ is D, A, or G, and $X_{26}$ is D or P; a CDR-H3 comprising the amino acid sequence of VRQSYGNSNYAMDH (SEQ ID NO: 90); and/or a VL comprising a CDR-L1 comprising the amino acid sequence of $RX_{28}SKX_{29}LX_{30}HSNGNTYLY$ (SEQ ID NO: 130), wherein $X_{28}$ is S or T, $X_{29}$ is S or R, and $X_{30}$ is L or Q; a CDR-L2 comprising the amino acid sequence of $X_{31}X_{32}SNLAS$ (SEQ ID NO: 131), wherein $X_{31}$ is R or K, and $X_{32}$ is M, V, or K; and a CDR-L3 comprising the amino acid sequence of $MQHX_{33}EYPFT$ (SEQ ID NO: 132), wherein $X_{33}$ is L or F.

In some embodiments, an antibody described herein binds to a CCR8 and comprises a VH comprising a CDR-H1 comprising the amino acid sequence of FQFNAYAMN (SEQ ID NO: 88); a CDR-H2 comprising the amino acid sequence of $RIRSKSNNYATYYADSVKX_{26}$ (SEQ ID NO: 139), wherein $X_{26}$ is D or P; a CDR-H3 comprising the amino acid sequence of VRQSYGNSNYAMDH (SEQ ID NO: 90); and/or a VL comprising a CDR-L1 comprising the amino acid sequence of $RSSKSLX_{30}HSNGNTYLY$ (SEQ ID NO: 140), wherein $X_{30}$ is L or Q; a CDR-L2 comprising the amino acid sequence of RVSNLAS (SEQ ID NO: 92); and a CDR-L3 comprising the amino acid sequence of MQHFEYPFT (SEQ ID NO: 96).

In some embodiments, in an antibody described herein, the CDR-H1 comprises the amino acid sequence of SEQ ID NO: 88, the CDR-H2 comprises the amino acid sequence of SEQ ID NO: 26, the CDR-H3 comprises the amino acid sequence of SEQ ID NO: 90; and/or the CDR-L1 comprises the amino acid sequence of SEQ ID NO: 28, the CDR-L2 comprises the amino acid sequence of SEQ ID NO: 92, and the CDR-L3 comprises the amino acid sequence of SEQ ID NO: 96.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 99, and the VL comprises an amino acid sequence that is at least 80% (e.g., at least 80%, at least 85%, at least 90%, at least 95%, at least 99%) identical to the amino acid sequence of SEQ ID NO: 100. In some embodiments, in an antibody described herein, the VH comprises the amino acid sequence of SEQ ID NO: 99, and the VL comprises the amino acid sequence of SEQ ID NO: 100.

In some embodiments, in an antibody described herein, the CDR-H1 comprises the amino acid sequence of SEQ ID NO: 88, the CDR-H2 comprises the amino acid sequence of SEQ ID NO: 89, the CDR-H3 comprises the amino acid sequence of SEQ ID NO: 90; and/or the CDR-L1 comprises the amino acid sequence of SEQ ID NO: 102, the CDR-L2 comprises the amino acid sequence of SEQ ID NO: 92, and the CDR-L3 comprises the amino acid sequence of SEQ ID NO: 96.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 93, and the VL comprises an amino acid sequence that is at least 80% (e.g., at least 80%, at least 85%, at least 90%, at least 95%, at least 99%) identical to the amino acid sequence of SEQ ID NO: 103. In some embodiments, in an antibody described herein, the VH comprises the amino acid sequence of SEQ ID NO: 93, and the VL comprises the amino acid sequence of SEQ ID NO: 103.

In some embodiments, in an antibody described herein, the CDR-H1 comprises the amino acid sequence of SEQ ID NO: 88, the CDR-H2 comprises the amino acid sequence of SEQ ID NO: 89, the CDR-H3 comprises the amino acid sequence of SEQ ID NO: 90; and/or the CDR-L1 comprises the amino acid sequence of SEQ ID NO: 91, the CDR-L2 comprises the amino acid sequence of SEQ ID NO: 92, and the CDR-L3 comprises the amino acid sequence of SEQ ID NO: 30.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 93, and the VL comprises an amino acid sequence that is at least 80% (e.g., at least 80%, at least 85%, at least 90%, at least 95%, at least 99%) identical to the amino acid sequence of SEQ ID NO: 94. In some embodiments, in an antibody described herein, the VH comprises the amino acid sequence of SEQ ID NO: 93, and the VL comprises the amino acid sequence of SEQ ID NO: 94.

In some embodiments, in an antibody described herein, the CDR-H1 comprises the amino acid sequence of SEQ ID NO: 88, the CDR-H2 comprises the amino acid sequence of SEQ ID NO: 89, the CDR-H3 comprises the amino acid sequence of SEQ ID NO: 90; and/or the CDR-L1 comprises the amino acid sequence of SEQ ID NO: 91, the CDR-L2 comprises the amino acid sequence of SEQ ID NO: 95, and the CDR-L3 comprises the amino acid sequence of SEQ ID NO: 96.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 93, and the VL comprises an amino acid sequence that is at least 80% (e.g., at least 80%, at least 85%, at least 90%, at least 95%, at least 99%) identical to the amino acid sequence of SEQ ID NO: 97. In some embodiments, in an antibody described herein, the VH comprises the amino acid sequence of SEQ ID NO: 93, and the VL comprises the amino acid sequence of SEQ ID NO: 97.

In some embodiments, in an antibody described herein, the CDR-H1 comprises the amino acid sequence of SEQ ID NO: 88, the CDR-H2 comprises the amino acid sequence of SEQ ID NO: 26, the CDR-H3 comprises the amino acid sequence of SEQ ID NO: 27; and/or the CDR-L1 comprises the amino acid sequence of SEQ ID NO: 91, the CDR-L2 comprises the amino acid sequence of SEQ ID NO: 95, and the CDR-L3 comprises the amino acid sequence of SEQ ID NO: 96.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 98, and the VL comprises an amino acid sequence that is at least 80% (e.g., at least 80%, at least 85%, at least 90%, at least 95%, at least 99%) identical to the amino acid sequence of SEQ ID NO: 97. In some embodiments, in an antibody described herein, the VH comprises the amino acid sequence of SEQ ID NO: 98, and the VL comprises the amino acid sequence of SEQ ID NO: 97.

In some embodiments, in an antibody described herein, the CDR-H1 comprises the amino acid sequence of SEQ ID NO: 88, the CDR-H2 comprises the amino acid sequence of SEQ ID NO: 89, the CDR-H3 comprises the amino acid sequence of SEQ ID NO: 90; and/or the CDR-L1 comprises the amino acid sequence of SEQ ID NO: 28, the CDR-L2 comprises the amino acid sequence of SEQ ID NO: 95, and the CDR-L3 comprises the amino acid sequence of SEQ ID NO: 96.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 93, and the VL comprises an amino acid sequence that is at least 80% (e.g., at least 80%, at least 85%, at least 90%, at least 95%, at least 99%) identical to the amino acid sequence of SEQ ID NO: 101. In some embodiments, in an antibody described herein, the VH comprises the amino acid sequence of SEQ ID NO: 93, and the VL comprises the amino acid sequence of SEQ ID NO: 101.

In some embodiments, in an antibody described herein, the CDR-H1 comprises the amino acid sequence of SEQ ID NO: 88, the CDR-H2 comprises the amino acid sequence of SEQ ID NO: 104, the CDR-H3 comprises the amino acid sequence of SEQ ID NO: 27; and/or the CDR-L1 comprises the amino acid sequence of SEQ ID NO: 28, the CDR-L2 comprises the amino acid sequence of SEQ ID NO: 105, and the CDR-L3 comprises the amino acid sequence of SEQ ID NO: 96.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 106, and the VL comprises an amino acid sequence that is at least 80% (e.g., at least 80%, at least 85%, at least 90%, at least 95%, at least 99%) identical to the amino acid sequence of SEQ ID NO: 107. In some embodiments, in an antibody described herein, the VH comprises the amino acid sequence of SEQ ID NO: 106, and the VL comprises the amino acid sequence of SEQ ID NO: 107.

In some embodiments, in an antibody described herein, the CDR-H1 comprises the amino acid sequence of SEQ ID NO: 88, the CDR-H2 comprises the amino acid sequence of SEQ ID NO: 104, the CDR-H3 comprises the amino acid sequence of SEQ ID NO: 27; and/or the CDR-L1 comprises the amino acid sequence of SEQ ID NO: 91, the CDR-L2 comprises the amino acid sequence of SEQ ID NO: 92, and the CDR-L3 comprises the amino acid sequence of SEQ ID NO:30.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 106, and the VL comprises an amino acid sequence that is at least 80% (e.g., at least 80%, at least 85%, at least 90%, at least 95%, at least 99%) identical to the amino acid sequence of SEQ ID NO: 94. In some embodiments, in an antibody described herein, the VH comprises the amino acid sequence of SEQ ID NO: 106, and the VL comprises the amino acid sequence of SEQ ID NO: 94.

In some embodiments, in an antibody described herein, the CDR-H1 comprises the amino acid sequence of SEQ ID NO: 88, the CDR-H2 comprises the amino acid sequence of SEQ ID NO: 104, the CDR-H3 comprises the amino acid sequence of SEQ ID NO: 27; and/or the CDR-L1 comprises the amino acid sequence of SEQ ID NO: 102, the CDR-L2 comprises the amino acid sequence of SEQ ID NO: 92, and the CDR-L3 comprises the amino acid sequence of SEQ ID NO:30.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 106, and the VL comprises an amino acid sequence that is at least 80% (e.g., at least 80%, at least 85%, at least 90%, at least 95%, at least 99%) identical to the amino acid sequence of SEQ ID NO: 108. In some embodiments, in an antibody described herein, the VH comprises the amino acid sequence of SEQ ID NO: 106, and the VL comprises the amino acid sequence of SEQ ID NO: 108.

In some embodiments, in an antibody described herein, the CDR-H1 comprises the amino acid sequence of SEQ ID NO: 109, the CDR-H2 comprises the amino acid sequence of SEQ ID NO: 104, the CDR-H3 comprises the amino acid sequence of SEQ ID NO: 27; and/or the CDR-L1 comprises the amino acid sequence of SEQ ID NO: 110, the CDR-L2 comprises the amino acid sequence of SEQ ID NO: 92, and the CDR-L3 comprises the amino acid sequence of SEQ ID NO: 96.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 111, and the VL comprises an amino acid sequence that is at least 80% (e.g., at least 80%, at least 85%, at least 90%, at least 95%, at least 99%) identical to the amino acid sequence of SEQ ID NO: 112. In some embodiments, in an antibody described herein, the VH comprises the amino acid sequence of SEQ ID NO: 111, and the VL comprises the amino acid sequence of SEQ ID NO: 112.

In some embodiments, in an antibody described herein, the CDR-H1 comprises the amino acid sequence of SEQ ID NO: 25, the CDR-H2 comprises the amino acid sequence of SEQ ID NO: 113, the CDR-H3 comprises the amino acid sequence of SEQ ID NO: 90; and/or the CDR-L1 comprises the amino acid sequence of SEQ ID NO: 91, the CDR-L2 comprises the amino acid sequence of SEQ ID NO: 92, and the CDR-L3 comprises the amino acid sequence of SEQ ID NO: 30.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 114, and the VL comprises an amino acid sequence that is at least 80% (e.g., at least 80%, at least 85%, at least 90%, at least 95%, at least 99%) identical to the amino acid sequence of SEQ ID NO: 94. In some embodiments, in an antibody described herein, the VH comprises the amino acid sequence of SEQ ID NO: 114, and the VL comprises the amino acid sequence of SEQ ID NO: 94.

In some embodiments, an antibody described herein binds to CCR8 and comprises a VH comprising a CDR-H1 comprising the amino acid sequence of YSISSGYYWG (SEQ ID NO: 9); a CDR-H2 comprising the amino acid sequence of SIYHSGNTYYRPSLKS (SEQ ID NO: 10); a CDR-H3 comprising the amino acid sequence of ARGKGGSWTAFGP (SEQ ID NO: 11); and/or a VL comprising a CDR-L1 comprising the amino acid sequence of RASQS$X_6$SS$X_7X_8$N (SEQ ID NO: 119), wherein $X_6$ is I, P, or L, $X_7$ is F, L, I, W, or Y, and $X_8$ is L, A, I, or V; a CDR-L2 comprising the amino acid sequence of A$X_9X_{10}$SLQS (SEQ ID NO: 120), wherein $X_9$ is A, I, L, or V, and $X_{10}$ is S, E, T, or D; and CDR-L3 comprising the amino acid sequence of QQG$X_{11}$STPPT (SEQ ID NO: 121), wherein $X_{11}$ is H, I, or L; wherein, if $X_6$ is I, $X_7$ is not F, $X_8$ is not L, $X_9$ is not A, $X_{10}$ is not S, and $X_{11}$ is not H.

In some embodiments, an antibody described herein binds to CCR8 and comprises a VH comprising a CDR-H1 comprising the amino acid sequence of YSISSGYYWG (SEQ ID NO: 9); a CDR-H2 comprising the amino acid sequence of SIYHSGNTYYRPSLKS (SEQ ID NO: 10); a CDR-H3 comprising the amino acid sequence of ARGKGGSWTAFGP (SEQ ID NO: 11); and/or a VL comprising a CDR-L1 comprising the amino acid sequence of RASQS$X_6$SS$X_7X_8$N (SEQ ID NO: 119), wherein $X_6$ is I or P, $X_7$ is F or L, and $X_8$ is L or A; a CDR-L2 comprising the amino acid sequence of A$X_9X_{10}$SLQS (SEQ ID NO: 120), wherein $X_9$ is A or I, and $X_{10}$ is S or E; and CDR-L3 comprising the amino acid sequence of QQG$X_{11}$STPPT (SEQ ID NO: 121), wherein $X_{11}$ is H or I; wherein if $X_6$ is I, $X_7$ is not F, $X_8$ is not L, $X_9$ is not A, $X_{10}$ is not S, and $X_{11}$ is not H.

In some embodiments, an antibody described herein binds to CCR8 and comprises a VH comprising a CDR-H1 comprising the amino acid sequence of YSISSGYYWG (SEQ ID NO: 9); a CDR-H2 comprising the amino acid sequence of SIYHSGNTYYRPSLKS (SEQ ID NO: 10); a CDR-H3 comprising the amino acid sequence of ARGKGGSWTAFGP (SEQ ID NO: 11); and/or a VL comprising a CDR-L1 comprising the amino acid sequence of RASQS$X_6$SS$X_7X_8$N (SEQ ID NO: 119), wherein $X_6$ is P, $X_7$ is F or L, and $X_8$ is L or A; a CDR-L2 comprising the amino acid sequence of A$X_9X_{10}$SLQS (SEQ ID NO: 120), wherein $X_9$ is A or I, and $X_{10}$ is S or E; and CDR-L3 comprising the amino acid sequence of QQG$X_{11}$STPPT (SEQ ID NO: 121), wherein $X_{11}$ is H or I.

In some embodiments, an antibody described herein binds to CCR8 and comprises a VH comprising a CDR-H1 comprising the amino acid sequence of YSISSGYYWG (SEQ ID NO: 9); a CDR-H2 comprising the amino acid sequence of SIYHSGNTYYRPSLKS (SEQ ID NO: 10); a CDR-H3 comprising the amino acid sequence of ARGKGGSWTAFGP (SEQ ID NO: 11); and/or a VL comprising a CDR-L1 comprising the amino acid sequence of RASQS$X_6$SS$X_7X_8$N (SEQ ID NO: 119), wherein $X_6$ is I or P, $X_7$ is L, and $X_8$ is L or A; a CDR-L2 comprising the amino acid sequence of A$X_9X_{10}$SLQS (SEQ ID NO: 120), wherein $X_9$ is A or I, and $X_{10}$ is S or E; and CDR-L3 comprising the amino acid sequence of QQG$X_{11}$STPPT (SEQ ID NO: 121), wherein $X_{11}$ is H or I.

In some embodiments, an antibody described herein binds to CCR8 and comprises a VH comprising a CDR-H1 comprising the amino acid sequence of YSISSGYYWG (SEQ ID NO: 9); a CDR-H2 comprising the amino acid sequence of SIYHSGNTYYRPSLKS (SEQ ID NO: 10); a CDR-H3 comprising the amino acid sequence of ARGKGGSWTAFGP (SEQ ID NO: 11); and/or a VL comprising a CDR-L1 comprising the amino acid sequence of RASQS$X_6$SS$X_7X_8$N (SEQ ID NO: 119), wherein $X_6$ is I or P, $X_7$ is F or L, and $X_8$ is A; a CDR-L2 comprising the amino acid sequence of A$X_9X_{10}$SLQS (SEQ ID NO: 120), wherein $X_9$ is A or I, and $X_{10}$ is S or E; and CDR-L3 comprising the amino acid sequence of QQG$X_{11}$STPPT (SEQ ID NO: 121), wherein $X_{11}$ is H or I.

In some embodiments, an antibody described herein binds to CCR8 and comprises a VH comprising a CDR-H1 comprising the amino acid sequence of YSISSGYYWG (SEQ ID NO: 9); a CDR-H2 comprising the amino acid sequence of SIYHSGNTYYRPSLKS (SEQ ID NO: 10); a CDR-H3 comprising the amino acid sequence of ARGKGGSWTAFGP (SEQ ID NO: 11); and/or a VL comprising a CDR-L1 comprising the amino acid sequence of RASQSX$_6$SSX$_7$X$_8$N (SEQ ID NO: 119), wherein X$_6$ is I or P, X$_7$ is F or L, and X$_8$ is L or A; a CDR-L2 comprising the amino acid sequence of AX$_9$X$_{10}$SLQS (SEQ ID NO: 120), wherein X$_9$ is I, and X$_{10}$ is S or E; and CDR-L3 comprising the amino acid sequence of QQGX$_{11}$STPPT (SEQ ID NO: 121), wherein X$_{11}$ is H or I.

In some embodiments, in an antibody described herein, the CDR-H1 comprises the amino acid sequence of SEQ ID NO: 9, the CDR-H2 comprises the amino acid sequence of SEQ ID NO: 10, the CDR-H3 comprises the amino acid sequence of SEQ ID NO: 11; and/or the CDR-L1 comprises the amino acid sequence of SEQ ID NO: 47, the CDR-L2 comprises the amino acid sequence of SEQ ID NO: 5, and the CDR-L3 comprises the amino acid sequence of SEQ ID NO: 13.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 14, and the VL comprises an amino acid sequence that is at least 80% (e.g., at least 80%, at least 85%, at least 90%, at least 95%, at least 99%) identical to the amino acid sequence of SEQ ID NO: 48. In some embodiments, in an antibody described herein, the VH comprises the amino acid sequence of SEQ ID NO: 14, and the VL comprises the amino acid sequence of SEQ ID NO: 48.

In some embodiments, in an antibody described herein, the CDR-H1 comprises the amino acid sequence of SEQ ID NO: 9, the CDR-H2 comprises the amino acid sequence of SEQ ID NO: 10, the CDR-H3 comprises the amino acid sequence of SEQ ID NO: 11; and/or the CDR-L1 comprises the amino acid sequence of SEQ ID NO: 49, the CDR-L2 comprises the amino acid sequence of SEQ ID NO: 5, and the CDR-L3 comprises the amino acid sequence of SEQ ID NO: 13.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 14, and the VL comprises an amino acid sequence that is at least 80% (e.g., at least 80%, at least 85%, at least 90%, at least 95%, at least 99%) identical to the amino acid sequence of SEQ ID NO: 50. In some embodiments, in an antibody described herein, the VH comprises the amino acid sequence of SEQ ID NO: 14, and the VL comprises the amino acid sequence of SEQ ID NO: 50.

In some embodiments, in an antibody described herein, the CDR-H1 comprises the amino acid sequence of SEQ ID NO: 9, the CDR-H2 comprises the amino acid sequence of SEQ ID NO: 10, the CDR-H3 comprises the amino acid sequence of SEQ ID NO: 11; and/or the CDR-L1 comprises the amino acid sequence of SEQ ID NO: 12, the CDR-L2 comprises the amino acid sequence of SEQ ID NO: 51, and the CDR-L3 comprises the amino acid sequence of SEQ ID NO: 13.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 14, and the VL comprises an amino acid sequence that is at least 80% (e.g., at least 80%, at least 85%, at least 90%, at least 95%, at least 99%) identical to the amino acid sequence of SEQ ID NO: 52. In some embodiments, in an antibody described herein, the VH comprises the amino acid sequence of SEQ ID NO: 14, and the VL comprises the amino acid sequence of SEQ ID NO: 52.

In some embodiments, in an antibody described herein, the CDR-H1 comprises the amino acid sequence of SEQ ID NO: 9, the CDR-H2 comprises the amino acid sequence of SEQ ID NO: 10, the CDR-H3 comprises the amino acid sequence of SEQ ID NO: 11; and/or the CDR-L1 comprises the amino acid sequence of SEQ ID NO: 53, the CDR-L2 comprises the amino acid sequence of SEQ ID NO: 54, and the CDR-L3 comprises the amino acid sequence of SEQ ID NO: 55.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 14, and the VL comprises an amino acid sequence that is at least 80% (e.g., at least 80%, at least 85%, at least 90%, at least 95%, at least 99%) identical to the amino acid sequence of SEQ ID NO: 56. In some embodiments, in an antibody described herein, the VH comprises the amino acid sequence of SEQ ID NO: 14, and the VL comprises the amino acid sequence of SEQ ID NO: 56.

In some embodiments, an antibody described herein binds to CCR8 and comprises a VH comprising a CDR-H1 comprising the amino acid sequence of GSISX$_{12}$SSX$_{13}$AWX$_{14}$ (SEQ ID NO: 122), wherein X$_{12}$ is S, Q, T, or N, X$_{13}$ is Y, N, I, L, W, F, or Q, and X$_{14}$ is G, L, S, T, or I; a CDR-H2 comprising the amino acid sequence of SIYYTGSTYYNPSLKS (SEQ ID NO: 17); a CDR-H3 comprising the amino acid sequence of X$_{15}$RGHRRDYIAFDI (SEQ ID NO: 123), wherein X$_{15}$ is L, V, I, or A; and/or a VL comprising CDR-L1 comprising the amino acid sequence of RAX$_{16}$QSIX$_{17}$X$_{18}$X$_{19}$LN (SEQ ID NO: 124), wherein X$_{16}$ is S, D, T, or E, X$_{17}$ is S, L, T, or I, X$_{18}$ is S, D, E, or T, and X$_{19}$ is Y, L, I, W, or F; a CDR-L2 comprising the amino acid sequence of X$_{20}$ASSLX$_{21}$X$_{22}$ (SEQ ID NO: 125), wherein X$_{20}$ is A, D, E, or V, X$_{21}$ is Q, D, F, Y, W, N, or E, and X$_{22}$ is S, E, T, or D; and a CDR-L3 comprising the amino acid sequence of QQSHNLPX$_{23}$ (SEQ ID NO: 126), wherein X$_{23}$ is T or S; wherein if X$_{12}$ is S, X$_{13}$ is not Y, X$_{14}$ is not G, X$_{15}$ is not L, X$_{16}$ is not S, X$_{17}$ is not S, X$_{18}$ is not S, X$_{19}$ is not Y, X$_{20}$ is not A, X$_{21}$ is not Q, X$_{22}$ is not S, and X$_{23}$ is not T, and/or if X$_{12}$ is S, X$_{13}$ is not Y, X$_{14}$ is not G, X$_{15}$ is not V, X$_{16}$ is not S, X$_{17}$ is not S, X$_{18}$ is not S, X$_{19}$ is not Y, X$_{20}$ is not A, X$_{21}$ is not Q, X$_{22}$ is not S, and X$_{23}$ is not T.

In some embodiments, an antibody described herein binds to CCR8 and comprises a VH comprising a CDR-H1 comprising the amino acid sequence of GSISX$_{12}$SSX$_{13}$AWX$_{14}$ (SEQ ID NO: 122), wherein X$_{12}$ is S or Q, X$_{13}$ is Y, N, or I, and X$_{14}$ is G, L, or S; a CDR-H2 comprising the amino acid sequence of SIYYTGSTYYNPSLKS (SEQ ID NO: 17); a CDR-H3 comprising the amino acid sequence of X$_{15}$RGHRRDYIAFDI (SEQ ID NO: 123), wherein X$_{15}$ is L or V; and/or a VL comprising CDR-L1 comprising the amino acid sequence of RAX$_{16}$QSIX$_{17}$X$_{18}$X$_{19}$LN (SEQ ID NO: 124), wherein X$_{16}$ is S or D, X$_{17}$ is S or L, X$_{18}$ is S, D or E, and X$_{19}$ is Y or L; a CDR-L2 comprising the amino acid sequence of X$_{20}$ASSLX$_{21}$X$_{22}$ (SEQ ID NO: 125), wherein X$_{20}$ is A or D, X$_{21}$ is Q, D, F, or Y, and X$_{22}$ is S or E; and a CDR-L3 comprising the amino acid sequence of QQSHNLPX$_{23}$ (SEQ ID NO: 126), wherein X$_{23}$ is T or S; wherein if X$_{12}$ is S, X$_{13}$ is not Y, X$_{14}$ is not G, X$_{15}$ is not L, X$_{16}$ is not S, X$_{17}$ is not S, X$_{18}$ is not S, X$_{19}$ is not Y, X$_{20}$ is not A, X$_{21}$ is not Q, X$_{22}$ is not S, and X$_{23}$ is not T, and/or if X$_{12}$ is S, X$_{13}$ is not Y, X$_{14}$ is not G, X$_{15}$ is not V, X$_{16}$ is not S, $X_{17}$ is not S, $X_{18}$ is not S, $X_{19}$ is not Y, $X_{20}$ is not A, $X_{21}$ is not Q, $X_{22}$ is not S, and $X_{23}$ is not T.

In some embodiments, an antibody described herein binds to CCR8 and comprises a VH comprising a CDR-H1 comprising the amino acid sequence of GSISX$_{12}$SSX$_{13}$AWX$_{14}$ (SEQ ID NO: 122), wherein $X_{12}$ is S or Q, $X_{13}$ is Y, N, or I, and $X_{14}$ is S or L; a CDR-H2 comprising the amino acid sequence of SIYYTGSTYYNPSLKS (SEQ ID NO: 17); a CDR-H3 comprising the amino acid sequence of X$_{15}$RGHRRDYIAFDI (SEQ ID NO: 123), wherein $X_{15}$ is L or V; and/or a VL comprising CDR-L1 comprising the amino acid sequence of RAX$_{16}$QSIX$_{17}$X$_{18}$X$_{19}$LN (SEQ ID NO: 124), wherein $X_{16}$ is S or D, $X_{17}$ is S or L, $X_{18}$ is S, D or E, and $X_{19}$ is Y or L; a CDR-L2 comprising the amino acid sequence of X$_{20}$ASSLX$_{21}$X$_{22}$ (SEQ ID NO: 125), wherein $X_{20}$ is A or D, $X_{21}$ is Q, D, F, or Y, and $X_{22}$ is S or E; and a CDR-L3 comprising the amino acid sequence of QQSHNLPX$_{23}$ (SEQ ID NO: 126), wherein $X_{23}$ is T or S.

In some embodiments, an antibody described herein binds to CCR8 and comprises a VH comprising a CDR-H1 comprising the amino acid sequence of GSISX$_{12}$SSX$_{13}$AWX$_{14}$ (SEQ ID NO: 122), wherein $X_{12}$ is S or Q, $X_{13}$ is N or I, and $X_{14}$ is G, S, or L; a CDR-H2 comprising the amino acid sequence of SIYYTGSTYYNPSLKS (SEQ ID NO: 17); a CDR-H3 comprising the amino acid sequence of X$_{15}$RGHRRDYIAFDI (SEQ ID NO: 123), wherein $X_{15}$ is L or V; and/or a VL comprising CDR-L1 comprising the amino acid sequence of RAX$_{16}$QSIX$_{17}$X$_{18}$X$_{19}$LN (SEQ ID NO: 124), wherein $X_{16}$ is S or D, $X_{17}$ is S or L, $X_{18}$ is S, D or E, and $X_{19}$ is Y or L; a CDR-L2 comprising the amino acid sequence of X$_{20}$ASSLX$_{21}$X$_{22}$ (SEQ ID NO: 125), wherein $X_{20}$ is A or D, $X_{21}$ is Q, D, F, or Y, and $X_{22}$ is S or E; and a CDR-L3 comprising the amino acid sequence of QQSHNLPX$_{23}$ (SEQ ID NO: 126), wherein $X_{23}$ is T or S.

In some embodiments, an antibody described herein binds to CCR8 and comprises a VH comprising a CDR-H1 comprising the amino acid sequence of GSISX$_{12}$SSX$_{13}$AWX$_{14}$ (SEQ ID NO: 122), wherein $X_{12}$ is S or Q, $X_{13}$ is Y, N, or I, and $X_{14}$ is G, S, or L; a CDR-H2 comprising the amino acid sequence of SIYYTGSTYYNPSLKS (SEQ ID NO: 17); a CDR-H3 comprising the amino acid sequence of X$_{15}$RGHRRDYIAFDI (SEQ ID NO: 123), wherein $X_{15}$ is L or V; and/or a VL comprising CDR-L1 comprising the amino acid sequence of RAX$_{16}$QSIX$_{17}$X$_{18}$X$_{19}$LN (SEQ ID NO: 124), wherein $X_{16}$ is S or D, $X_{17}$ is S or L, $X_{18}$ is S, D or E, and $X_{19}$ is Y or L; a CDR-L2 comprising the amino acid sequence of X$_{20}$ASSLX$_{21}$X$_{22}$ (SEQ ID NO: 125), wherein $X_{20}$ is A or D, $X_{21}$ is D, F, or Y, and $X_{22}$ is S or E; and a CDR-L3 comprising the amino acid sequence of QQSHNLPX$_{23}$ (SEQ ID NO: 126), wherein $X_{23}$ is T or S.

In some embodiments, an antibody described herein binds to a CCR8 and comprises a VH comprising a CDR-H1 comprising the amino acid sequence of GSISX$_{12}$SSX$_{13}$AWX$_{14}$ (SEQ ID NO: 122), wherein $X_{12}$ is S or Q, $X_{13}$ is Y, N, or I, and $X_{14}$ is G, S, or L; a CDR-H2 comprising the amino acid sequence of SIYYTG-STYYNPSLKS (SEQ ID NO: 17); a CDR-H3 comprising the amino acid sequence of X$_{15}$RGHRRDYIAFDI (SEQ ID NO: 123), wherein $X_{15}$ is L or V; and/or a VL comprising CDR-L1 comprising the amino acid sequence of RAX$_{16}$QSIX$_{17}$X$_{18}$X$_{19}$LN (SEQ ID NO: 124), wherein $X_{16}$ is S or D, $X_{17}$ is S or L, $X_{18}$ is D or E, and $X_{19}$ is Y or L; a CDR-L2 comprising the amino acid sequence of X$_{20}$ASSLX$_{21}$X$_{22}$ (SEQ ID NO: 125), wherein $X_{20}$ is A or D, $X_{21}$ is Q, D, F, or Y, and $X_{22}$ is S or E; and a CDR-L3 comprising the amino acid sequence of QQSHNLPX$_{23}$ (SEQ ID NO: 126), wherein $X_{23}$ is T or S.

In some embodiments, in an antibody described herein, the CDR-H1 comprises the amino acid sequence of SEQ ID NO: 57, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 19, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 58, and the VL comprises an amino acid sequence that is at least 80% (e.g., at least 80%, at least 85%, at least 90%, at least 95%, at least 99%) identical to the amino acid sequence of SEQ ID NO: 22. In some embodiments, in an antibody described herein, the VH comprises the amino acid sequence of SEQ ID NO: 58, and the VL comprises the amino acid sequence of SEQ ID NO: 22.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 59, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 21, and the VL comprises an amino acid sequence that is at least 80% (e.g., at least 80%, at least 85%, at least 90%, at least 95%, at least 99%) identical to the amino acid sequence of SEQ ID NO: 60. In some embodiments, in an antibody described herein, the VH comprises the amino acid sequence of SEQ ID NO: 21, and the VL comprises the amino acid sequence of SEQ ID NO: 60.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 61, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 21, and the VL comprises an amino acid sequence that is at least 80% (e.g., at least 80%, at least 85%, at least 90%, at least 95%, at least 99%) identical to the amino acid sequence of SEQ ID NO: 62. In some embodiments, in an antibody described herein, the VH comprises the amino acid sequence of SEQ ID NO: 21, and the VL comprises the amino acid sequence of SEQ ID NO: 62.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 19, the CDR-L2 comprises the amino acid sequence of SEQ ID NO: 63, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 21, and the VL comprises an amino acid sequence that is at least 80% (e.g., at least 80%, at least 85%, at least 90%, at least 95%, at least 99%) identical to the amino acid sequence of SEQ ID NO: 64. In some embodiments, in an antibody described herein, the VH comprises the amino acid sequence of SEQ ID NO: 21, and the VL comprises the amino acid sequence of SEQ ID NO: 64.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 19, the CDR-L2 comprises the amino acid sequence of SEQ ID NO: 65, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 21, and the VL comprises an amino acid sequence that is at least 80% (e.g., at least 80%, at least 85%, at least 90%, at least 95%, at least 99%) identical to the amino acid sequence of SEQ ID NO: 66. In some embodiments, in an antibody described herein, the VH comprises the amino acid sequence of SEQ ID NO: 21, and the VL comprises the amino acid sequence of SEQ ID NO: 66.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 19, the CDR-L2 comprises the amino acid sequence of SEQ ID NO: 67, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 21, and the VL comprises an amino acid sequence that is at least 80% (e.g., at least 80%, at least 85%, at least 90%, at least 95%, at least 99%) identical to the amino acid sequence of SEQ ID NO: 68. In some embodiments, in an antibody described herein, the VH comprises the amino acid sequence of SEQ ID NO: 21, and the VL comprises the amino acid sequence of SEQ ID NO: 68.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 19, the CDR-L2 comprises the amino acid sequence of SEQ ID NO: 5, and the CDR-L3 comprises the amino acid sequence of SEQ ID NO: 69.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 21, and the VL comprises an amino acid sequence that is at least 80% (e.g., at least 80%, at least 85%, at least 90%, at least 95%, at least 99%) identical to the amino acid sequence of SEQ ID NO: 70. In some embodiments, in an antibody described herein, the VH comprises the amino acid sequence of SEQ ID NO: 21, and the VL comprises the amino acid sequence of SEQ ID NO: 70.

In some embodiments, in an antibody described herein, the CDR-H1 comprises the amino acid sequence of SEQ ID NO: 71, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 19, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO:72, and the VL comprises an amino acid sequence that is at least 80% (e.g., at least 80%, at least 85%, at least 90%, at least 95%, at least 99%) identical to the amino acid sequence of SEQ ID NO: 22. In some embodiments, in an antibody described herein, the VH comprises the amino acid sequence of SEQ ID NO: 72, and the VL comprises the amino acid sequence of SEQ ID NO: 22.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 18; and/or the CDR-L1 comprises the amino acid sequence of SEQ ID NO: 73, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 21, and the VL comprises an amino acid sequence that is at least 80% (e.g., at least 80%, at least 85%, at least 90%, at least 95%, at least 99%) identical to the amino acid sequence of SEQ ID NO: 74. In some embodiments, in an antibody described herein, the VH comprises the amino acid sequence of SEQ ID NO: 21, and the VL comprises the amino acid sequence of SEQ ID NO: 74.

In some embodiments, in an antibody described herein, the CDR-H1 comprises the amino acid sequence of SEQ ID NO: 75, the CDR-H2 comprises the amino acid sequence of SEQ ID NO: 17, the CDR-H3 comprises the amino acid sequence of SEQ ID NO: 23; and/or the CDR-L1 comprises the amino acid sequence of SEQ ID NO: 19, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 76, and the VL comprises an amino acid sequence that is at least 80% (e.g., at least 80%, at least 85%, at least 90%, at least 95%, at least 99%) identical to the amino acid sequence of SEQ ID NO: 22. In some embodiments, in an antibody described herein, the VH comprises the amino acid sequence of SEQ ID NO: 76, and the VL comprises the amino acid sequence of SEQ ID NO: 22.

In some embodiments, in an antibody described herein, the CDR-H1 comprises the amino acid sequence of SEQ ID NO: 77, the CDR-H2 comprises the amino acid sequence of SEQ ID NO: 17, the CDR-H3 comprises the amino acid sequence of SEQ ID NO: 23; and/or the CDR-L1 comprises the amino acid sequence of SEQ ID NO: 19, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 78, and the VL comprises an amino acid sequence that is at least 80% (e.g., at least 80%, at least 85%, at least 90%, at least 95%, at least 99%) identical to the amino acid sequence of SEQ ID NO: 22. In some embodiments, in an antibody described herein, the VH comprises the amino acid sequence of SEQ ID NO: 78, and the VL comprises the amino acid sequence of SEQ ID NO: 22.

In some embodiments, in an antibody described herein, the CDR-H1 comprises the amino acid sequence of SEQ ID NO: 79, the CDR-H2 comprises the amino acid sequence of SEQ ID NO: 17, the CDR-H3 comprises the amino acid sequence of SEQ ID NO: 23; and/or the CDR-L1 comprises the amino acid sequence of SEQ ID NO: 19, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 80, and the VL comprises an amino acid sequence that is at least 80% (e.g., at least 80%, at least 85%, at least 90%, at least 95%, at least 99%) identical to the amino acid sequence of SEQ ID NO: 22. In some embodiments, in an antibody described herein, the VH comprises the amino acid sequence of SEQ ID NO: 80, and the VL comprises the amino acid sequence of SEQ ID NO: 22.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 23; and/or the CDR-L1 comprises the amino acid sequence of SEQ ID NO: 81, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 24, and the VL comprises an amino acid sequence that is at least 80% (e.g., at least 80%, at least 85%, at least 90%, at least 95%, at least 99%) identical to the amino acid sequence of SEQ ID NO: 82. In some embodiments, in an antibody described herein, the VH comprises the amino acid sequence of SEQ ID NO: 24, and the VL comprises the amino acid sequence of SEQ ID NO: 82.

In some embodiments, in an antibody described herein, the CDR-H1 comprises the amino acid sequence of SEQ ID NO:16, the CDR-H2 comprises the amino acid sequence of SEQ ID NO: 17, the CDR-H3 comprises the amino acid sequence of SEQ ID NO: 23; and/or the CDR-L1 comprises the amino acid sequence of SEQ ID NO: 49, the CDR-L2 comprises the amino acid sequence of SEQ ID NO: 5, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 24, and the VL comprises an amino acid sequence that is at least 80% (e.g., at least 80%, at least 85%, at least 90%, at least 95%, at least 99%) identical to the amino acid sequence of SEQ ID NO: 83. In some embodiments, in an antibody described herein, the VH comprises the amino acid sequence of SEQ ID NO: 24, and the VL comprises the amino acid sequence of SEQ ID NO: 83.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 23; and/or the CDR-L1 comprises the amino acid sequence of SEQ ID NO: 19, the CDR-L2 comprises the amino acid sequence of SEQ ID NO: 84, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 24, and the VL comprises an amino acid sequence that is at least 80% (e.g., at least 80%, at least 85%, at least 90%, at least 95%, at least 99%) identical to the amino acid sequence of SEQ ID NO: 85. In some embodiments, in an antibody described herein, the VH comprises the amino acid sequence of SEQ ID NO: 24, and the VL comprises the amino acid sequence of SEQ ID NO: 85.

In some embodiments, in an antibody described herein, the CDR-H1 comprises the amino acid sequence of SEQ ID NO: 16, the CDR-H2 comprises the amino acid sequence of SEQ ID NO: 17, the CDR-H3 comprises the amino acid sequence of SEQ ID NO: 23; and/or the CDR-L1 comprises the amino acid sequence of SEQ ID NO: 19, the CDR-L2 comprises the amino acid sequence of SEQ ID NO: 86, and the CDR-L3 comprises the amino acid sequence of SEQ ID NO: 20.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 24, and the VL comprises an amino acid sequence that is at least 80% (e.g., at least 80%, at least 85%, at least 90%, at least 95%, at least 99%) identical to the amino acid sequence of SEQ ID NO: 87. In some embodiments, in an antibody described herein, the VH comprises the amino acid sequence of SEQ ID NO: 24, and the VL comprises the amino acid sequence of SEQ ID NO: 87.

In some embodiments, an antibody described herein binds to CCR8 and comprises a VH comprising a CDR-H1 comprising the amino acid sequence of FTFSS$X_1$GMH (SEQ ID NO: 115), wherein $X_1$ is Y, H, W, or F; CDR-H2 comprising the amino acid sequence of VISYDGSNKYYAFSVKG (SEQ ID NO: 2); a CDR-H3 comprising the amino acid sequence of ARVRRIAGRAGYGMDV (SEQ ID NO: 3); and/or a VL comprising a CDR-L1 comprising the amino acid sequence of RASQSI$X_2$SYLN (SEQ ID NO: 116), wherein $X_2$ is N, V, Q, or A; a CDR-L2 comprising the amino acid sequence of $X_3$AS$X_4$LQS (SEQ ID NO: 117), wherein $X_3$ is A, S, N, T, or V, and $X_4$ is S, I, T, or L; and a CDR-L3 comprising the amino acid sequence of QESYS- TPI$X_5$ (SEQ ID NO: 118), wherein $X_5$ is T, F, S, W, or Y; wherein, if $X_1$ is Y, $X_2$ is not N, $X_3$ is not A, $X_4$ is not S, and $X_5$ is not T.

In some embodiments, an antibody described herein binds to CCR8 and comprises a VH comprising a CDR-H1 comprising the amino acid sequence of FTFSS$X_1$GMH (SEQ ID NO: 115), wherein $X_1$ is Y or H; a CDR-H2 comprising the amino acid sequence of VISYDGSNKYYAFSVKG (SEQ ID NO: 2); a CDR-H3 comprising the amino acid sequence of ARVRRIAGRAGYGMDV (SEQ ID NO: 3); and/or a VL comprising a CDR-L1 comprising the amino acid sequence of RASQSI$X_2$SYLN (SEQ ID NO: 116), wherein $X_2$ is N or V; a CDR-L2 comprising the amino acid sequence of $X_3$AS$X_4$LQS (SEQ ID NO: 117), wherein $X_3$ is A or S, and $X_4$ is S or I; and a CDR-L3 comprising the amino acid sequence of QESYSTPI$X_5$ (SEQ ID NO: 118), wherein $X_5$ is T or F; wherein if $X_1$ is Y, $X_2$ is not N, $X_3$ is not A, $X_4$ is not S, and $X_5$ is not T.

In some embodiments, an antibody described herein binds to CCR8 and comprises a VH comprising a CDR-H1 comprising the amino acid sequence of FTFSSHGMH (SEQ ID NO: 39); a CDR-H2 comprising the amino acid sequence of VISYDGSNKYYAFSVKG (SEQ ID NO: 2); a CDR-H3 comprising the amino acid sequence of ARVRRIAGRAGYGMDV (SEQ ID NO: 3); and/or a VL comprising a CDR-L1 comprising the amino acid sequence of RASQSI$X_2$SYLN (SEQ ID NO: 116), wherein $X_2$ is N or V; a CDR-L2 comprising the amino acid sequence of $X_3$AS$X_4$LQS (SEQ ID NO: 117), wherein $X_3$ is A or S, and $X_4$ is S or I; and a CDR-L3 comprising the amino acid sequence of QESYSTPI$X_5$ (SEQ ID NO: 118), wherein $X_5$ is T or F.

In some embodiments, in an antibody described herein, the CDR-H1 comprises the amino acid sequence of SEQ ID NO: 39, the CDR-H2 comprises the amino acid sequence of SEQ ID NO: 2, the CDR-H3 comprises the amino acid sequence of SEQ ID NO: 3; and/or the CDR-L1 comprises the amino acid sequence of SEQ ID NO: 4, the CDR-L2 comprises the amino acid sequence of SEQ ID NO: 40, and the CDR-L3 comprises the amino acid sequence of SEQ ID NO: 41.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 42, and the VL comprises an amino acid sequence that is at least 80% (e.g., at least 80%, at least 85%, at least 90%, at least 95%, at least 99%) identical to the amino acid sequence of SEQ ID NO: 43. In some embodiments, in an antibody described herein, the VH comprises the amino acid sequence of SEQ ID NO: 42, and the VL comprises the amino acid sequence of SEQ ID NO: 43.

In some embodiments, in an antibody described herein, the CDR-H1 comprises the amino acid sequence of SEQ ID NO: 39, the CDR-H2 comprises the amino acid sequence of SEQ ID NO: 2, the CDR-H3 comprises the amino acid sequence of SEQ ID NO: 3; and/or the CDR-L1 comprises the amino acid sequence of SEQ ID NO: 44, the CDR-L2 comprises the amino acid sequence of SEQ ID NO: 45, and the CDR-L3 comprises the amino acid sequence of SEQ ID NO: 6.

In some embodiments, in an antibody described herein, the VH comprises an amino acid sequence that is at least 80% (e.g., at least 80%, at least 85%, at least 90%, at least 95%, at least 99%) identical to the amino acid sequence of SEQ ID NO: 42, and the VL comprises an amino acid sequence that is at least 80% (e.g., at least 80%, at least 85%, at least 90%, at least 95%, at least 99%) identical to the amino acid sequence of SEQ ID NO: 46. In some embodiments, in an antibody described herein, the VH comprises the amino acid sequence of SEQ ID NO: 42, and the VL comprises the amino acid sequence of SEQ ID NO: 46.

In some embodiments, an antibody described herein is a full-length IgG, a Fab fragment, a F(ab') fragment, a $F(ab')_2$ fragment, an scFv, or an Fv. In some embodiments, an antibody described herein is a full-length IgG. In further embodiments, the full-length IgG is IgG1, IgG2, IgG3, or IgG4. In some embodiments, the antibody is a Fab. In some embodiments, the antibody is a humanized antibody. In some embodiments, the antibody is a human antibody.

In some embodiments, any one of the antibodies described herein may comprise a heavy chain constant region (CH) or a portion thereof (e.g., CH1, CH2, CH3, or a combination thereof) fused to the heavy chain variable region. The heavy chain constant region can be of any suitable origin, e.g., human, mouse, rat, or rabbit. In one specific example, the heavy chain constant region is from a human IgG (a gamma heavy chain), e.g., IgG1, IgG2, or IgG4. A non-limiting example of an IgG constant region is given below:

```
                                         (SEQ ID NO: 133)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG
```

In some embodiments, an antibody described herein comprises a heavy chain comprising a heavy chain constant region comprising an L235A (EU numbering) mutation and a G237A (EU numbering) mutation relative to the heavy chain constant region set forth in SEQ ID NO: 133. In some embodiments, an antibody described herein comprises a heavy chain comprising a heavy chain constant region comprising a D265C (EU numbering) mutation relative to the heavy chain constant region set forth in SEQ ID NO: 133. In some embodiments, an antibody described herein comprises a heavy chain comprising a heavy chain constant region comprising an L235A (EU numbering) mutation, a G237A (EU numbering) mutation, and a D265C (EU numbering) mutation relative to the heavy chain constant region set forth in SEQ ID NO: 133. In some embodiments, an antibody described herein comprises a heavy chain comprising a heavy chain constant region as set forth in SEQ ID NO: 134:

```
                                         (SEQ ID NO: 134)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELAGAPSVFLFPPKPKDTLMISRTPEVTCVVV

CVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ
```

-continued

VSLTCLVKGFYPSDIAVEWESNGQPENNYKTTPPVLDSDGSFFLYSKLT

VDKSRWQQGNVFSCSVMHEALHNHYTQKSLSLSPG.

In some embodiments, any one of the antibodies described herein may comprise a light chain comprising a light chain constant region (CL) fused to the light chain variable region. The CL can be any CL known in the art. In some examples, the CL is a hukappa light chain. In other examples, the CL is a lambda light chain. In some embodiments, the CL is a hukappa light chain, the sequence of which is provided below:

(SEQ ID NO: 135)

RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC.

Other antibody heavy and light chain constant regions that may be used in accordance with the antibodies described herein are known in the art, e.g., those provided in the IMGT database (imgt.org) or at vbase2.org/vbstat.php.

In some embodiments, one, two or more mutations (e.g., amino acid substitutions) are introduced into the Fc region of an antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425.

In some embodiments, one, two or more mutations (e.g., amino acid substitutions) are introduced into the Fc region of a CCR8-targeting antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of an antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of an antibody in vivo. In some embodiments, an antibody described herein can have one or more amino acid mutations (e.g., substitutions) in the second constant (CH2) domain (residues 231-340 of human IgG1) and/or (e.g., and) the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of an antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of an antibody described herein can be replaced with a different amino acid residue such that the antibody has altered Clq binding and/or reduced or abolished complement dependent cytotoxicity (CDC). This approach is described in further detail in U.S. Pat. No. 6,194,551 (Idusogie et al.). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcγ receptor. This approach is described further in International Publication No. WO 00/42072.

In some embodiments, an antibody provided herein may comprise mutations that confer desirable properties to the antibodies. For example, to avoid potential complications due to Fab-arm exchange, which is known to occur with native IgG4 mAbs, an antibody provided herein may comprise a stabilizing 'Adair' mutation (Angal S. et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecules are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecules are monosaccharides, disaccharides, oligosaccharides, or glycans. In some embodiments, the one or more sugar or carbohydrate molecules are a branched oligosaccharide or a branched glycan. In some embodiments, the one or more sugar or carbohydrate molecules includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O- glycosylation pathway, e.g., a glycosyltransferase. In some embodiments, an antibody is functionalized with sugar or carbohydrate molecules as described in International Patent Application Publication WO2014065661, titled, "Modified antibody, antibody-conjugate and process for the preparation thereof".

Non-limiting examples of full length IgG antibodies described herein are provided in Table 2.

Nucleic Acid Sequences, Vectors and Cells

In some aspects, the present disclosure provides nucleic acid sequences encoding any one of the antibodies disclosed herein (e.g., the antibodies of Table 1 or Table 2). In some embodiments, the nucleic acid sequence encodes the VH of any one of the antibodies of Table 1 or Table 2. In some embodiments, the nucleic acid sequence encodes the VL of any one of the antibodies of Table 1 or Table 2. In some embodiments, the nucleic acid sequence encodes the VH and VL of any one of the antibodies of Table 1 or Table 2.

In some embodiments, the nucleic acid molecule is a vector. In some embodiments, the nucleic acid molecule is an expression vector (e.g., an expression vector suitable for expression of the protein in mammalian cells such as human cells).

As will be appreciated by those in the art, the nucleic acid compositions will depend on the format of the proteins. In general, a protein described herein is encoded by a single nucleic acid molecule in a single expression vector for production.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art. Examples of polyadenylation signals useful to practice the methods described herein include, but are not limited to, human collagen I polyadenylation signal, human collagen II polyadenylation signal, and SV40 polyadenylation signal.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV promoter, and the herpes simplex tk virus promoter.

Regulatable promoters can also be used. Such regulatable promoters include those using the lac repressor from *E. coli* as a transcription modulator to regulate transcription from lac operator bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-555115 (1992); Yao, F. et al., Human Gene Therapy, 9:1939-1950 (1998); Shockelt, P. et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from commercial suppliers.

The nucleic acids and/or expression vectors encoding the antibodies disclosed herein are then transformed into any number of different types of host cells known in the art, including mammalian, bacterial, yeast, insect and/or fungal cells.

The antibody compositions described herein are made by culturing host cells comprising the expression vector(s). Once produced, traditional antibody purification steps may be performed, including a Protein A affinity chromatography step and/or an ion exchange chromatography step.

Preparation of the CCR8 Antibodies

Antibodies capable of binding CCR8 as described herein can be made by any method known in the art. See, for example, Harlow and Lane, (1998) Antibodies: A Laboratory Manual, Cold Spring Harbor Laboratory, New York.

In some embodiments, the sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to manipulate the antibody sequence to obtain greater affinity to the target antigen and greater efficacy.

Antigen-binding fragments of an intact antibody (full-length antibody) can be prepared via routine methods. For example, $F(ab')_2$ fragments can be produced by pepsin digestion of an antibody molecule, and Fab fragments that can be generated by reducing the disulfide bridges of $F(ab')_2$ fragments. Genetically engineered antibodies, such as humanized antibodies, chimeric antibodies, single-chain antibodies, and bi-specific antibodies, can be produced via recombinant technology. In one example, DNA encoding a monoclonal antibody specific to a target antigen can be isolated and sequenced (e.g., by using oligonucleotide probes that are capable of binding specifically to genes encoding the heavy and light chains of the monoclonal antibodies). Once isolated, the DNA may be placed into one or more expression vectors, which are then transfected into host cells such as *E. coli* cells, simian COS cells, Chinese hamster ovary (CHO) cells, human HEK293 cells, or myeloma cells that do not otherwise produce immunoglobulin protein, to obtain the synthesis of monoclonal antibodies in the recombinant host cells. See, e.g., International Publication. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Alternatively, techniques described for the production of single chain antibodies (U.S. Pat. Nos. 4,946,778 and 4,704, 692) can be adapted to produce a phage or yeast scFv library and scFv antibodies specific to CCR8 can be identified from the library.

In some embodiments, an antibody is prepared by recombinant technology. Nucleic acids encoding the heavy and light chain of an anti-CCR8 antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some embodiments, methods for preparing an antibody described herein involve a recombinant expression vector that encodes both the heavy chain and the light chain of an anti-CCR8 antibody, as also described herein. The recombinant expression vector can be introduced into a suitable host cell by a conventional method, e.g., calcium phosphate mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

Alternatively, each of the expression vectors can be introduced into suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

In some embodiments, standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Antibody Drug Conjugates (ADC)

In some aspects, the present disclosure provides antibody-drug conjugates (ADCs) comprising an anti-CCR8 antibody, or an antigen-binding fragment thereof, as described herein (including, e.g., an antibody provided in Table 1 or Table 2), conjugated to a payload via a linker. In some embodiments, the linker is a cleavable linker. In some embodiments, the linker is a non-cleavable linker. In some embodiments, the payload is an amatoxin. In some embodiments, the payload is an amanitin.

In some embodiments, an ADC described herein has the structure of Formula (A):

(A)

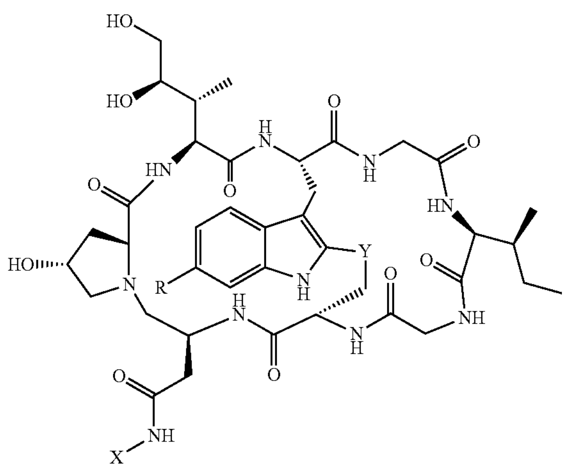

or a pharmaceutically acceptable salt, solvate, hydrate, tautomer, stereoisomer, diastereomer, or enantiomer thereof, wherein:

Y is —S—, —S(=O)—, or —$SO_2$—;

R is H, —OH, or —O-L-Z-Ab; and

X is H or -L-Z-Ab, wherein:

L is a linker;

Ab is an anti-CCR8 antibody as described herein (including, e.g., in Table 1 or Table 2), or an antigen binding fragment thereof;

Z is a chemical moiety formed by a coupling reaction between a first reactive substituent previously bound to L and a second reactive substituent previously present within the anti-CCR8 antibody, or antigen-binding fragment thereof;

provided that:

if X is H then R is —O-L-Z-Ab, and if X is -L-Z-Ab then R is H or —OH.

In some embodiments, the ADC of Formula (A) is of Formula (A-I):

(A-I)

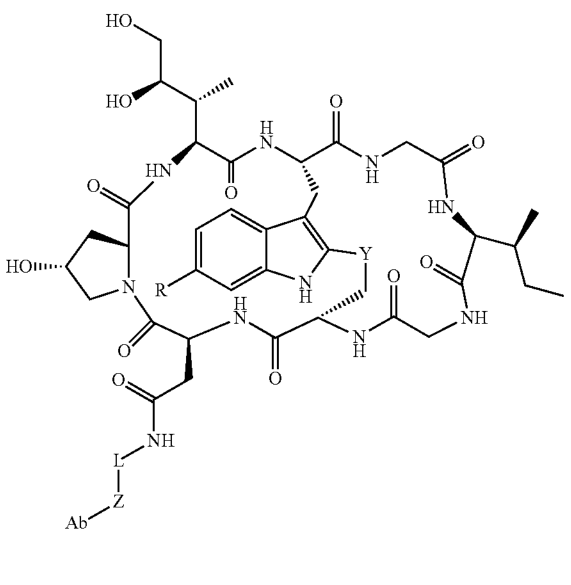

or a pharmaceutically acceptable salt, solvate, hydrate, tautomer, stereoisomer, diastereomer, or enantiomer thereof, wherein R is H or OH.

In some embodiments, the ADC of Formula (A) is of the Formula (A-I-a):

(A-I-a)

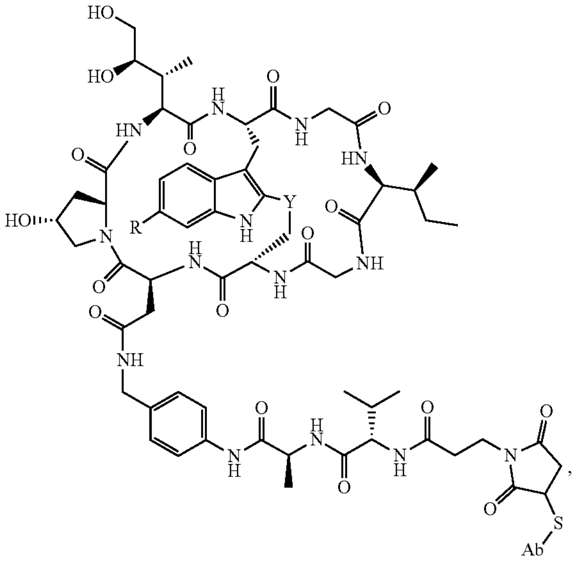

or a pharmaceutically acceptable salt, solvate, hydrate, tautomer, stereoisomer, diastereomer, or enantiomer thereof, wherein R is H or OH.

In some embodiments, the ADC of Formula (A) is of the Formula (A-I-b):

(A-I-b)

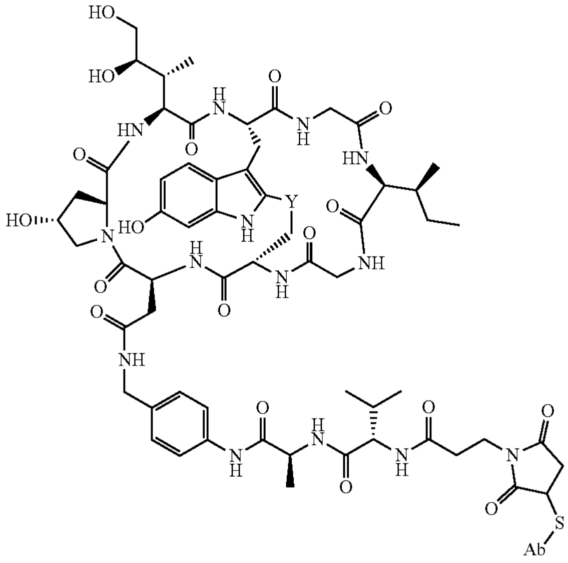

or a pharmaceutically acceptable salt, solvate, hydrate, tautomer, stereoisomer, diastereomer, or enantiomer thereof.

In some embodiments, the ADC of Formula (A) is of the Formula (A-I-c):

(A-I-c)

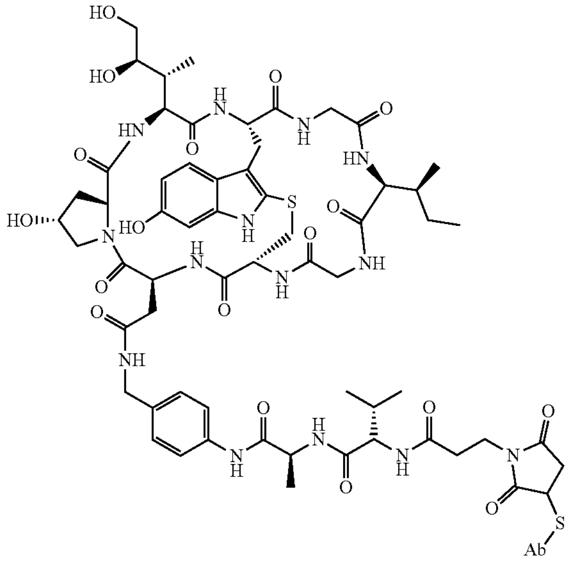

or a pharmaceutically acceptable salt, solvate, hydrate, tautomer, stereoisomer, diastereomer, or enantiomer thereof.

In some embodiments, the ADC of Formula (A) is of the Formula (A-I-d):

(A-I-d)

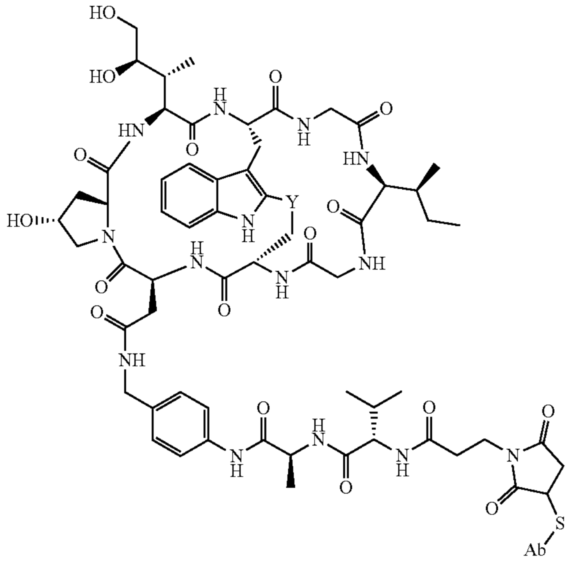

or a pharmaceutically acceptable salt, solvate, hydrate, tautomer, stereoisomer, diastereomer, or enantiomer thereof.

In some embodiments, the ADC of Formula (A) is of the Formula (A-I-e):

(A-I-e)

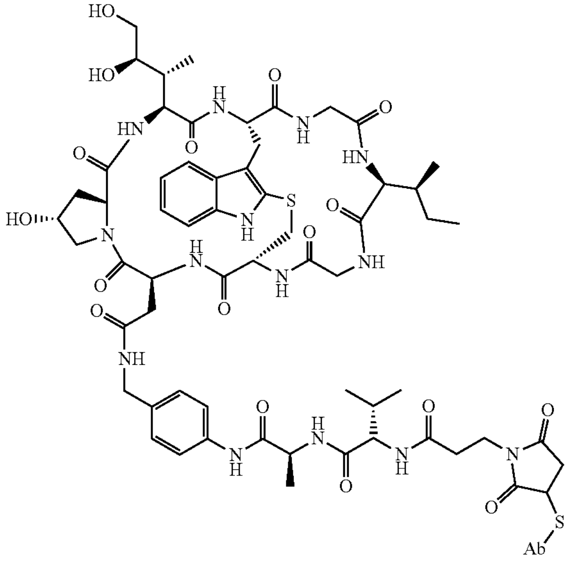

or a pharmaceutically acceptable salt, solvate, hydrate, tautomer, stereoisomer, diastereomer, or enantiomer thereof.

In some embodiments, the ADC of Formula (A) is of the Formula (A-II):

(A-II)

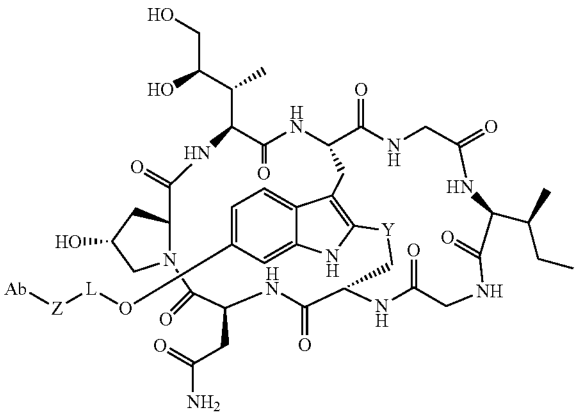

or a pharmaceutically acceptable salt, solvate, hydrate, tautomer, stereoisomer, diastereomer, or enantiomer thereof.

In some embodiments, the ADC of Formula (A) is of the Formula (A-II-a):

(A-II-a)

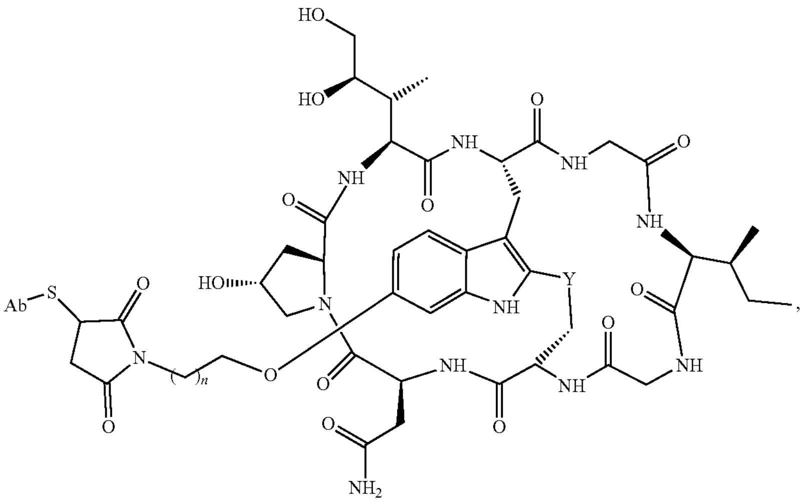

or a pharmaceutically acceptable salt, solvate, hydrate, tautomer, stereoisomer, diastereomer, or enantiomer thereof, wherein n is 2, 3, 4, 5, 6, 7, 8, 9, or 10.

In some embodiments, the ADC of Formula (A) is of Formula (A-II-b):

(A-II-b)

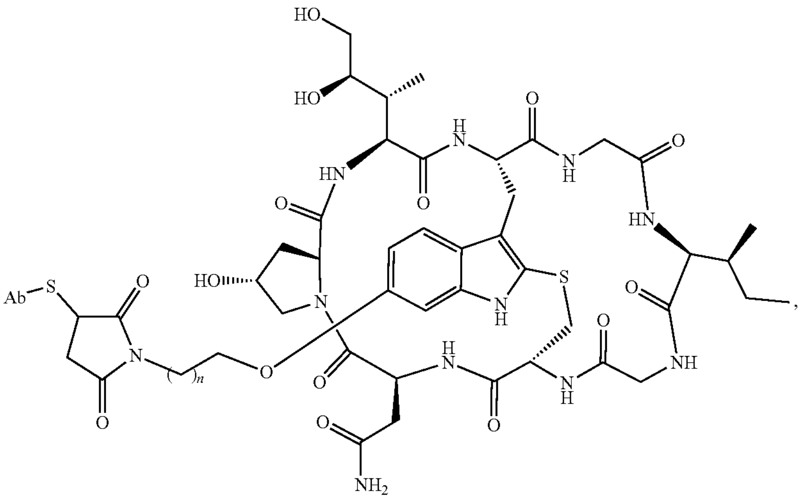

or a pharmaceutically acceptable salt, solvate, hydrate, tautomer, stereoisomer, diastereomer, or enantiomer thereof, wherein n is 1, 2, 3, 4, 5, 6, 7, 8, 9, or 10.

In some embodiments, the ADC described herein contains the substituent R (e.g., Formulae (A), (A-I), (A-I-a)). In some embodiments, R is —H. In some embodiments, R is —OH. In some embodiments, R is —O-L-Z-Ab.

In some aspects, the ADC described herein contains the substituent Y (e.g., Formulae (A), (A-I), (A-I-a), (A-I-b), (A-I-d), (A-II), (A-II-a)). In some embodiments, Y is —S—. In some embodiments, Y is —S(═O)—. In some embodiments, Y is —$SO_2$—.

In some embodiments, in an ADC comprising a structure of any one of Formulae (A), (A-I), (A-I-a), (A-I-b), (A-I-c), (A-I-d), (A-I-e), (A-II), (A-II-a), and (A-II-b), and the Ab is an anti-CCR8 antibody as described herein (including, e.g., in Table 1 or Table 2), or antigen binding fragment thereof. In some embodiments, in an ADC comprising a structure of any one of Formulae (A), (A-I), (A-I-a), (A-I-b), (A-I-c), (A-I-d), (A-I-e), (A-II), (A-II-a), and (A-II-b), the Ab is an anti-CCR8 antibody comprising a VH comprising the amino acid sequence of SEQ ID NO: 99 and a VL comprising the amino acid sequence of SEQ ID NO: 100. In some embodiments, in an ADC comprising a structure of any one of Formulae (A), (A-I), (A-I-a), (A-I-b), (A-I-c), (A-I-d), (A-I-e), (A-II), (A-II-a), and (A-II-b), the Ab is an anti-CCR8 antibody comprising a VH comprising the amino acid sequence of SEQ ID NO: 93 and a VL comprising the amino acid sequence of SEQ ID NO: 103. In some embodiments, in an ADC comprising a structure of any one of Formulae (A), (A-I), (A-I-a), (A-I-b), (A-I-c), (A-I-d), (A-I-e), (A-II), (A-II-a), and (A-II-b), the Ab is an anti-CCR8 antibody comprising a heavy chain comprising the amino acid sequence of SEQ ID NO: 145 and a light chain comprising the amino acid sequence of SEQ ID NO: 146. In some embodiments, in an ADC comprising a structure of any one of Formulae (A), (A-I), (A-I-a), (A-I-b), (A-I-c), (A-I-d), (A-I-e), (A-II), (A-II-a), and (A-II-b), the Ab is an anti-CCR8 antibody comprising a heavy chain comprising the amino acid sequence of SEQ ID NO: 147 and a light chain comprising the amino acid sequence of SEQ ID NO: 148.

In some embodiments, in an ADC comprising a structure of any one of Formulae (A), (A-I), (A-I-a), (A-I-b), (A-I-c), (A-I-d), (A-I-e), (A-II), (A-II-a), and (A-II-b), the payload is covalently linked to the anti-CCR8 antibody via a cysteine of the anti-CCR8 antibody. In some embodiments, in an ADC comprising a structure of any one of Formulae (A), (A-I), (A-I-a), (A-I-b), (A-I-c), (A-I-d), (A-I-e), (A-II), (A-II-a), and (A-II-b), the payload is covalently linked to the anti-CCR8 antibody via the cysteine at position 265 (EU numbering) in the heavy chain constant region.

In some embodiments, an ADC described herein has the structure of Formula (A):

(A)

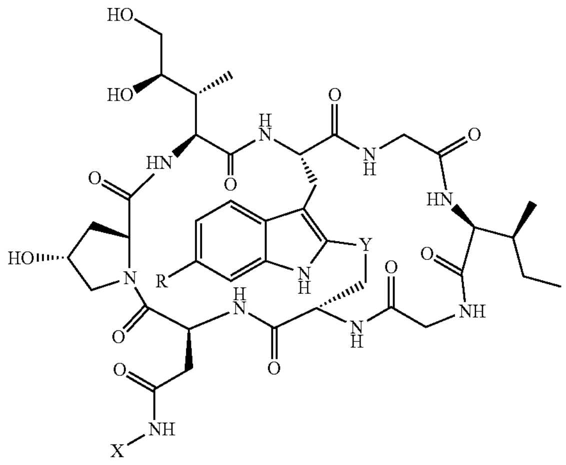

or a pharmaceutically acceptable salt, solvate, hydrate, tautomer, stereoisomer, diastereomer, or enantiomer thereof, wherein:

Ab is an anti-CCR8 antibody comprising a VH comprising a CDR-H1 comprising the amino acid sequence of SEQ ID NO: 127, a CDR-H2 comprising the amino acid sequence of SEQ ID NO: 128, and a CDR-H3 comprising the amino acid sequence of SEQ ID NO: 129; and a VL comprising a CDR-L1 comprising the amino acid sequence of SEQ ID NO: 130, a CDR-L2 comprising the amino acid sequence of SEQ ID NO: 131, and a CDR-L3 comprising the amino acid sequence of SEQ ID NO: 132; wherein if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L; and wherein if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, the ADC of Formula (A) is of the Formula (A-I-c):

(A-I-c)

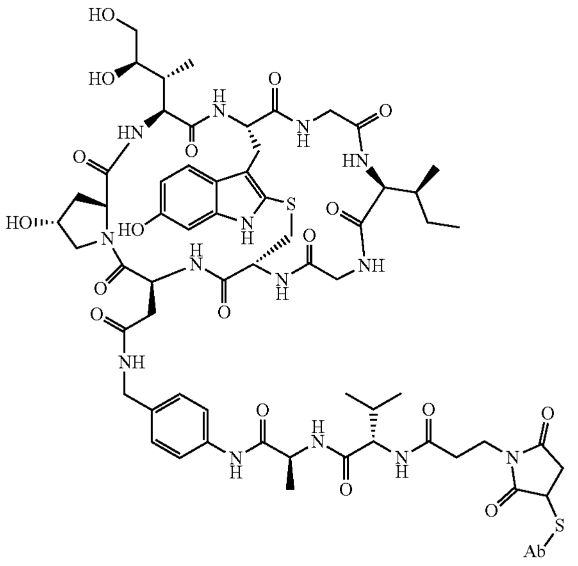

or a pharmaceutically acceptable salt, solvate, hydrate, tautomer, stereoisomer, diastereomer, or enantiomer, thereof, wherein:

Ab is an anti-CCR8 antibody comprising a VH comprising a CDR-H1 comprising the amino acid sequence of SEQ ID NO: 127, a CDR-H2 comprising the amino acid sequence of SEQ ID NO: 128, and a CDR-H3 comprising the amino acid sequence of SEQ ID NO: 129; and a VL comprising a CDR-L1 comprising the amino acid sequence of SEQ ID NO: 130, a CDR-L2 comprising the amino acid sequence of SEQ ID NO: 131, and a CDR-L3 comprising the amino acid sequence of SEQ ID NO: 132; wherein if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L; and wherein if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, the ADC of Formula (A) is of the Formula (A-I-e):

(A-I-e)

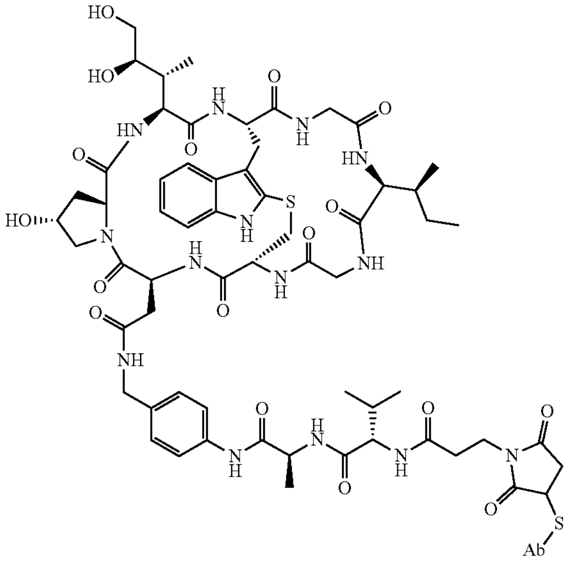

or a pharmaceutically acceptable salt, solvate, hydrate, tautomer, stereoisomer, diastereomer, or enantiomer, thereof, wherein:

Ab is an anti-CCR8 antibody comprising a VH comprising a CDR-H1 comprising the amino acid sequence of SEQ ID NO: 127, a CDR-H2 comprising the amino acid sequence of SEQ ID NO: 128, and a CDR-H3 comprising the amino acid sequence of SEQ ID NO: 129; and a VL comprising a CDR-L1 comprising the amino acid sequence of SEQ ID NO: 130, a CDR-L2 comprising the amino acid sequence of SEQ ID NO: 131, and a CDR-L3 comprising the amino acid sequence of SEQ ID NO: 132; wherein if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L; and wherein if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, the ADC of Formula (A) is of Formula (A-II-b):

(A-II-b)

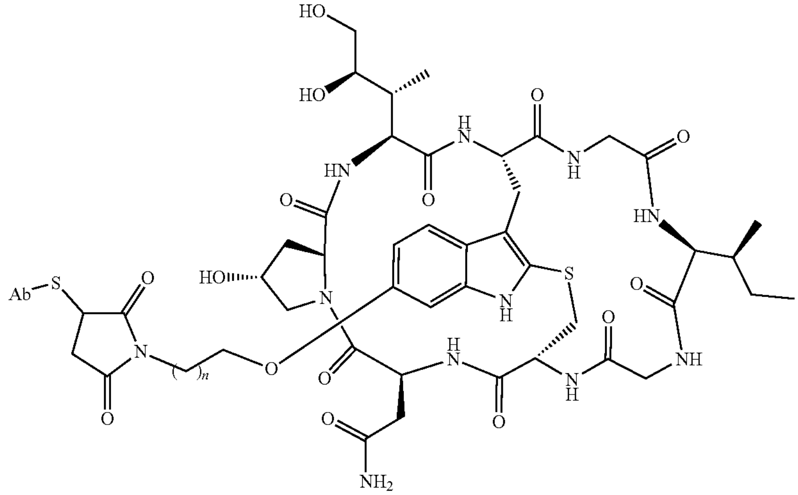

, or a pharmaceutically acceptable salt, solvate, hydrate, tautomer, stereoisomer, diastereomer, or enantiomer, thereof, wherein:

n is 5; and

Ab is an anti-CCR8 antibody comprising a VH comprising a CDR-H1 comprising the amino acid sequence of SEQ ID NO: 127, a CDR-H2 comprising the amino acid sequence of SEQ ID NO: 128, and a CDR-H3 comprising the amino acid sequence of SEQ ID NO: 129; and a VL comprising a CDR-L1 comprising the amino acid sequence of SEQ ID NO: 130, a CDR-L2 comprising the amino acid sequence of SEQ ID NO: 131, and a CDR-L3 comprising the amino acid sequence of SEQ ID NO: 132; wherein if $X_{24}$ is T, $X_{25}$ is not D, $X_{26}$ is not D, $X_{27}$ is not Y, $X_{28}$ is not S, $X_{29}$ is not S, $X_{30}$ is not L, $X_{31}$ is not R, $X_{32}$ is not M, and $X_{33}$ is not L; and wherein if $X_{24}$ is T, $X_{25}$ is not A, $X_{26}$ is not D, $X_{27}$ is not Y, $X_{28}$ is not S, $X_{29}$ is not S, $X_{30}$ is not L, $X_{31}$ is not R, $X_{32}$ is not K, and $X_{33}$ is not L.

In some embodiments, an ADC described herein has the structure of Formula (A):

(A)

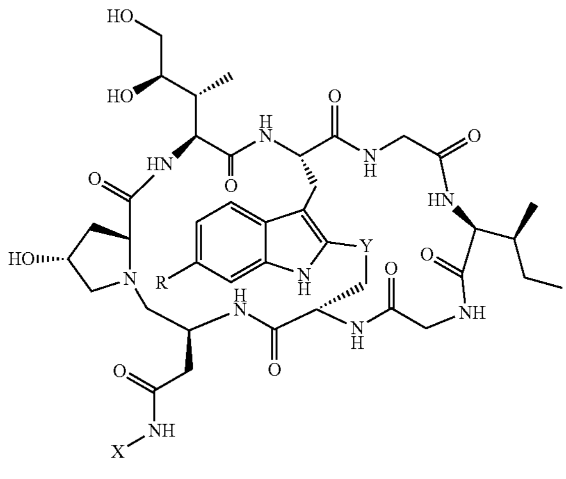

or a pharmaceutically acceptable salt, solvate, hydrate, tautomer, stereoisomer, diastereomer, or enantiomer thereof, wherein:

Ab is an anti-CCR8 antibody comprising a VH comprising a CDR-H1 comprising the amino acid sequence of SEQ ID NO: 88, a CDR-H2 comprising the amino acid sequence of SEQ ID NO: 139, and a CDR-H3 comprising the amino acid sequence of SEQ ID NO: 90; and a VL comprising a CDR-L1 comprising the amino acid sequence of SEQ ID NO: 140, a CDR-L2 comprising the amino acid sequence of SEQ ID NO: 92, and a CDR-L3 comprising the amino acid sequence of SEQ ID NO: 69; wherein $X_{26}$ is D or P and $X_{30}$ is L or Q.

In some embodiments, the ADC of Formula (A) is of the Formula (A-I-c):

(A-I-c)

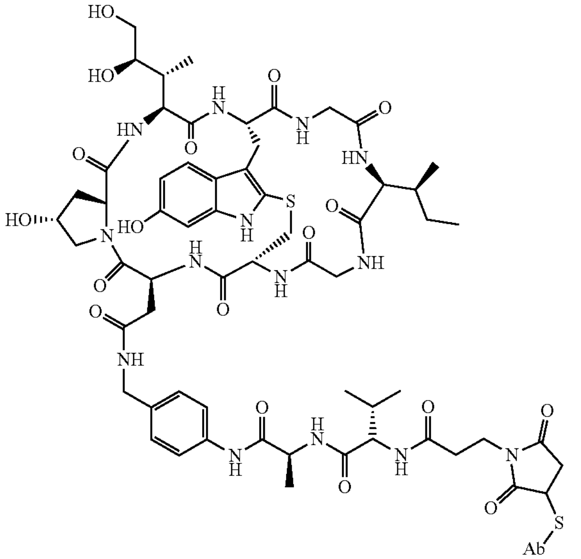

or a pharmaceutically acceptable salt, solvate, hydrate, tautomer, stereoisomer, diastereomer, or enantiomer, thereof, wherein:

Ab is an anti-CCR8 antibody comprising a VH comprising a CDR-H1 comprising the amino acid sequence of SEQ ID NO: 88, a CDR-H2 comprising the amino acid sequence of SEQ ID NO: 139, and a CDR-H3 comprising the amino acid sequence of SEQ ID NO: 90; and a VL comprising a CDR-L1 comprising the amino acid sequence of SEQ ID NO: 140, a CDR-L2 comprising the amino acid sequence of SEQ ID NO: 92, and a CDR-L3 comprising the amino acid sequence of SEQ ID NO: 69; wherein $X_{26}$ is D or P and $X_{30}$ is L or Q.

In some embodiments, the ADC of Formula (A) is of the Formula (A-I-e):

(A-I-e)

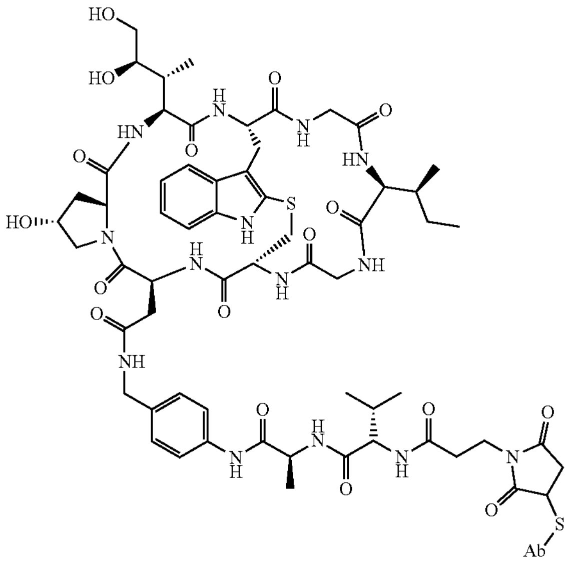

or a pharmaceutically acceptable salt, solvate, hydrate, tautomer, stereoisomer, diastereomer, or enantiomer, thereof, wherein:

Ab is an anti-CCR8 antibody comprising a VH comprising a CDR-H1 comprising the amino acid sequence of SEQ ID NO: 88, a CDR-H2 comprising the amino acid sequence of SEQ ID NO: 139, and a CDR-H3 comprising the amino acid sequence of SEQ ID NO: 90; and a VL comprising a CDR-L1 comprising the amino acid sequence of SEQ ID NO: 140, a CDR-L2 comprising the amino acid sequence of SEQ ID NO: 92, and a CDR-L3 comprising the amino acid sequence of SEQ ID NO: 69; wherein $X_{26}$ is D or P and $X_{30}$ is L or Q.

In some embodiments, the ADC of Formula (A) is of Formula (A-II-b):

(A-II-b)

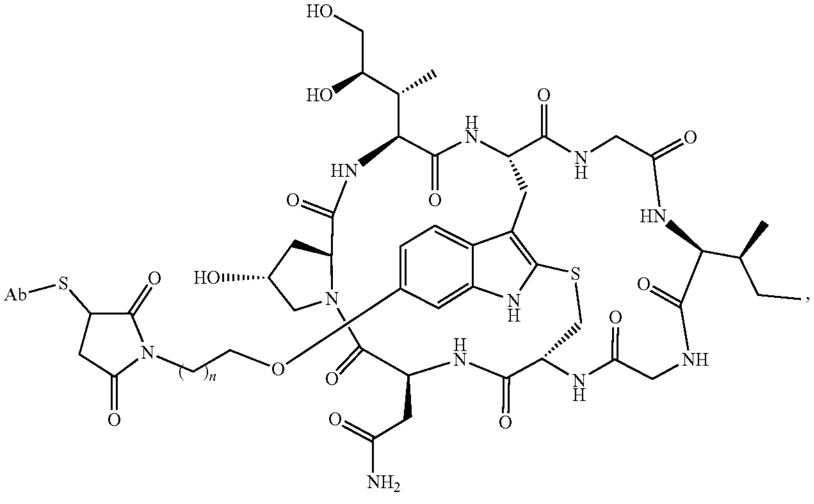

or a pharmaceutically acceptable salt, solvate, hydrate, tautomer, stereoisomer, diastereomer, or enantiomer, thereof, wherein:

n is 5; and

Ab is an anti-CCR8 antibody comprising a VH comprising a CDR-H1 comprising the amino acid sequence of SEQ ID NO: 88, a CDR-H2 comprising the amino acid sequence of SEQ ID NO: 139, and a CDR-H3 comprising the amino acid sequence of SEQ ID NO: 90; and a VL comprising a CDR-L1 comprising the amino acid sequence of SEQ ID NO: 140, a CDR-L2 comprising the amino acid sequence of SEQ ID NO: 92, and a CDR-L3 comprising the amino acid sequence of SEQ ID NO: 69; wherein $X_{26}$ is D or P and $X_{30}$ is L or Q.

In some embodiments, an ADC described herein has the structure of Formula (A):

(A)

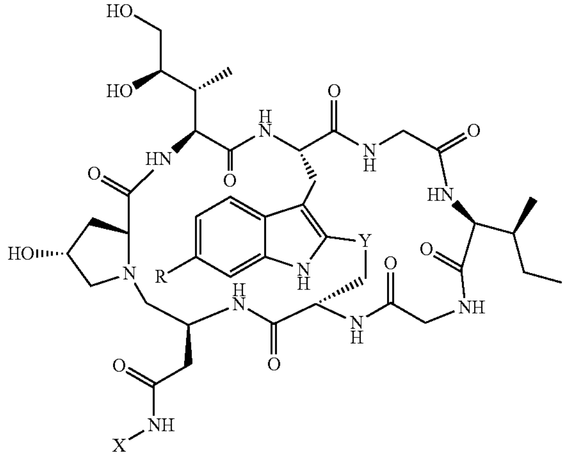

or a pharmaceutically acceptable salt, solvate, hydrate, tautomer, stereoisomer, diastereomer, or enantiomer thereof, wherein:

Ab is an anti-CCR8 antibody comprising a VH comprising the amino acid sequence of SEQ ID NO: 99 and a VL comprising the amino acid sequence of SEQ ID NO: 100.

In some embodiments, the ADC of Formula (A) is of the Formula (A-I-c):

(A-I-c)

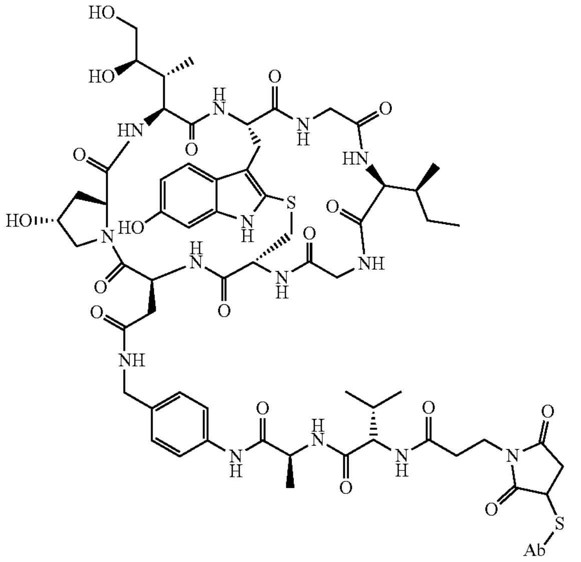

or a pharmaceutically acceptable salt, solvate, hydrate, tautomer, stereoisomer, diastereomer, or enantiomer, thereof, wherein:

Ab is an anti-CCR8 antibody comprising a VH comprising the amino acid sequence of SEQ ID NO: 99 and a VL comprising the amino acid sequence of SEQ ID NO: 100.

In some embodiments, the ADC of Formula (A) is of the Formula (A-I-e):

(A-I-e)

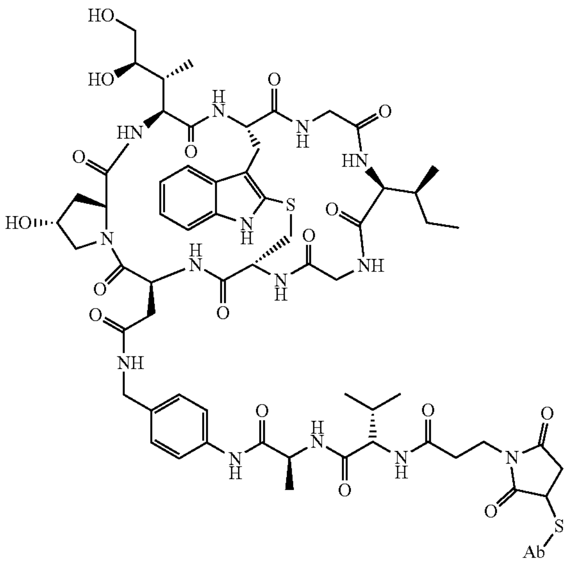

or a pharmaceutically acceptable salt, solvate, hydrate, tautomer, stereoisomer, diastereomer, or enantiomer, thereof, wherein:

Ab is an anti-CCR8 antibody comprising a VH comprising the amino acid sequence of SEQ ID NO: 99 and a VL comprising the amino acid sequence of SEQ ID NO: 100.

In some embodiments, the ADC of Formula (A) is of Formula (A-II-b):

(A-II-b)

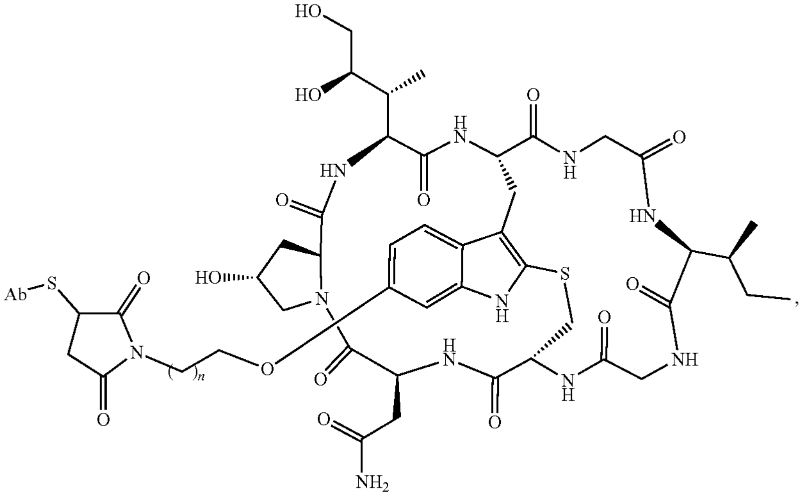

or a pharmaceutically acceptable salt, solvate, hydrate, tautomer, stereoisomer, diastereomer, or enantiomer, thereof, wherein:

n is 5; and

Ab is an anti-CCR8 antibody comprising a VH comprising the amino acid sequence of SEQ ID NO: 90 and a VL comprising the amino acid sequence of SEQ ID NO: 100.

In some embodiments, an ADC described herein has the structure of Formula (A):

(A)

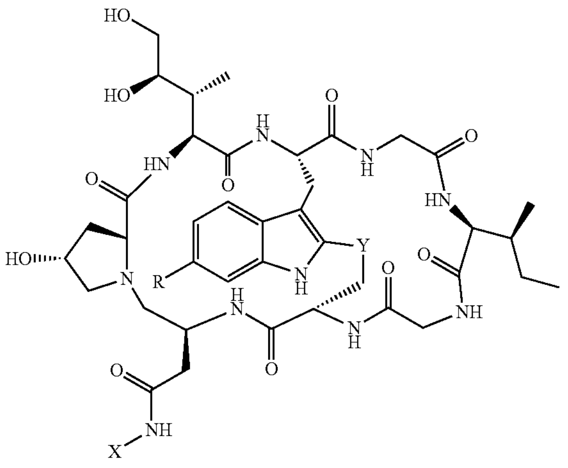

or a pharmaceutically acceptable salt, solvate, hydrate, tautomer, stereoisomer, diastereomer, or enantiomer thereof, wherein:

Ab is an anti-CCR8 antibody comprising a VH comprising the amino acid sequence of SEQ ID NO: 93 and a VL comprising the amino acid sequence of SEQ ID NO: 103.

In some embodiments, the ADC of Formula (A) is of the Formula (A-I-c):

(A-I-c)

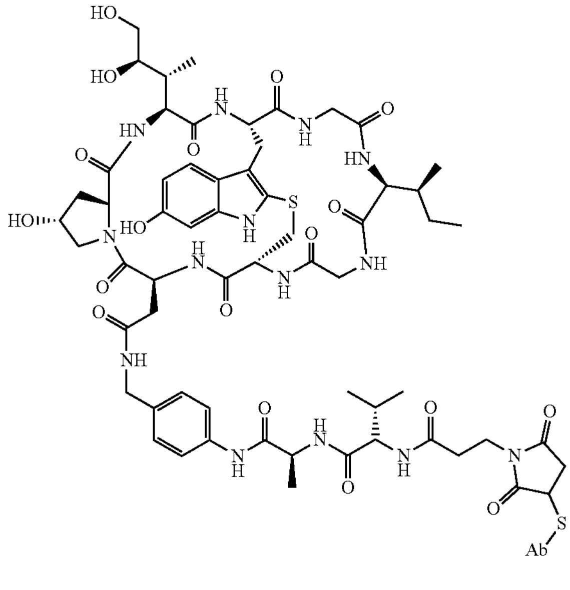

or a pharmaceutically acceptable salt, solvate, hydrate, tautomer, stereoisomer, diastereomer, or enantiomer, thereof, wherein:

Ab is an anti-CCR8 antibody comprising a VH comprising the amino acid sequence of SEQ ID NO: 93 and a VL comprising the amino acid sequence of SEQ ID NO: 103.

In some embodiments, the ADC of Formula (A) is of the Formula (A-I-e):

(A-I-e)

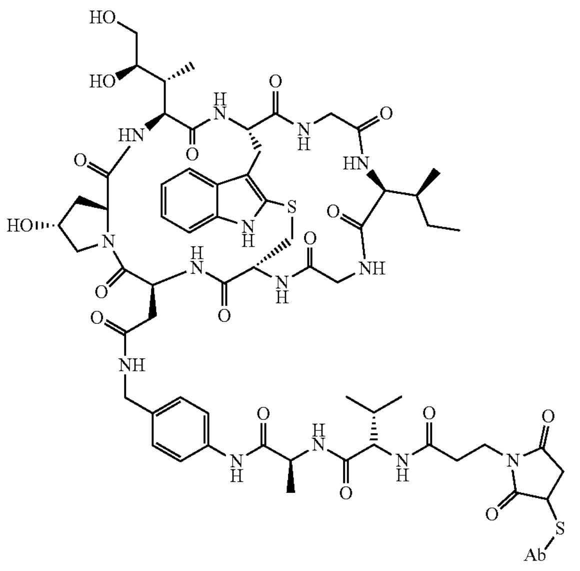

or a pharmaceutically acceptable salt, solvate, hydrate, tautomer, stereoisomer, diastereomer, or enantiomer, thereof, wherein:

Ab is an anti-CCR8 antibody comprising a VH comprising the amino acid sequence of SEQ ID NO: 93 and a VL comprising the amino acid sequence of SEQ ID NO: 103.

In some embodiments, the ADC of Formula (A) is of Formula (A-II-b):

(A-II-b)

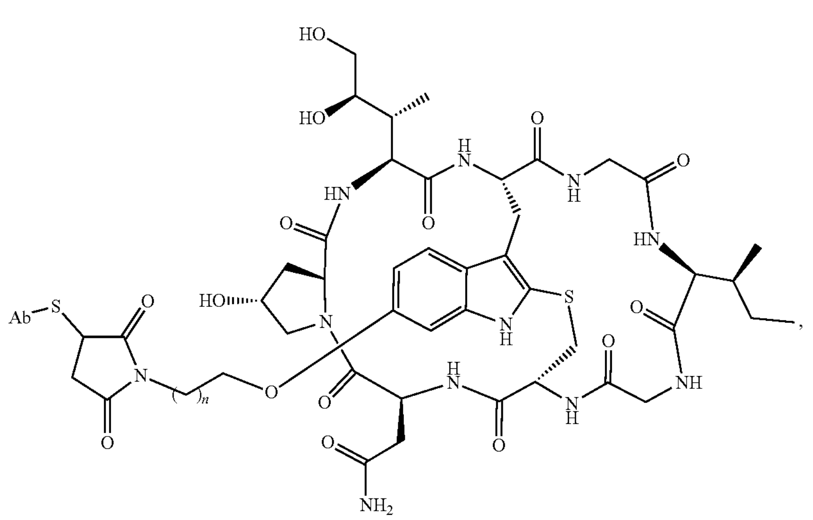

or a pharmaceutically acceptable salt, solvate, hydrate, tautomer, stereoisomer, diastereomer, or enantiomer, thereof, wherein:

n is 5; and

Ab is an anti-CCR8 antibody comprising a VH comprising the amino acid sequence of SEQ ID NO: 93 and a VL comprising the amino acid sequence of SEQ ID NO: 103.

In some embodiments, an ADC described herein has the structure of Formula (A):

(A)

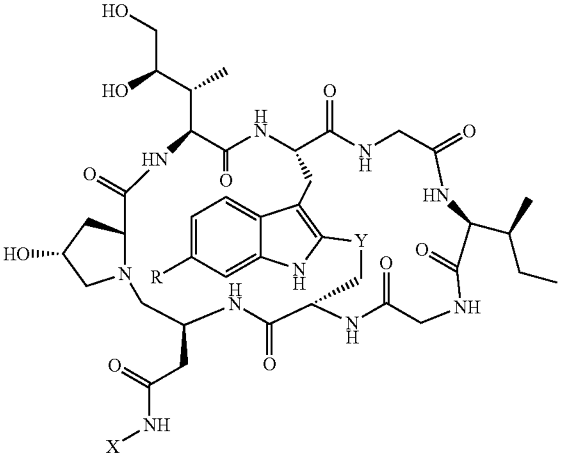

or a pharmaceutically acceptable salt, solvate, hydrate, tautomer, stereoisomer, diastereomer, or enantiomer thereof, wherein:

Ab is an anti-CCR8 antibody comprising a heavy chain comprising the amino acid sequence of SEQ ID NO: 145 and a light chain comprising the amino acid sequence of SEQ ID NO: 146.

In some embodiments, the ADC of Formula (A) is of the Formula (A-I-c):

(A-I-c)

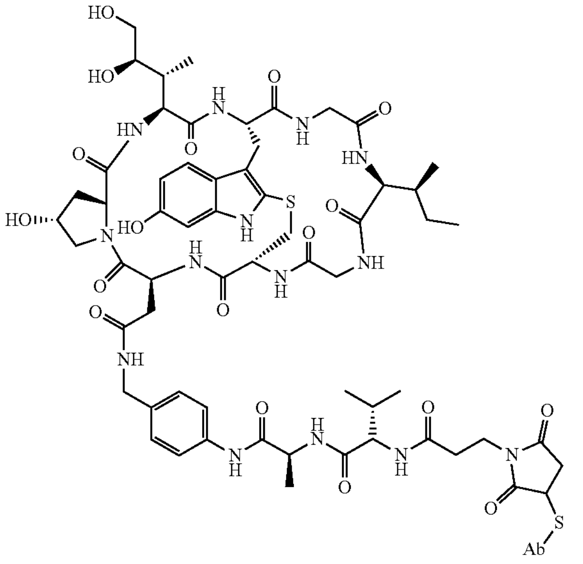

or a pharmaceutically acceptable salt, solvate, hydrate, tautomer, stereoisomer, diastereomer, or enantiomer, thereof, wherein:

Ab is an anti-CCR8 antibody comprising a heavy chain comprising the amino acid sequence of SEQ ID NO: 145 and a light chain comprising the amino acid sequence of SEQ ID NO: 146.

In some embodiments, the ADC of Formula (A) is of the Formula (A-I-e):

(A-I-e)

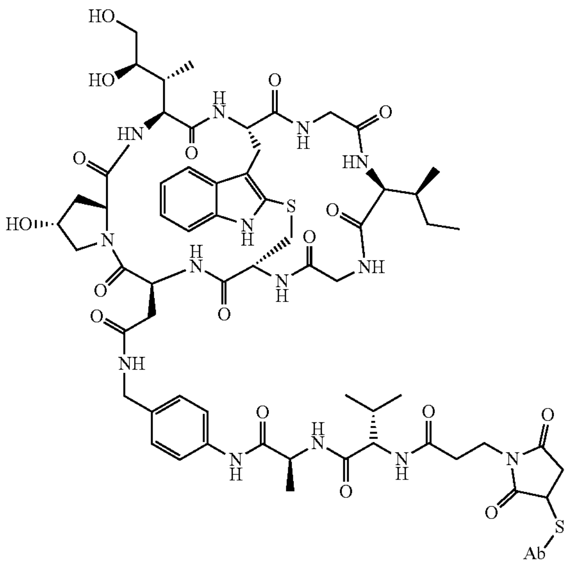

or a pharmaceutically acceptable salt, solvate, hydrate, tautomer, stereoisomer, diastereomer, or enantiomer, thereof, wherein:

Ab is an anti-CCR8 antibody comprising a heavy chain comprising the amino acid sequence of SEQ ID NO: 145 and a light chain comprising the amino acid sequence of SEQ ID NO: 146.

In some embodiments, the ADC of Formula (A) is of Formula (A-II-b):

(A-II-b)

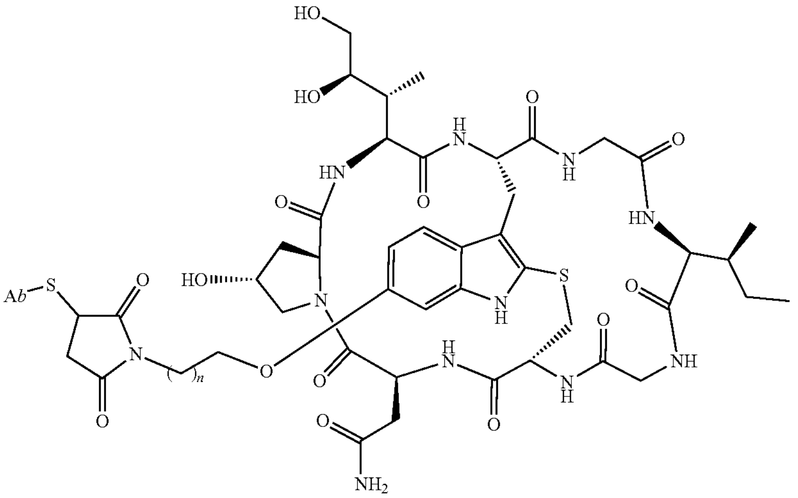

, or a pharmaceutically acceptable salt, solvate, hydrate, tautomer, stereoisomer, diastereomer, or enantiomer, thereof, wherein:

n is 5; and

Ab is an anti-CCR8 antibody comprising a heavy chain comprising the amino acid sequence of SEQ ID NO: 145 and a light chain comprising the amino acid sequence of SEQ ID NO: 146.

In some embodiments, an ADC described herein has the structure of Formula (A):

(A)

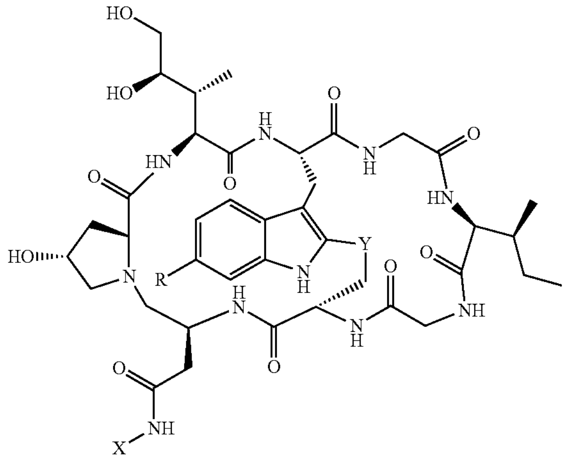

or a pharmaceutically acceptable salt, solvate, hydrate, tautomer, stereoisomer, diastereomer, or enantiomer thereof, wherein:

Ab is an anti-CCR8 antibody comprising a heavy chain comprising the amino acid sequence of SEQ ID NO: 147 and a light chain comprising the amino acid sequence of SEQ ID NO: 148.

In some embodiments, the ADC of Formula (A) is of the Formula (A-I-c):

(A-I-c)

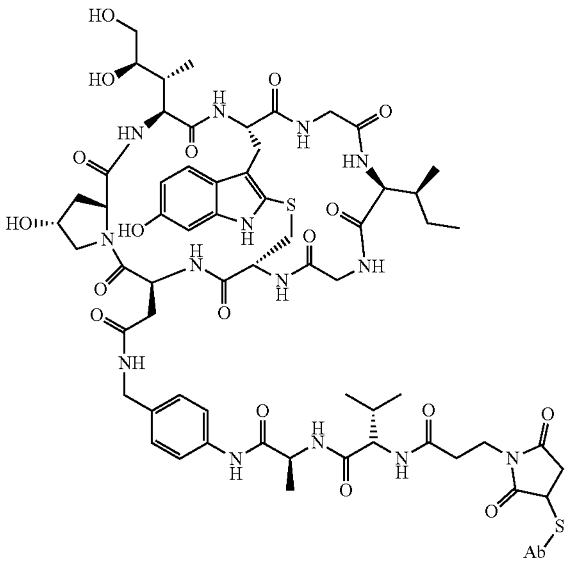

or a pharmaceutically acceptable salt, solvate, hydrate, tautomer, stereoisomer, diastereomer, or enantiomer, thereof, wherein:

Ab is an anti-CCR8 antibody comprising a heavy chain comprising the amino acid sequence of SEQ ID NO: 147 and a light chain comprising the amino acid sequence of SEQ ID NO: 148.

In some embodiments, the ADC of Formula (A) is of the Formula (A-I-e):

(A-I-e)

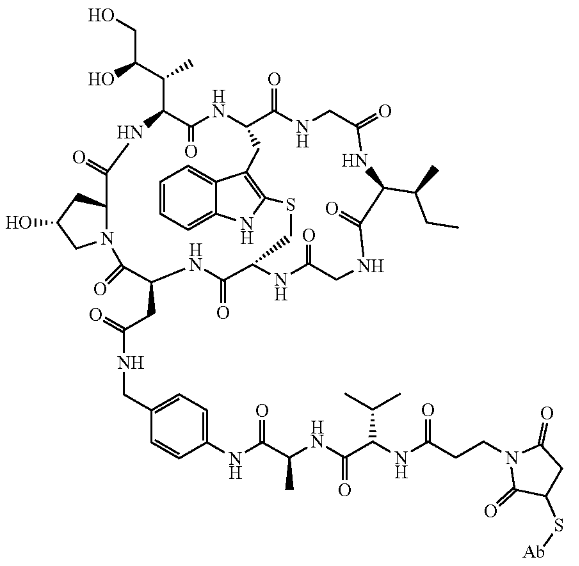

or a pharmaceutically acceptable salt, solvate, hydrate, tautomer, stereoisomer, diastereomer, or enantiomer, thereof, wherein:

Ab is an anti-CCR8 antibody comprising a heavy chain comprising the amino acid sequence of SEQ ID NO: 147 and a light chain comprising the amino acid sequence of SEQ ID NO: 148.

In some embodiments, the ADC of Formula (A) is of Formula (A-II-b):

(A-II-b)

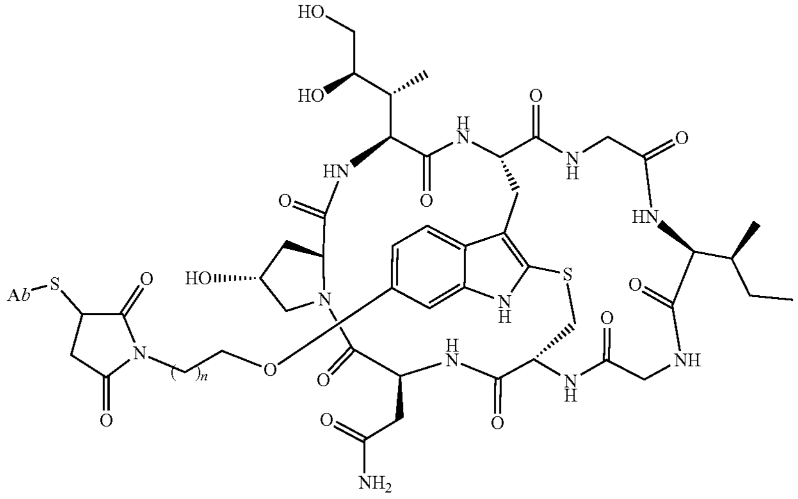

, or a pharmaceutically acceptable salt, solvate, hydrate, tautomer, stereoisomer, diastereomer, or enantiomer, thereof, wherein:

n is 5; and

Ab is an anti-CCR8 antibody comprising a heavy chain comprising the amino acid sequence of SEQ ID NO: 147 and a light chain comprising the amino acid sequence of SEQ ID NO: 148. In some embodiments, the ADC is of the depicted formula or a pharmaceutically acceptable salt thereof.

Linkers

The term "Linker" as used herein means a divalent chemical moiety comprising a covalent bond or a chain of atoms that forms an antibody-drug conjugate (ADC) by covalently attaching an anti-CCR8 antibody as described herein (including, e.g., in Table 1 or Table 2), or antigen binding fragment thereof (through one or more chemical moieties, e.g., a chemical moiety formed by a coupling reaction between a first reactive substituent previously bound to the linker and a second reactive substituent previously present within the anti-CCR8 antibody, or antigen-binding fragment thereof) to a payload (e.g., a cytotoxic moiety, such as an amatoxin or amanitin).

Covalent attachment of an anti-CCR8 antibody described herein (including, e.g., in Table 1 or Table 2), or antigen-binding fragment thereof, to the payload can be achieved by forming the from two reactive functional groups, i.e., bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Accordingly, in some embodiments, formation of the linkers disclosed herein is achieved using two reactive termini, one for conjugation to an anti-CCR8 antibody described herein (including, e.g., in Table 1 or Table 2), and the other for conjugation to the payload. In some embodiments, the reactive termini are simultaneously present in the synthesis of the ADC. In some embodiments, the reactive termini are installed at separate times during the synthesis of the ADC. Similarly, in some embodiments, the reactive termini are reacted with their complementary reactive substituents simultaneously. In some embodiments, the reactive termini are reacted with their complementary reactive substituents at separate times.

In some embodiments, the anti-CCR8 antibody conjugation reactive terminus of the linker comprises a chemical moiety that is capable of conjugation to an anti-CCR8 antibody described herein (including, e.g., in Table 1 or Table 2), through formation of a bond with a complementary reactive substituent present on the anti-CCR8 antibody, or antigen-binding fragment thereof. In some embodiments, conjugation of the linker to an anti-CCR8 antibody described herein (including, e.g., in Table 1 or Table 2), is accomplished by forming a chemical moiety though a coupling reaction between a first reactive substituent on the linker and a second reactive substituent present on an anti-CCR8 antibody described herein (including, e.g., in Table 1 or Table 2). In some embodiments, the complementary reactive substituent present on an anti-CCR8 antibody described herein (including e.g., in Table 1 or Table 2), comprises a thiol, alcohol, or amine group. In some embodiments, the thiol group is present on a cysteine residue. In some embodiments, the alcohol group is present on a serine, tyrosine, or threonine residue. In some embodiments, the amine group is present on a lysine, or proline residue. In some embodiments, the anti-CCR8 antibody conjugation reactive terminus comprises a thiol-reactive group. In some embodiments, the anti-CCR8 antibody conjugation reactive terminus comprises a Michael acceptor, a leaving group, or an amine-reactive group. In some embodiments, the anti-CCR8 antibody conjugation reactive terminus comprises a maleimide. In some embodiments, the anti-CCR8 antibody conjugation reactive terminus comprises a chloro, bromo, iodo, or a sulfanyl group. In some embodiments, the anti-CCR8 antibody conjugation reactive terminus comprises a carboxyl group. Conjugation of the linker to the anti-CCR8 antibody, or antigen-binding fragment thereof, is described more fully herein below.

In some embodiments, the payload conjugation reactive terminus of the linker comprises a chemical moiety that is capable of conjugation to the payload through formation of a bond with a complementary reactive substituent present on the payload. In some embodiments, the conjugation of the linker to the payload comprises an amide bond formed between a basic amine or carboxyl group on the payload via a carboxyl or basic amine group on the linker, respectively. In some embodiments, the conjugation of the linker to the payload comprises an ether bond formed by alkylation of an alcohol group on the payload via a leaving group on the linker. In some embodiments, the conjugation of the linker to the payload comprises an ether bond formed by alkylation of a leaving group on the payload via an alcohol group on the linker.

When the term "linker" is used in describing the linker in conjugated form, one or both of the reactive termini will be absent or incomplete (such as being only the carbonyl of the carboxylic acid) because of the formation of the bonds between the linker and/or the compound, and between the linker and/or an anti-CCR8 antibody described herein (including, e.g., in Table 1 or Table 2). Such conjugation reactions are described further herein below.

A variety of linkers can be used to conjugate an anti-CCR8 antibody described herein (including, e.g., in Table 1 or Table 2), and ligands described to a payload. Generally, linkers suitable for the present disclosure may be substantially stable in circulation within the subject, but allow for release of the payload within or in close proximity to the target cells. In some embodiments, some linkers suitable for the present disclosure may be categorized as "cleavable" or "non-cleavable." Generally, cleavable linkers contain one or more functional groups that is cleaved in response to a physiological environment. For example, a cleavable linker may contain an enzymatic substrate (e.g., valine-alanine) that degrades in the presence of an intracellular enzyme (e.g., cathepsin B), an acid-cleavable group (e.g., a hydrozone) that degrades in the acidic environment of a cellular compartment, or a reducible group (e.g., a disulfide) that degrades in an intracellular reducing environment. By contrast, generally, non-cleavable linkers are released from the ADC during degradation (e.g., lysosomal degradation) of the anti-CCR8 antibody moiety of the ADC inside the target cell.

In some embodiments, the linker L comprises one or more of a bond, —(C═O)—, a —C(O)NH— group, an —OC(O)NH— group, alkylene, heteroalkylene, alkenylene, heteroalkenylene, alkynylene, heteroalkynylene, cycloalkylene, heterocycloalkylene, arylene, heteroarylene, a $-(CH_2CH_2O)_p-$ group where p is an integer from 1-10.

In some embodiments, the alkylene is $C_1$-$C_{10}$ alkylene. In some embodiments, the alkylene is $C_1$-$C_6$ alkylene. In some embodiments, the alkylene is unsubstituted. In some embodiments, the alkylene is substituted.

In some embodiments, the heteroalkylene is $C_1$-$C_{10}$ heteroalkylene. In some embodiments, the heteroalkylene is $C_1$-$C_6$ heteroalkylene. In some embodiments, the heteroalkylene is unsubstituted. In some embodiments, the heteroalkylene is substituted.

In some embodiments, the alkenylene is $C_2$-$C_{10}$ alkenylene. In some embodiments, the alkenylene is $C_2$-$C_6$ alkenylene. In some embodiments, the alkenylene is unsubstituted. In some embodiments, the alkenylene is substituted.

In some embodiments, the heteroalkenylene is $C_2$-$C_{10}$ heteroalkenylene. In some embodiments, the heteroalkenylene is $C_2$-$C_6$ heteroalkenylene. In some embodiments, the heteroalkenylene is unsubstituted. In some embodiments, the heteroalkenylene is substituted.

In some embodiments, the alkynylene is $C_2$-$C_{10}$ alkynylene. In some embodiments, the alkynylene is $C_2$-$C_6$ alkynylene. In some embodiments, the alkynylene is unsubstituted. In some embodiments, the alkynylene is substituted.

In some embodiments, the heteroalkynylene is $C_2$-$C_{10}$ heteroalkynylene. In some embodiments, the heteroalkynylene is $C_2$-$C_6$ heteroalkynylene. In some embodiments, the heteroalkynylene is unsubstituted. In some embodiments, the heteroalkynylene is substituted.

In some embodiments, the cycloalkylene is $C_3$-$C_{10}$ cycloalkylene. In some embodiments, the cycloalkylene is $C_3$-$C_5$ cycloalkylene. In some embodiments, the cycloalkylene is unsubstituted. In some embodiments, the cycloalkylene is substituted.

In some embodiments, the heterocycloalkylene is 3- to 14-membered heterocycloalkylene. In some embodiments, the heterocycloalkylene is 3- to 7-membered heterocycloalkylene. In some embodiments, the heterocycloalkylene is 3- to 10-membered heterocycloalkylene. In some embodiments, the heterocycloalkylene is 5- to 10-membered heterocycloalkylene. In some embodiments, the heterocycloalkylene is 5- to 8-membered heterocycloalkylene. In some embodiments, the heterocycloalkylene is 5- to 6-membered heterocycloalkylene. In some embodiments, the heterocycloalkylene is monocyclic. In some embodiments, the heterocycloalkylene is polycyclic. In some embodiments, one or more heteroatoms is disposed in one ring. In some embodiments, one or more heteroatoms is disposed in more than one ring. In some embodiments, the heterocycloalkylene includes ring carbon atoms and 1-4 ring heteroatoms. In some embodiments, each heteroatom is independently selected from nitrogen, oxygen, and sulfur, as valency permits. In some embodiments, 1, 2, or 3 atoms in the heterocycloalkylene ring system are independently oxygen, nitrogen, or sulfur, as valency permits. In some embodiments, 1 or 2 atoms in the heterocycloalkylene ring system are independently oxygen, nitrogen, or sulfur, as valency permits. In some embodiments, one atom in the heterocycloalkylene ring system is oxygen, nitrogen, or sulfur, as valency permits. In some embodiments, each atom in the heterocycloalkylene ring system is independently oxygen or nitrogen. In some embodiments, each atom in the heterocycloalkylene ring system is nitrogen. In some embodiments, the 5-6 membered heterocycloalkylene has 1-3 ring heteroatoms selected from nitrogen, oxygen, and sulfur. In some embodiments, the 5-6 membered heterocycloalkylene has 1-2 ring heteroatoms selected from nitrogen, oxygen, and sulfur. In some embodiments, the 5-6 membered heterocycloalkylene has 1 ring heteroatom selected from nitrogen, oxygen, and sulfur.

In some embodiments, the heterocycloalkylene is azirdinylene, oxiranylene, or thiiranylene. In some embodiments, the heterocycloalkylene is azetidinylene, oxetanylene, or thietanylene. In some embodiments, the heterocycloalkylene is tetrahydrofuranylene, dihydrofuranylene, tetrahydrothiophenylene, dihydrothiophenylene, pyrrolidinylene, dihydropyrrolylene, or pyrrolyl-2,5-dionylene. In some embodiments, the heterocycloalkylene is dioxolanylene, oxathiolanylene, or dithiolanylene. In some embodiments, the heterocycloalkylene is triazolinylene, oxadiazolinylene, or thiadiazolinylene. In some embodiments, the heterocycloalkylene is piperidinylene, tetrahydropyranylene, dihydropyridinylene, or thianylene. In some embodiments, the heterocycloalkylene is piperazinylene, morpholinylene, dithianylene, or dioxanylene. In some embodiments, the heterocycloalkylene is triazinylene. In some embodiments, the heterocycloalkylene is azepanylene, oxepanylene or thiepanylene. In some embodiments, the heterocycloalkylene is azocanylene, oxecanylene or thiocanylene. In some embodiments, the heterocycloalkylene is indolinylene, isoindolinylene, dihydrobenzofuranylene, dihydrobenzothienylene, tetrahydrobenzothienylene, tetrahydrobenzofuranylene, tetrahydroindolylene, tetrahydroquinolinylene, tetrahydroisoquinolinylene, decahydroquinolinylene, decahydroisoquinolinylene, octahydrochromenylene, octahydroisochromenylene, decahydronaphthyridinylene, decahydro-1,8-naphthyridinylene, octahydropyrrolo[3,2-b]pyrrole, indolinylene, phthalimidylene, naphthalimidylene, chromanylene, chromenylene, 1H-benzo[e][1,4]diazepinylene, 1,4,5,7-tetrahydropyrano[3,4-b]pyrrolylene, 5,6-dihydro-4H-furo[3,2-b]pyrrolylene, 6,7-dihydro-5H-furo[3,2-b]pyranylene, 5,7-dihydro-4H-thieno[2,3-c]pyranylene, 2,3-dihydro-1H-pyrrolo[2,3-b]pyridinylene, 2,3-dihydrofuro[2,3-b]pyridinylene, 4,5,6,7-tetrahydro-1H-pyrrolo[2,3-b]pyridinylene, 4,5,6,7-tetrahydrofuro[3,2-c]pyridinylene, 4,5,6,7-tetrahydrothieno[3,2-b]pyridinylene, or 1,2,3,4-tetrahydro-1,6-naphthyridinylene. In some embodiments, the point of attachment is a carbon atom. In some embodiments, the point of attachment is a nitrogen atom. In some embodiments, the heterocycloalkylene is unsubstituted. In some embodiments, the heterocycloalkylene is substituted with one or more substituents.

In some embodiments, the arylene is $C_{6-14}$ arylene. In some embodiments, the arylene is phenylene. In some embodiments, the arylene is $C_{10}$ arylene. In some embodiments, the arylene is naphthylene. In some embodiments, the arylene is 1-naphthylene. In some embodiments, the arylene is 2-naphthylene. In some embodiments, the arylene is $C_{14}$ arylene. In some embodiments, the arylene is anthracylene. In some embodiments, the arylene is unsubstituted. In some embodiments, the arylene is substituted with one or more substituents. In some embodiments, the arylene is an unsubstituted $C_{6-14}$ arylene. In some embodiments, the arylene is a substituted $C_{6-14}$ arylene. In some embodiments, the arylene is unsubstituted. In some embodiments, the arylene is substituted.

In some embodiments, the heteroarylene is 5- to 14-membered heteroarylene. In some embodiments, the heteroarylene is 5- to 10-membered heteroarylene. In some embodiments, the heteroarylene is 5- to 8-membered heteroarylene. In some embodiments, the heteroarylene is 5- or 6-membered heteroarylene. In some embodiments, the heteroarylene is 9- or 10-membered heteroarylene. In some embodiments, the heteroarylene is monocyclic. In some embodiments, the heteroarylene is polycyclic. In some embodiments, one or more heteroatoms is disposed in one ring. In some embodiments, one or more heteroatoms is disposed in more than one ring. In some embodiments, the heteroarylene includes ring carbon atoms and 1-4 ring heteroatoms. In some embodiments, each heteroarylene is independently selected from nitrogen, oxygen, and sulfur, as valency permits. In some embodiments, 1, 2, or 3 atoms in the heteroarylene ring system are independently oxygen, nitrogen, or sulfur, as valency permits. In some embodiments, 1 or 2 atoms in the heteroarylene ring system are independently oxygen, nitrogen, or sulfur, as valency permits. In some embodiments, one atom in the heteroarylene ring system is oxygen, nitrogen, or sulfur, as valency permits. In some embodiments, each atom in the heteroarylene ring system is independently oxygen or nitrogen. In some embodiments, each atom in the heteroarylene ring system is nitrogen. In some embodiments, the 5-6 membered heteroarylene has 1-3 ring heteroatoms selected from nitrogen, oxygen, and sulfur. In some embodiments, the 5-6 membered heteroarylene has 1-2 ring heteroatoms selected from nitrogen, oxygen, and sulfur. In some embodiments, the 5-6 membered heteroarylene has 1 ring heteroatom selected from nitrogen, oxygen, and sulfur. In some embodiments, the 9- or 10-membered heteroarylene has 1, 2, 3, or 4 atoms in the heteroaryl ring system selected from independently oxygen, nitrogen, or sulfur. In some embodiments, the heteroarylene group is an unsubstituted 5-14 membered heteroarylene. In some embodiments, the heteroarylene group is a substituted 5-14 membered heteroarylene. In some embodiments, the point of attachment is a carbon atom. In some embodiments, the point of attachment is a nitrogen atom. In some embodiments, the heteroarylene is unsubstituted. In some embodiments, the heteroarylene is substituted with one or more substituents with one or more substituents.

In some embodiments, the heteroarylene is pyrrolylene, furanylene, or thiophenylene. In some embodiments, the heteroarylene is imidazolylene, pyrazolylene, oxazolylene, isoxazolylene, thiazolylene, or isothiazolylene. In some embodiments, the heteroarylene is triazolylene, oxadiazolylene, or thiadiazolylene. In some embodiments, the heteroarylene is tetrazolylene. In some embodiments, the heteroarylene is pyridinylene. In some embodiments, the heteroarylene is pyridazinylene, pyrimidinylene, or pyrazinylene. In some embodiments, the heteroarylene is triazinylene or tetrazinylene. In some embodiments, the heteroarylene is azepinylene, oxepinylene, or thiepinylene. In some embodiments, the heteroarylene is indolylene, isoindolylene, indazolylene, benzotriazolylene, benzothiophenylene, isobenzothiophenylene, benzofuranylene, benzoisofuranylene, benzimidazolylene, benzoxazolylene, benzisoxazolylene, benzoxadiazolylene, benzthiazolylene, benzisothiazolylene, benzthiadiazolylene, indolizinylene, or purinylene. In some embodiments, the heteroarylene is naphthyridinylene, pteridinylene, quinolinylene, isoquinolinylene, cinnolinylene, quinoxalinylene, phthalazinylene, or quinazolinylene. In some embodiments, the heteroarylene is phenanthridinylene, dibenzofuranylene, carbazolylene, acridinylene, phenothiazinylene, phenoxazinylene, or phenazinylene.

In some embodiments, p is an integer from 1-6. In some embodiments, p is an integer from 1-5. In some embodiments, p is an integer from 1-4. In some embodiments, p is an integer from 1-3. In some embodiments, p is an integer from 1-2. In some embodiments, p is 1.

In some embodiments, wherein the group is substituted, the group is substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro. In some embodiments, each alkylene, heteroalkylene, alkenylene, heteroalkenylene, alkynylene, heteroalkynylene, cycloalkylene, heterocycloalkylene, arylene, or heteroarylene is optionally interrupted by one or more heteroatoms selected from O, S, and N.

Non-Cleavable Linkers

In some embodiments, the non-cleavable linker comprises one or more of a bond, —(C═O)—, alkylene, heteroalkylene, alkenylene, heteroalkenylene, alkynylene, heteroalkynylene, cycloalkylene, heterocycloalkylene, arylene, heteroarylene, and combinations thereof, each of which is optionally substituted. In some embodiments, the non-cleavable linker includes one or more heteroatoms (e.g., S, N, or O) in place of one or more carbon atoms. In some embodiments, the non-cleavable linker comprises $(CH_2)_p$, $(C{=}O)(CH_2)_p$, or polyethyleneglycol (PEG; $(CH_2CH_2O)_p$), units, wherein p is an integer from 1-10, independently selected for each occasion. In some embodiments, the non-cleavable linker comprises one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, and $C_3$-$C_5$ cycloalkylene.

In some embodiments, the non-cleavable linker comprises a $—(CH_2)_n—$ unit, where n is an integer from 1-20. In some embodiments, n is an integer from 1-20. In some embodiments, n is an integer from 2-6. In some embodiments, the non-cleavable linker comprises a $—(CH_2)_n—$ where n is 1, 2, 3, 4, 5, or 6. In some embodiments, the non-cleavable linker is $—(CH_2)_n—$ where n is 6, represented by the formula:

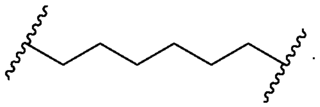 [SMILES: *CCCCCC*]

In some embodiments, the non-cleavable linker is $—(CH_2)_n—$ where n is 6, represented by the formula:

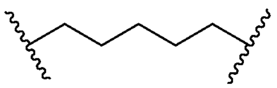 [SMILES: *CCCCC*]

Cleavable Linkers

In some embodiments, the linker conjugating an anti-CCR8 antibody described herein (including, e.g., in Table 1 or Table 2), and the payload is cleavable under intracellular conditions, such that cleavage of the linker releases the drug unit from an anti-CCR8 antibody described herein (including, e.g., in Table 1 or Table 2), in the intracellular environment. Cleavable linkers are designed to exploit the differences in local environments, e.g., extracellular and intracellular environments, including, for example, pH, reduction potential or enzyme concentration, to trigger the release of the payload in the target cell. Generally, cleavable linkers are relatively stable in circulation, but are particularly susceptible to cleavage in the intracellular environment through one or more mechanisms (e.g., including, but not limited to, activity of proteases, peptidases, and glucuronidases). Cleavable linkers used herein are substantially stable in circulating plasma and/or outside the target cell and may be cleaved at some efficacious rate inside the target cell or in close proximity to the target cell.

In some embodiments, the cleavable linker may be cleaved by enzymatic hydrolysis, photolysis, hydrolysis under acidic conditions, hydrolysis under basic conditions, oxidation, disulfide reduction, nucleophilic cleavage, or organometallic cleavage (see, e.g., Leriche et al. Bioorg. Med. Chem. 2012, 20:571-582). In some embodiments, the cleavable linker comprises a hydrazine, a disulfide, a thioether or a dipeptide.

In some embodiments, the cleavable linker is hydrolyzable under acidic conditions. In some embodiments, the cleavable linker is a hydrazone, semicarbazone, thiosemicarbazone, cis-aconitic amide, orthoester, acetal, ketal, or the like (see, e.g., U.S. Pat. Nos. 5,122,368; 5,824,805; 5,622,929; Dubowchik and Walker, *Pharm. Therapeutics* 1999, 83:67-123; Neville et al. *Biol. Chem.* 1989, 264: 14653-14661, the disclosures of each of which are incorporated herein by reference in their entireties as they pertain to linkers suitable for covalent conjugation). Such linkers are relatively stable under neutral pH conditions, such as those in the blood, but are unstable at below pH 5.5 or 5.0, the approximate pH of the lysosome.

In some embodiments, the linker is cleavable under reducing conditions. In some embodiments, the cleavable linker comprises a disulfide. In some embodiments, the cleavable disulfide linker is formed using SATA (N-succinimidyl-S-acetylthioacetate), SPDP (N-succinimidyl-3-(2 pyridyldithio) propionate), SPDB (N-succinimidyl-3-(2-pyridyldithio)butyrate) and SMPT (N- succinimidyl-oxycarbonyl-alpha-methyl-alpha-(2-pyridyl-dithio)toluene), SPDB and SMPT (see, e.g., Thorpe et al. Cancer Res. 1987, 47:5924-5931; Wawrzynczak et al. In lmmunoconjugates: Antibody Conjugates in Radioimagery and Therapy of Cancer (C. W. Vogel ed., Oxford U. Press, 1987; see also U.S. Pat. No. 4,880,935).

In some embodiments, the cleavable linker is a linker susceptible to enzymatic hydrolysis. In some embodiments, the cleavable linker is a peptide-containing linker that is cleaved by an intracellular peptidase or protease enzyme. In some cases, the protease enzyme is a lysosomal or endosomal protease. One advantage of using intracellular proteolytic release of the therapeutic agent is that the agent is typically attenuated when conjugated and the serum stabilities of the conjugates are typically high. In some embodiments, the cleavable peptidyl linker is at least two amino acids long. In some embodiments, the cleavable peptidyl linker is at least three amino acids long. In some embodiments, the cleavable amino acid linker is a dipeptide, a tripeptide, a tetrapeptide, or a pentapeptide. In some embodiments, the peptide comprises one or more amino acids selected from the group consisting of Valine, Alanine, Citrulline (Cit), Phenylalanine, Lysine, Leucine, and Glycine. Amino acid residues which comprise an amino acid linker component include those occurring naturally, as well as minor amino acids and non- naturally occurring amino acid analogs, such as citrulline. In some embodiments, the dipeptide includes valine-citrulline or alanine-phenylalanine (af or ala-phe). In some embodiments, the tripeptide includes glycine-valine-citrulline (gly-val-cit) or glycine-glycine-glycine (gly-gly-gly). In some embodiments, the cleavable linker includes a dipeptide such as Val-Cit, Ala-Val, or Phe-Lys, Val-Lys, Ala-Lys, Phe-Cit, Leu-Cit, lie-Cit, Phe-Arg, or Trp-Cit. Linkers containing dipeptides such as Val-Cit or Phe-Lys are disclosed in, for example, U.S. Pat. No. 6,214,345. In some embodiments, the cleavable linker comprises a dipeptide selected from Val-Ala and Val-Cit.

Cleavable linkers suitable for conjugating the antibodies, antigen-binding fragments, described herein to a payload include those capable of releasing a compound by a 1,6-elimination process. Chemical moieties capable of this elimination process include the p-aminobenzyl (PAB) group, 6-maleimidohexanoic acid, pH-sensitive carbonates, and other reagents as described in Jain et al. Pharm. Res. 2015, 32:3526-3540.

In some embodiments, the cleavable linker comprises one or more of a hydrazine, a disulfide, a thioether, an amino acid, a peptide consisting of up to 10 amino acids, a p-aminobenzyl (PAB) group, a heterocyclic self-immolative group, alkyl, heteroalkyl, alkenyl, heteroalkenyl, alkynyl, heteroalkynyl, cycloalkyl, heterocycloalkyl, aryl, heteroaryl, a $-(C{=}O)-$ group, a $-C(O)NH-$ group, an $-OC(O)NH-$ group, or a $-(CH_2CH_2O)_p-$ group.

In some embodiments, the cleavable linker includes a p-aminobenzyl group (PAB). In some embodiments, the p-aminobenzyl group is disposed between the payload and a protease cleavage site in the linker. In some embodiments, the p-aminobenzyl group is part of a p-aminobenzyloxycarbonyl unit. In some embodiments, the p-aminobenzyl group is part of a p-aminobenzylamido unit.

In some embodiments, the cleavable linker comprises a dipeptide selected from the group consisting of Phe-Lys, Val-Lys, Phe-Ala, Phe-Cit, Val-Ala, Val-Cit, and Val-Arg. In some embodiments, the cleavable linker comprises one or more of PAB, Val-Cit-PAB, Val-Ala-PAB, Val- Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the cleavable linker comprises a combination of one or more of a peptide, oligosaccharide, $-(CH_2)_p-$, $-(CH_2CH_2O)_p-$, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB. In some embodiments, the cleavable linker comprises a $-(C{=}O)(CH_2)_p-$ unit, wherein p is an integer from 1-10. In some embodiments, the cleavable linker comprises a $-(C{=}O)(CH_2)_p-$ unit, wherein p is an integer from 2-8. In some embodiments, the cleavable linker comprises a $-(C{=}O)(CH_2)_p-$ unit, wherein p is an integer from 1-6. In some embodiments, the cleavable linker comprises a $-(C{=}O)(CH_2)_p-$ unit, wherein p is an integer from 4-6.

Linkers L

In some embodiments, an ADC described herein comprises a linker L. In some embodiments, L is of the formula: $-Q^{L1}-Q^1-Q^{L2}$ wherein each of $Q^{L1}$ and $Q^{L2}$ is optionally substituted alkylene; and $Q^1$ is a peptide. In some embodiments, $Q^{L1}$ comprises an arylene group. In some embodiments, $Q^{L1}$ is phenylene. In some embodiments, $Q^{L1}$ is benzylene. In some embodiments, $Q^{L1}$ is phenylethylene. In some embodiments, $Q^1$ is a dipeptide. In some embodiments, $Q^1$ is a dipeptide comprising at least one of an alanine and a valine residue. In some embodiments, $Q^1$ is a Ala-Val dipeptide. In some embodiments, $Q^{L2}$ is an alkanoylene group. In some embodiments, $Q^{L2}$ is a propanoylene group. In some embodiments, L is of the formula:

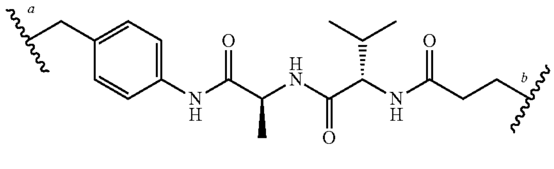
, wherein a is the portion of L bonded to the amide moiety linked to L in Formula (A), Formula (A-I), Formula (A-I-a), Formula (A-I-b), Formula (A-I-c), Formula (A-I-d), Formula (A-I-e), Formula (A-II), Formula (A-II-a), or Formula (A-II-b) and b is the portion of L bonded to Z. In some embodiments, -L-first reactive substituent is of the formula:

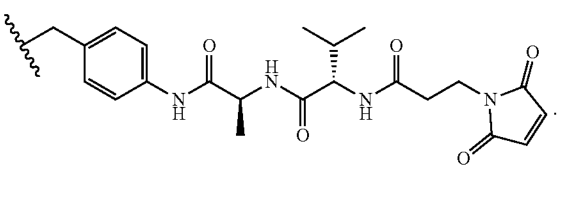 [SMILES: *Cc1ccc(NC(=O)[C@H](C)NC(=O)[C@@H](NC(=O)CCN2C(=O)C=CC2=O)C(C)C)cc1]

Chemical Moiety Z

In some aspects, the ADC of Formula (A) as disclosed herein comprises the substituent Z, a chemical moiety formed by a coupling reaction between a first reactive substituent previously bound to L and a second reactive substituent previously present within the anti-CCR8 antibody, or antigen-binding fragment thereof.

In some embodiments, the reactive substituent previously bound to L comprises an olefin. In some embodiments, the reactive substituent previously bound to L comprises an olefin disposed within a ring. In some embodiments, the reactive substituent previously bound to L comprises an olefin disposed within a heterocyclic ring. In some embodiments, the reactive substituent previously bound to L comprises an olefin disposed within a heterocyclic ring comprising an imide. In some embodiments, the reactive substituent previously bound to L comprises a maleimide. In some embodiments, the reactive substituent previously bound to L comprises 1H-pyrrol-1-yl-2,5-dione.

In some embodiments, the reactive substituent previously present within the anti-CCR8 antibody is a thiol. In some embodiments, the reactive substituent previously present within the anti-CCR8 antibody is a thiol of a cysteine.

In some embodiments, Z comprises a sulfide bond. In some embodiments, Z comprises a pyrrolidine-1-yl-2,5-dione moiety. In some embodiments, Z is of the formula:

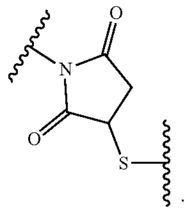 [SMILES: *SC1CC(=O)N(*)C1=O]

Pharmaceutical Compositions

In some aspects, the present disclosure also provides a composition (e.g., pharmaceutical composition) comprising an anti-CCR8 antibody described herein (including, e.g., in Table 1 or Table 2) and a pharmaceutically acceptable excipient. In some aspects, the present disclosure also provides a composition (e.g., pharmaceutical composition) comprising an ADC provided herein and a pharmaceutically acceptable excipient.

Pharmaceutically acceptable excipients are well known in the art. Pharmaceutically acceptable excipients are safe for administration to humans in accordance with generally established government standards, including those published by the US Food and Drug Administration.

Pharmaceutical compositions described herein can be prepared by any method known in the art. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents or fillers, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents or fillers include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, starches (such as dry starch, cornstarch), sugars (such as powdered sugar), calcium trisulfate, carboxymethylcellulose calcium, dextrate, dextrin, dextrose, fructose, lactitol, lactose, magnesium carbonate, magnesium, maltitol, maltodextrin, maltose, sucrose, glucose, mannitol, silicic acid, xylitol, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary disintegrating agents or disintegrants include agar, algin, alginic acid, sodium alginate, silicates, sodium carbonate, calcium carbonate, carboxymethylcellulose, cellulose, clay, colloidal silicon dioxide, croscarmellose sodium, crospovidone, rubber, magnesium silicate, methylcellulose, potassium krillin, hydroxypropylcellulose (e.g., low substituted Hydroxypropylcellulose), crosslinked polyvinylpyrrolidone, hydroxypropylcellulose, and starch (e.g., sodium glycolate starch, potato or tapioca starch).

Exemplary binding agents include starch (e.g., glycolate starch, cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof.

Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include agar, ethyl oleate, ethyl laurate, glycerin, blyceryl palmitostearate, magnesium oxide, magnesium stearate, mannitol, poloxamer, glycol, sodium stearyl, sorbitol, zinc stearate, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, surfactants, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In some embodiments, injectable preparations of the compositions disclosed herein are in the form of a ready-to-use ("RTU") preparation that can be directly administered to a subject. In some embodiments, the RTU preparation is a suspension. In some embodiments, the RTU preparation is a solution. In some embodiments, the RTU preparation is an emulsion. In some embodiments, injectable preparations of the compositions disclosed herein are in the form of a solid that is reconstituted prior to administration. In some embodiments, the solid is a lyophilized solid. In some embodiments, injectable preparations of the compositions disclosed herein are in the form of a liquid or suspension that is diluted prior to administration.

In some embodiments, the pharmaceutical compositions disclosed herein comprise a bulking agent. Bulking agents can be used, e.g., to improve the appearance of a solid composition, to provide visible "bulk" to demonstrate product quality or to facilitate preparation, e.g., of a solid composition prepared for reconstitution prior to administration. Bulking agents can be used for low dose (high potency) drugs that do not have the necessary bulk to support their own structure or provide a visible composition in a unit dosage form. Bulking agents are used in lyophilized formulations. Bulking agents provide a desirable structure for a lyophilized cake comprising pores that provide the means for vapor to escape from the product during lyophilization cycles, and facilitate dissolution on reconstitution. In some embodiments, the bulking agent is mannitol, lactose, sucrose, dextran, trehalose, povidone, dextran, glycine, isoleucine, methionine, or a cyclodextrin (e.g., (2-hydroxypropyl)-O-cyclodextrin).

In some embodiments, a pharmaceutical composition disclosed herein is in the form of a solid dosage form. Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

Use of Anti-CCR8 Antibodies and Antibody Conjugates

In some aspects, the present disclosure provides methods of diagnosing a subject having a disease or disorder associated with, e.g., CCR8 expression or overexpression.

Antibodies provided in the present disclosure are also suitable for in vitro applications, such as immunoassays.

In some aspects, the present disclosure provides a method of treating a subject having cancer, the method comprising administering to a subject an ADC provided herein. In some embodiments, the subject has a cancer with tumor infiltrating CCR8+ regulatory T cells (Tregs). In some embodiments, the cancer is a solid tumor. In some embodiments, the cancer expresses CCR8. In some embodiments, the cancer is colorectal cancer (including, for example, microsatellite stable colorectal cancer, non-small cell lung cancer, pancreatic cancer, head and neck squamous cell carcinoma, gastric/esophageal cancer, triple negative breast cancer, or renal cell carcinoma. In some embodiments, the cancer is a lymphoma expressing CCR8. In some embodiments, the lymphoma expressing CCR8 is cutaneous T cell lymphoma or Sezary syndrome. In some embodiments, the subject is a human subject. In some embodiments, the subject has an underlying condition that increases the risk of developing cancer. In some embodiments, the ADC is administered intravenously or subcutaneously. In some embodiments, the method further comprising administering an additional therapeutic for treatment of cancer. In some embodiments, the additional therapeutic comprises chemotherapy, radiation therapy, targeted therapy, immunotherapy, hormonal therapy, targeted therapies, hyperthermia, or photodynamic therapy In some aspects, the present provides kits for the ADCs disclosed herein. Such kits can include one or more containers comprising an anti- CCR8 antibody, e.g., any of those described herein or an ADC, e.g., any of those described herein.

In some embodiments, the kit comprises instructions for use in accordance with any of the methods described herein. The included instructions can comprise a description of administration of the ADC to treat, delay the onset, or alleviate a target disease as those described herein (e.g., cancer). The kit may further comprise a description of selecting an individual suitable for treatment based on identifying whether that individual has the target disease. In some embodiments, the instructions comprise a description of administering an ADC to an individual at risk of the target disease.

The instructions relating to the use of an ADC generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder treatable by modulating immune responses, such as cancer. Instructions may be provided for practicing any of the methods described herein.

The kits of the present disclosure are in suitable packaging. Suitable packaging includes, but is not limited to, vials, bottles, jars, flexible packaging (e.g., sealed Mylar or plastic bags), and the like.

Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an ADC as those described herein.

Kits may optionally provide additional components such as buffers and interpretive information. Normally, the kit comprises a container and a label or package insert(s) on or associated with the container. In some embodiments, the present disclosure provides articles of manufacture comprising contents of the kits described above.

TABLE 1

Optimized CCR8 Antibodies

| Identifier* | Antibody Part | Sequence | SEQ ID NO: |
|---|---|---|---|
| A1.1 | VH CDR1 | FTFSSHGMH | 39 |
| | VH CDR2 | VISYDGSNKYYAFSVKG | 2 |
| | VH CDR3 | ARVRRIAGRAGYGMDV | 3 |
| | VL CDR1 | RASQSINSYLN | 4 |
| | VL CDR2 | SASSLQS | 40 |
| | VL CDR3 | QESYSTPIF | 41 |
| | VH | QVQLVESGGGVVQPGRSLRLSCAASGFTFSSHGM HWVRQAPGKGLEWVAVISYDGSNKYYAFSVKGR FTISRDNSKNTLYLQMNSLRVEDTAVYYCARVRRI AGRAGYGMDVWGQGTTVTVSS | 42 |
| | VL | DIQMTQSPSSLSASVGDRVTITCRASQSINSYLNWY QQKPGKAPKLLIYSASSLQSGVPSRFSGSGSGTDFT LTISSLQPEDFATYYCQESYSTPIFFGGGTKVEIK | 43 |
| A1.2 | VH CDR1 | FTFSSHGMH | 39 |
| | VH CDR2 | VISYDGSNKYYAFSVKG | 2 |
| | VH CDR3 | ARVRRIAGRAGYGMDV | 3 |
| | VL CDR1 | RASQSIVSYLN | 44 |
| | VL CDR2 | AASILQS | 45 |
| | VL CDR3 | QESYSTPIT | 6 |
| | VH | QVQLVESGGGVVQPGRSLRLSCAASGFTFSSHGM HWVRQAPGKGLEWVAVISYDGSNKYYAFSVKGR FTISRDNSKNTLYLQMNSLRVEDTAVYYCARVRRI AGRAGYGMDVWGQGTTVTVSS | 42 |
| | VL | DIQMTQSPSSLSASVGDRVTITCRASQSIVSYLNWY QQKPGKAPKLLIYAASILQSGVPSRFSGSGSGTDFT LTISSLQPEDFATYYCQESYSTPITFGGGTKVEIK | 46 |
| A2.1 | VH CDR1 | YSISSGYYWG | 9 |
| | VH CDR2 | SIYHSGNTYYRPSLKS | 10 |
| | VH CDR3 | ARGKGGSWTAFGP | 11 |
| | VL CDR1 | RASQSISSFAN | 47 |
| | VL CDR2 | AASSLQS | 5 |

TABLE 1-continued

Optimized CCR8 Antibodies

| Identifier* | Antibody Part | Sequence | SEQ ID NO: |
|---|---|---|---|
| | VL CDR3 | QQGHSTPPT | 13 |
| | VH | QVQLQESGPGLVKPSETLSLTCAVSGYSISSGYYW GWIRQPPGKGLEWIGSIYHSGNTYYRPSLKSRVTIS VDTSKNQFSLKLSSVTAADTAVYYCARGKGGSWT AFGPWGQGTLVTVSS | 14 |
| | VL | DIQMTQSPSSLSASVGDRVTITCRASQSISSFANWY QQKPGKAPKLLISAASSLQSGVPSRFSGSGSGTDFT LTISSLQPEDFATYYCQQGHSTPPTFGGGTKVEIK | 48 |
| A2.2 | VH CDR1 | YSISSGYYWG | 9 |
| | VH CDR2 | SIYHSGNTYYRPSLKS | 10 |
| | VH CDR3 | ARGKGGSWTAFGP | 11 |
| | VL CDR1 | RASQSISSLLN | 49 |
| | VL CDR2 | AASSLQS | 5 |
| | VL CDR3 | QQGHSTPPT | 13 |
| | VH | QVQLQESGPGLVKPSETLSLTCAVSGYSISSGYYW GWIRQPPGKGLEWIGSIYHSGNTYYRPSLKSRVTIS VDTSKNQFSLKLSSVTAADTAVYYCARGKGGSWT AFGPWGQGTLVTVSS | 14 |
| | VL | DIQMTQSPSSLSASVGDRVTITCRASQSISSLLNWY QQKPGKAPKLLISAASSLQSGVPSRFSGSGSGTDFT LTISSLQPEDFATYYCQQGHSTPPTFGGGTRVEIK | 50 |
| A2.3 | VH CDR1 | YSISSGYYWG | 9 |
| | VH CDR2 | SIYHSGNTYYRPSLKS | 10 |
| | VH CDR3 | ARGKGGSWTAFGP | 11 |
| | VL CDR1 | RASQSISSFLN | 12 |
| | VL CDR2 | AAESLQS | 51 |
| | VL CDR3 | QQGHSTPPT | 13 |
| | VH | QVQLQESGPGLVKPSETLSLTCAVSGYSISSGYYW GWIRQPPGKGLEWIGSIYHSGNTYYRPSLKSRVTIS VDTSKNQFSLKLSSVTAADTAVYYCARGKGGSWT AFGPWGQGTLVTVSS | 14 |
| | VL | DIQMTQSPSSLSASVGDRVTITCRASQSISSFLNWY QQKPGKAPKLLISAAESLQSGVPSRFSGSGSGTDFT LTISSLQPEDFATYYCQQGHSTPPTFGGGTKVEIK | 52 |
| A2.4 | VH CDR1 | YSISSGYYWG | 9 |
| | VH CDR2 | SIYHSGNTYYRPSLKS | 10 |
| | VH CDR3 | ARGKGGSWTAFGP | 11 |
| | VL CDR1 | RASQSPSSFLN | 53 |
| | VL CDR2 | AISSLQS | 54 |
| | VL CDR3 | QQGISTPPT | 55 |
| | VH | QVQLQESGPGLVKPSETLSLTCAVSGYSISSGYYW GWIRQPPGKGLEWIGSIYHSGNTYYRPSLKSRVTIS VDTSKNQFSLKLSSVTAADTAVYYCARGKGGSWT AFGPWGQGTLVTVSS | 14 |
| | VI | DIQMTQSPSSLSASVGDRVTITCRASQSPSSFLNWY QQKPGKAPKLLISAISSLQSGVPSRFSGSGSGTDFTL TISSLQPEDFATYYCQQGISTPPTFGGGTKVEIK | 56 |
| A3.1 | VH CDR1 | GSISSSSYAWS | 57 |
| | VH CDR2 | SIYYTGSTYYNPSLKS | 17 |
| | VH CDR3 | LRGHRRDYIAFDI | 18 |
| | VL CDR1 | RASQSISSYLN | 19 |
| | VL CDR2 | AASSLQS | 5 |
| | VL CDR3 | QQSHNLPT | 20 |
| | VH | QLQLQESGPGLVKPSETLSLTCTVSGGSISSSSYAW SWIRQPPGKRLEWIGSIYYTGSTYYNPSLKSRVTIS VDTSKNQFSLKLSSVTAADTAVYYCLRGHRRDYI AFDIWGQGTMVTVSS | 58 |
| | VL | DIQMTQSPSSLSASVGDRVTITCRASQSISSYLNWY QQKPGKAPKLLIYAASSLQSGVPSRFSGSGSGTDFT LTISSLQPEDFATYYCQQSHNLPTFGGGTKVEIK | 22 |
| A3.2 | VH CDR1 | GSISSSSYAWG | 16 |
| | VH CDR2 | SIYYTGSTYYNPSLKS | 17 |
| | VH CDR3 | LRGHRRDYIAFDI | 18 |
| | VL CDR1 | RASQSISDYLN | 59 |

TABLE 1-continued

Optimized CCR8 Antibodies

| Identifier* | Antibody Part | Sequence | SEQ ID NO: |
|---|---|---|---|
| | VL CDR2 | AASSLQS | 5 |
| | VL CDR3 | QQSHNLPT | 20 |
| | VH | QLQLQESGPGLVKPSETLSLTCTVSGGSISSSSYAWGWIRQPPGKRLEWIGSIYYTGSTYYNPSLKSRVTISVDTSKNQFSLKLSSVTAADTAVYYCLRGHRRDYIAFDIWGQGTMVTVSS | 21 |
| | VL | DIQMTQSPSSLSASVGDRVTITCRASQSISDYLNWYQQKPGKAPKLLIYAASSLQSGVPSRFSGSGSGTDFTLTISSLQPEDFATYYCQQSHNLPTFGGGTKVEIK | 60 |
| A3.3 | VH CDR1 | GSISSSSYAWG | 16 |
| | VH CDR2 | SIYYTGSTYYNPSLKS | 17 |
| | VH CDR3 | LRGHRRDYIAFDI | 18 |
| | VL CDR1 | RASQSISEYLN | 61 |
| | VL CDR2 | AASSLQS | 5 |
| | VL CDR3 | QQSHNLPT | 20 |
| | VH | QLQLQESGPGLVKPSETLSLTCTVSGGSISSSSYAWGWIRQPPGKRLEWIGSIYYTGSTYYNPSLKSRVTISVDTSKNQFSLKLSSVTAADTAVYYCLRGHRRDYIAFDIWGQGTMVTVSS | 21 |
| | VL | DIQMTQSPSSLSASVGDRVTITCRASQSISEYLNWYQQKPGKAPKLLIYAASSLQSGVPSRFSGSGSGTDFTLTISSLQPEDFATYYCQQSHNLPTFGGGTKVEIK | 62 |
| A3.4 | VH CDR1 | GSISSSSYAWG | 16 |
| | VH CDR2 | SIYYTGSTYYNPSLKS | 17 |
| | VH CDR3 | LRGHRRDYIAFDI | 18 |
| | VL CDR1 | RASQSISSYLN | 19 |
| | VL CDR2 | DASSLQS | 63 |
| | VL CDR3 | QQSHNLPT | 20 |
| | VH | QLQLQESGPGLVKPSETLSLTCTVSGGSISSSSYAWGWIRQPPGKRLEWIGSIYYTGSTYYNPSLKSRVTISVDTSKNQFSLKLSSVTAADTAVYYCLRGHRRDYIAFDIWGQGTMVTVSS | 21 |
| | VL | DIQMTQSPSSLSASVGDRVTITCRASQSISSYLNWYQQKPGKAPKLLIYDASSLQSGVPSRFSGSGSGTDFTLTISSLQPEDFATYYCQQSHNLPTFGGGTKVEIK | 64 |
| A3.5 | VH CDR1 | GSISSSSYAWG | 16 |
| | VH CDR2 | SIYYTGSTYYNPSLKS | 17 |
| | VH CDR3 | LRGHRRDYIAFDI | 18 |
| | VL CDR1 | RASQSISSYLN | 19 |
| | VL CDR2 | AASSLDS | 65 |
| | VL CDR3 | QQSHNLPT | 20 |
| | VH | QLQLQESGPGLVKPSETLSLTCTVSGGSISSSSYAWGWIRQPPGKRLEWIGSIYYTGSTYYNPSLKSRVTISVDTSKNQFSLKLSSVTAADTAVYYCLRGHRRDYIAFDIWGQGTMVTVSS | 21 |
| | VL | DIQMTQSPSSLSASVGDRVTITCRASQSISSYLNWYQQKPGKAPKLLIYAASSLDSGVPSRFSGSGSGTDFTLTISSLQPEDFATYYCQQSHNLPTFGGGTKVEIK | 66 |
| A3.6 | VH CDR1 | GSISSSSYAWG | 16 |
| | VH CDR2 | SIYYTGSTYYNPSLKS | 17 |
| | VH CDR3 | LRGHRRDYIAFDI | 18 |
| | VL CDR1 | RASQSISSYLN | 19 |
| | VL CDR2 | AASSLQE | 67 |
| | VL CDR3 | QQSHNLPT | 20 |
| | VH | QLQLQESGPGLVKPSETLSLTCTVSGGSISSSSYAWGWIRQPPGKRLEWIGSIYYTGSTYYNPSLKSRVTISVDTSKNQFSLKLSSVTAADTAVYYCLRGHRRDYIAFDIWGQGTMVTVSS | 21 |
| | VL | DIQMTQSPSSLSASVGDRVTITCRASQSISSYLNWYQQKPGKAPKLLIYAASSLQEGVPSRFSGSGSGTDFTLTISSLQPEDFATYYCQQSHNLPTFGGGTKVEIK | 68 |
| A3.7 | VH CDR1 | GSISSSSYAWG | 16 |
| | VH CDR2 | SIYYTGSTYYNPSLKS | 17 |
| | VH CDR3 | LRGHRRDYIAFDI | 18 |
| | VL CDR1 | RASQSISSYLN | 19 |
| | VL CDR2 | AASSLQS | 5 |
| | VL CDR3 | QQSHNLPS | 69 |
| | VH | QLQLQESGPGLVKPSETLSLTCTVSGGSISSSSYAWGWIRQPPGKRLEWIGSIYYTGSTYYNPSLKSRVTIS | 21 |

TABLE 1-continued

Optimized CCR8 Antibodies

| Identifier* | Antibody Part | Sequence | SEQ ID NO: |
|---|---|---|---|
| | | VDTSKNQFSLKLSSVTAADTAVYYCLRGHRRDYIAFDIWGQGTMVTVSS | |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSHNLPSFGGGTKVEIK | 70 |
| A3.8 | VH CDR1 | GSISSSSNAWG | 71 |
| | VH CDR2 | SIYYTGSTYYNPSLKS | 17 |
| | VH CDR3 | LRGHRRDYIAFDI | 18 |
| | VL CDR1 | RASQSISSYLN | 19 |
| | VL CDR2 | AASSLQS | 5 |
| | VL CDR3 | QQSHNLPT | 20 |
| | VH | QLQLQESGPGLVKPSETLSLTCTVSGGSISSSSNAWGWIRQPPGKRLEWIGSIYYTGSTYYNPSLKSRVTISVDTSKNQFSLKLSSVTAADTAVYYCLRGHRRDYIAFDIWGQGTMVTVSS | 72 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSHNLPTFGGGTKVEIK | 22 |
| A3.9 | VH CDR1 | GSISSSSYAWG | 16 |
| | VH CDR2 | SIYYTGSTYYNPSLKS | 17 |
| | VH CDR3 | LRGHRRDYIAFDI | 18 |
| | VL CDR1 | RASQSILSYLN | 73 |
| | VL CDR2 | AASSLQS | 5 |
| | VL CDR3 | QQSHNLPT | 20 |
| | VH | QLQLQESGPGLVKPSETLSLTCTVSGGSISSSSYAWGWIRQPPGKRLEWIGSIYYTGSTYYNPSLKSRVTISVDTSKNQFSLKLSSVTAADTAVYYCLRGHRRDYIAFDIWGQGTMVTVSS | 21 |
| | VL | DIQMTQSPSSLSASVGDRVTITCRASQSILSYLNWYQQKPGKAPKLLIYAASSLQSGVPSRFSGSGSGTDFTLTISSLQPEDFATYYCQQSHNLPTFGGGTKVEIK | 74 |
| A4.1 | VH CDR1 | GSISQSSYAWG | 75 |
| | VH CDR2 | SIYYTGSTYYNPSLKS | 17 |
| | VH CDR3 | VRGHRRDYIAFDI | 23 |
| | VL CDR1 | RASQSISSYLN | 19 |
| | VL CDR2 | AASSLQS | 5 |
| | VL CDR3 | QQSHNLPT | 20 |
| | VH | QLQLQESGPGLVKPSETLSLTCTVSGGSISQSSYAWGWIRQPPGKRLEWIGSIYYTGSTYYNPSLKSRVTISVDTSKNQFSLKLSSVTAADTAVYYCVRGHRRDYIAFDIWGQGTMVTVSS | 76 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSHNLPTFGGGTKVEIK | 22 |
| A4.2 | VH CDR1 | GSISSSSIAWG | 77 |
| | VH CDR2 | SIYYTGSTYYNPSLKS | 17 |
| | VH CDR3 | VRGHRRDYIAFDI | 23 |
| | VL CDR1 | RASQSISSYLN | 19 |
| | VL CDR2 | AASSLQS | 5 |
| | VL CDR3 | QQSHNLPT | 20 |
| | VH | QLQLQESGPGLVKPSETLSLTCTVSGGSISSSSIAWGWIRQPPGKRLEWIGSIYYTGSTYYNPSLKSRVTISVDTSKNQFSLKLSSVTAADTAVYYCVRGHRRDYIAFDIWAQGTMVTVSS | 78 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSHNLPTFGGGTKVEIK | 22 |

TABLE 1-continued

Optimized CCR8 Antibodies

| Identifier* | Antibody Part | Sequence | SEQ ID NO: |
|---|---|---|---|
| A4.3 | VH CDR 1 | GSISSSSYAWL | 79 |
| | VH CDR2 | SIYYTGSTYYNPSLKS | 17 |
| | VH CDR3 | VRGHRRDYIAFDI | 23 |
| | VL CDR1 | RASQSISSYLN | 19 |
| | VL CDR2 | AASSLQS | 5 |
| | VL CDR3 | QQSHNLPT | 20 |
| | VH | QLQLQESGPGLVKPSETLSLTCTVSGGSISSSSYAW LWIRQPPGKRLEWIGSIYYTGSTYYNPSLKSRVTIS VDTSKNQFSLKLSSVTAADTAVYYCVRGHRRDYI AFDIWGQGTMVTVSS | 80 |
| | VL | DIQMTQSPSSLSASVGDRVTITCRASQSISSYLNWY QQKPGKAPKLLIYAASSLQSGVPSRFSGSGSGTDFT LTISSLQPEDFATYYCQQSHNLPTFGGGTKVEIK | 22 |
| A4.4 | VH CDR1 | GSISSSSYAWG | 16 |
| | VH CDR2 | SIYYTGSTYYNPSLKS | 17 |
| | VH CDR3 | VRGHRRDYIAFDI | 23 |
| | VL CDR1 | RADQSISSYLN | 81 |
| | VL CDR2 | AASSLQS | 5 |
| | VL CDR3 | QQSHNLPT | 20 |
| | VH | QLQLQESGPGLVKPSETLSLTCTVSGGSISSSSYAW GWIRQPPGKRLEWIGSIYYTGSTYYNPSLKSRVTIS VDTSKNQFSLKLSSVTAADTAVYYCVRGHRRDYI AFDIWGQGTMVTVSS | 24 |
| | VL | DIQMTQSPSSLSASVGDRVTITCRADQSISSYLNWY QQKPGKAPKLLIYAASSLQSGVPSRFSGSGSGTDFT LTISSLQPEDFATYYCQQSHNLPTFGGGTKVEIK | 82 |
| A4.5 | VH CDR1 | GSISSSSYAWG | 16 |
| | VH CDR2 | SIYYTGSTYYNPSLKS | 17 |
| | VH CDR3 | VRGHRRDYIAFDI | 23 |
| | VL CDR1 | RASQSISSLLN | 49 |
| | VL CDR2 | AASSLQS | 5 |
| | VL CDR3 | QQSHNLPT | 20 |
| | VH | QLQLQESGPGLVKPSETLSLTCTVSGGSISSSSYAW GWIRQPPGKRLEWIGSIYYTGSTYYNPSLKSRVTIS VDTSKNQFSLKLSSVTAADTAVYYCVRGHRRDYI AFDIWGQGTMVTVSS | 24 |
| | VL | DIQMTQSPSSLSASVGDRVTITCRASQSISSLLNWY QQKPGKAPKLLIYAASSLQSGVPSRFSGSGSGTDFT LTISSLQPEDFATYYCQQSHNLPTFGGGTKVEIK | 83 |
| A4.6 | VH CDR1 | GSISSSSYAWG | 16 |
| | VH CDR2 | SIYYTGSTYYNPSLKS | 17 |
| | VH CDR3 | VRGHRRDYIAFDI | 23 |
| | VL CDR1 | RASQSISSYLN | 19 |
| | VL CDR2 | AASSLFS | 84 |
| | VL CDR3 | QQSHNLPT | 20 |
| | VH | QLQLQESGPGLVKPSETLSLTCTVSGGSISSSSYAW GWIRQPPGKRLEWIGSIYYTGSTYYNPSLKSRVTIS VDTSKNQFSLKLSSVTAADTAVYYCVRGHRRDYI AFDIWGQGTMVTVSS | 24 |
| | VL | DIQMTQSPSSLSASVGDRVTITCRASQSISSYLNWY QQKPGKAPKLLIYAASSLFSGVPSRFSGSGSGTDFT LTISSLQPEDFATYYCQQSHNLPTFGGGTKVEIK | 85 |
| A4.7 | VH CDR1 | GSISSSSYAWG | 16 |
| | VH CDR2 | SIYYTGSTYYNPSLKS | 17 |
| | VH CDR3 | VRGHRRDYIAFDI | 23 |
| | VL CDR1 | RASQSISSYLN | 19 |
| | VL CDR2 | AASSLYS | 86 |
| | VL CDR3 | QQSHNLPT | 20 |
| | VH | QLQLQESGPGLVKPSETLSLTCTVSGGSISSSSYAW GWIRQPPGKRLEWIGSIYYTGSTYYNPSLKSRVTIS VDTSKNQFSLKLSSVTAADTAVYYCVRGHRRDYI AFDIWGQGTMVTVSS | 24 |
| | VL | DIQMTQSPSSLSASVGDRVTITCRASQSISSYLNWY QQKPGKAPKLLIYAASSLYSGVPSRFSGSGSGTDFT LTISSLQPEDFATYYCQQSHNLPTFGGGTKVEIK | 87 |
| A5.1 | VH CDR1 | FQFNAYAMN | 88 |
| | VH CDR2 | RIRSKSNNYATYYADSVKP | 89 |
| | VH CDR3 | VRQSYGNSNYAMDH | 90 |
| | VL CDR1 | RSSKRLLHSNGNTYLY | 91 |

TABLE 1-continued

Optimized CCR8 Antibodies

| Identifier* | Antibody Part | Sequence | SEQ ID NO: |
|---|---|---|---|
| | VL CDR2 | RVSNLAS | 92 |
| | VL CDR3 | MQHLEYPFT | 30 |
| | VH | EVQLVESGGGLVQPGGSLRLSCAASGFQFNAYAMNWVRQAPGKGLEWVARIRSKSNNYATYYADSVKPRFTISRDDSKNSLYLQMNSLKTEDTAVYYCVRQSYGNSNYAMDHWGQGTTVTVSS | 93 |
| | VL | DIVMTQSPLSLPVTPGEPASISCRSSKRLLHSNGNTYLYWYLQKPGQSPQLLIYRVSNLASGVPDRESGSGSGTDFTLKISRVEAEDVGVYYCMQHLEYPFTFGGGTKVEIK | 94 |
| A5.2 | VH CDR1 | FQFNAYAMN | 88 |
| | VH CDR2 | RIRSKSNNYATYYADSVKP | 89 |
| | VH CDR3 | VRQSYGNSNYAMDH | 90 |
| | VL CDR1 | RSSKRLLHSNGNTYLY | 91 |
| | VL CDR2 | KMSNLAS | 95 |
| | VL CDR3 | MQHFEYPFT | 96 |
| | VH | EVQLVESGGGLVQPGGSLRLSCAASGFQFNAYAMNWVRQAPGKGLEWVARIRSKSNNYATYYADSVKPRFTISRDDSKNSLYLQMNSLKTEDTAVYYCVRQSYGNSNYAMDHWGQGTTVTVSS | 93 |
| | VL | DIVMTQSPLSLPVTPGEPASISCRSSKRLLHSNGNTYLYWYLQKPGQSPQLLIYKMSNLASGVPDRESGSGSGTDFTLKISRVEAEDVGVYYCMQHFEYPFTFGGGTKVEIK | 97 |
| A5.3 | VH CDR1 | FQFNAYAMN | 88 |
| | VH CDR2 | RIRSKSNNYATYYADSVKD | 26 |
| | VH CDR3 | VRQSYGNSNYAMDY | 27 |
| | VL CDR1 | RSSKRLLHSNGNTYLY | 91 |
| | VL CDR2 | KMSNLAS | 95 |
| | VL CDR3 | MQHFEYPFT | 96 |
| | VH | EVQLVESGGGLVQPGGSLRLSCAASGFQFNAYAMNWVRQAPGKGLEWVARIRSKSNNYATYYADSVKDRFTISRDDSKNSLYLQMNSLKTEDTAVYYCVRQSYGNSNYAMDYWGQGTTVTVSS | 98 |
| | VL | DIVMTQSPLSLPVTPGEPASISCRSSKRLLHSNGNTYLYWYLQKPGQSPQLLIYKMSNLASGVPDRFSGSGSGTDFTLKISRVEAEDVGVYYCMQHFEYPFTFGGGTKVEIK | 97 |
| A5.4 | VH CDR1 | FQFNAYAMN | 88 |
| | VH CDR2 | RIRSKSNNYATYYADSVKD | 26 |
| | VH CDR3 | VRQSYGNSNYAMDH | 90 |
| | VL CDR1 | RSSKSLLHSNGNTYLY | 28 |
| | VL CDR2 | RVSNLAS | 92 |
| | VL CDR3 | MQHFEYPFT | 96 |
| | VH | EVQLVESGGGLVQPGGSLRLSCAASGFQFNAYAMNWVRQAPGKGLEWVARIRSKSNNYATYYADSVKDRFTISRDDSKNSLYLQMNSLKTEDTAVYYCVRQSYGNSNYAMDHWGQGTTVTVSS | 99 |
| | VL | DIVMTQSPLSLPVTPGEPASISCRSSKSLLHSNGNTYLYWYLQKPGQSPQLLIYRVSNLASGVPDRESGSGSGTDFTLKISRVEAEDVGVYYCMQHFEYPFTFGGGTKVEIK | 100 |
| A5.5 | VH CDR1 | FQFNAYAMN | 88 |
| | VH CDR2 | RIRSKSNNYATYYADSVKP | 89 |
| | VH CDR3 | VRQSYGNSNYAMDH | 90 |
| | VL CDR1 | RSSKSLLHSNGNTYLY | 28 |
| | VL CDR2 | KMSNLAS | 95 |
| | VL CDR3 | MQHFEYPFT | 96 |
| | VH | EVQLVESGGGLVQPGGSLRLSCAASGFQFNAYAMNWVRQAPGKGLEWVARIRSKSNNYATYYADSVKPRFTISRDDSKNSLYLQMNSLKTEDTAVYYCVRQSYGNSNYAMDHWGQGTTVTVSS | 93 |
| | VL | DIVMTQSPLSLPVTPGEPASISCRSSKSLLHSNGNTYLYWYLQKPGQSPQLLIYKMSNLASGVPDRESGSGSGTDFTLKISRVEAEDVGVYYCMQHFEYPFTFGGGTKVEIK | 101 |
| A5.6 | VH CDR1 | FQFNAYAMN | 88 |
| | VH CDR2 | RIRSKSNNYATYYADSVKP | 89 |
| | VH CDR3 | VRQSYGNSNYAMDH | 90 |

TABLE 1-continued

| Optimized CCR8 Antibodies | | | |
|---|---|---|---|
| Identifier* | Antibody Part | Sequence | SEQ ID NO: |
| | VL CDR1 | RSSKSLQHSNGNTYLY | 102 |
| | VL CDR2 | RVSNLAS | 92 |
| | VL CDR3 | MQHFEYPFT | 96 |
| | VH | EVQLVESGGGLVQPGGSLRLSCAASGFQFNAYAM NWVRQAPGKGLEWVARIRSKSNNYATYYADSVK PRFTISRDDSKNSLYLQMNSLKTEDTAVYYCVRQS YGNSNYAMDHWGQGTTVTVSS | 93 |
| | VL | DIVMTQSPLSLPVTPGEPASISCRSSKSLQHSNGNT YLYWYLQKPGQSPQLLIYRVSNLASGVPDRESGSG SGTDFTLKISRVEAEDVGVYYCMQHFEYPFTFGGG TKVEIK | 103 |
| A6.1 | VH CDR1 | FQFNAYAMN | 88 |
| | VH CDR2 | RIRSKSNNYATYYAGSVKD | 104 |
| | VH CDR3 | VRQSYGNSNYAMDY | 27 |
| | VL CDR1 | RSSKSLLHSNGNTYLY | 28 |
| | VL CDR2 | KKSNLAS | 105 |
| | VL CDR3 | MQHFEYPFT | 96 |
| | VH | EVQLVESGGGLVQPGGSLRLSCAASGFQFNAYAM NWVRQAPGKGLEWVARIRSKSNNYATYYAGSVK DRFTISRDDSKNSLYLQMNSLKTEDTAVYYCVRQS YGNSNYAMDYWGQGTTVTVSS | 106 |
| | VL | DIVMTQSPLSLPVTPGEPASISCRSSKSLLHSNGNT YLYWYLQKPGQSPQLLIYKKSNLASGVPDRFSGSG SGTDFTLKISRVEAEDVGVYYCMQHFEYPFTFGGG TKVEIK | 107 |
| A6.2 | VH CDR1 | FQFNAYAMN | 88 |
| | VH CDR2 | RIRSKSNNYATYYAGSVKD | 104 |
| | VH CDR3 | VRQSYGNSNYAMDY | 27 |
| | VL CDR1 | RSSKRLLHSNGNTYLY | 91 |
| | VL CDR2 | RVSNLAS | 92 |
| | VL CDR3 | MQHLEYPFT | 30 |
| | VH | EVQLVESGGGLVQPGGSLRLSCAASGFQFNAYAM NWVRQAPGKGLEWVARIRSKSNNYATYYAGSVK DRFTISRDDSKNSLYLQMNSLKTEDTAVYYCVRQS YGNSNYAMDYWGQGTTVTVSS | 106 |
| | VL | DIVMTQSPLSLPVTPGEPASISCRSSKRLLHSNGNT YLYWYLQKPGQSPQLLIYRVSNLASGVPDRESGSG SGTDFTLKISRVEAEDVGVYYCMQHLEYPFTFGGG TKVEIK | 94 |
| A6.3 | VH CDR1 | FQFNAYAMN | 88 |
| | VH CDR2 | RIRSKSNNYATYYAGSVKD | 104 |
| | VH CDR3 | VRQSYGNSNYAMDY | 27 |
| | VL CDR1 | RSSKSLQHSNGNTYLY | 102 |
| | VL CDR2 | RVSNLAS | 92 |
| | VL CDR3 | MQHLEYPFT | 30 |
| | VH | EVQLVESGGGLVQPGGSLRLSCAASGFQFNAYAM NWVRQAPGKGLEWVARIRSKSNNYATYYAGSVK DRFTISRDDSKNSLYLQMNSLKTEDTAVYYCVRQS YGNSNYAMDYWGQGTTVTVSS | 106 |
| | VL | DIVMTQSPLSLPVTPGEPASISCRSSKSLQHSNGNT YLYWYLQKPGQSPQLLIYRVSNLASGVPDRFSGSG SGTDFTLKISRVEAEDVGVYYCMQHLEYPFTFGGG TKVEIK | 108 |
| A6.4 | VH CDR1 | FSFNAYAMN | 109 |
| | VH CDR2 | RIRSKSNNYATYYAGSVKD | 104 |
| | VH CDR3 | VRQSYGNSNYAMDY | 27 |
| | VL CDR1 | RTSKSLLHSNGNTYLY | 110 |
| | VL CDR2 | RVSNLAS | 92 |
| | VL CDR3 | MQHFEYPFT | 96 |
| | VH | EVQLVESGGGLVQPGGSLRLSCAASGFSFNAYAM NWVRQAPGKGLEWVARIRSKSNNYATYYAGSVK DRFTISRDDSKNSLYLQMNSLKTEDTAVYYCVRQS YGNSNYAMDYWGQGTTVTVSS | 111 |
| | VL | DIVMTQSPLSLPVTPGEPASISCRTSKSLLHSNGNT YLYWYLQKPGQSPQLLIYRVSNLASGVPDRESGSG SGTDFTLKISRVEAEDVGVYYCMQHFEYPFTFGGG TKVEIK | 112 |
| A6.5 | VH CDR1 | FTFNAYAMN | 25 |
| | VH CDR2 | RIRSKSNNYATYYAASVKP | 113 |

TABLE 1-continued

Optimized CCR8 Antibodies

| Identifier* | Antibody Part | Sequence | SEQ ID NO: |
|---|---|---|---|
| | VH CDR3 | VRQSYGNSNYAMDH | 90 |
| | VL CDR1 | RSSKRLLHSNGNTYLY | 91 |
| | VL CDR2 | RVSNLAS | 92 |
| | VL CDR3 | MQHLEYPFT | 30 |
| | VH | EVQLVESGGGLVQPGGSLRLSCAASGFTFNAYAM NWVRQAPGKGLEWVARIRSKSNNYATYYAASVK PRFTISRDDSKNSLYLQMNSLKTEDTAVYYCVRQS YGNSNYAMDHWGQGTTVTVSS | 114 |
| | VL | DIVMTQSPLSLPVTPGEPASISCRSSKRLLHSNGNT YLYWYLQKPGQSPQLLIYRVSNLASGVPDRESGSG SGTDFTLKISRVEAEDVGVYYCMQHLEYPFTFGGG TKVEIK | 94 |

*A1.1-A6.5 include affinity matured progenies of certain antibodies disclosed in WO2012178749

TABLE 2

Non-limiting examples of full length IgG antibodies

| Antibody | Sequence |
|---|---|
| A5.4 with WT IgG1 heavy chain constant region | Heavy Chain (VH underlined)<br>EVQLVESGGGLVQPGGSLRLSCAASGFQFNAYAMNWVRQAPGK<br>GLEWVARIRSKSNNYATYYADSVKDRFTISRDDSKNSLYLQMNSL<br>KTEDTAVYYCVRQSYGNSNYAMDHWGQGTTVTVSSASTKGPSV<br>FPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVYTL<br>PPSRDELTKNQVSLTCLVKGFYPSDIA VEWESNGQPENNYKTTPP<br>VLDSDGSFFLYSKLTVDKSRWQQGNVFSCSVMHEALHNHYTQKS<br>LSLSPG (SEQ ID NO: 141)<br>Light Chain (VL underlined)<br>DIVMTQSPLSLPVTPGEPASISCRSSKSLLHSNGNTYLYWYLQKPG<br>QSPQLLIYRVSNLASGVPDRESGSGSGTDFTLKISRVEAEDVGVYY<br>CMQHFEYPFTFGGGTKVEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGEC (SEQ ID<br>NO: 142) |
| A5.6 with WT IgG1 heavy chain constant region | Heavy Chain (VH underlined)<br>EVQLVESGGGLVQPGGSLRLSCAASGFQFNAYAMNWVRQAPGK<br>GLEWVARIRSKSNNYATYYADSVKPRFTISRDDSKNSLYLQMNSL<br>KTEDTAVYYCVRQSYGNSNYAMDHWGQGTTVTVSSASTKGPSV<br>FPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVYTL<br>PPSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPG (SEQ ID NO: 143)<br>Light Chain (VL underlined)<br>DIVMTQSPLSLPVTPGEPASISCRSSKSLQHSNGNTYLYWYLQKPG<br>QSPQLLIYRVSNLASGVPDRESGSGSGTDFTLKISRVEAEDVGVYY<br>CMQHFEYPFTFGGGTKVEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGEC (SEQ ID<br>NO: 144) |

TABLE 2-continued

Non-limiting examples of full length IgG antibodies

| Antibody | Sequence |
|---|---|
| A5.4 with IgG1 heavy chain constant region containing mutations L235A/G237A/ D265C (EU numbering) | Heavy Chain (VH underlined)<br>EVQLVESGGGLVQPGGSLRLSCAASGFQFNAYAMNWVRQAPGK<br>GLEWVARIRSKSNNYATYYADSVKDRFTISRDDSKNSLYLQMNSL<br>KTEDTAVYYCVRQSYGNSNYAMDHWGQGTTVTVSSASTKGPSV<br>FPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEP<br>KSCDKTHTCPPCPAPELAGAPSVFLFPPKPKDTLMISRTPEVTCVV<br>VCVSHEDPEVKFNWYVDGVEVHNAKTKPREEQYNSTYRVVSVL<br>TVLHQDWLNGKEYKCKVSNKALPAPIEKTISKAKGQPREPQVYTL<br>PPSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPG (SEQ ID NO: 145)<br><br>Light Chain (VL underlined)<br>DIVMTQSPLSLPVTPGEPASISCRSSKSLLHSNGNTYLYWYLQKPG<br>QSPQLLIYRVSNLASGVPDRFSGSGSGTDFTLKISRVEAEDVGVYY<br>CMQHFEYPFTFGGGTKVEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGEC (SEQ ID NO: 146) |
| A5.6 with IgG1 heavy chain constant region containing mutations L235A/G237A/ D265C (EU numbering) | Heavy Chain (VH underlined)<br>EVQLVESGGGLVQPGGSLRLSCAASGFQFNAYAMNWVRQAPGK<br>GLEWVARIRSKSNNYATYYADSVKPRFTISRDDSKNSLYLQMNSL<br>KTEDTAVYYCVRQSYGNSNYAMDHWGQGTTVTVSSASTKGPSV<br>FPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEP<br>KSCDKTHTCPPCPAPELAGAPSVFLFPPKPKDTLMISRTPEVTCVV<br>VCVSHEDPEVKFNWYVDGVEVHNAKTKPREEQYNSTYRVVSVL<br>TVLHQDWLNGKEYKCKVSNKALPAPIEKTISKAKGQPREPQVYTL<br>PPSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPG (SEQ ID NO: 147)<br>Light Chain (VL underlined)<br>DIVMTQSPLSLPVTPGEPASISCRSSKSLQHSNGNTYLYWYLQKPG<br>QSPQLLIYRVSNLASGVPDRESGSGSGTDFTLKISRVEAEDVGVYY<br>CMQHFEYPFTFGGGTKVEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGEC (SEQ ID NO: 148) |

EXAMPLES

It should be understood that the following Examples, while indicating preferred embodiments of the present disclosure, are given by way of illustration only. The present disclosure is not limited to the material, proportions, conditions and procedures set forth in the Examples. From the above discussion and these Examples, one skilled in the art can ascertain the essential characteristics of the subject technology, and without departing from the spirit and scope thereof, can make various changes and modifications of the subject technology to adapt it to various uses and conditions.

Example 1: Generation of Optimized CCR8 Antibodies

Antibodies that bind CCR8 were developed by generating library diversity around a single parental antibody and performing selections to enrich improved progeny antibodies. The objective was to produce improved affinity progeny antibodies that bind to human CCR8, have reduced off-target binding (e.g., do not bind to other chemokine receptors such as CCR5), are preferably cross-reactive with cynomolgus (*Macaca fascicularis*) CCR8, have decreased poly-specific reagent (PSR) score, and/or are able to internalize upon binding to CCR8.

Libraries containing CDR diversity based around a single parental antibody were first subjected to saturated mutagenesis and screening to identify positions that mitigate or improve binding to CCR8 while mitigating CCR5 and EV cross-reactivity, with a subsequent step that combined selected heavy and light chains followed by screening and sequencing. The resulting antibodies were produced for primary characterization in an IgG format. Secondary characterization was then performed on selected antibodies, by producing them in a Fab format. To characterize the affinity matured antibodies, CHO cells that overexpressed either CCR8 or CCR5 (or CHO cells expressing an empty vector) were used (FIGS. 1A-1D). Many progeny had increased affinity for CCR8 (FIG. 1A and FIG. 1D), and lower affinity for CCR5 (FIG. 1B) without substantial off target binding to CHO cells transfected with an empty vector (EV).

Figure 2A:
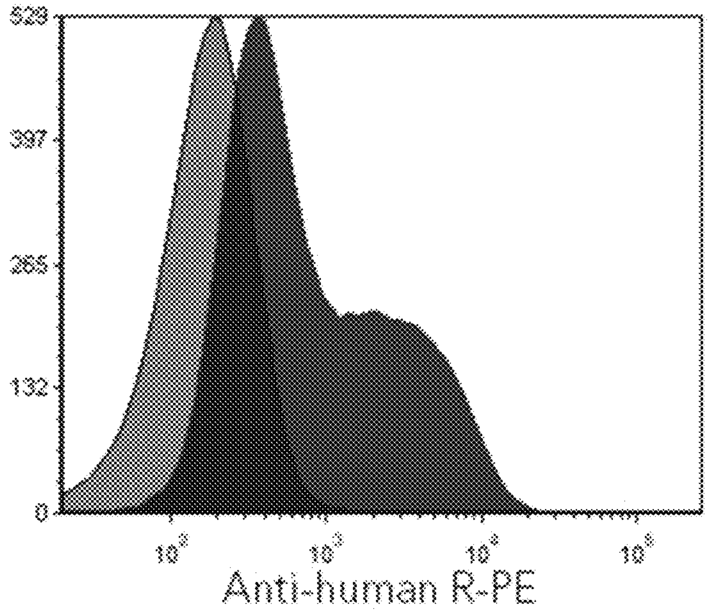
FIGS. 2A-2G show image overlays of CCR5 binding.
Figure 2B:
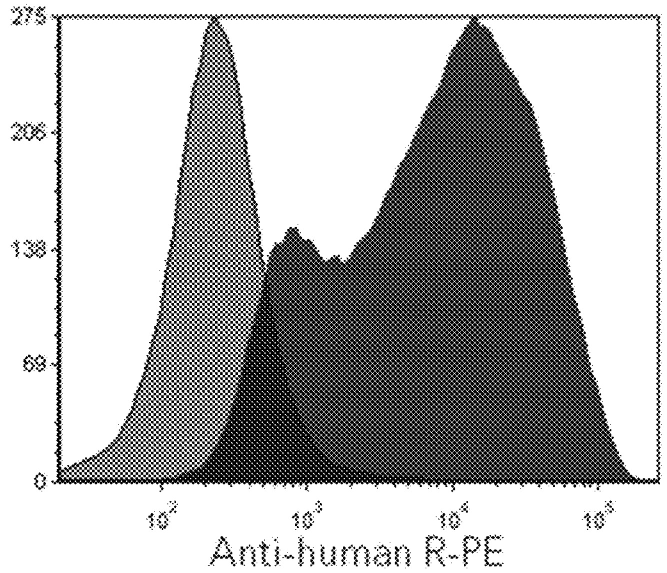
Figure 2C:
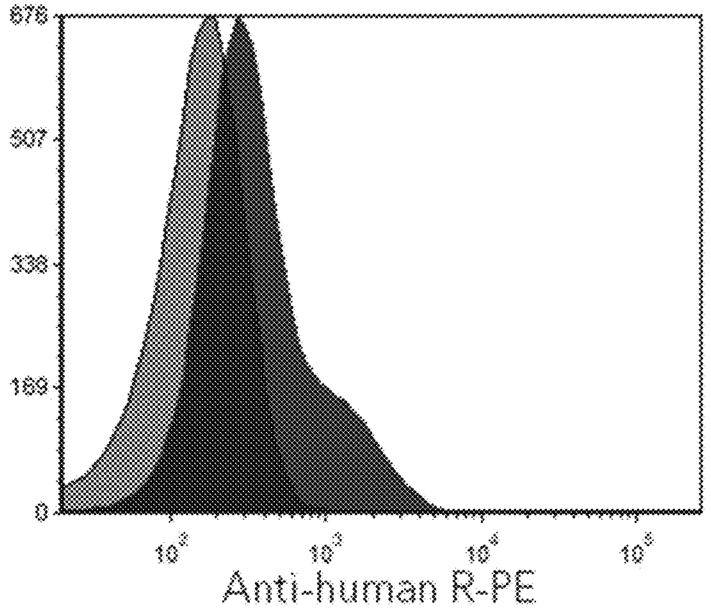
Figure 2D:
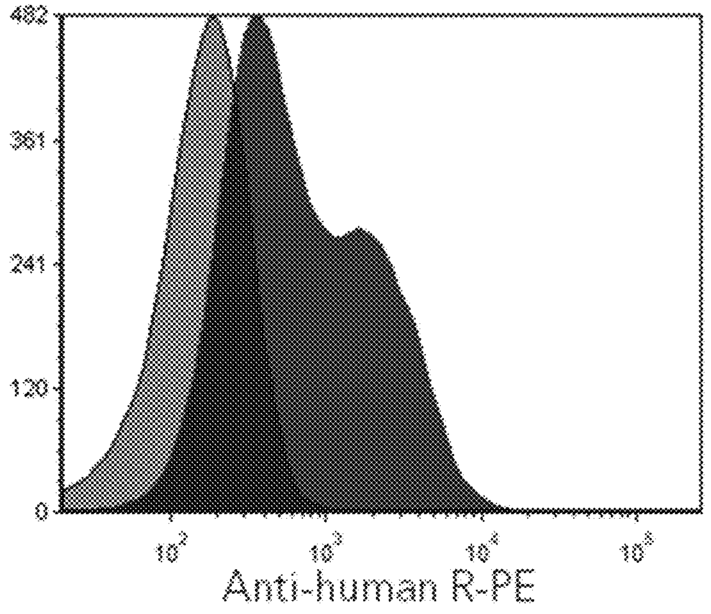
Figure 2E:
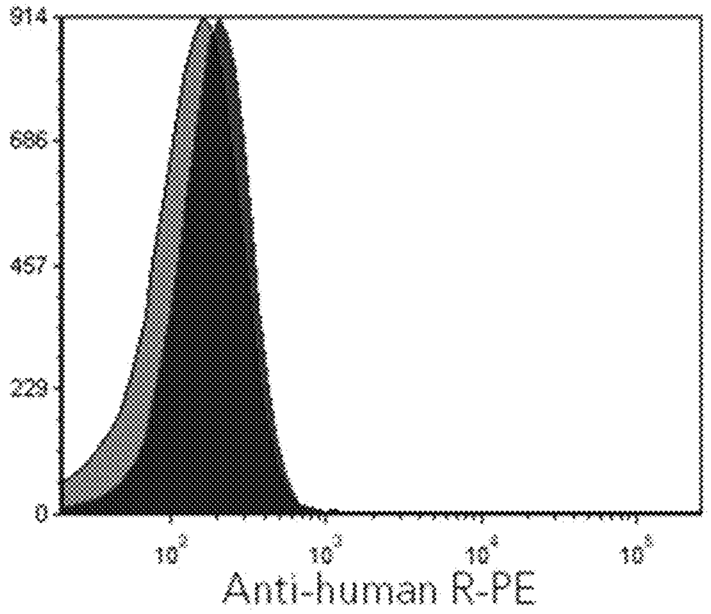
Figure 2F:
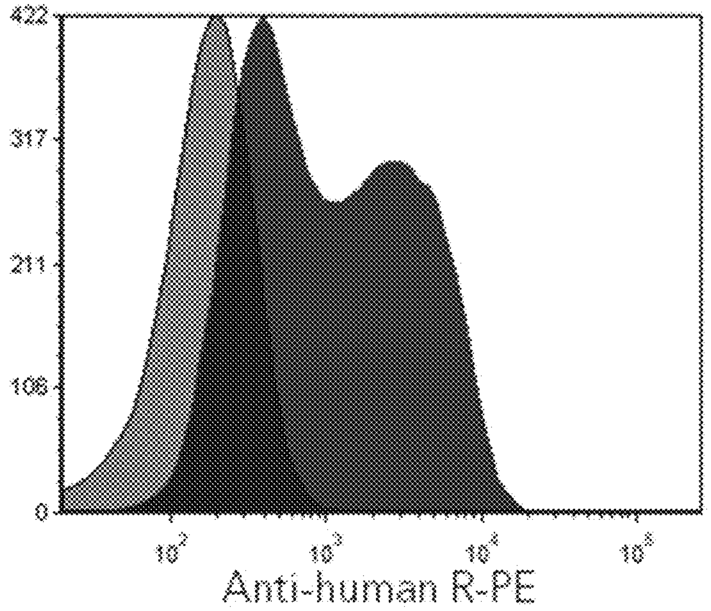
Figure 2G:
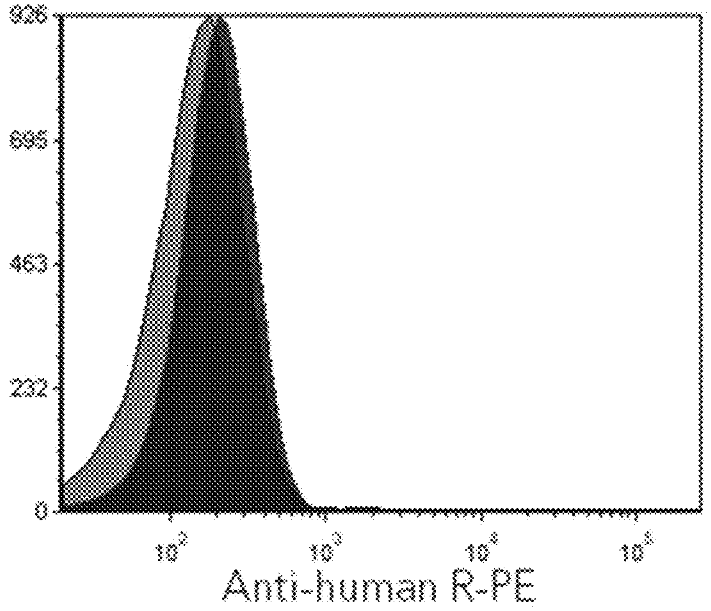

Further characterization results using CHO cells overexpressing CCR8 or CCR5 are shown in FIG. 2A-2G, Table 3 and Table 4. FIG. 2A shows off target binding to CCR5 of the Parent 5 antibody represented by shift of the curve to the right (indicating binding), whereas in FIG. 2E and FIG. 2G, A5.4 and A5.6 progeny antibodies, respectively, show lower off-target binding of CCR5, represented by minimal shift of the curve into the binding area, therefore more overlap between the background and the tested antibody. All IgG1 antibodies were produced in yeast and purified by protein A capture. Flow-cytometry experiments were performed at a concentration of 100 nM, using a secondary anti-human IgG PE conjugate diluted 1/100. A Fab format for the anti-CCR8 antibodies were used to determine the apparent binding affinity to CCR8. To determine the EC50 of CCR8 binding, a cell binding titration assay was performed using CHO cells that overexpress CCR8 (Table 5), starting from the highest concentration of 100 nM. EC50 values were calculated using Graph-Pad Prism software. Fab molecules were produced by Papain digestion of IgG1 and subsequent removal of the Fc fragment. Binding was detected by using a secondary anti-human IgG, F(ab')2 specific—AlexaFluor 647 conjugated, diluted 1/500.

To assess the off-target binding of the affinity matured anti-CCR8 antibodies (in IgG format) to biomolecules, assays were performed to determine a Poly-Specificity Reagent (PSR) Score. Polyspecificity reagents include a mixture of biomolecules typically associated with cells, as described in Yingda Xu et al. Protein Engineering, Design & Selection vol. 26 no. 10 pp. 663-670, 2013. PSR scores for the tested anti-CCR8 antibodies determined by normalizing values against a set of control IgGs. The PSR score ranges from 0-1, with a higher score indicating more off target binding to biomolecules (Clean PSR: <0.10; Low PSR: ≥0.10 and <0.33; Medium PSR: ≥0.33 and <0.66; High PSR: ≥0.66 and ≤1.00). Many of the affinity matured progeny antibodies showed an improvement in PSR scores compared to the parent antibodies (Table 5). Together, these results identified antibodies with improved CCR8 affinity, and decreased off-target (e.g., CCR5 and PSR) binding.

Figure 3:
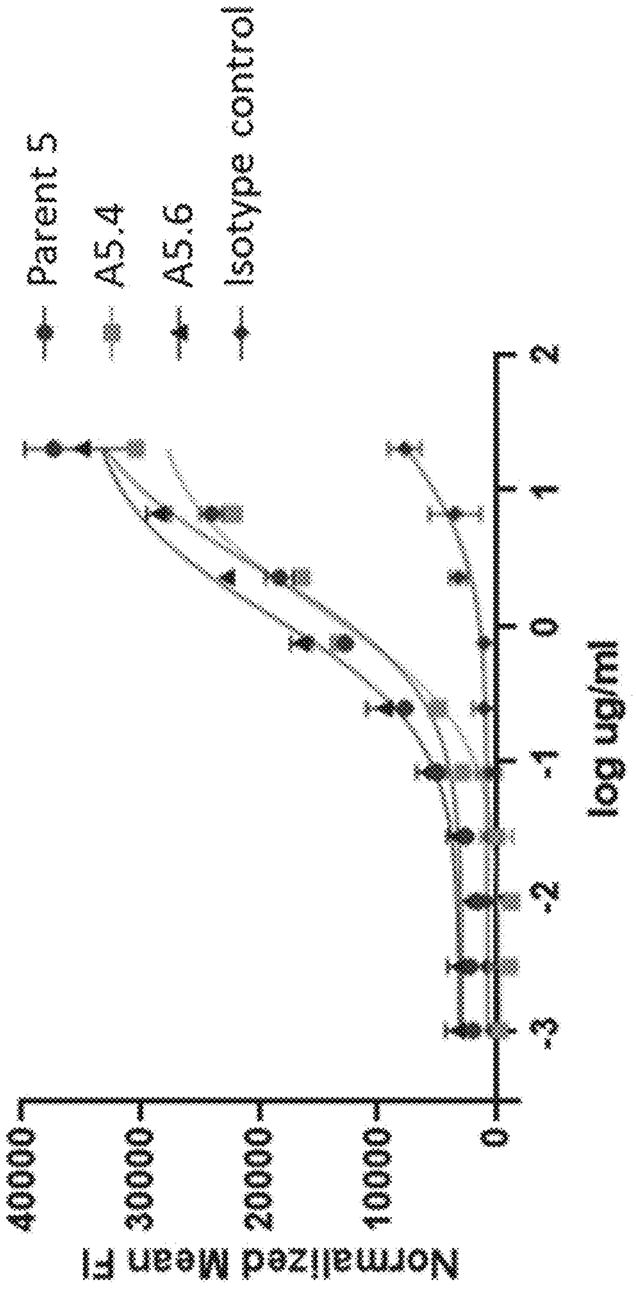
FIG. 3 shows the internalization of three anti-CCR8 antibodies, one parent and two progeny.

To determine anti-CCR8 antibody internalization, a pH sensitive dye-based internalization assay was used. CHO cells expressing human CCR8 were plated in a 384-well clear V-bottom plate (Greiner 781280) at 30,000 cells per well in cell culture media (Freestyle CHO, ThermoFisher 12651-014; 8 mM L-glutamine, Gibco 25030-081; and 5 ug/ml Puromycin, Gibco A11138-03). Antibodies to be tested were mixed with the pH-sensitive fluorescent dye (Zenon pHrodo iFL human IgG labeling Reagent Invitrogen Z25611) at 1:3 molarity ratio (antibody:dye) and incubated at room temperature for 15 minutes. The antibody-dye mixture was then serially diluted in cell culture media, and transferred to cells. The cells were incubated at 37° C. incubator with 5% $CO_2$ and 80% humidity for 6 hours. At the end of the incubation, the assay plate was centrifuged to allow cell pellets to form. The supernatants were removed, and cell pellets were resuspended in cold FACS buffer (PBS, 2% FBS). The assay plate was set on the iQue Flow Cytometer (Sartorius, Göttingen, Germany), and mean fluorescence intensity at 505 nm for excitation and 530 nm for emission was measured. The affinity matured progeny A5.4 and A5.6 showed increased internalization compared to the parent antibody Parent 5 (FIG. 3 and Table 6).

To identify species cross-reactivity, anti-CCR8 antibodies were tested for binding in CHO cells expressing human CCR8, cyno CCR8, murine CCR8, and an empty vector, respectively. Cells were plated in 384-well clear V-bottom plate (Greiner 781280) at 30,000 cells per well in FACS buffer. Antibodies were diluted to 2 working concentrations in FACS buffer to achieve final of 100 nM and 10 nM in-well concentrations. The antibodies were then transferred to cells in the assay plate. The plate was incubated at 4° C. for 1 hour. Following 3 wash cycles in FACS buffer to remove un-bound antibodies, a fluorescent labeled secondary antibody (Goat-anti-human Fc gamma IgG-AF647, Jackson ImmunoResearch Labs 109-605-098) was added to the cells followed by incubation at 4° C. for 30 minutes. After another 3 cycles of washes to remove excess secondary antibody, the cells were resuspended in FACS buffer and set on the iQue Flow Cytometer (Sartorius, Göttingen, Germany). Mean fluorescence intensity was measured at 650 nm for excitation and 668 nm for emission. (Table 7). Higher fluorescence intensity correlates to higher binding affinity.

TABLE 3

CCR5 Cell Binding (IgG)

| Identifier* | Human CCR5 CHO-S Fold Over Background (FOB) |
|---|---|
| Parent 1 | 23 |
| A1.1 | 43 |
| A1.2 | 39 |
| Parent 2 | 2 |
| A2.1 | 2 |
| A2.2 | 3 |
| A2.3 | 2 |
| A2.4 | 4 |
| Parent 3 | 21 |
| A3.1 | 2 |
| A3.2 | 6 |
| A3.3 | 12 |
| A3.4 | 2 |
| A3.5 | 14 |
| A3.6 | 13 |
| A3.7 | 9 |
| A3.8 | 35 |
| A3.9 | 48 |
| Parent 4 | 16 |
| A4.1 | 5 |
| A4.2 | 3 |
| A4.3 | 3 |
| A4.4 | 4 |
| A4.5 | 3 |
| A4.6 | 41 |
| A4.7 | 42 |
| Parent 5 | 4 |
| A5.1 | 40 |
| A5.2 | 2 |
| A5.3 | 4 |
| A5.4 | 2 |
| A5.5 | 6 |
| A5.6 | 2 |
| Parent 6 | 2 |
| A6.1 | 2 |
| A6.2 | 2 |
| A6.3 | 1 |
| A6.4 | 1 |
| A6.5 | 2 |
| Control | 1 |

*Antibody identifiers correspond to the identifiers in Table 1

TABLE 4

CCR8 Cell Binding (Fab)

| | Cell Binding Titration Equilibrium EC50 (M) Human CCR8 CHO cells incubated with Fab |
|---|---|
| Parent 1 | 2.0E−08 |
| A1.1 | 7.8E−09 |
| A1.2 | 8.1E−09 |
| Parent 2 | 2.5E−08 |
| A2.1 | 3.8E−08 |
| A2.2 | 6.2E−08 |
| A2.3 | 4.3E−08 |
| A2.4 | 3.0E−09 |
| Parent 3 | 6.5E−09 |
| A3.1 | 1.8E−08 |
| A3.2 | 2.1E−08 |
| A3.3 | 8.0E−09 |
| A3.4 | 3.8E−08 |
| A3.5 | 9.2E−09 |

TABLE 4-continued

| CCR8 Cell Binding (Fab) | Cell Binding Titration Equilibrium EC50 (M) Human CCR8 CHO cells incubated with Fab |
|---|---|
| A3.6 | 9.8E−09 |
| A3.7 | 2.9E−08 |
| A3.8 | 1.3E−09 |
| A3.9 | 2.0E−09 |
| Parent 4 | 7.4E−09 |
| A4.1 | 1.6E−08 |
| A4.2 | 1.2E−08 |
| A4.3 | 2.1E−08 |
| A4.4 | 2.5E−08 |
| A4.5 | 2.3E−08 |
| A4.6 | 5.0E−09 |
| A4.7 | 5.0E−09 |
| Parent 5 | 1.0E−09 |
| A5.1 | 4.9E−10 |
| A5.2 | 5.2E−10 |
| A5.3 | 4.8E−10 |
| A5.4 | 6.9E−10 |
| A5.5 | 4.6E−10 |
| A5.6 | 5.8E−10 |
| Parent 6 | 5.8E−10 |
| A6.1 | 3.4E−10 |
| A6.2 | 4.5E−10 |
| A6.3 | 5.1E−10 |
| A6.4 | 5.5E−10 |
| A6.5 | 4.8E−10 |
| Control | 6.9E−07 |

*Antibody identifiers correspond to the identifiers in Table 1

TABLE 5

IgG Poly-Specificity Reagent (PSR) Score (0-1)

| Identifier | PSR Score (0-1) |
|---|---|
| Parent 1 | 0.25 |
| A1.1 | 0.18 |
| A1.2 | 0.21 |
| Parent 2 | 0.24 |
| A2.1 | 0.27 |
| A2.2 | 0.17 |
| A2.3 | 0.21 |
| A2.4 | 0.15 |
| Parent 3 | 0.14 |

TABLE 5-continued

IgG Poly-Specificity Reagent (PSR) Score (0-1)

| Identifier | PSR Score (0-1) |
|---|---|
| A3.1 | 0.13 |
| A3.2 | 0.07 |
| A3.3 | 0.10 |
| A3.4 | 0.01 |
| A3.5 | 0.11 |
| A3.6 | 0.11 |
| A3.7 | 0.14 |
| A3.8 | 0.11 |
| A3.9 | 0.13 |
| Parent 4 | 0.20 |
| A4.1 | 0.24 |
| A4.2 | 0.19 |
| A4.3 | 0.13 |
| A4.4 | 0.15 |
| A4.5 | 0.07 |
| A4.6 | 0.14 |
| A4.7 | 0.14 |
| Parent 5 | 0.38 |
| A5.1 | 0.13 |
| A5.2 | 0.15 |
| A5.3 | 0.22 |
| A5.4 | 0.11 |
| A5.5 | 0.20 |
| A5.6 | 0.15 |
| Parent 6 | 0.62 |
| A6.1 | 0.49 |
| A6.2 | 0.25 |
| A6.3 | 0.32 |
| A6.4 | 0.38 |
| A6.5 | 0.38 |
| Control | 0.08 |

*Antibody identifiers correspond to the identifiers in Table 1

TABLE 6

Internalization of Anti-CCR8 antibody

| Anti-CCR8 Antibody | EC50 ug/ml |
|---|---|
| Parent 5 | 2.56 |
| A5.4 | 1.26 |
| A5.6 | 1.18 |
| Isotype control | 19.91 |

*Antibody identifiers correspond to the identifiers in Table 1

TABLE 7

Species Cross Reactivity (Mean Fluorescence Intensity/100,000)

| | Human CCR8 | | Cyno CCR8 | | Murine CCR8 | | Vector | |
|---|---|---|---|---|---|---|---|---|
| Identifier | 100 nM | 10 nM | 100 nM | 10 nM | 100 nM | 10 nM | 100 nM | 10 nM |
| Parent 2 | 17.7 | 14.1 | 61.7 | 37.2 | 41.9 | 22.6 | 3.3 | 2.0 |
| A2.1 | 16.7 | 12.3 | 49.6 | 26.2 | 31.5 | 11.7 | 3.4 | 1.6 |
| A2.2 | 16.1 | 11.8 | 49.2 | 25.5 | 20.5 | 4.5 | 2.7 | 1.5 |
| A2.3 | 16.2 | 12.3 | 54.8 | 29.2 | 30.9 | 11.7 | 3.5 | 2.3 |
| A2.4 | 24.2 | 18.0 | 89.2 | 56.3 | 97.2 | 84.4 | 5.2 | 3.0 |
| Parent 3 | 22.3 | 18.4 | 28.9 | 4.8 | 19.6 | 3.5 | 2.2 | 0.5 |
| A3.1 | 18.4 | 16.3 | 10.3 | 1.3 | 9.4 | 1.4 | 0.9 | 0.2 |
| A3.2 | 19.3 | 15.5 | 13.2 | 1.6 | 1.6 | 0.2 | 1.2 | 0.3 |
| A3.3 | 21.3 | 17.3 | 21.2 | 2.9 | 7.3 | 0.9 | 1.5 | 0.3 |
| A3.4 | 12.1 | 7.6 | 0.5 | 0.1 | 0.2 | 0.2 | 0.2 | 0.1 |
| A3.5 | 21.6 | 17.0 | 23.5 | 3.2 | 7.8 | 1.0 | 1.7 | 0.4 |
| A3.6 | 20.7 | 16.5 | 22.2 | 3.3 | 5.4 | 0.6 | 1.9 | 0.4 |
| A3.7 | 17.5 | 13.1 | 15.4 | 2.2 | 13.0 | 2.5 | 1.2 | 0.3 |

TABLE 7-continued
| Species Cross Reactivity (Mean Fluorescence Intensity/100,000) | | | | | | | | |
|---|---|---|---|---|---|---|---|---|
| | Human CCR8 | | Cyno CCR8 | | Murine CCR8 | | Vector | |
| Identifier | 100 nM | 10 nM | 100 nM | 10 nM | 100 nM | 10 nM | 100 nM | 10 nM |
| A3.8 | 28.3 | 21.6 | 28.0 | 6.0 | 43.1 | 22.5 | 1.9 | 0.7 |
| A3.9 | 24.8 | 19.2 | 25.8 | 5.3 | 17.8 | 1.7 | 2.0 | 0.5 |
| Parent 4 | 22.0 | 17.8 | 25.0 | 3.4 | 6.7 | 0.9 | 1.8 | 0.4 |
| A4.1 | 20.9 | 16.0 | 17.4 | 2.1 | 2.1 | 0.2 | 1.5 | 0.3 |
| A4.2 | 19.7 | 15.7 | 9.9 | 1.3 | 2.8 | 0.4 | 0.9 | 0.3 |
| A4.3 | 19.0 | 14.1 | 6.7 | 0.9 | 8.9 | 1.2 | 0.7 | 0.2 |
| A4.4 | 19.2 | 14.3 | 15.9 | 3.0 | 2.6 | 0.3 | 1.4 | 0.4 |
| A4.5 | 18.1 | 14.1 | 12.9 | 2.1 | 9.4 | 1.4 | 1.5 | 0.3 |
| A4.6 | 23.6 | 19.3 | 31.6 | 9.9 | 16.3 | 2.1 | 2.5 | 0.9 |
| A4.7 | 24.5 | 20.0 | 30.5 | 9.0 | 17.1 | 2.1 | 2.6 | 0.8 |
| Parent 6 | 23.6 | 18.8 | 3.6 | 0.8 | 0.5 | 0.1 | 0.5 | 0.2 |
| A6.1 | 24.1 | 19.6 | 6.8 | 1.5 | 1.4 | 0.2 | 0.7 | 0.2 |
| A6.2 | 23.8 | 20.6 | 7.1 | 1.4 | 3.5 | 0.5 | 0.6 | 0.2 |
| A6.3 | 23.6 | 19.5 | 8.2 | 1.9 | 4.8 | 0.7 | 0.7 | 0.2 |
| A6.4 | 23.8 | 19.6 | 11.2 | 2.9 | 5.3 | 0.8 | 0.9 | 0.2 |
| A6.5 | 23.9 | 19.9 | 11.7 | 4.0 | 8.7 | 1.8 | 0.9 | 0.4 |
| Control | 1.8 | 0.6 | 0.1 | 0.1 | 0.1 | 0.1 | 0.1 | 0.1 |
| Parent 5 | 22.2 | 18.5 | 0.9 | 0.1 | 0.3 | 0.1 | 0.3 | 0.1 |
| A5.1 | 24.3 | 20.9 | 11.0 | 1.8 | 10.0 | 0.9 | 1.1 | 0.2 |
| A5.2 | 24.6 | 20.5 | 2.8 | 0.6 | 0.4 | 0.1 | 0.4 | 0.2 |
| A5.3 | 23.9 | 20.3 | 1.4 | 0.3 | 0.4 | 0.2 | 0.3 | 0.1 |
| A5.4 | 22.1 | 19.0 | 2.6 | 0.5 | 0.3 | 0.1 | 0.3 | 0.2 |
| A5.5 | 21.7 | 18.8 | 4.3 | 0.8 | 0.7 | 0.2 | 0.4 | 0.2 |
| A5.6 | 23.5 | 20.9 | 6.8 | 1.7 | 3.7 | 0.6 | 0.5 | 0.2 |
| Parent 1 | 5.4 | 1.4 | 25.0 | 9.9 | 16.7 | 2.3 | 2.3 | 0.7 |
| A1.1 | 16.9 | 15.6 | 40.3 | 31.2 | 54.8 | 33.9 | 2.8 | 1.9 |
| A1.2 | 16.9 | 14.5 | 41.5 | 26.7 | 61.9 | 36.7 | 3.8 | 1.9 |
* Antibody identifiers correspond to the identifiers in Table 1
Example 2: General Synthesis Schemes
General Synthesis Scheme 1.
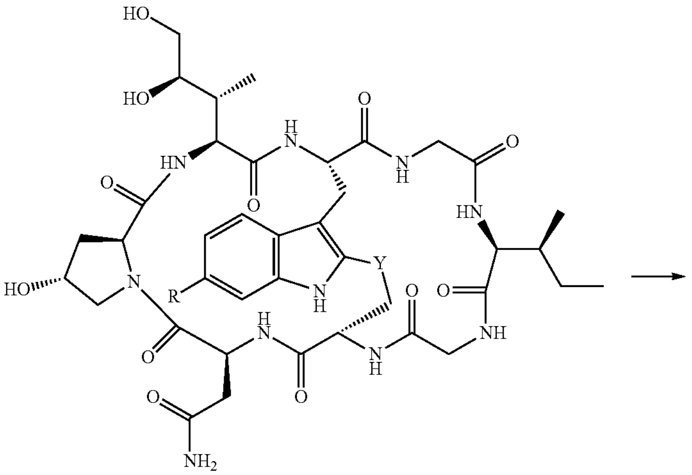

-continued
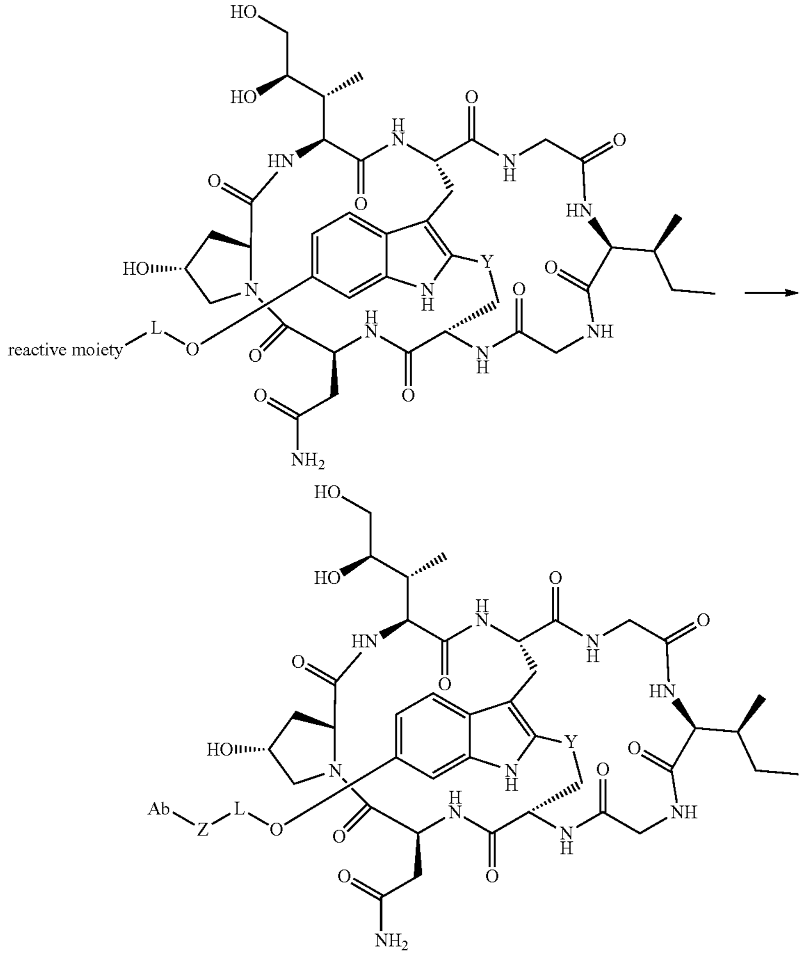
(A-I)
General Synthesis Scheme 2.
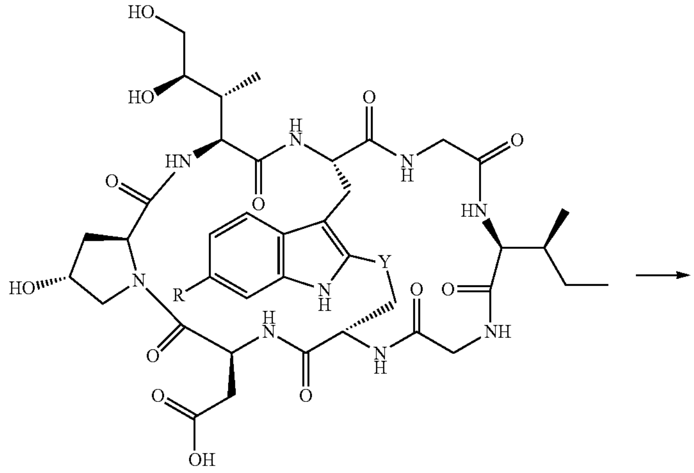

-continued
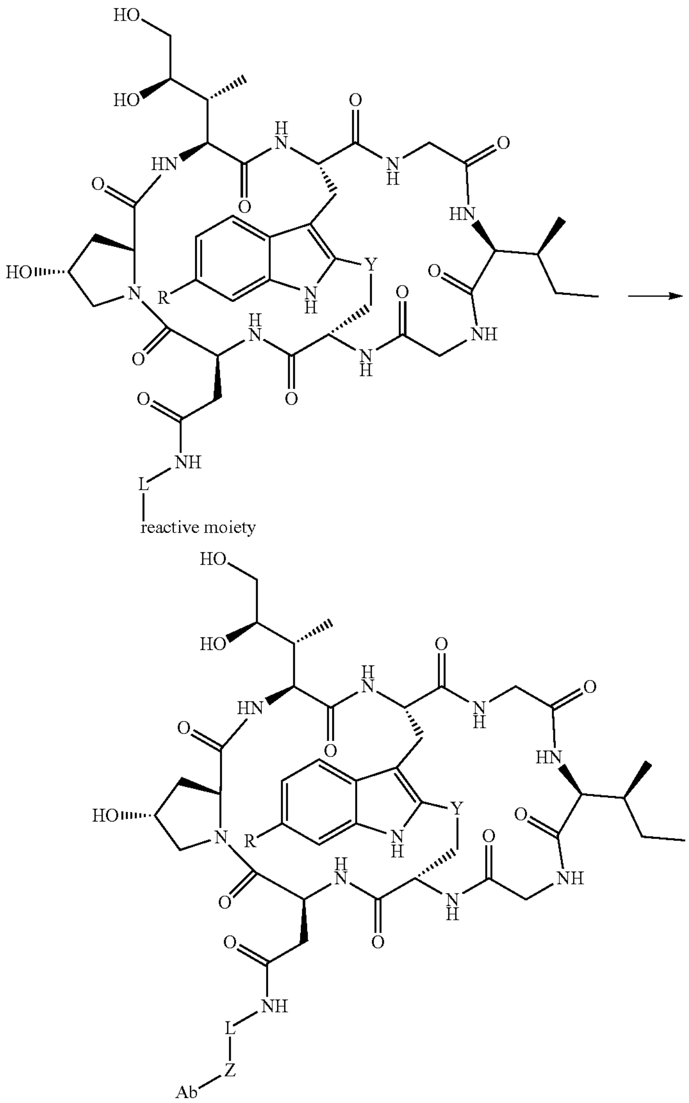
(A-II)
Example 3. Synthesis of Linker-Payload I
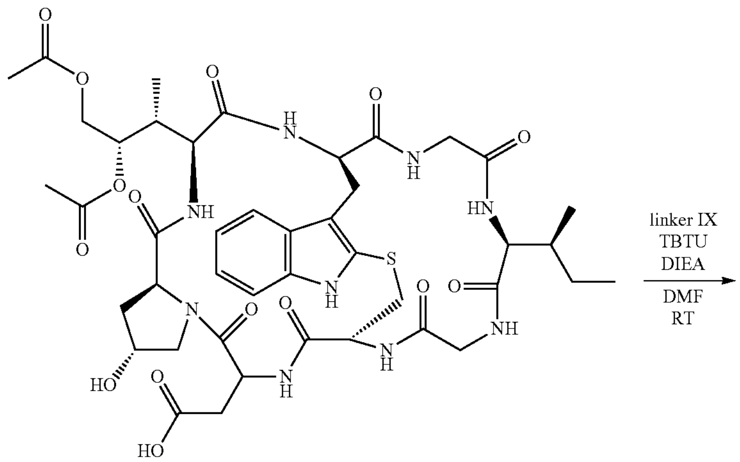

-continued

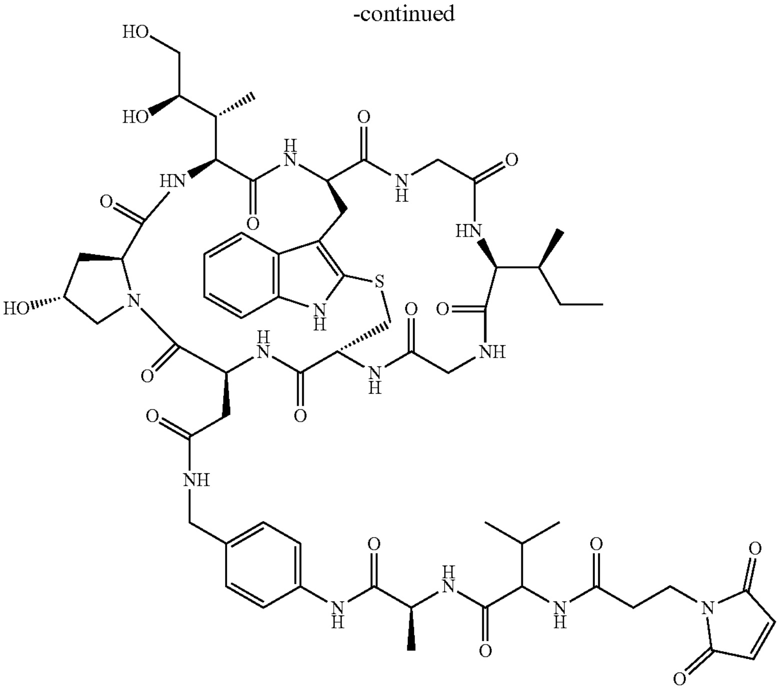

Linker-Payload I

The synthesis of linker-payload I was performed according to the procedure below as disclosed in WO 2017/149077.

Compound VI was treated with a 0.1 M solution of linker IX (1.5 eq), 0.1 M TBTU (1.5 eq) and 0.2 M DIEA (3.0 eq) at RT. After completion the reaction is quenched with $H_2O$ stirred for 15 minutes and injected onto a preparative RP-HPLC.

Example 4. Synthesis of Linker-Payloads II and III

Scheme 1. Synthesis of Cleavable and Non-Cleavable S-Deoxo-Amanitin Linker-Payloads II and III.

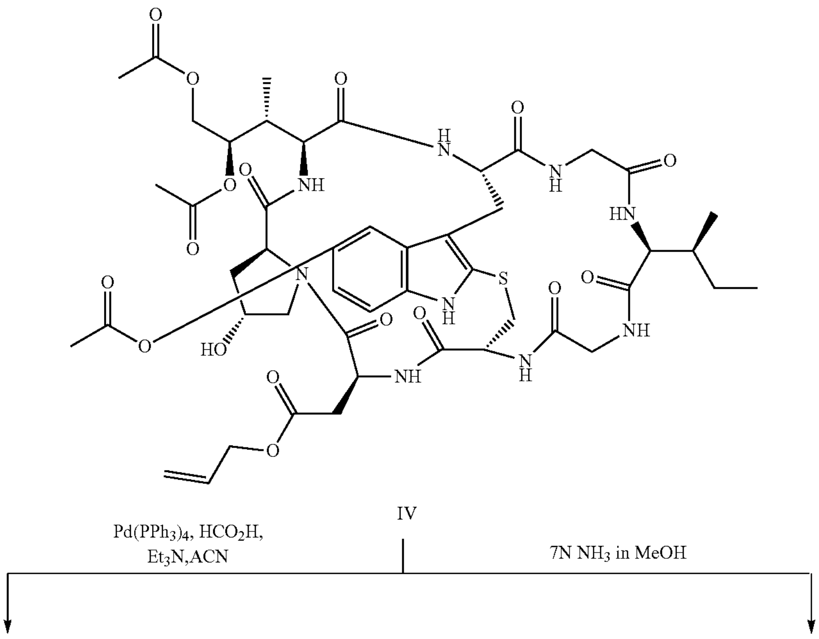

-continued
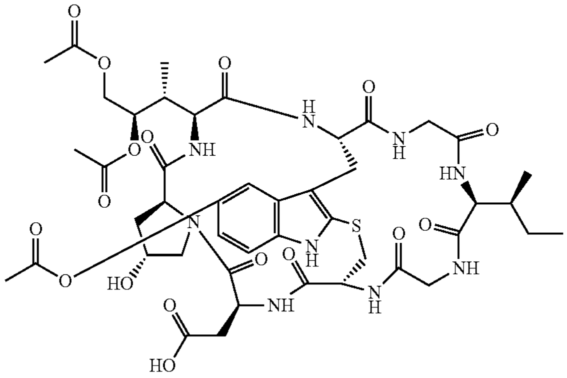
V
7N $NH_3$ in MeOH
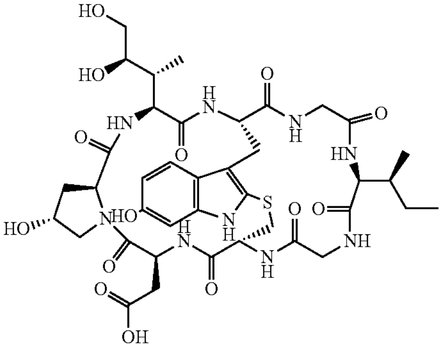
VI
DIC/HOBt
IX, DIPEA, DMF
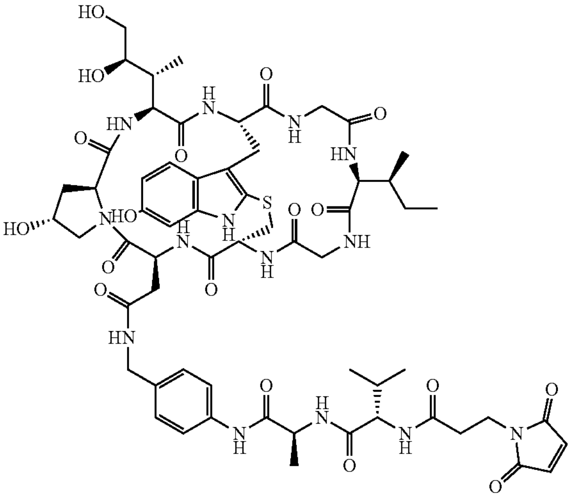
II
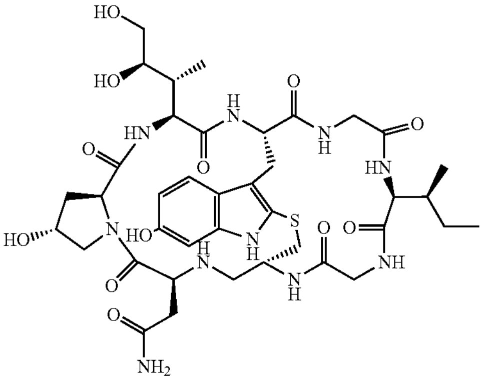
VII
X, LiOH, DMSO
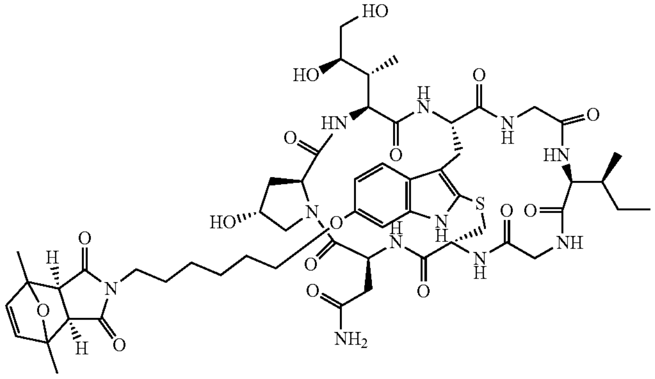
VIII
toluene, 90° C.
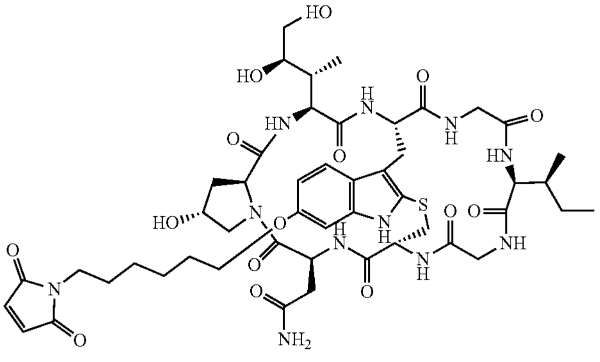
III -continued

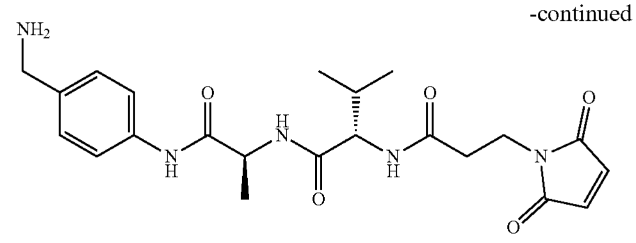

IX

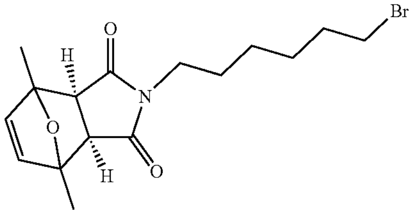

X

Synthesis of Linker IX

IX

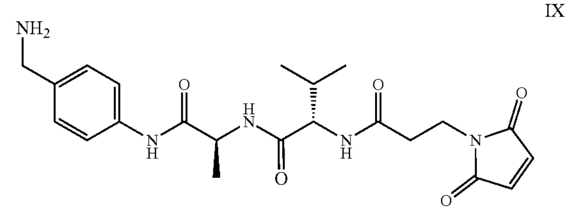 [SMILES: CC(C)[C@H](NC(=O)CCN1C(=O)C=CC1=O)C(=O)N[C@@H](C)C(=O)Nc1ccc(CN)cc1]

Synthesis of linker IX was performed according to the procedures below as disclosed in WO 2017/149077.

Accordingly, the dideoxy precursor molecule comprising a thiol reactive group with cleavable linker can be synthesized in 7 steps as follows:

Step 1: Fmoc-Val-OSu

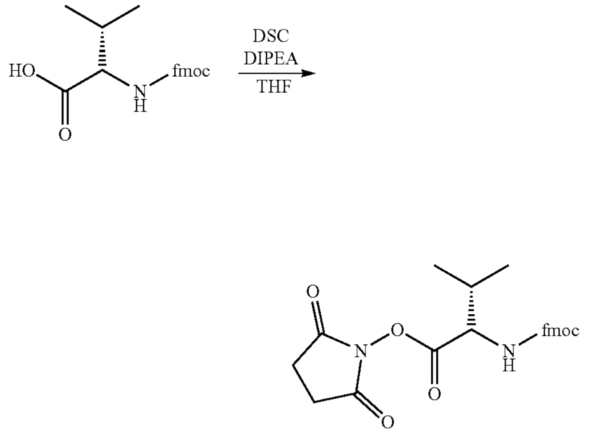

This compound is prepared according to R. A. Firestone et al., U.S. Pat. No. 6,214,345. Fmoc-Val-OH and N-hydroxysuccinimide (1.0 eq.) in tetrahydrofuran at 0° C. is treated with N,N'-dicyclohexylcarbodiimide (1.0 eq.). The mixture is stirred at RT under argon atmosphere and then the solid dicyclohexyl urea (DCU) by-product is filtered off and washed with THF and the solvent is removed in vacuo. The residue is dissolved in dichloromethane, cooled in an ice bath and filtered again to remove additional DCU. The dichloromethane is evaporated and the solid foam is used in the next step without further purification.

Step 2: Fmoc-Val-Ala-OH

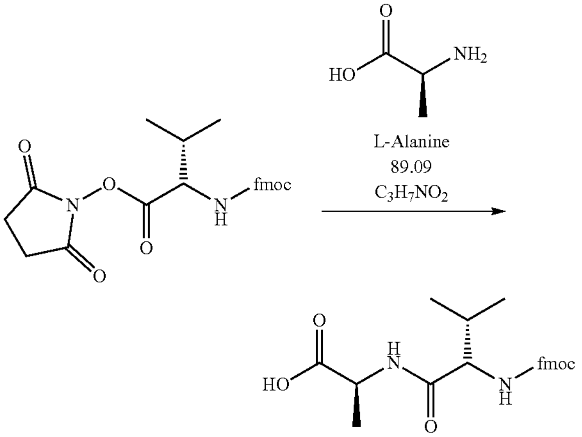

Step 2 product was prepared in analogy to P. W. Howard et al. US 2011/0256157. A solution of L-alanine (1.05 eq.) and sodium hydrogen carbonate (1.1 eq.) in water is prepared and added to a solution of Step 1 product in tetrahydrofuran. The mixture is stirred at RT. After consumption of starting material the solution is partitioned between 0.2 M citric acid and ethyl acetate. The aqueous layer is separated and extracted with ethyl acetate. The combined organic layers are washed with water and brine, dried ($MgSO_4$), and the solvent is evaporated. Pure product precipitated at this time and is filtered off. The mother liquor is evaporated to dryness and the residue is stirred with MTBE to result additional crystalline material.

Step 3: Fmoc-Val-Ala-PAB-NHBoc

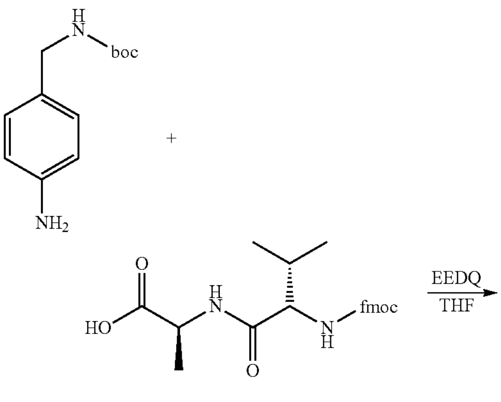

-continued

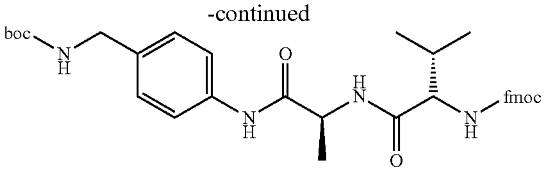

Step 2 product and 4-[(N- Boc)aminomethyl]aniline (1.05 eq.) are dissolved in abs. tetrahydrofuran. 2-Ethoxy-N-(ethoxycarbonyl)-1,2-dihydroquinoline (EEDQ, 1.05 eq.) is added and the mixture is stirred at RT, protected from light. With ongoing reaction a gelatinous matter is formed from the initially clear solution. After 40 h the reaction mixture is diluted with tert-butylmethyl ether (MTBE) and stirred for 1 h. Subsequently the precipitation is filtered off with suction, washed with MTBE and dried in vacuo.

-continued

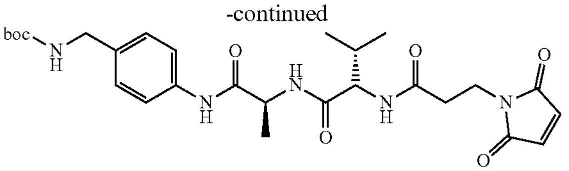

Crude step 4 product is dissolved in 40 ml DMF, 3-(maleimido)propionic acid N-hydroxysuccinimide ester (BMPS; 1.0 eq.) and N-ethyldiisopropylamine (1.5 eq.) are added and the mixture is stirred at RT After consumption of starting material, the volatiles are evaporated and the residue is stirred with MTBE until a fine suspension is formed. The precipitate is filtered off with suction, washed with MTBE and dried. The crude product is dissolved in 20 ml dichloromethane/methanol 1:1, kieselgur is added and the solvents are stripped off. The solid material is placed on top of an 80 g silica gel column and eluted with a linear gradient of 0-10% methanol in dichloromethane.

Step 6: BMP-Val-Ala-PAB-$NH_2$

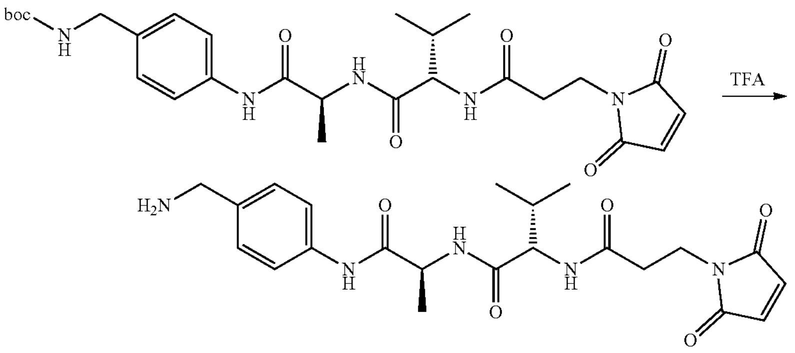

Step 4: H-Val-Ala-PAB-NHBoc

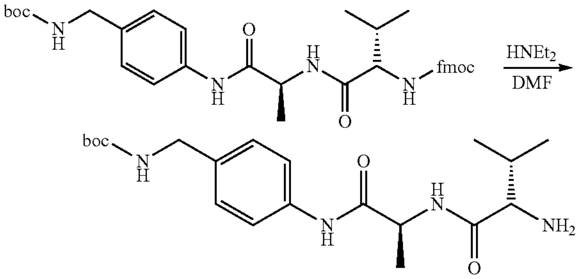

Step 3 compound (2.00 mmol) is placed in a 100 ml flask and dissolved in 40 ml dimethylformamide (DMF). Diethyl amine (7.5 ml) is added and the mixture is stirred at RT. The reaction is monitored by TLC (chloroform/methanol/HOAc 90:8:2). After consumption of starting material the volatiles are evaporated and the residue is co-evaporated with 40 ml fresh DMF to remove traces of diethyl amine. The crude product is used without further purification for the next step.

Step 5: BMP-Val-Ala-PAB-NHBoc

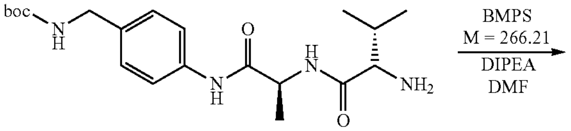

Step 5 product is dissolved in trifluoroacetic acid and stirred. Subsequently the volatiles are evaporated at RT and the remainders are co-evaporated twice with toluene. The residue is dissolved in 1,4-dioxane/water 4:1, solidified in liquid nitrogen and freeze-dried.

Synthesis of Linker X

X

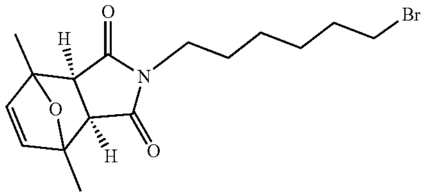

Synthesis of linker X was performed according to the procedure below as disclosed in WO 2016/142049.

Step 1: 4,7-dimethyl-3a,4,7,7a-tetrahydro-1H-4,7-epoxyisoindole-1,3(2H)-dione, Exo Isomer

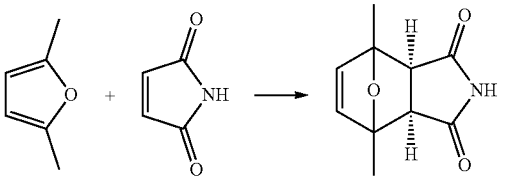

2,5-dimethyl furan and maleimide (1.5 eq.) are dissolved in diethyl ether and heated in a Parr reactor. The resulting precipitate is filtered off and re-crystallized from methanol.

Step 2: 4-(6-Bromohexyl)-1,7-dimethyl-10-oxa-4-azatricyclo[5.2.1.02·6]dec-8-en-3,5-dione, Exo Isomer

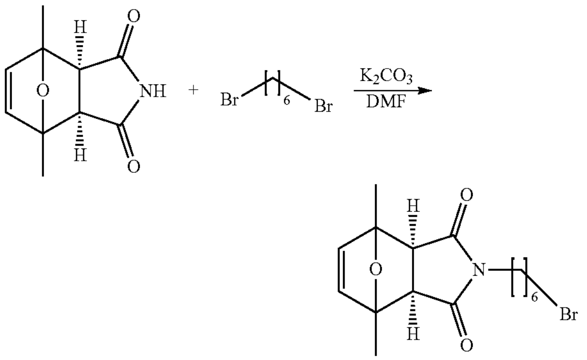

Step 1 product and 1,6-dibromohexane were dissolved in DMF. Potassium carbonate is added and the suspension heated to 50° C. Subsequently the DMF is evaporated, and the resulting the residue is taken up with dichloromethane. The inorganic salts are removed by filtration, kieselguhr is added to the filtrate and the solvent removed under vacuum. The residue is then purified by silica gel chromatography eluting with a gradient n-hexane-ethyl acetate Example 5: Synthesis of Linker-Payload II

II

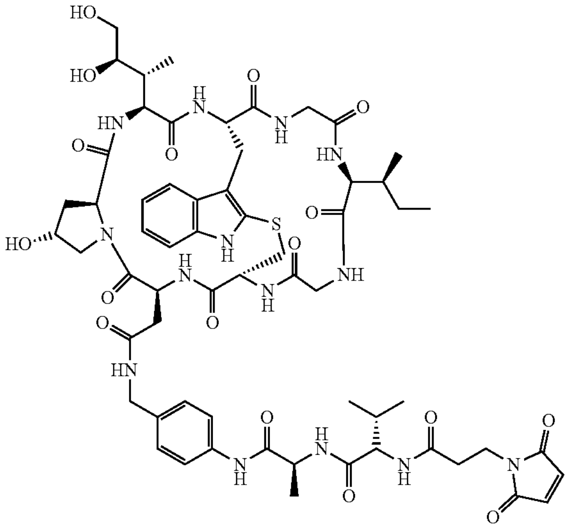

Scheme 2. Allyl—Deprotection

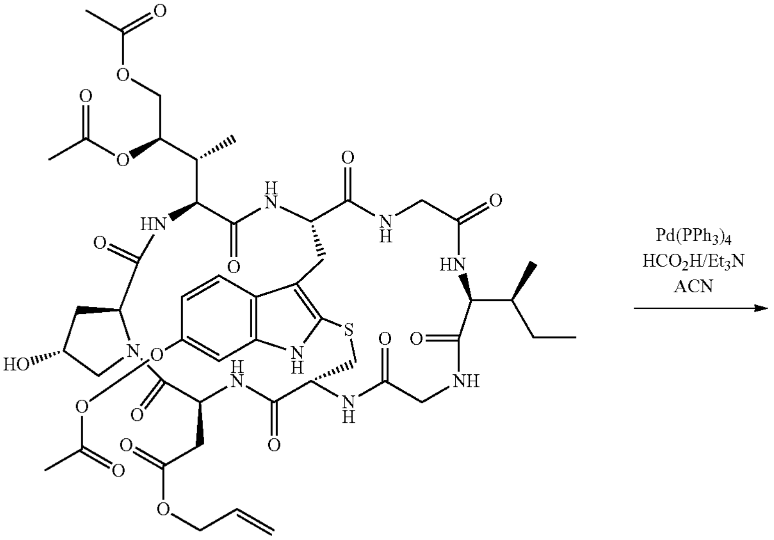

IV

Chemical Formula: $C_{48}H_{63}N_9O_{17}S$

Molecular Weight: 1070.14

-continued

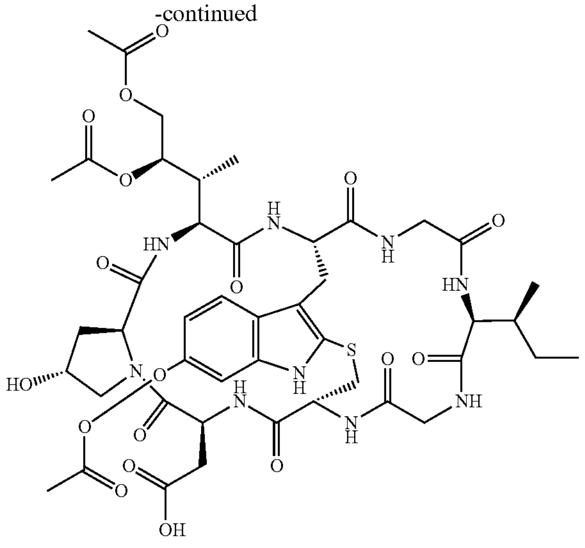

V
Chemical Formula: $C_{45}H_{59}N_9O_{17}S$
Molecular Weight: 1030.07

Synthesis of bicyclic precursor IV was performed as disclosed in Lutz et al. "Total Synthesis of α- and β-Amanitin" *Angew. Chem.* 2020, 59, 11390-11393.

IV was dissolved in acetonitrile (50 μL/μmol) and formic acid (5 eq.), triethylamine (7 eq.) and $Pd(PPh_3)_4$ (0.1 eq.) were added. The reaction was stirred at ambient temperature until completion. For precipitation of the crude product, the reaction mixture was dropped into precooled methyl tert-butyl ether (MTBE). The isolated crude product V was used without further purification. ESI-MS (positive mode): m/z=1030.4 $[M+H]^+$ (found), 1030.4 $[M+H]^+$ (calculated).

Scheme 3. Acetate Deprotection

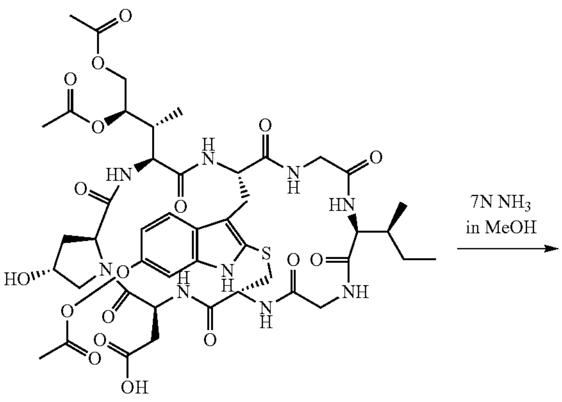

V
Chemical Formula: $C_{45}H_{59}N_9O_{17}S$
Molecular Weight: 1030.07

-continued

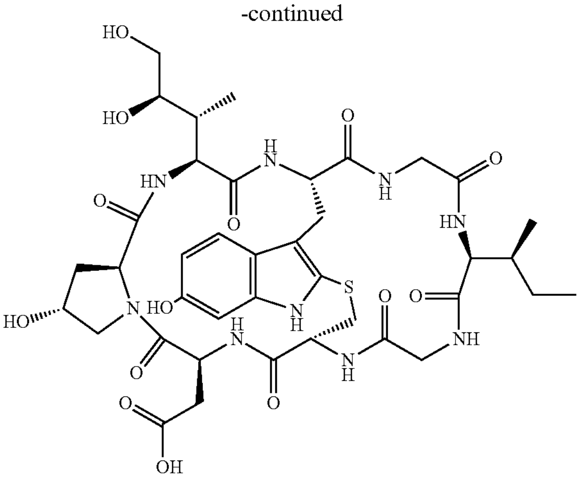

VI
Chemical Formula: $C_{39}H_{53}N_9O_{14}S$
Molecular Weight: 903.96

V (227 mg) was dissolved in 23 mL 7N ammonia solution in methanol. The reaction mixture was stirred at room temperature upon completion and the conversion to VI monitored by HPLC. The reaction mixture was concentrated at about 30° C. and under reduced pressure. The residue was re-dissolved in methanol, then concentrated to dryness at about 30° C. and under reduced pressure. The crude product was purified on a Luna® 10 μm C18(2) 100 Å, 250×21.2 mm column (Phenomenex) with water/0.1% formic acid and acetonitrile as mobile phase (gradient from 5 to 35% ACN in 14 min). Fractions were isolated, concentrated and freeze dried to a yield VI (129 mg, 64%). ESI-MS (positive mode): m/z=904.3 $[M+H]^+$ (found), 904.4 $[M+H]^+$ (calculated).

Scheme 4. Linker Attachment

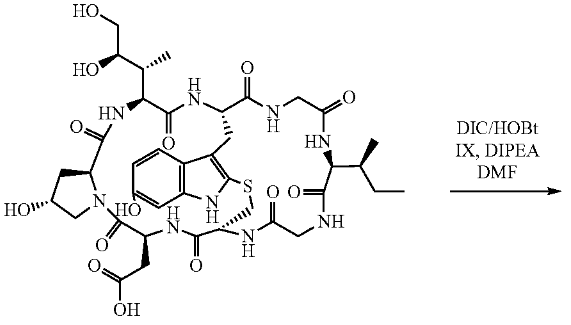

VI

Chemical Formula: $C_{39}H_{53}N_9O_{14}S$

Molecular Weight: 903.96

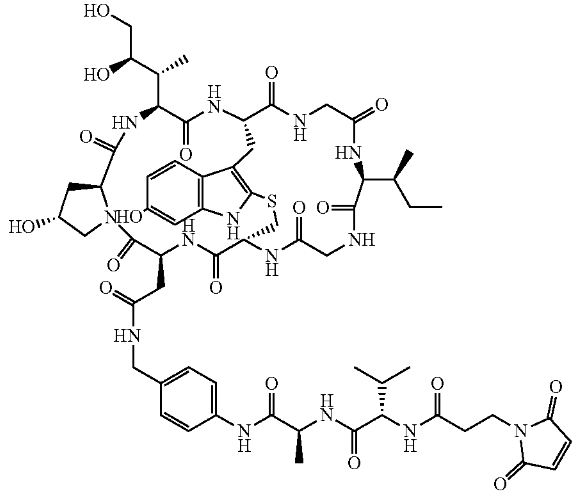

II

Chemical Formulal: $C_{61}H_{80}N_{14}O_{18}S$

Molecular Weight: 1329.45

VI (78.1 mg, 86 μmol) and HOBt (133 mg, 0.87 mmol) were dissolved in DMF (abs.) and concentrated in vacuo. The residue was dried in high vacuum overnight. The residue was dissolved in 3 mL DMF (abs.) under argon, 134 μL N,N'-diisopropylcarbodiimide (0.86 mmol) were added and the solution stirred at room temperature for 60 min. Then, a solution of IX (72.3 mg, 0.13 mmol) in 5 mL DMF (abs.) and 45.2 μL DIPEA (0.26 mmol) were added. After 23 hours, DMF is evaporated in vacuo and the residue re-dissolved in DMF. For precipitation, the solution was added to ice-cold MTBE and the crude product isolated by centrifugation. The crude product was purified on a Luna® 10 μm C18(2) 100 Å, 250×21.2 mm column (Phenomenex) with water/0.05% TFA and acetonitrile as mobile phase (gradient from 5 to 50% ACN in 14.8 min). Fractions were isolated, concentrated and freeze dried to yield linker-payload II (77.3 mg, 67%). ESI-MS (positive mode): m/z=1329.5 $[M+H]^+$ (found), 1329.6 $[M+H]^+$ (calculated).

$^1$H NMR (500 MHz, DMSO-d6): δ [ppm]=10.79 (s, 1H), 9.70 (s, 1H), 8.96 (s, 1H), 8.92 (t, J=5.7 Hz, 1H), 8.78 (t, J=6.3 Hz, 1H), 8.46 (d, J=4.4 Hz, 1H), 8.34 (d, J=3.7 Hz, 1H), 8.13 (d, J=8.0 Hz, 1H), 8.05 (d, J=7.0 Hz, 1H), 7.95 (d, J=8.4 Hz, 1H), 7.93-7.87 (m, 2H), 7.82 (d, J=9.0 Hz, 1H), 7.41 (d, J=8.5 Hz, 2H), 7.35 (d, J=8.6 Hz, 1H), 7.10 (d, J=8.7 Hz, 2H), 6.97 (s, 2H), 6.61 (d, J=2.2 Hz, 1H), 6.54 (dd, J=8.6, 2.2 Hz, 1H), 5.20 (s, 1H), 5.06 (dt, J=13.1, 8.8 Hz, 1H), 4.77-4.70 (m, 1H), 4.63-4.48 (m, 2H), 4.42-4.25 (m, 4H), 4.17 (dd, J=18.6, 8.1 Hz, 1H), 4.11 (dd, J=8.4, 6.7 Hz, 1H), 3.98 (dd, J=14.8, 5.0 Hz, 1H), 3.91 (dd, J=17.2, 7.4 Hz, 1H), 3.79-3.67 (m, 3H), 3.67-3.52 (m, 3H), 3.49-3.22 (m, 6H), 3.07-2.97 (m, 2H), 2.94-2.84 (m, 1H), 2.77 (dd, J=10.9, 3.7 Hz, 1H), 2.49-2.40 (m, 1H), 2.25-2.12 (m, 2H), 2.00-1.81 (m, 2H), 1.64-1.48 (m, 2H), 1.27 (d, J=7.1 Hz, 2H), 1.20-1.07 (m, 1H), 0.90 (d, J=7.0 Hz, 3H), 0.87-0.75 (m, 11H).

$^{13}$C NMR (126 MHz, DMSO-d6): δ [ppm]=171.88, 171.08, 170.78, 170.63, 170.61, 170.41, 170.18, 169.88, 169.72, 169.30, 167.97, 167.56, 153.91, 137.74, 134.44, 132.86, 128.07, 121.61, 120.80, 120.60, 118.91, 115.79, 109.58, 95.82, 72.73, 68.56, 63.49, 61.90, 58.96, 57.70, 55.79, 54.51, 53.24, 52.18, 50.28, 48.90, 42.32, 41.46, 38.51, 37.74, 37.41, 34.76, 34.38, 33.96, 33.64, 30.61, 30.14, 25.06, 18.99, 18.04, 17.77, 14.74, 13.45, 10.48.

Example 6: Synthesis of Linker-Payload III

III

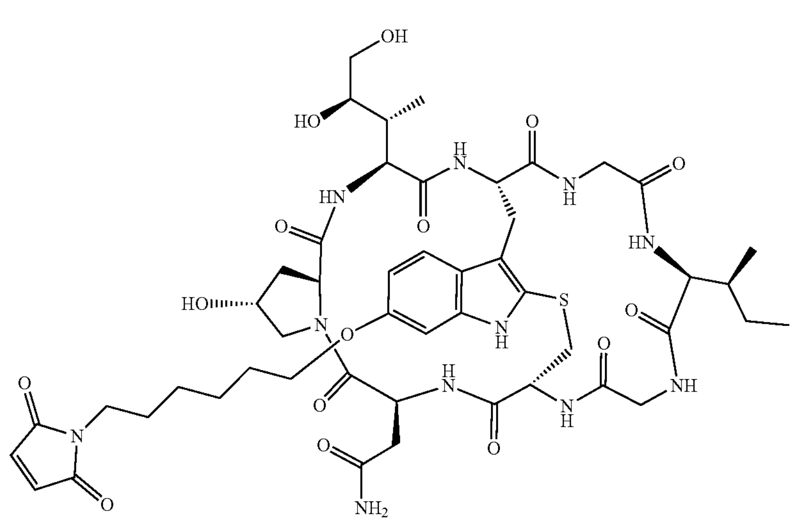

Step 1: Acetate Deprotection and Amide Formation

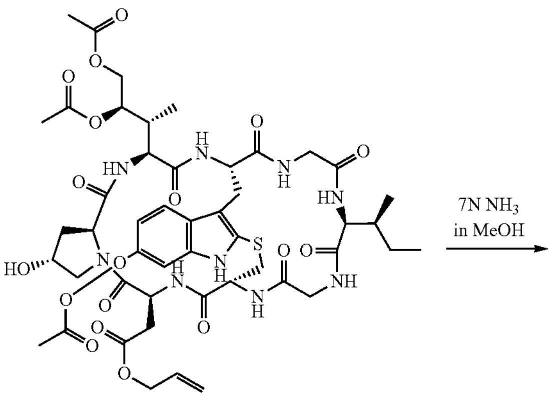

IV

Chemical Formula: $C_{48}H_{63}N_9O_{17}S$

Molecular Weight: 1070.14

-continued

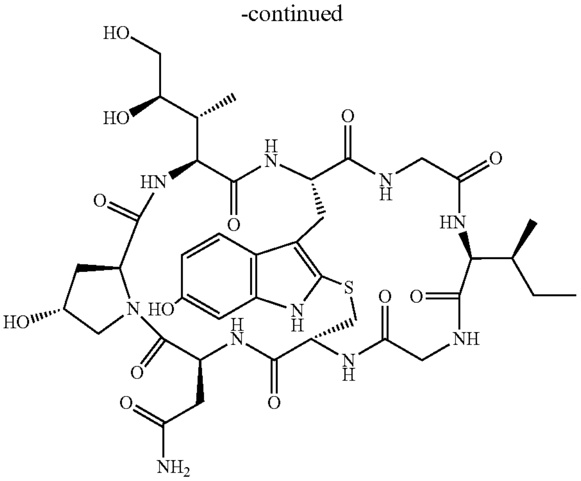

VII

Chemical Formula: $C_{39}H_{53}N_9O_{14}S$

Molecular Weight: 903.96

IV (475.2 mg) was dissolved in 47.5 mL 7N ammonia solution in methanol. The reaction mixture was stirred at room temperature upon completion and the conversion to VII monitored by analytical RP-HPLC. The reaction mixture was transferred to a round bottom flask and concentrated at about 30° C. and under reduced pressure. The resulting residue was re-dissolved in methanol, concentrated to dryness at about 30° C. and under reduced pressure. The crude product was purified on a Luna® 10 μm C18(2) 100 Å, 250×21.2 mm column (Phenomenex) with water and acetonitrile as mobile phase (gradient to 40% ACN in 11 min). Fractions were isolated, concentrated and freeze dried to yield VII (288.7 mg, 71%) as colorless lyophilizate. ESI-MS (positive mode): m/z=903.6 $[M+H]^+$ (found), 903.4 $[M+H]^+$ (calculated).

Step 2: Alkylation of 6-OH-Trp

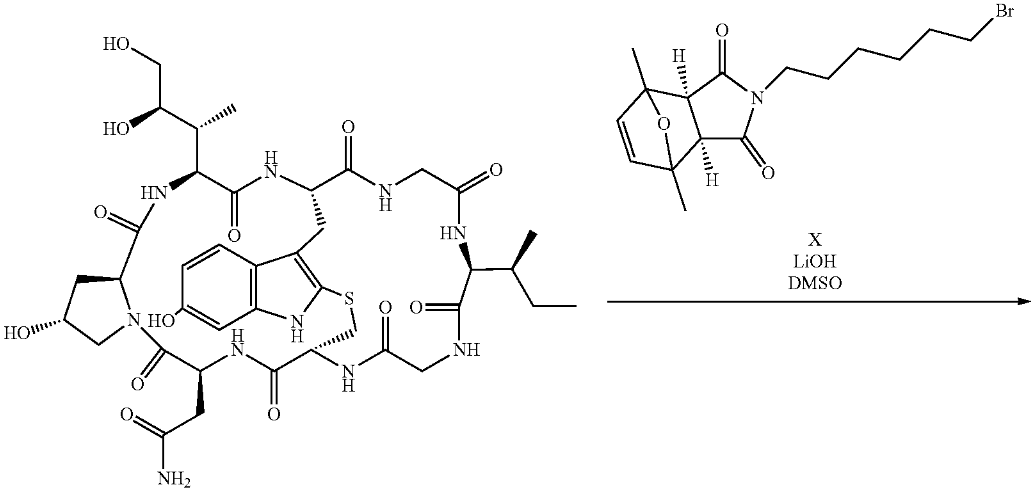

VII

Chemical Formula: $C_{39}H_{54}N_{10}O_{13}S$

Molecular Weight: 902.98

-continued

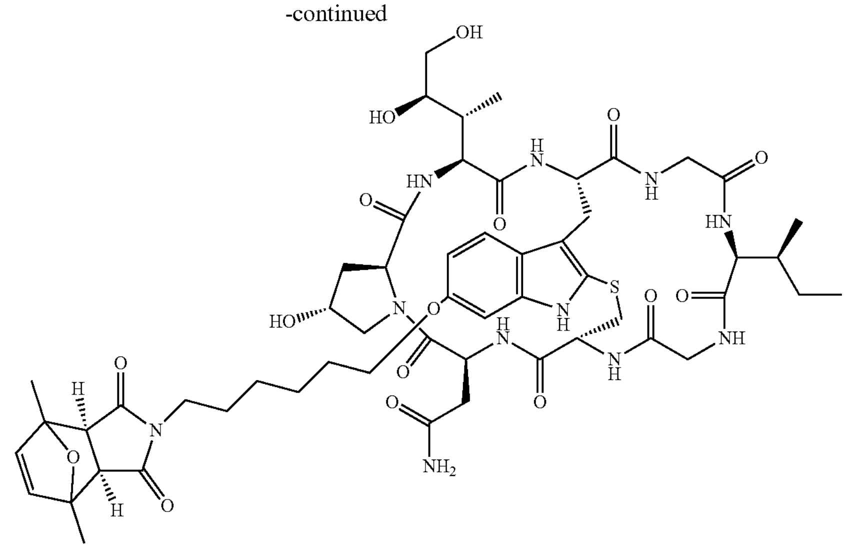

VIII
Chemical Formula: $C_{55}H_{75}N_{11}O_{16}S$
Molecular Weight: 1178.33

To a solution of VII (91.8 mg, 0.102 mmol) in 1.76 mL DMSO (abs.) was added to a solution of linker X (291 mg, 0.816 mmol) in 0.6 mL DMSO (abs.). A 2 M LiOH-solution in water (61.2 μL, 0.122 mmol) was added to start the reaction. Conversion was monitored by RP-HPLC and additional 2M LiOH added if necessary. The reaction was quenched by the addition of acetic acid (3 equiv. relating to total amount of LiOH) and concentrated in vacuo. The crude product was purified on a Luna® 10 μm C18(2) 100 Å, 250×21.2 mm column (Phenomenex) with water and acetonitrile as mobile phase (gradient to 30% ACN in 3 min followed by a gradient to 45% ACN in additional 9 min). Fractions were isolated, concentrated and freeze dried to a yield VIII (76.3 mg, 63%) as colourless lyophilizate. ESI-MS (positive mode): m/z=1178.7 $[M+H]^+$ (found), 1178.5 $[M+H]^+$ (calculated).

Step 3: Retro-Diels-Alder Reaction

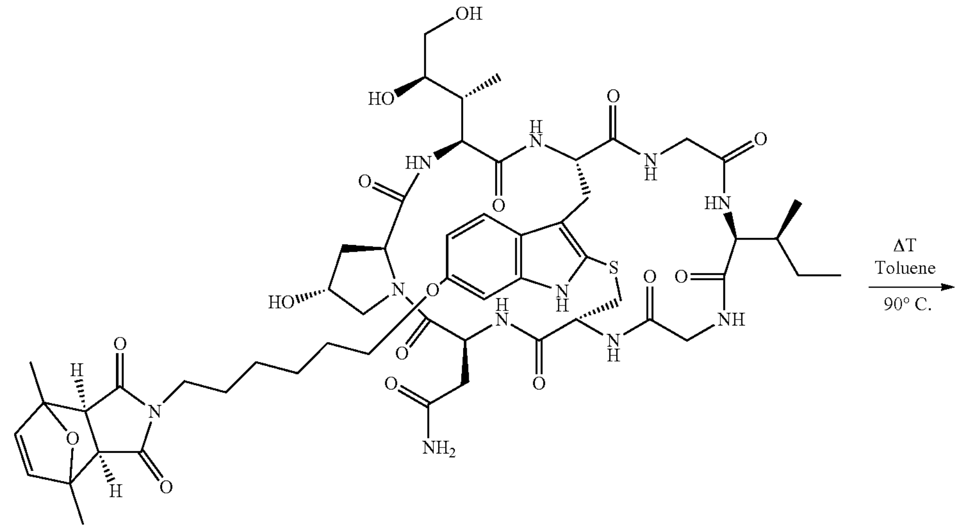

VIII
Chemical Formula: $C_{55}H_{75}N_{11}O_{16}S$
Molecular Weight: 1178.33

-continued

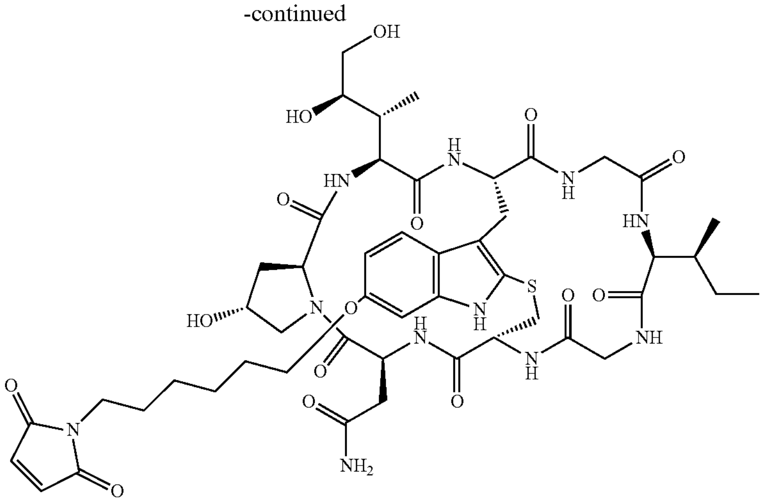

III

Chemical Formula: $C_{49}H_{67}N_{11}O_{15}S$

Molecular Weight: 1082.20

VIII (76.3 mg, 65 μmol, 1 equiv.) was suspended in 16.7 mL acetonitrile and the solvent removed in vacuo. The procedure was repeated once. The residue was suspended in 16.7 mL toluene and the solvent removed in vacuo. The procedure was repeated once. The residue was then suspended in 64.7 mL toluene under argon and heated to 90° C. The reaction progress was monitored by analytical RP-HPLC and after 5 h, and the solvent was removed in vacuo. The crude product was purified on a Luna® 10 μm C18(2) 100 Å, 250×21.2 mm column (Phenomenex) with water and acetonitrile as mobile phase (gradient to 30% ACN in 3 min followed by a gradient to 45% ACN in additional 9 min). Fractions were isolated, concentrated and freeze dried to a yield III (70.3 mg, 91%) as slightly yellowish lyophilizate. ESI-MS (positive mode): m/z=1082.7 $[M+H]^+$ (found), 1082.5 $[M+H]^+$ (calculated).

$^1H$ NMR (500 MHz, DMSO-d6) δ 10.94 (s, 1H), 8.78 (t, J=6.4 Hz, 1H), 8.46 (d, J=4.4 Hz, 1H), 8.40 (d, J=3.7 Hz, 1H), 8.13-8.01 (m, 2H), 8.01-7.90 (dd, J=9.6, 7.0 Hz, 2H), 7.84 (d, J=8.3 Hz, 1H), 7.43 (d, J=8.7 Hz, 1H), 7.41-7.35 (m, 1H), 6.98 (s, 2H), 6.70 (d, J=2.2 Hz, 1H), 6.66 (dd, J=8.7, 2.2 Hz, 1H), 4.94 (ddd, J=13.9, 8.3, 6.2 Hz, 1H), 4.72 (q, J=4.2 Hz, 1H), 4.57 (ddd, J=11.9, 9.9, 3.6 Hz, 1H), 4.46 (dd, J=9.4, 5.5 Hz, 1H), 4.40 (d, J=4.2 Hz, 1H), 4.29 (dd, J=11.4, 7.0 Hz, 1H), 4.17 (dd, J=18.5, 8.2 Hz, 1H), 3.98-3.86 (m, 3H), 3.80 (dd, J=11.3, 3.2 Hz, 1H), 3.76-3.69 (m, 2H), 3.51 (dt, J=6.6, 3.2 Hz, 1H), 3.46-3.35 (m, 5H), 3.34-3.28 (m, 2H), 3.28-3.20 (t, J=13.9 Hz, 1H), 3.05 (t, J=11.5 Hz, 1H), 2.96 (ddd, J=20.2, 15.2, 5.4 Hz, 2H), 2.77 (dd, J=11.0, 3.5 Hz, 1H), 2.21 (td, J=12.5, 12.1, 6.6 Hz, 2H), 1.88 (td, J=12.5, 3.7 Hz, 1H), 1.71 (p, J=6.7 Hz, 2H), 1.64-1.49 (m, 4H), 1.48-1.39 (m, 2H), 1.35-1.22 (m, 2H), 1.17-1.06 (m, 1H), 0.89 (d, J=7.0 Hz, 3H), 0.86-0.74 (m, 6H).

$^{13}C$ NMR (126 MHz, DMSO-d6) δ 172.26, 171.88, 170.98, 170.77, 170.44, 170.20, 170.09, 169.72, 168.00, 167.66, 155.52, 137.25, 134.34, 122.34, 121.40, 120.82, 116.12, 109.65, 94.46, 72.36, 68.54, 67.48, 63.41, 61.84, 58.94, 55.72, 54.97, 53.29, 52.24, 50.43, 42.25, 41.35, 38.37, 37.75, 37.51, 36.93, 34.33, 34.19, 30.07, 28.53, 27.77, 25.81, 25.05, 14.73, 13.52, 10.45.

Example 7: Temporal Cytotoxicity of Anti-CCR8 Antibody Conjugates

Figure 4A:
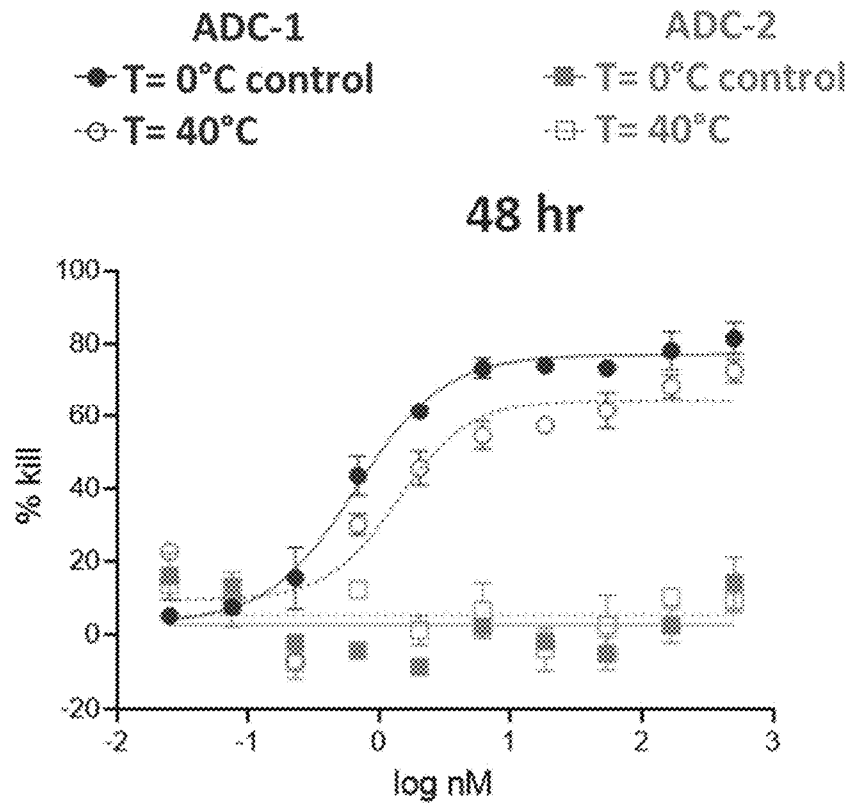
FIGS. 4A-4B shows the cytotoxicity of two anti-CCR8 antibody drug conjugates (ADCs) over time under developability stressing conditions.
Figure 4B:
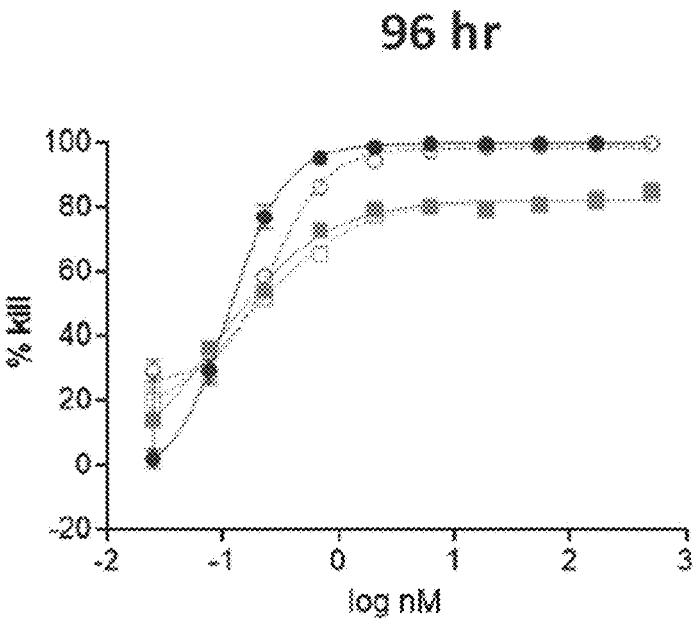

The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a linker (e.g., a cleavable linker or a non-cleavable linker). First, the antibody was diluted, and the solution adjusted with EDTA. Next, the cysteines were uncapped through an antibody reaction with tris(2-carboxyethyl)phosphine (TCEP), followed by incubation and two consecutive dialyses. The antibody then went through re-oxidation by adding dehydroascorbic acid (dhAA) followed by an incubation. Next, using an amanitin-linker derivative, Amanitin was conjugated to the antibody. To quench the reaction N-acetyl-L-cysteine was added followed by incubation and purification. The ADC was then purified by centrifugation, with the supernatant collected. Next, the reaction mix was purified by preparative fast protein liquid chromatography (FPLC) using HiLoad 26/600 Superdex 200 pg and a XK26-column equilibrated with 50 mM histidine, 125 mM Arginine, and pH 6.3. Fractions were collected by UV absorption at 280 nm. Lastly, the protein concentration was adjusted, and brought to sterile conditions by filtration. The resulting ADC with the cleavable linker has a structure of Formula (A-I-c) (ADC-1), and the resulting ADC with the non-cleavable linker has a structure of Formula (A-II-b) (wherein n is 5) (ADC-2). ADC-1 and ADC-2 were stress-treated at 40° C. for two weeks. Samples kept at 0° C. during the same time period was used as the stress-free control. To assess the ADC's ability to kill CCR8+ cells in the in vitro settings, CHO-S cells were transfected with human CCR8 (hCCR8). The hCCR8-CHO cells were plated in 384-well white plate (Corning 356661) in cell culture media (Freestyle CHO, ThermoFisher 12651-014; 8 mM L-glutamine, Gibco 25030-081; and 5 ug/ml Puromycin, Gibco A11138-03) at the density of 1000 cells per well. ADC-1 and ADC-2 with (40° C.) and without (0° C.) stress-treatment were serially diluted in cell culture media and then transferred to the cell-containing plate. The cell viability indicating reagent RealTime-Glo (Promega G9713) was reconstituted per manufacturer's recommendations in cell culture media, and then added to the cell-ADC mix in the plate. The plate was incubated at 37° C. incubator with 5% $CO_2$ and 80% humidity for 96 hours with luminescence intensity measured at the 48 and 96 hour. (FIG. 4). Percentage kill was calculated using the Relative Luminescence Intensity (RLU) value of each sample in referencing to the positive control (2 μM free payload) and negative control (cell culture media) using the below formula:

% kill=(1−(ADC−free payload)/(Media control−free payload))×100

ADC-1 showed a higher percentage of hCCR8 CHO cells killed at both the 48- and 96-hour timepoints. ADC-1 also had higher levels of cytotoxicity at lower doses, 48 hours post treatment when compared to ADC-2. Developability stressing, lowered the cytotoxicity potency (EC50) of ADC-1 approximately 2 to 10-fold. However, the maximum effect of both ADC-1 and ADC-2 was not impacted.

Example 8: Evaluation of ADC on Treg Depletion, Killing CCR8+ Tregs, and Antitumor Activity The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a linker (e.g., a cleavable linker or a non-cleavable linker). The resulting ADC with the cleavable linker has a structure of Formula (A-I-c) (ADC-1) or Formula (A-I-e) (ADC-3), and the resulting ADC with the non-cleavable linker has a structure of Formula (A-II-b) (wherein n is 5) (ADC-2). The ADCs were then assessed for their ability to deplete Tregs, kill CCR8+ Tregs, and inhibit tumor growth.

Figure 5A:
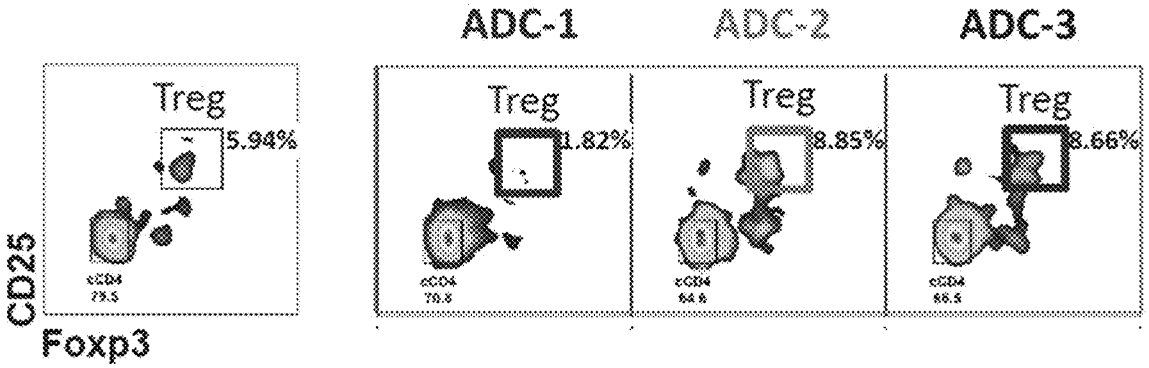
FIGS. 5A-5C show the evaluation of an ADC comprising an anti-CCR8 antibody conjugated to amanitin with three different linkers (ADC-1, ADC-2, and ADC-3).

To assess the ability to deplete Tregs, Dispersed Tumor Cells (DTCs) were generated from a breast cancer patient tumor sample by digestion with the Miltenyi Human Tumor Dissociation Kit, according to the manufacturer's protocol. The DTCs were then cultured in complete RPMI media with 2000U IL-2 and treated with control (PBS), ADC-1, ADC-2, or ADC-3 at a dose of 20 nM for 96 hours (FIG. 5A). Cells were labeled with antibodies for immune cell markers at 4° C., and the percent Treg population (CD25+Foxp3+ out of bulk CD4+ cells) was then assessed by flow cytometry. Data were analyzed using FlowJo software. Treatment with ADC-1 resulted in a large decrease in the percent of tumor infiltrating Tregs, while treatment with ADC-2 and ADC-3 showed no decrease in comparison to the mock treated control.

Figure 5B:
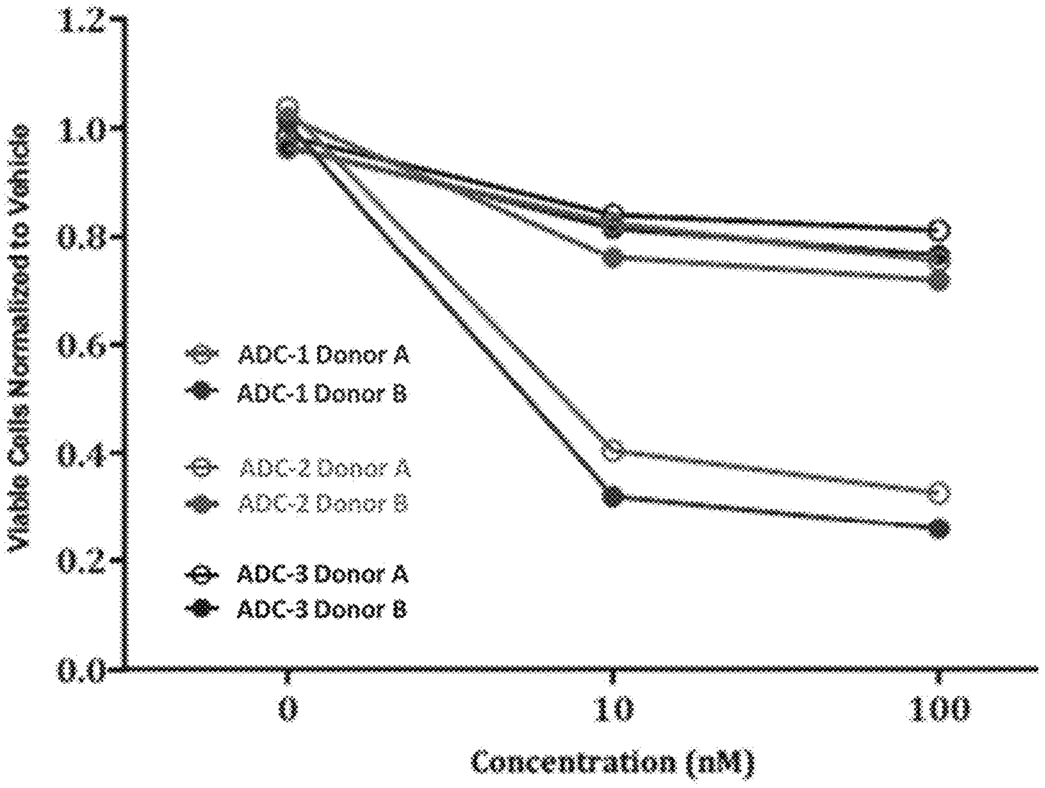

Next, to assess the ADC's ability to specifically kill CCR8+ Tregs a CellTiter-Glo® (CTG) assay was performed. A CTG assay is a method to determine the number of viable cells in a culture based on the quantity of ATP. nTregs were first isolated from PBMCs of two healthy donors using the EasySep Human CD4+CD127lowCD25+ Regulatory T Cell Isolation Kit from StemCell Technologies according to the manufacturer's protocol. Cells were plated in Expansion Media (XVIVO-15 from Lonza with 5% HI-FBS) at 80,000 cells/well in 200 uL with CD3/CD28 Human Treg Expander Dynabeads (4:1 beads to cells), rapamycin (10 nM), and anti-TNFR2 antibody (3 ug/mL) in a 96 well plate to induce CCR8 expression over the course of expansion. On Day 2, the media was refreshed, and IL-2 (20 ng/mL) was added to the culture. On Day 4, the Complete T Cell Media (XVIVO-15, 5% HI-FBS, rapamycin, anti-TNFR2, IL-2) was refreshed and cells were expanded to a 48 well plate. On Day 6, the Complete T Cell Media was refreshed, and cells were expanded to a 24 well plate. On Day 8, the Complete T Cell Media was refreshed, cells were restimulated with CD3/CD28 Human Treg Expander Dynabeads (1:1 beads to cells), and cells were expanded to a 12 well plate. On Day 10, expanded nTreg were counted and seeded at 80,000 cells/well in an Ultra Low Bind 96 well plate in Complete T Cell Media without IL-2 and treated for 96 hours with 0, 10, and 100 nM concentrations of ADC-1, ADC-2, and ADC-3 (FIG. 5B). At 96 hours, 25,000 cells from each well were moved to a black-walled clear bottom plate for the CTG assay (Promega), which was performed according to the manufacturer's protocol. Luminescence was normalized to vehicle control, and treatment with ADC-2 and ADC-3 resulted in a mild decrease in viable cells, while treatment with ADC-1 showed a strong decrease in viable cells (killing of nTreg) for both donors.

Figure 5C:
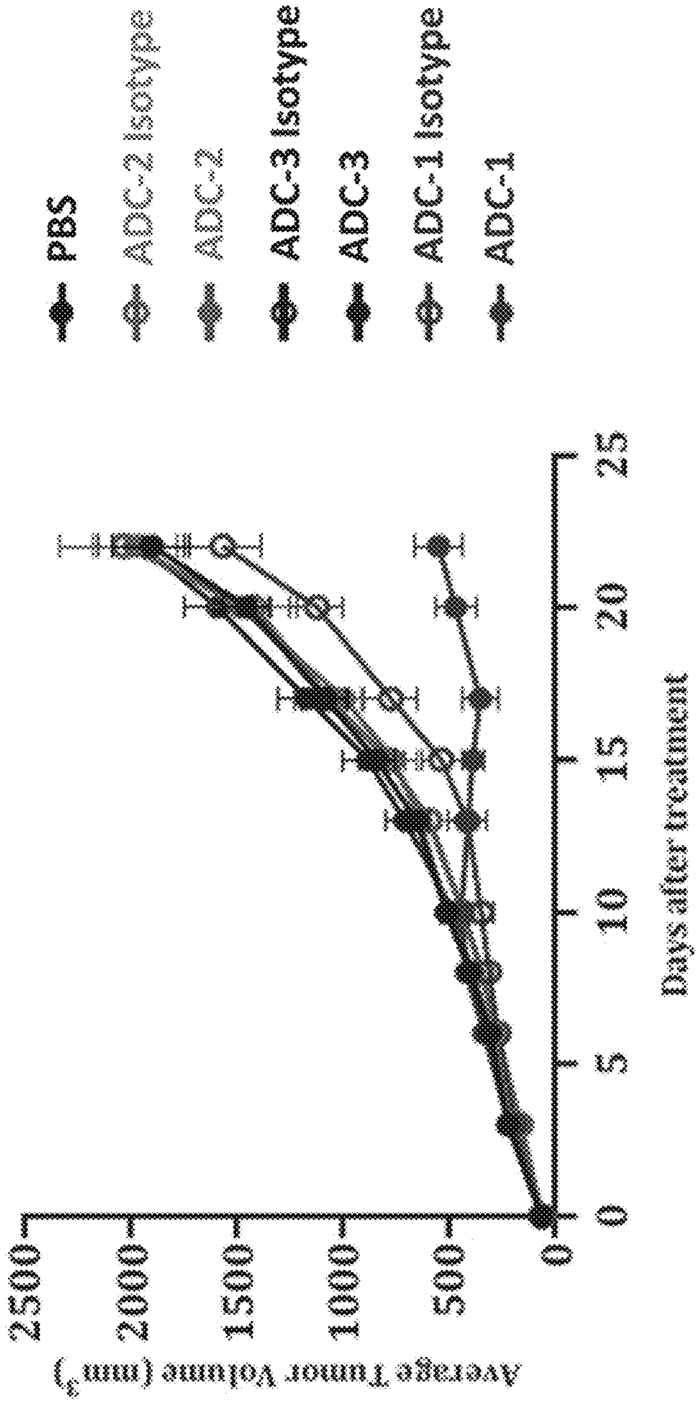

Lastly, the ADC's antitumor ability in vivo was assessed in a model of MC38 tumors in human CCR8 knock-in mice (Biocytogen). MC38 cells (Obio Technology) were cultured in 90% DMEM +10% FBS. Female huCCR8 KI mice were inoculated subcutaneously with $1\times10^6$ MC38 cells in 0.1 mL in the right flank, and tumor growth was measured three times per week using calipers (using the formula $V=W^2\times L/2$). Mice were randomly grouped when the average tumor volume was ~50 $mm^3$, with Day 0 being the day of grouping. On Day 0, mice were treated with a single dose, intravenously (IV), of either vehicle (PBS), an ADC at 5 mg/kg (ADC-1, ADC-2, ADC-3), or controls in which the antibody is a non-specific antibody conjugated to the same linker-payloads (ADC-1 isotype, ADC-2 isotype, ADC-3 isotype) (FIG. 5C). Tumor volume was assessed over time. Mice treated with ADC-1 had reduced tumor size in comparison to vehicle and isotype control treated mice.

Example 9: CCR8-Amanitin ADC Demonstrates CCR8 Specific Anti-Tumor Efficacy

The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a cleavable linker, resulting in ADCs having a structure of Formula (A-I-c) (ADC-1). The ADCs were then assessed for their antitumor ability.

Figure 6A:
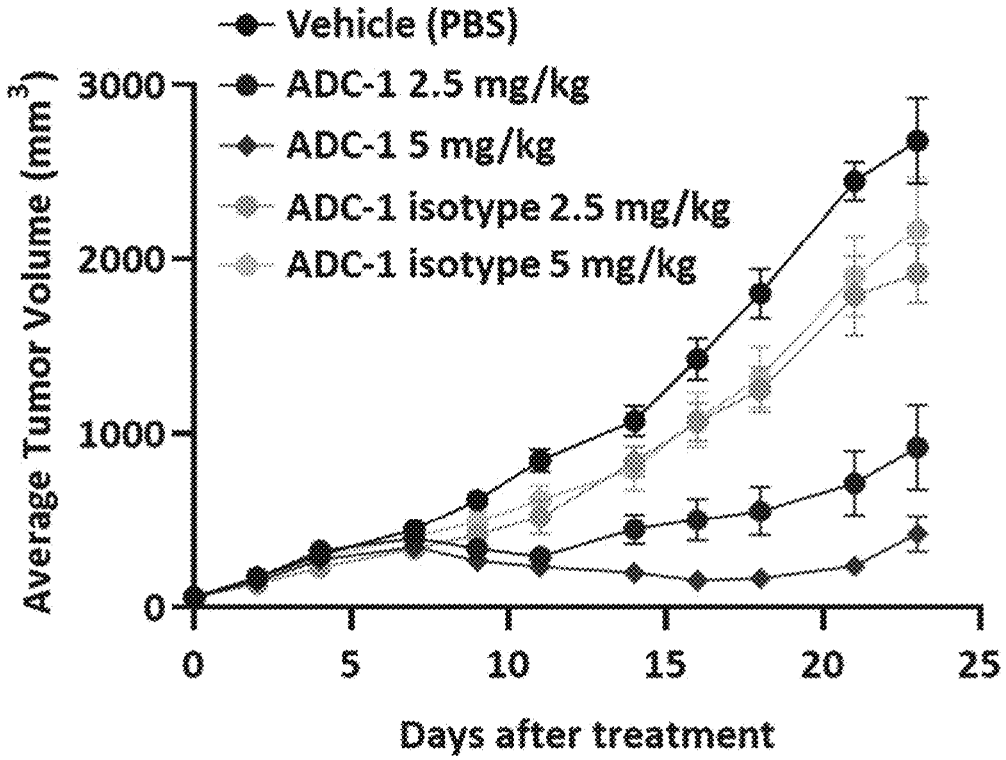
FIGS. 6A-6C show the CCR8-specific antitumor efficacy of an anti-CCR8 antibody-amanitin ADC.

MC38 cells (Obio Technology) were cultured in 90% DMEM +10% FBS. Female huCCR8 KI mice were inoculated subcutaneously with $1\times10^6$ MC38 cells in 0.1 mL in the right flank, and tumor growth was measured three times per week using calipers (using the formula $V=W^2\times L/2$). Mice were randomly grouped when the average tumor volume was ~55 $mm^3$, with Day 0 being the day of grouping. On Day 0, mice were treated with a single IV dose of either vehicle (PBS), ADC-1 (2.5 mg/kg or 5 mg/kg), or a control ADC with a non-specific antibody conjugated to the same linker-payload (ADC-1 isotype) at matched concentrations. Tumor volume was assessed over time (FIG. 6A). ADC-1 showed dose-dependent tumor growth inhibition compared to isotype or vehicle control.

Figure 6B:
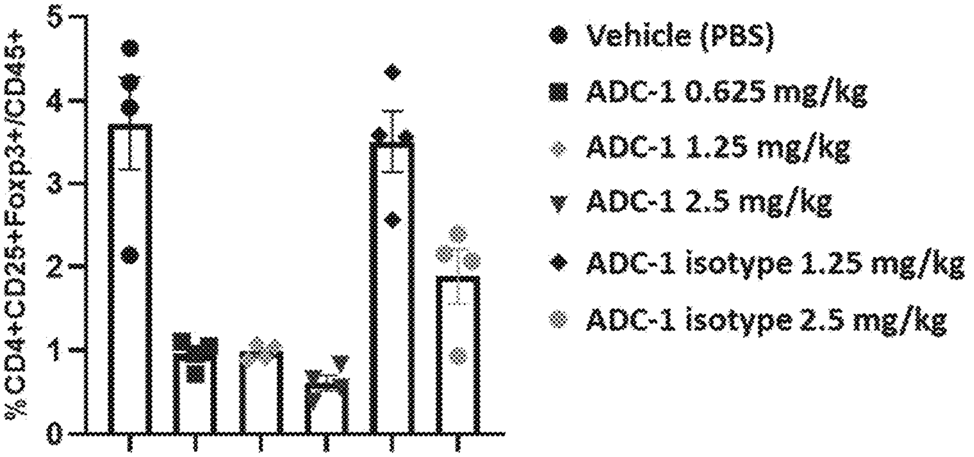
Figure 6C:
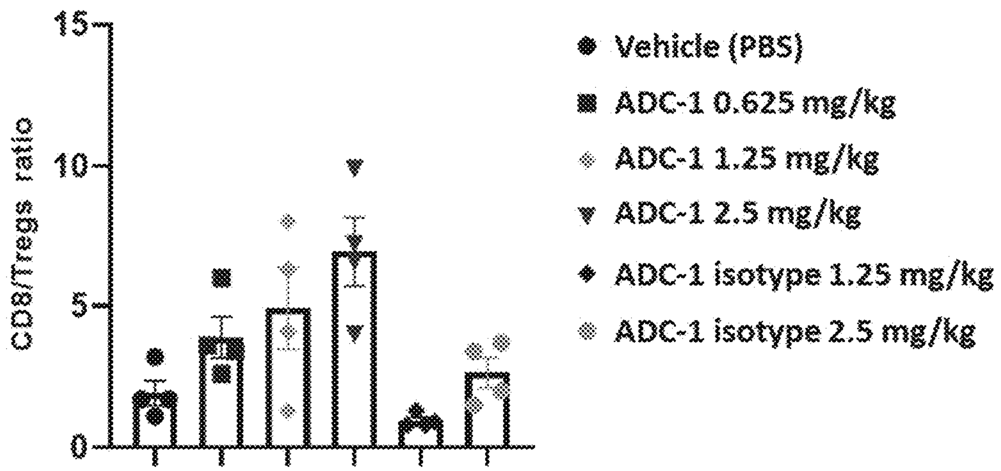

Next, the intra-tumoral Treg and CD8+ T cell profile was assessed 72 hours post treatment. Female huCCR8 KI mice were inoculated subcutaneously with $1\times10^6$ MC38 cells, and tumor growth was measured using calipers. Mice were randomly grouped when the average tumor volume was ~290 mm3, with Day 0 being the day of grouping. On Day 1, the mice were treated IV with (PBS), ADC-1 (0.625 mg/kg, 1.25 mg/kg, and 2.5 mg/kg), or a control ADC with a non-specific antibody conjugated to the same linker-payload (ADC-1 isotype, 1.25 mg/kg and 2.5 mg/kg). On Day 4, tumors were harvested and digested using the Mouse Tumor Dissociation Kit (Miltenyi) and GentleMACS Octo Dissociator with heaters (Miltenyi) according to the manufacturer's protocol. $5\times10^6$ cells (or all cells if less were obtained) from each tumor sample were labeled with antibodies for immune cell markers at 4° C., and flow cytometry was performed to identify Treg (TCRb+CD4+Foxp3+CD25+ out of CD45+ cells) and CD8+ T cells (TCRb+CD8+ out of CD45+ cells). Data were analyzed using FlowJo software. Mice treated with ADC-1 had enhanced Treg depletion (FIG. 6B) in comparison to vehicle and control groups, and an increase in effector CD8+ T cell infiltration, as demonstrated by an increase in the tumor CD8/Tregs ratio (FIG. 6C). Together, this data indicates the CCR8-amanitin ADC depletes tumor infiltrating Treg and demonstrates anti-tumor efficacy.

Example 10: CCR8-Amanitin ADC Demonstrates Selective Killing of Tregs in Patient Tumor Samples The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a cleavable linker, resulting in ADCs having a structure of Formula (A-I-c) (ADC-1). The ADCs were then assessed for their ability to kill Treg in human tumor samples.

Figure 7:
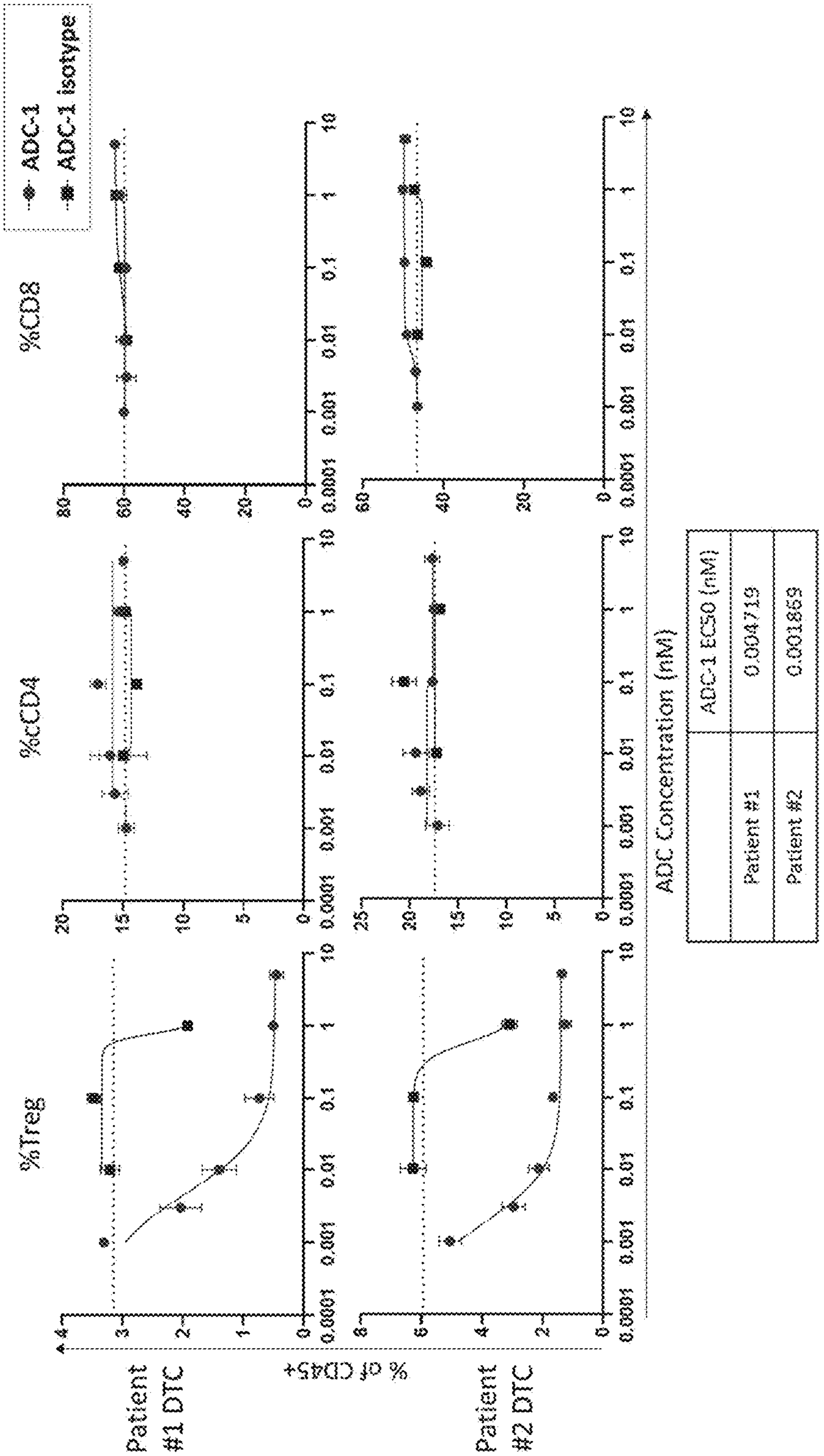
FIG. 7 shows the selectivity of the ADC to kill T regulatory cell (Treg) in patient tumor samples.

To assess the ADC's ability to selectively kill Tregs in patient tumor samples, frozen DTCs from two kidney cancer patients were obtained from Discovery Life Sciences and treated with multiple concentrations of ADC-1 and a non-specific antibody conjugated to the same linker-payload (ADC-1 isotype). DTCs were first thawed at 37° C., transferred to Culture Media (RPMI 1640+10% HI FBS+1× Penn/Strep+L-glutamine (2 mM)+1× sodium pyruvate (1 mM)+1× NEAA+HEPES+β-ME), centrifuged, and filtered through a 30 μM cell strainer before counting. DNAse I (StemCell Technologies) was added prior to counting according to the manufacturer's protocol if cell clumping was observed. $2\times10^5$ cells/well in 100 μL Culture Media +400 ng/mL IL-2 were added to each well of a 96 well (round bottom) plate. DTCs were treated with PBS (vehicle control) or ADC-1 and ADC-1 isotype at concentrations of 5, 1, 0.1, 0.01, 0.003, and 0.001 nM for 96 hours. After 96 hours, cells were labeled with antibodies for immune cell markers at 4° C., and the percent Treg (CD4+Foxp3+CD25+), percent cCD4 (conventional CD4+ T cells, CD4+Foxp3−), and percent CD8+ T cells were enumerated out of CD45+ cells by flow cytometry (FIG. 7). The dashed black line on each plot indicates the average percent of cells for vehicle control treated samples. ADC-1 shows specific depletion of human tumor Treg, with no depletion/decrease of conventional CD4+ (cCD4) or CD8+ T cells, showing the selectivity of the killing for tumor Treg. ADC-1 demonstrates potent killing of tumor Treg, with EC50 values of ~0.0047 and ~0.0019 nM. EC50 was calculated using non-linear regression (curve fit), variable slope (4 parameters) in PRISM.

Example 11: CCR8-ADC Potently and Specifically Depletes Human Treg in NSCLC Dispersed Tumor Cells (DTCs)

The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a cleavable linker, resulting in ADCs having a structure of Formula (A-I-c) (ADC-1). The ADCs were then assessed for their ability to kill Tregs in non-small cell lung cancer (NSCLC) samples.

Figure 8A:
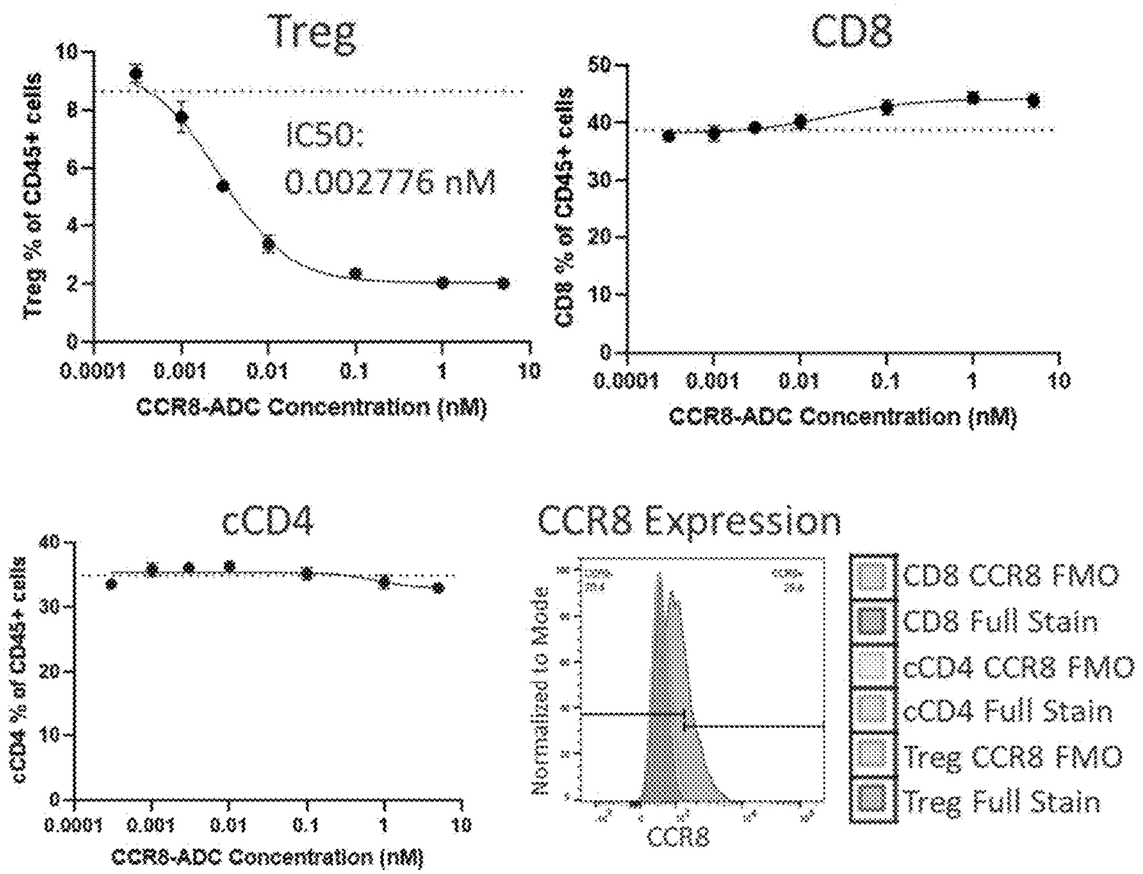
FIGS. 8A-8C show the evaluation of an ADC comprising an anti-CCR8 antibody on T cell populations.
Figure 8B:
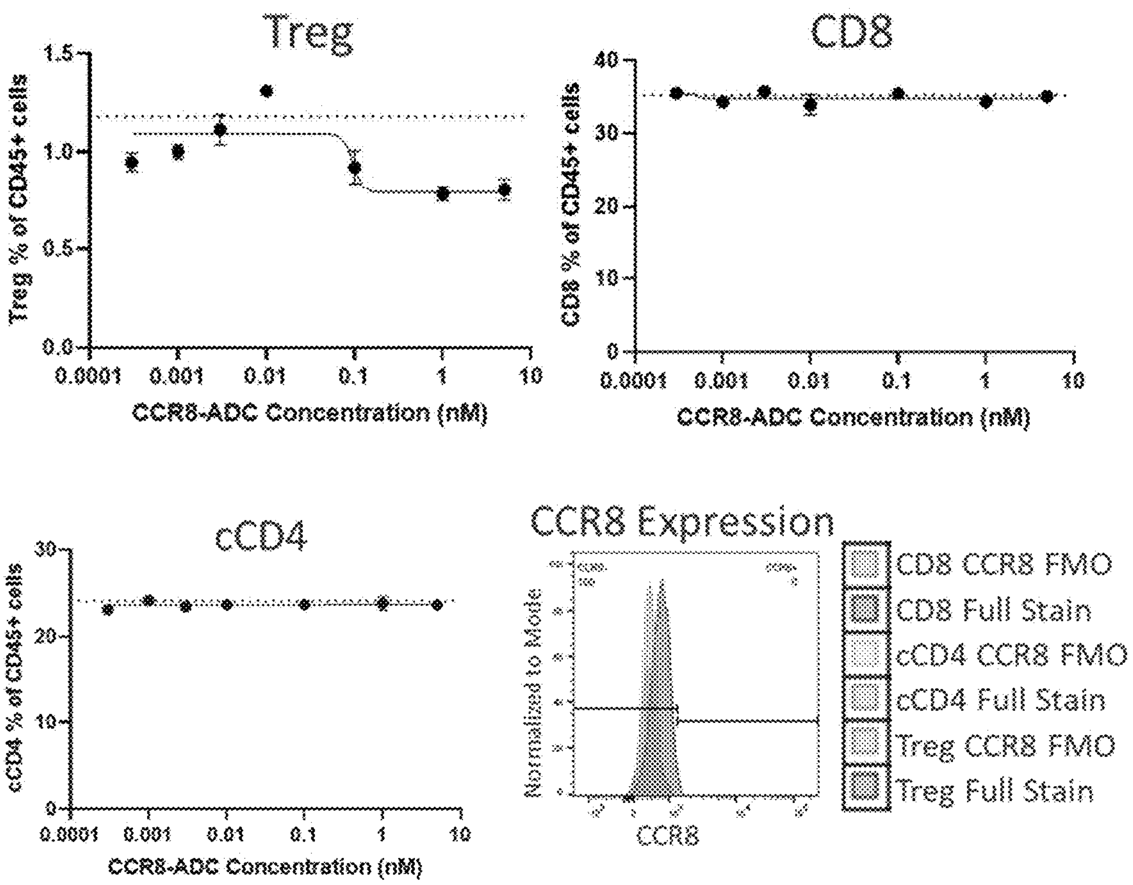
Figure 8C:
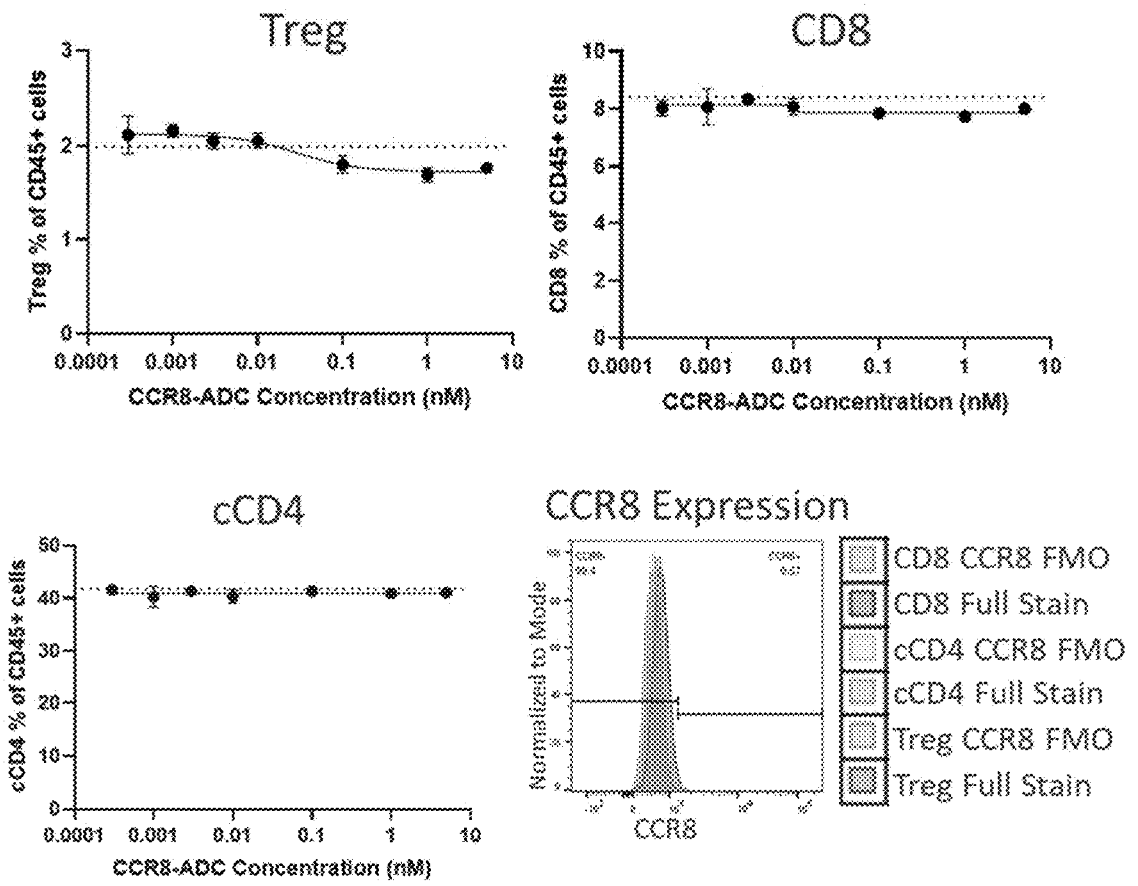

To assess the ADC's ability to kill Tregs in NSCLC samples, a portion of NSCLC cancer dispersed tumor cells (DTCs), matched NSCLC cancer PBMCs, and non-cancer PBMCs were stained for flow cytometry (Day 0 time point) to assess CCR8 expression on T cell populations (FIGS. 8A-8C, bottom right plot). Specifically, CD8, cCD4 cells, and Treg cells were analyzed following staining with the CCR8 FMO (fluorescence minus one) panel and with the full panel (Full Stain). Another portion of the same samples were treated with either vehicle control (PBS) or CCR8-ADC at concentrations of 5, 1, 0.1, 0.01, 0.003, 0.001, and 0.0003 nM for 96 hours. The samples were then stained for flow cytometry to quantify the percentage of Tregs, CD8 Tcells, and cCD4 T cells after treatment (FIGS. 8A-8C).

Compared to the FMO panel, the only T cell population that expressed CCR8 with the Tregs from the NSCLC cancer DTC sample (FIG. 8A). Additionally, the Tregs from the NSCLC cancer DTC samples were the only T cell population depleted by treatment with the CCR8-ADC (IC50: 0.002776 nM, as calculated by GraphPad Prism software).

These data show that CCR8-ADC potently and specifically depletes only CCR8-expressing Tregs in DTC samples and has minimal impact on Tregs from PBMC that do not express CCR8 and minimal impact on CD8 and cCD4 T cells. Together, these data demonstrate that CCR8-ADC is effective at killing Tregs in NSCLC tumor samples and can enhance anti-tumor immunity in NSCLC by eliminating immunosuppressive CCR8+ Tregs.

Example 12: CCR8-ADC Decreases M2 Macrophages in the Tumor Microenvironment

The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a cleavable linker, resulting in ADCs having a structure of Formula (A-I-c) (ADC-1). The ADCs were then assessed for their ability to modulate macrophage populations in tumor samples.

To assess the ADC's ability to modulate macrophage populations in tumor samples, the mechanism of action of Fc-enabled CCR8 antibodies was compared to that of CCR8-ADC. Briefly, a CCR8 monoclonal antibody was generated by engineering the binding portions of a CCR8-ADC (CCR8 Ab #1) with mIgG2a Fc to engage mouse Fc-receptors in in vivo mouse models. Human CCR8 knock-in (huCCR8-KI) mice were inoculated subcutaneously with MC38 tumors. When the tumors reached ~80-120 $mm^3$ (Day 0), the mice were treated intravenously with either vehicle control (PBS), CCR8 mAb (CCR8 Ab #1) mIgG2a (1.25 mg/kg or 5 mg/kg), or CCR8-ADC (1.25 mg/kg or 2.5 mg/kg). CCR8 mAb (CCR8 Ab #1) mIgG2a was administered twice weekly for two weeks (4 total doses) and CCR8-ADC was administered once weekly for two weeks (2 total doses). On Day 14, tumors were harvested and processed into single cell suspensions for flow cytometry staining to analyze macrophage phenotype.

Figure 9A:
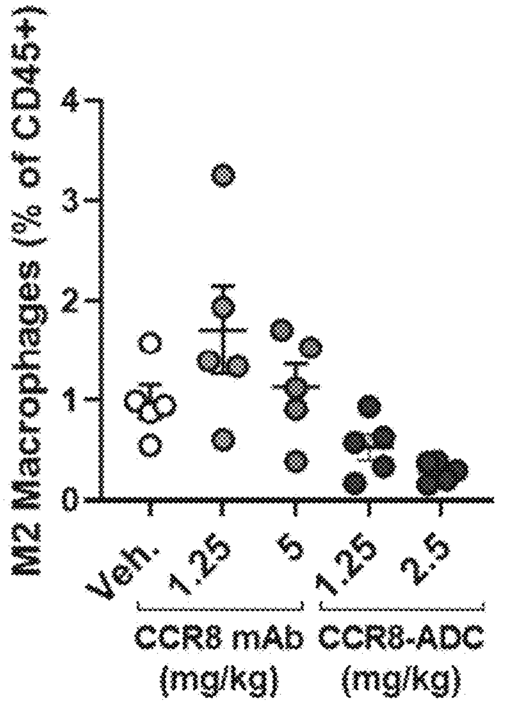
FIGS. 9A-9B show the evaluation of an ADC comprising an anti-CCR8 antibody on macrophage populations.
Figure 9B:
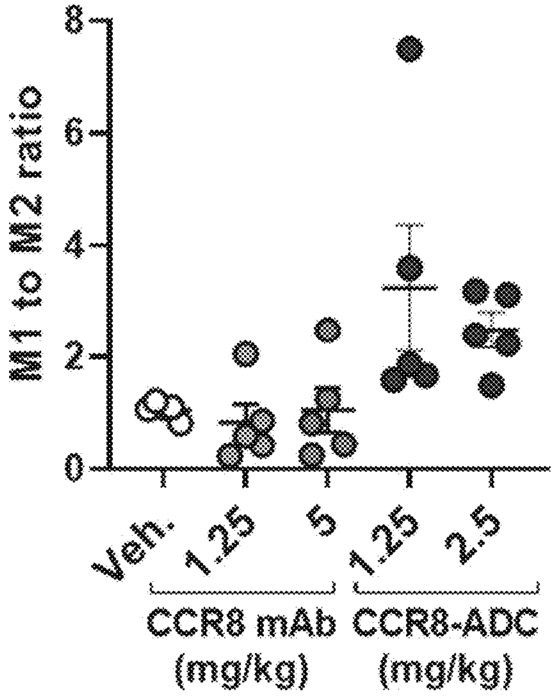

Treg depletion via CCR8-ADC decreased M2 macrophages in the tumor, shifting the balance to a more favorable increase in M1/M2 ratio, while the CCR8 monoclonal antibody did not impact macrophages in the tumor microenvironment (FIGS. 9A-9B). These data show that CCR8-ADC modulates macrophage phenotype in the tumor microenvironment in a manner not achieved by Fc-enabled CCR8 monoclonal antibodies. Together, this Example demonstrates that Treg depletion by CCR8-ADC can overcome additional macrophage-driven suppressive mechanisms in the tumor microenvironment.

Example 13: CCR8-ADC Specifically Depletes CCR8+ Cells without the Need for Exogenously Added NK Cells The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a cleavable linker, resulting in ADCs having a structure of Formula (A-I-c) (ADC-1). The ADCs were then assessed for their ability to specifically deplete CCR8+ cells without the need for exogenously added natural killer (NK) cells.

To assess the ADC's ability to specifically deplete CCR8+ cells without the need for exogenously added natural killer (NK) cells, NK cells were isolated from frozen PBMCs to use as effector cells in a co-culture killing assay with HUT-78 target cells that endogenously express human CCR8. HUT-78 wild-type cells alone, HUT-78 wild-type cells+NK cells (5:1 NK cell:HUT-78 cell ratio), or CCR8 Knockout HUT-78 cells+NK cells (5:1 NK cell:HUT-78 cell ratio) were treated with vehicle control (PBS), CCR8-ADC, or Fc-enabled aFucosylated (aFuc) mAbs at 1000, 10, 0.1, and 0.01 ng/mL for 96 hours. CellTiter-Glo (CTG) was used to assess viability and was normalized to vehicle control treated samples.

Figure 10:
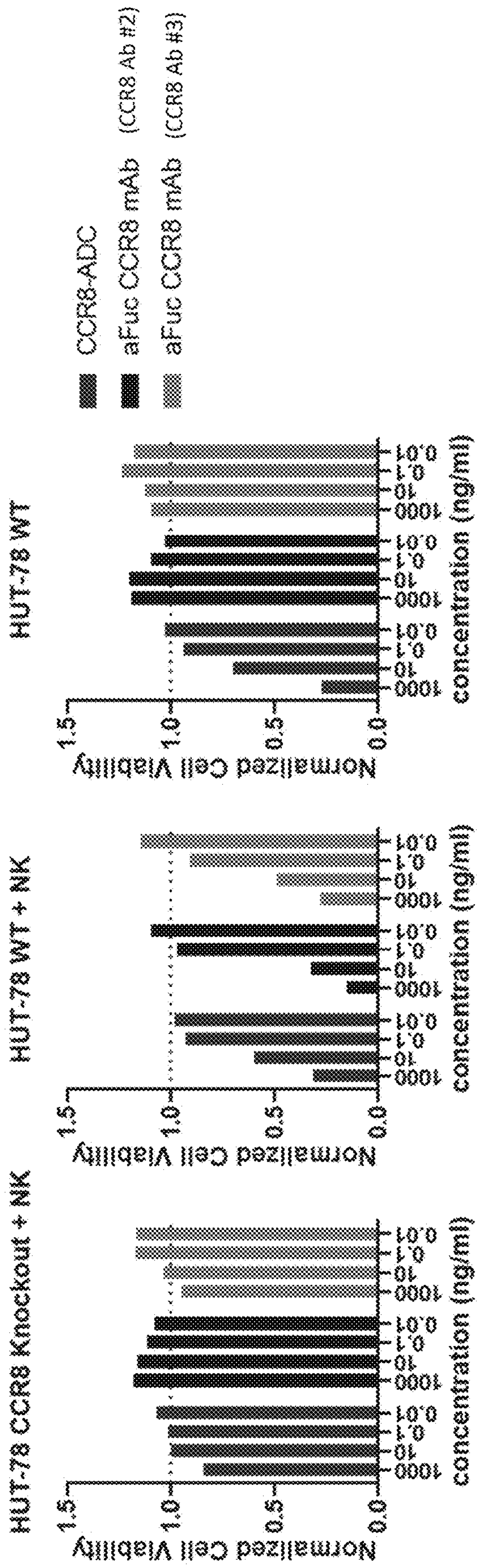
FIG. 10 shows normalized cell viability (CellTiter-Glo-normalized to PBS vehicle control treated samples) of HUT-78 CCR8 knockout cells+NK cells (left panel), HUT-78 wild-type cells+NK cells (middle panel), or HUT-78 wild-type cells alone (right panel) treated with either CCR8-ADC, aFuc CCR8 mAb (CCR8 Ab #2), or aFuc CCR8 mAb (CCR8 Ab #3) for 96 hours.

HUT-78 target cell killing by CCR8-ADC and both aFuc CCR8 mAbs (CCR8 Ab #2 and CCR8 Ab #3) was CCR8-dependent, as minimal impacts on cell viability were observed in CCR8 Knockout HUT-78 cells, even in the presence of NK cells (FIG. 10, left panel). All three CCR8-targeting agents [CCR8-ADC, aFuc CCR8 mAb (CCR8 Ab #2), and aFuc CCR8 mAb (CCR8 Ab #3)] killed HUT-78 WT cells in the presence of NK cells (FIG. 10 middle panel). However, in HUT-78 wild-type cells alone, only CCR8-ADC was able to kill CCR8-expressing target cells (FIG. 10, right panel).

These data demonstrate that, unlike Fc-enabled aFucosylated CCR8 mAbs, CCR8-ADC specifically depletes CCR8+ cells in the absence of exogenously added NK cells. These data suggest that CCR8-ADC is more effective than Fc-enabled CCR8 mAbs in patients whose solid tumors are not infiltrated with effector cells, such as NK cells, that can vary in frequency and may be functionally inhibited in the tumor microenvironment.

Example 14: CCR8-ADC is More Efficacious than CCR8 Monoclonal Antibody In Vivo The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a cleavable linker, resulting in ADCs having a structure of Formula (A-I-c) (ADC-1). The in vivo efficacy of CCR8-ADC was compared to CCR8 monoclonal antibodies.

Figure 11A:
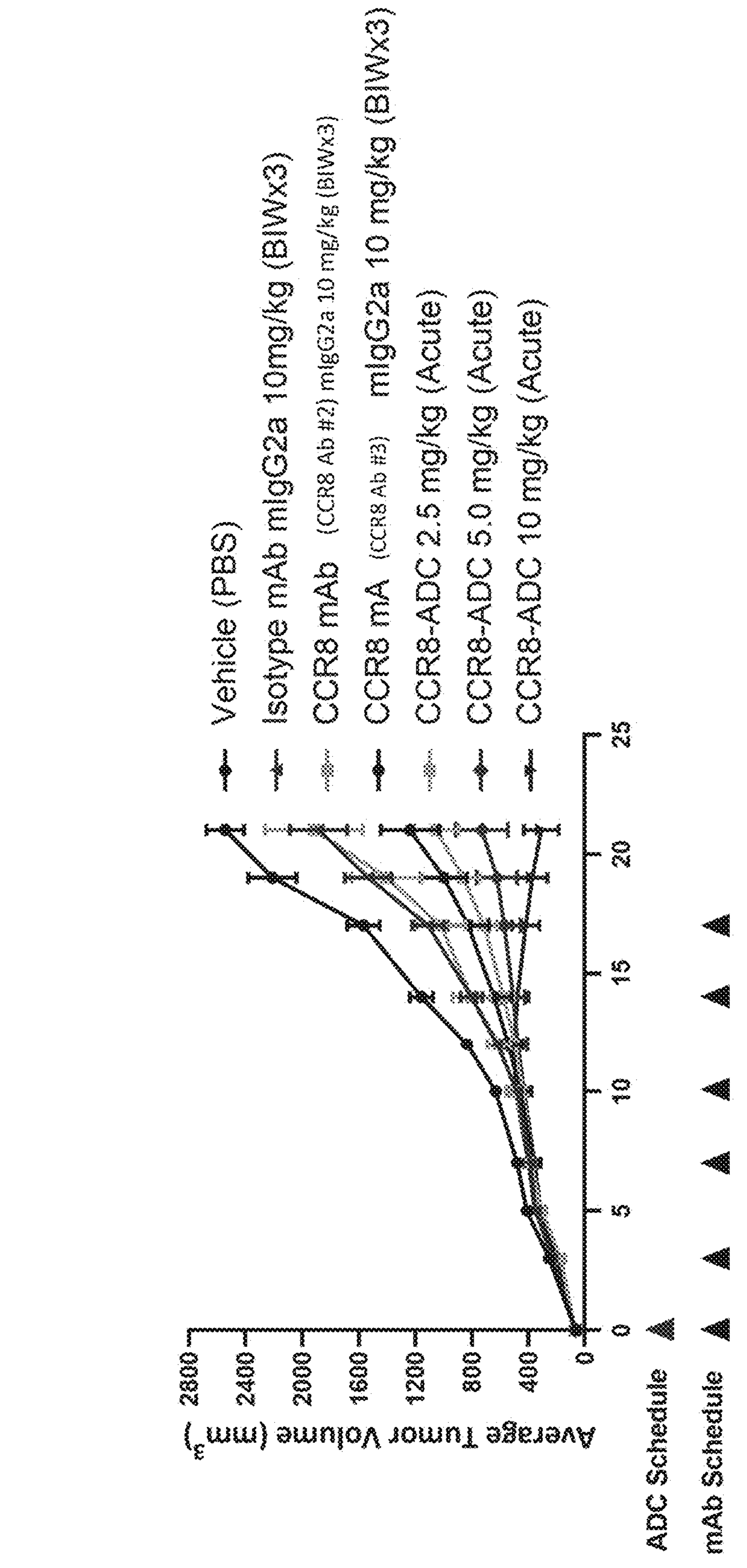
FIGS. 11A-11B show a comparison of the in vivo efficacy of a CCR8-ADC and a CCR8 monclonal antibody.
Figure 11B:
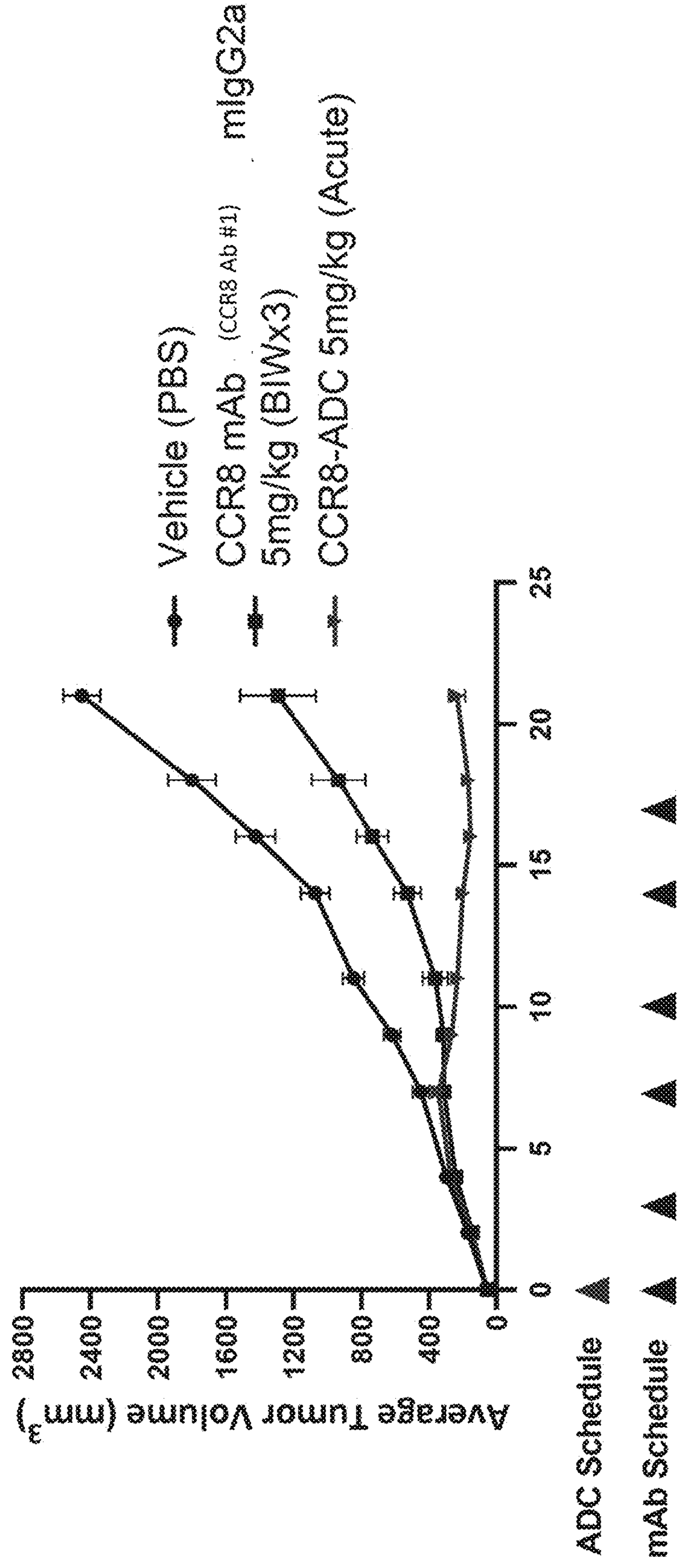

To assess the in vivo efficacy of CCR8-ADC compared to CCR8 monoclonal antibodies, multiple CCR8 monoclonal antibodies (mAbs) were engineered with mIgG2a Fc to engage mouse Fc-receptors in in vivo mouse models. CCR8 mAb (CCR8 Ab #2) and CCR8 mAb (CCR8 Ab #3) mIgG2a have distinct binding regions, whereas the binding regions of CCR8 Ab #1 mIgG2a overlaps with the binding regions of CCR8-ADC. Human CCR8 knock-in (huCCR8-KI) mice were inoculated subcutaneously with MC38 tumors. When the tumors reached ~65 $mm^3$ (FIG. 11A) or ~55 mm3 (FIG. 111B) (Day 0), the mice were randomized and treated intravenously with either vehicle control (PBS), isotype mAb mIgG2a (10 mg/kg), CCR8 mAb (CCR8 Ab #2) mIgG2a (10 mg/kg), CCR8 mAb (CCR8 Ab #3) mIgG2a (10 mg/kg), or CCR8-ADC (2.5, 5, or 10 mg/kg) (FIG. 11A), or vehicle control (PBS), CCR8 mAb (CCR8 Ab #1) mIgG2a (5 mg/kg), or CCR8-ADC (5 mg/kg) (FIG. 11B). The Fc-enabled mAbs were administered twice weekly for three weeks (6 total doses) and CCR8-ADC was administered acutely (1 total dose).

The data demonstrate that even when given as a single acute dose, CCR8-ADC was more efficacious in vivo than either Fc-enabled CCR8 mAbs with distinct binding regions (FIG. 11A) or Fc-enabled CCR8 mAb, which comprises binding regions that overlap with those of CCR8-ADC (FIG. 11B), given twice weekly for 3 weeks. These data suggest that direct Treg depletion by CCR8-ADC is more efficacious than Treg depletion via Fc-enabled mAbs.

Example 15: CCR8-ADC Demonstrates a More Robust Intratumoral Treg Depletion and Increase in CD8/Treg Ratio Compared to Fc-Enabled Anti-CCR8 Monoclonal Antibody Upon Repeat Dosing The anti-CCR8 antibody conjugates (ADCs) were prepared by conjugating an anti-CCR8 antibody comprising a heavy chain region of SEQ ID NO: 145 and a light chain region of SEQ ID NO: 146 to amanitin via a cleavable linker, resulting in ADCs having a structure of Formula (A-I-c) (ADC-1). The efficacy of CCR8-ADC was compared to a CCR8 monoclonal antibody.

To assess the efficacy of CCR8-ADC compared to a CCR8 monoclonal antibody (mAb), a CCR8 mAb was generated by engineering the binding portion of a CCR8-ADC (CCR8 Ab #1) with mIgG2a Fc to engage mouse Fc-receptors in in vivo mouse models. Human CCR8 knock-in (huCCR8-KI) mice were inoculated subcutaneously with MC38 tumors. When the tumors reached ~80-120 $mm^3$ (Day 0), the mice were treated intravenously with either vehicle control (PBS), CCR8 mAb (CCR8 Ab #1) mIgG2a (1.25 or 5 mg/kg), or CCR8-ADC (1.25 or 2.5 mg/kg). CCR8 mAb (CCR8 Ab #1) mIgG2a was administered twice weekly for two weeks (4 total doses) and CCR8-ADC was administered once weekly for two weeks (2 total doses). On Day 14, tumors were harvested and processed into single cell suspensions for flow cytometry staining to analyze T cell populations.

Figure 12:
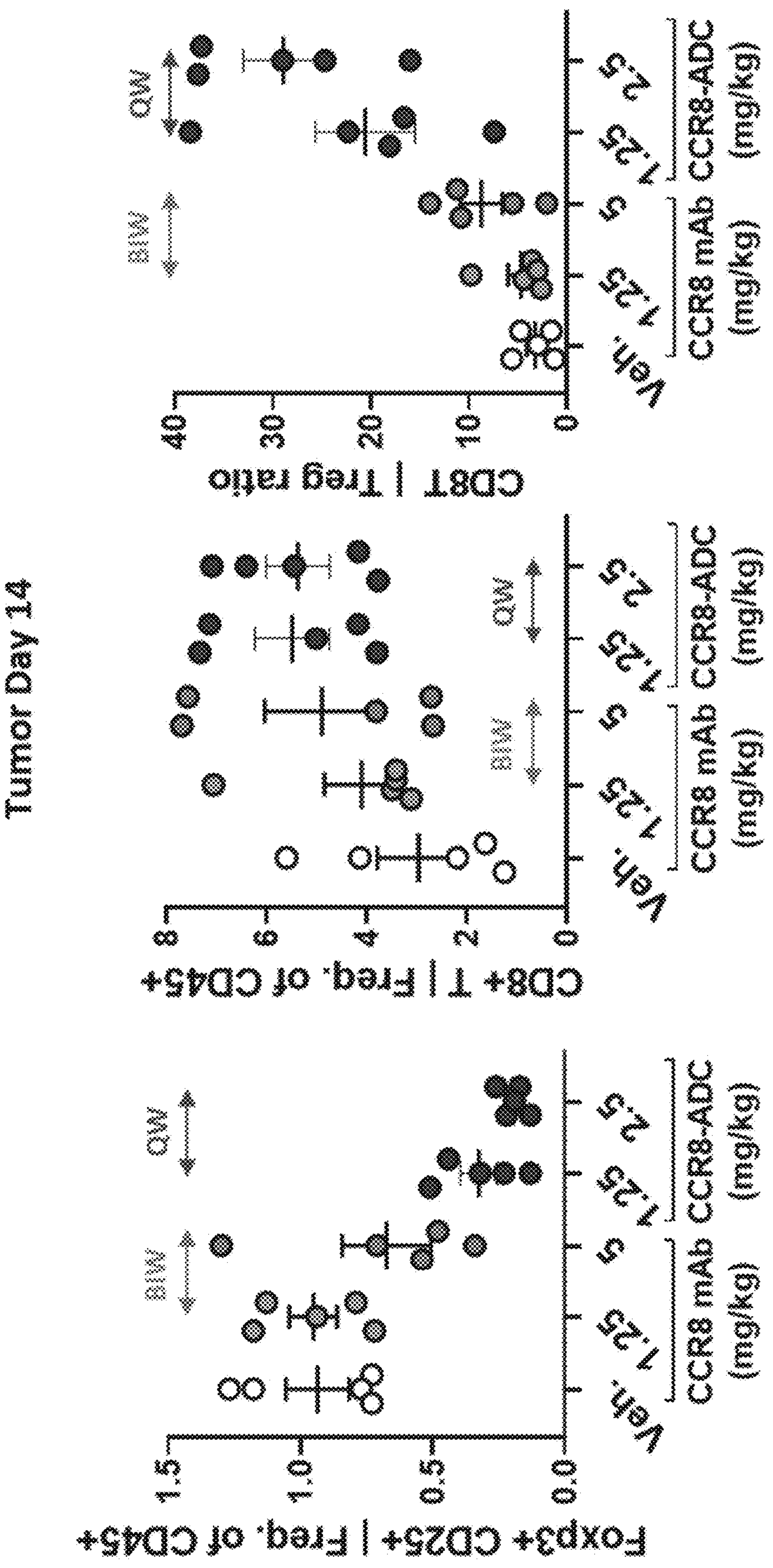
FIG. 12 shows quantification of Foxp3+CD25+Tregs (as a percentage of CD45+ cells), CD8 (as a percentage of CD45+ cells), and the CD8/Treg Ratio in the tumor of MC38 tumor-bearing huCCR8-KI mice 14 days post-treatment with either vehicle control [PBS] (Veh.), CCR8 mAb (CCR8 Ab #1) mIgG2a (CCR8 mAb), or CCR8-ADC.

CCR8-ADC given once weekly for two weeks (2 total doses) demonstrated a more robust Treg depletion and increase in the CD8/Treg ratio in the tumor than CCR8 mAb given twice weekly for two weeks (4 total doses) (FIG. 12). These data demonstrate that CCR8-ADC induces more potent intratumoral Treg depletion than CCR8 mAb and suggest that CCR8-ADC may potentially trigger enhanced anti-tumor immunity by increasing the CD8/Treg ratio when compared to Fc-enabled mAbs.

What is claimed is:

1. An antibody that binds to CCR8 wherein the antibody comprises:

a heavy chain variable domain (VH) comprising a heavy chain complementary determining region 1 (CDR-H1) comprising the amino acid sequence FQFNAYAMN (SEQ ID NO: 88); a heavy chain complementary determining region 2 (CDR-H2) comprising the amino acid sequence RIRSKSNNYATYYADSVKD (SEQ ID NO: 26); a heavy chain complementary determining region 3 (CDR-H3) comprising the amino acid sequence VRQSYGNSNYAMDH (SEQ ID NO: 90); and a light chain variable domain (VL) comprising a light chain complementary determining region 1 (CDR-L1) comprising the amino acid sequence RSSKSLLHSNGNTYLY (SEQ ID NO: 28); a light chain complementary determining region 2 (CDR-L2) comprising the amino acid sequence RVSNLAS (SEQ ID NO: 92); a light chain complementary determining region 3 (CDR-L3) comprising the amino acid sequence MQHFEYPFT (SEQ ID NO: 96).

2. The antibody of claim 1, wherein the VH comprises the amino acid sequence SEQ ID NO: 99, and the VL comprises the amino acid sequence SEQ ID NO: 100.

3. The antibody of claim 1, wherein the antibody is a full-length IgG.

4. The antibody of claim 3, wherein the full-length IgG comprises a heavy chain constant region of isotype IgG1.

5. The antibody of claim 4, wherein the heavy chain constant region comprises the amino acid sequence SEQ ID NO: 133.

6. The antibody of claim 4, wherein the heavy chain constant region comprises an L235A (EU numbering) and a G237A (EU numbering) mutation relative to the heavy chain constant region as set forth in SEQ ID NO: 133.

7. The antibody of claim 6, wherein the heavy chain constant region further comprises a D265C (EU numbering) mutation relative to the heavy chain constant region as set forth in SEQ ID NO: 133.

8. The antibody of claim 1, wherein the antibody comprises a light chain constant region comprising the amino acid sequence SEQ ID NO: 135.

9. An antibody-drug conjugate (ADC) having the structure of Formula (A):

(A)

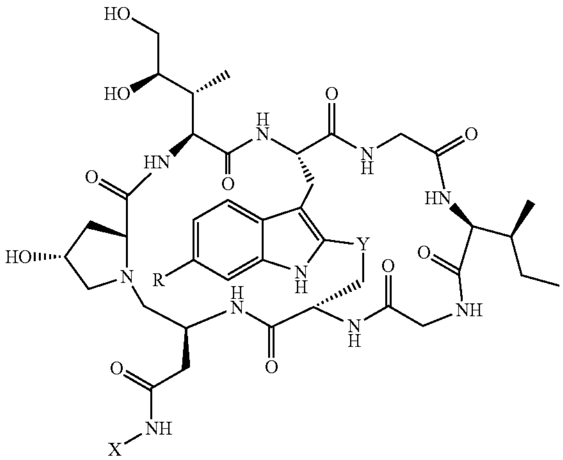

or a pharmaceutically acceptable salt, solvate, hydrate, tautomer, stereoisomer, diastereomer, or enantiomer thereof, wherein:

R is H, —OH, or —O-L-Z-Ab;

Y is —S—, —S(═O)—, or —$SO_2$—;

X is H or -L-Z-Ab, wherein:

L is a linker of the formula: —$(CH_2)_n$— or -$Q^{L1}$-$Q^1$-$Q^{L2}$-, wherein:

n is 2, 3, 4, 5, 6, 7, 8, 9, or 10; or each of $Q^{L1}$ and $Q^{L2}$ is optionally substituted alkylene and $Q^1$ is a dipeptide;

Z is

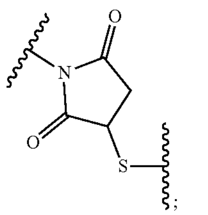 [SMILES: *SC1CC(=O)N(*)C1=O]

provided that:

if X is H then R is —O-L-Z-Ab, and if X is -L-Z-Ab then R is H or —OH; and wherein Ab is an antibody comprising:

a heavy chain variable domain (VH) comprising a heavy chain complementary determining region 1 (CDR-H1) comprising the amino acid sequence FQFNAYAMN (SEQ ID NO: 88); a heavy chain complementary determining region 2 (CDR-H2) comprising the amino acid sequence RIRSKSNNYATYYADSVKD (SEQ ID NO: 26); a heavy chain complementary determining region 3 (CDR-H3) comprising the amino acid sequence VRQSYGNSNYAMDH (SEQ ID NO: 90); and a light chain variable domain (VL) comprising a light chain complementary determining region 1 (CDR-L1) comprising the amino acid sequence RSSKSLLHSNGNTYLY (SEQ ID NO: 28); a light chain complementary determining region 2 (CDR-L2) comprising the amino acid sequence RVSNLAS (SEQ ID NO: 92); a light chain complementary determining region 3 (CDR-L3) comprising the amino acid sequence MQHFEYPFT (SEQ ID NO: 96).

10. The ADC of claim 9, wherein the ADC is of the Formula (A-I-c):

(A-I-c)

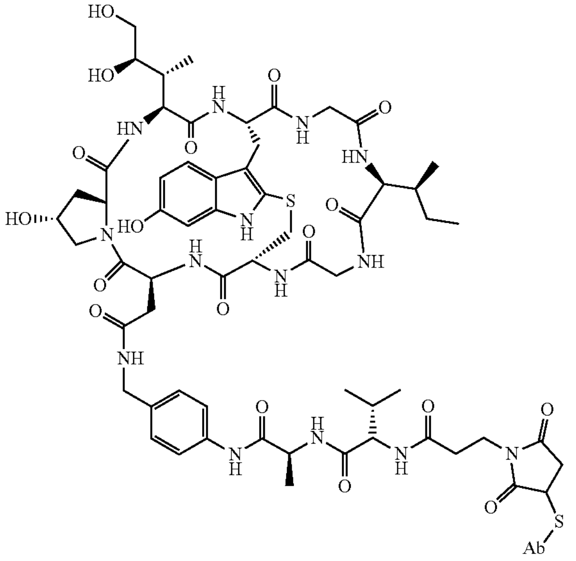

or a pharmaceutically acceptable salt, solvate, hydrate, tautomer, stereoisomer, diastereomer, or enantiomer thereof.

11. The ADC of claim 9, wherein the ADC is of the Formula (A-I-e):

(A-I-e)

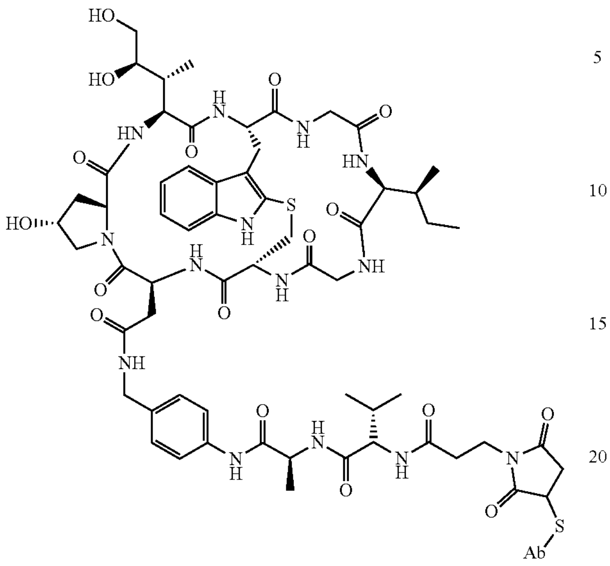

or a pharmaceutically acceptable salt, solvate, hydrate, tautomer, stereoisomer, diastereomer, or enantiomer thereof.

12. The ADC of claim 9, wherein the ADC is of Formula (A-II-b):

or a pharmaceutically acceptable salt, solvate, hydrate, tautomer, stereoisomer, diastereomer, or enantiomer thereof, wherein n is 1, 2, 3, 4, 5, 6, 7, 8, 9, or 10.

13. The ADC of claim 12, or a pharmaceutically acceptable salt, solvate, hydrate, tautomer, stereoisomer, diastereomer, or enantiomer thereof, wherein n is 5.

14. The ADC of claim 10, wherein the VH comprises the amino acid sequence SEQ ID NO: 99, and the VL comprises the amino acid sequence SEQ ID NO: 100.

15. The ADC of claim 11, wherein the antibody comprises a heavy chain comprising the amino acid sequence of SEQ ID NO: 145 and a light chain comprising the amino acid sequence of SEQ ID NO: 146.

16. The ADC of claim 12, wherein n is 5 and the antibody comprises a heavy chain comprising the amino acid sequence of SEQ ID NO: 145 and a light chain comprising the amino acid sequence of SEQ ID NO: 146.

17. A method comprising administering to a subject the ADC of claim 9, or a pharmaceutically acceptable salt, solvate, hydrate, tautomer, stereoisomer, diastereomer, or enantiomer thereof, wherein the subject has cancer.

18. The method of claim 17 wherein the cancer is microsatellite stable colorectal cancer, non-small cell lung cancer, triple negative breast cancer, or renal cell carcinoma.

19. A method of treating a subject having non-small cell lung cancer, the method comprising administering to the subject the ADC of claim 9, or a pharmaceutically acceptable salt, solvate, hydrate, tautomer, stereoisomer, diastereomer, or enantiomer thereof.

20. An antibody-drug conjugate (ADC) having the structure of Formula (A-I-c):

(A-II-b)

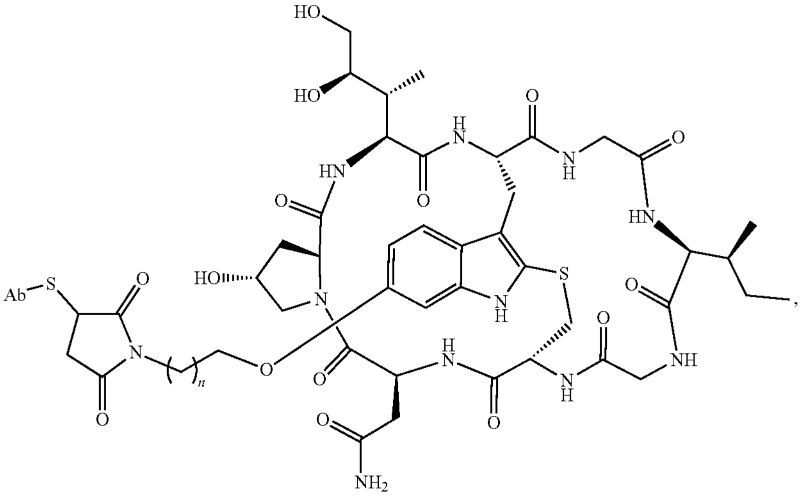

(A-I-c)
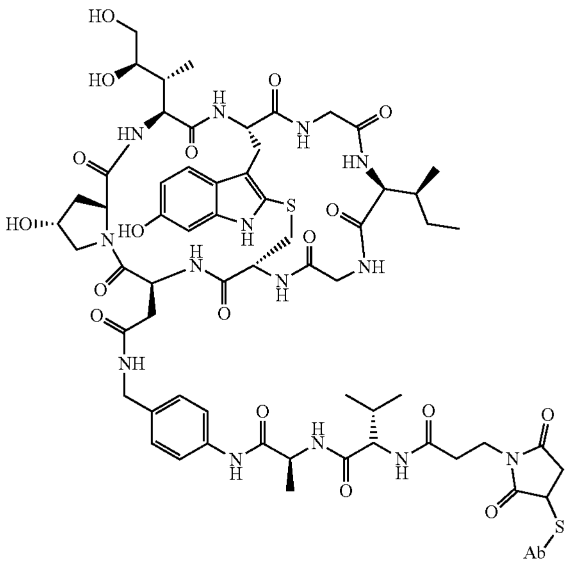
or a pharmaceutically acceptable salt, solvate, hydrate, tautomer, stereoisomer, diastereomer, or enantiomer thereof,
wherein the antibody comprises a heavy chain comprising the amino acid sequence of SEQ ID NO: 145 and a light chain comprising the amino acid sequence of SEQ ID NO: 146.
* * * * *

SEQUENCE LISTING

```
Sequence total quantity: 148
SEQ ID NO: 1            moltype =   length =
SEQUENCE: 1
000

SEQ ID NO: 2            moltype = AA  length = 17
FEATURE                 Location/Qualifiers
source                  1..17
                        mol_type = protein
                        organism = synthetic construct
SEQUENCE: 2
VISYDGSNKY YAFSVKG                                                 17

SEQ ID NO: 3            moltype = AA  length = 16
FEATURE                 Location/Qualifiers
source                  1..16
                        mol_type = protein
                        organism = synthetic construct
SEQUENCE: 3
ARVRRIAGRA GYGMDV                                                  16

SEQ ID NO: 4            moltype = AA  length = 11
FEATURE                 Location/Qualifiers
source                  1..11
                        mol_type = protein
                        organism = synthetic construct
SEQUENCE: 4
RASQSINSYL N                                                       11

SEQ ID NO: 5            moltype = AA  length = 7
FEATURE                 Location/Qualifiers
source                  1..7
                        mol_type = protein
                        organism = synthetic construct
SEQUENCE: 5
AASSLQS                                                            7

SEQ ID NO: 6            moltype = AA  length = 9
FEATURE                 Location/Qualifiers
source                  1..9
                        mol_type = protein
                        organism = synthetic construct
SEQUENCE: 6
QESYSTPIT                                                          9

SEQ ID NO: 7            moltype =   length =
SEQUENCE: 7
000

SEQ ID NO: 8            moltype =   length =
SEQUENCE: 8
000

SEQ ID NO: 9            moltype = AA  length = 10
FEATURE                 Location/Qualifiers
source                  1..10
                        mol_type = protein
                        organism = synthetic construct
SEQUENCE: 9
YSISSGYYWG                                                         10

SEQ ID NO: 10           moltype = AA  length = 16
FEATURE                 Location/Qualifiers
source                  1..16
                        mol_type = protein
                        organism = synthetic construct
SEQUENCE: 10
SIYHSGNTYY RPSLKS                                                  16

SEQ ID NO: 11           moltype = AA  length = 13
FEATURE                 Location/Qualifiers
source                  1..13
                        mol_type = protein
                        organism = synthetic construct
SEQUENCE: 11
ARGKGGSWTA FGP                                                     13

SEQ ID NO: 12           moltype = AA  length = 11
```

```
FEATURE                Location/Qualifiers
source                 1..11
                       mol_type = protein
                       organism = synthetic construct
SEQUENCE: 12
RASQSISSFL N                                               11

SEQ ID NO: 13          moltype = AA  length = 9
FEATURE                Location/Qualifiers
source                 1..9
                       mol_type = protein
                       organism = synthetic construct
SEQUENCE: 13
QQGHSTPPT                                                  9

SEQ ID NO: 14          moltype = AA  length = 120
FEATURE                Location/Qualifiers
source                 1..120
                       mol_type = protein
                       organism = synthetic construct
SEQUENCE: 14
QVQLQESGPG LVKPSETLSL TCAVSGYSIS SGYYWGWIRQ PPGKGLEWIG SIYHSGNTYY  60
RPSLKSRVTI SVDTSKNQFS LKLSSVTAAD TAVYYCARGK GGSWTAFGPW GQGTLVTVSS  120

SEQ ID NO: 15          moltype =   length =
SEQUENCE: 15
000

SEQ ID NO: 16          moltype = AA  length = 11
FEATURE                Location/Qualifiers
source                 1..11
                       mol_type = protein
                       organism = synthetic construct
SEQUENCE: 16
GSISSSSYAW G                                               11

SEQ ID NO: 17          moltype = AA  length = 16
FEATURE                Location/Qualifiers
source                 1..16
                       mol_type = protein
                       organism = synthetic construct
SEQUENCE: 17
SIYYTGSTYY NPSLKS                                          16

SEQ ID NO: 18          moltype = AA  length = 13
FEATURE                Location/Qualifiers
source                 1..13
                       mol_type = protein
                       organism = synthetic construct
SEQUENCE: 18
LRGHRRDYIA FDI                                             13

SEQ ID NO: 19          moltype = AA  length = 11
FEATURE                Location/Qualifiers
source                 1..11
                       mol_type = protein
                       organism = synthetic construct
SEQUENCE: 19
RASQSISSYL N                                               11

SEQ ID NO: 20          moltype = AA  length = 8
FEATURE                Location/Qualifiers
source                 1..8
                       mol_type = protein
                       organism = synthetic construct
SEQUENCE: 20
QQSHNLPT                                                   8

SEQ ID NO: 21          moltype = AA  length = 121
FEATURE                Location/Qualifiers
source                 1..121
                       mol_type = protein
                       organism = synthetic construct
SEQUENCE: 21
QLQLQESGPG LVKPSETLSL TCTVSGGSIS SSSYAWGWIR QPPGKRLEWI GSIYYTGSTY  60
YNPSLKSRVT ISVDTSKNQF SLKLSSVTAA DTAVYYCLRG HRRDYIAFDI WGQGTMVTVS  120
S                                                          121

SEQ ID NO: 22          moltype = AA  length = 106
```

```
FEATURE                 Location/Qualifiers
source                  1..106
                        mol_type = protein
                        organism = synthetic construct
SEQUENCE: 22
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SHNLPTFGGG TKVEIK                106

SEQ ID NO: 23           moltype = AA  length = 13
FEATURE                 Location/Qualifiers
source                  1..13
                        mol_type = protein
                        organism = synthetic construct
SEQUENCE: 23
VRGHRRDYIA FDI                                                     13

SEQ ID NO: 24           moltype = AA  length = 121
FEATURE                 Location/Qualifiers
source                  1..121
                        mol_type = protein
                        organism = synthetic construct
SEQUENCE: 24
QLQLQESGPG LVKPSETLSL TCTVSGGSIS SSSYAWGWIR QPPGKRLEWI GSIYYTGSTY  60
YNPSLKSRVT ISVDTSKNQF SLKLSSVTAA DTAVYYCVRG HRRDYIAFDI WGQGTMVTVS  120
S                                                                  121

SEQ ID NO: 25           moltype = AA  length = 9
FEATURE                 Location/Qualifiers
source                  1..9
                        mol_type = protein
                        organism = synthetic construct
SEQUENCE: 25
FTFNAYAMN                                                          9

SEQ ID NO: 26           moltype = AA  length = 19
FEATURE                 Location/Qualifiers
source                  1..19
                        mol_type = protein
                        organism = synthetic construct
SEQUENCE: 26
RIRSKSNNYA TYYADSVKD                                               19

SEQ ID NO: 27           moltype = AA  length = 14
FEATURE                 Location/Qualifiers
source                  1..14
                        mol_type = protein
                        organism = synthetic construct
SEQUENCE: 27
VRQSYGNSNY AMDY                                                    14

SEQ ID NO: 28           moltype = AA  length = 16
FEATURE                 Location/Qualifiers
source                  1..16
                        mol_type = protein
                        organism = synthetic construct
SEQUENCE: 28
RSSKSLLHSN GNTYLY                                                  16

SEQ ID NO: 29           moltype =   length =
SEQUENCE: 29
000

SEQ ID NO: 30           moltype = AA  length = 9
FEATURE                 Location/Qualifiers
source                  1..9
                        mol_type = protein
                        organism = synthetic construct
SEQUENCE: 30
MQHLEYPFT                                                          9

SEQ ID NO: 31           moltype =   length =
SEQUENCE: 31
000

SEQ ID NO: 32           moltype =   length =
SEQUENCE: 32
000

SEQ ID NO: 33           moltype =   length =
```

```
SEQUENCE: 33
000

SEQ ID NO: 34          moltype =   length =
SEQUENCE: 34
000

SEQ ID NO: 35          moltype =   length =
SEQUENCE: 35
000

SEQ ID NO: 36          moltype =   length =
SEQUENCE: 36
000

SEQ ID NO: 37          moltype =   length =
SEQUENCE: 37
000

SEQ ID NO: 38          moltype =   length =
SEQUENCE: 38
000

SEQ ID NO: 39          moltype = AA  length = 9
FEATURE                Location/Qualifiers
source                 1..9
                       mol_type = protein
                       organism = synthetic construct
SEQUENCE: 39
FTFSSHGMH                                                         9

SEQ ID NO: 40          moltype = AA  length = 7
FEATURE                Location/Qualifiers
source                 1..7
                       mol_type = protein
                       organism = synthetic construct
SEQUENCE: 40
SASSLQS                                                           7

SEQ ID NO: 41          moltype = AA  length = 9
FEATURE                Location/Qualifiers
source                 1..9
                       mol_type = protein
                       organism = synthetic construct
SEQUENCE: 41
QESYSTPIF                                                         9

SEQ ID NO: 42          moltype = AA  length = 123
FEATURE                Location/Qualifiers
source                 1..123
                       mol_type = protein
                       organism = synthetic construct
SEQUENCE: 42
QVQLVESGGG VVQPGRSLRL SCAASGFTFS SHGMHWVRQA PGKGLEWVAV ISYDGSNKYY  60
AFSVKGRFTI SRDNSKNTLY LQMNSLRVED TAVYYCARVR RIAGRAGYGM DVWGQGTTVT  120
VSS                                                               123

SEQ ID NO: 43          moltype = AA  length = 107
FEATURE                Location/Qualifiers
source                 1..107
                       mol_type = protein
                       organism = synthetic construct
SEQUENCE: 43
DIQMTQSPSS LSASVGDRVT ITCRASQSIN SYLNWYQQKP GKAPKLLIYS ASSLQSGVPS  60
RFSGSGSGTD FTLTISSLQP EDFATYYCQE SYSTPIFFGG GTKVEIK               107

SEQ ID NO: 44          moltype = AA  length = 11
FEATURE                Location/Qualifiers
source                 1..11
                       mol_type = protein
                       organism = synthetic construct
SEQUENCE: 44
RASQSIVSYL N                                                      11

SEQ ID NO: 45          moltype = AA  length = 7
FEATURE                Location/Qualifiers
source                 1..7
                       mol_type = protein
                       organism = synthetic construct
```

-continued

```
SEQUENCE: 45
AASILQS                                                      7

SEQ ID NO: 46          moltype = AA  length = 107
FEATURE                Location/Qualifiers
source                 1..107
                       mol_type = protein
                       organism = synthetic construct
SEQUENCE: 46
DIQMTQSPSS LSASVGDRVT ITCRASQSIV SYLNWYQQKP GKAPKLLIYA ASILQSGVPS  60
RFSGSGSGTD FTLTISSLQP EDFATYYCQE SYSTPITFGG GTKVEIK              107

SEQ ID NO: 47          moltype = AA  length = 11
FEATURE                Location/Qualifiers
source                 1..11
                       mol_type = protein
                       organism = synthetic construct
SEQUENCE: 47
RASQSISSFA N                                                 11

SEQ ID NO: 48          moltype = AA  length = 107
FEATURE                Location/Qualifiers
source                 1..107
                       mol_type = protein
                       organism = synthetic construct
SEQUENCE: 48
DIQMTQSPSS LSASVGDRVT ITCRASQSIS SFANWYQQKP GKAPKLLISA ASSLQSGVPS  60
RFSGSGSGTD FTLTISSLQP EDFATYYCQQ GHSTPPTFGG GTKVEIK              107

SEQ ID NO: 49          moltype = AA  length = 11
FEATURE                Location/Qualifiers
source                 1..11
                       mol_type = protein
                       organism = synthetic construct
SEQUENCE: 49
RASQSISSLL N                                                 11

SEQ ID NO: 50          moltype = AA  length = 107
FEATURE                Location/Qualifiers
source                 1..107
                       mol_type = protein
                       organism = synthetic construct
SEQUENCE: 50
DIQMTQSPSS LSASVGDRVT ITCRASQSIS SLLNWYQQKP GKAPKLLISA ASSLQSGVPS  60
RFSGSGSGTD FTLTISSLQP EDFATYYCQQ GHSTPPTFGG GTRVEIK              107

SEQ ID NO: 51          moltype = AA  length = 7
FEATURE                Location/Qualifiers
source                 1..7
                       mol_type = protein
                       organism = synthetic construct
SEQUENCE: 51
AAESLQS                                                      7

SEQ ID NO: 52          moltype = AA  length = 107
FEATURE                Location/Qualifiers
source                 1..107
                       mol_type = protein
                       organism = synthetic construct
SEQUENCE: 52
DIQMTQSPSS LSASVGDRVT ITCRASQSIS SFLNWYQQKP GKAPKLLISA AESLQSGVPS  60
RFSGSGSGTD FTLTISSLQP EDFATYYCQQ GHSTPPTFGG GTKVEIK              107

SEQ ID NO: 53          moltype = AA  length = 11
FEATURE                Location/Qualifiers
source                 1..11
                       mol_type = protein
                       organism = synthetic construct
SEQUENCE: 53
RASQSPSSFL N                                                 11

SEQ ID NO: 54          moltype = AA  length = 7
FEATURE                Location/Qualifiers
source                 1..7
                       mol_type = protein
                       organism = synthetic construct
SEQUENCE: 54
AISSLQS                                                      7
```

-continued

```
SEQ ID NO: 55          moltype = AA  length = 9
FEATURE                Location/Qualifiers
source                 1..9
                       mol_type = protein
                       organism = synthetic construct
SEQUENCE: 55
QQGISTPPT                                                          9

SEQ ID NO: 56          moltype = AA  length = 107
FEATURE                Location/Qualifiers
source                 1..107
                       mol_type = protein
                       organism = synthetic construct
SEQUENCE: 56
DIQMTQSPSS LSASVGDRVT ITCRASQSPS SFLNWYQQKP GKAPKLLISA ISSLQSGVPS  60
RFSGSGSGTD FTLTISSLQP EDFATYYCQQ GISTPPTFGG GTKVEIK                107

SEQ ID NO: 57          moltype = AA  length = 11
FEATURE                Location/Qualifiers
source                 1..11
                       mol_type = protein
                       organism = synthetic construct
SEQUENCE: 57
GSISSSSYAW S                                                       11

SEQ ID NO: 58          moltype = AA  length = 121
FEATURE                Location/Qualifiers
source                 1..121
                       mol_type = protein
                       organism = synthetic construct
SEQUENCE: 58
QLQLQESGPG LVKPSETLSL TCTVSGGSIS SSSYAWSWIR QPPGKRLEWI GSIYYTGSTY  60
YNPSLKSRVT ISVDTSKNQF SLKLSSVTAA DTAVYYCLRG HRRDYIAFDI WGQGTMVTVS  120
S                                                                  121

SEQ ID NO: 59          moltype = AA  length = 11
FEATURE                Location/Qualifiers
source                 1..11
                       mol_type = protein
                       organism = synthetic construct
SEQUENCE: 59
RASQSISDYL N                                                       11

SEQ ID NO: 60          moltype = AA  length = 106
FEATURE                Location/Qualifiers
source                 1..106
                       mol_type = protein
                       organism = synthetic construct
SEQUENCE: 60
DIQMTQSPSS LSASVGDRVT ITCRASQSIS DYLNWYQQKP GKAPKLLIYA ASSLQSGVPS  60
RFSGSGSGTD FTLTISSLQP EDFATYYCQQ SHNLPTFGGG TKVEIK                 106

SEQ ID NO: 61          moltype = AA  length = 11
FEATURE                Location/Qualifiers
source                 1..11
                       mol_type = protein
                       organism = synthetic construct
SEQUENCE: 61
RASQSISEYL N                                                       11

SEQ ID NO: 62          moltype = AA  length = 106
FEATURE                Location/Qualifiers
source                 1..106
                       mol_type = protein
                       organism = synthetic construct
SEQUENCE: 62
DIQMTQSPSS LSASVGDRVT ITCRASQSIS EYLNWYQQKP GKAPKLLIYA ASSLQSGVPS  60
RFSGSGSGTD FTLTISSLQP EDFATYYCQQ SHNLPTFGGG TKVEIK                 106

SEQ ID NO: 63          moltype = AA  length = 7
FEATURE                Location/Qualifiers
source                 1..7
                       mol_type = protein
                       organism = synthetic construct
SEQUENCE: 63
DASSLQS                                                            7

SEQ ID NO: 64          moltype = AA  length = 106
FEATURE                Location/Qualifiers
```

```
source                  1..106
                        mol_type = protein
                        organism = synthetic construct
SEQUENCE: 64
DIQMTQSPSS LSASVGDRVT ITCRASQSIS SYLNWYQQKP GKAPKLLIYD ASSLQSGVPS  60
RFSGSGSGTD FTLTISSLQP EDFATYYCQQ SHNLPTFGGG TKVEIK                 106

SEQ ID NO: 65           moltype = AA  length = 7
FEATURE                 Location/Qualifiers
source                  1..7
                        mol_type = protein
                        organism = synthetic construct
SEQUENCE: 65
AASSLDS                                                            7

SEQ ID NO: 66           moltype = AA  length = 106
FEATURE                 Location/Qualifiers
source                  1..106
                        mol_type = protein
                        organism = synthetic construct
SEQUENCE: 66
DIQMTQSPSS LSASVGDRVT ITCRASQSIS SYLNWYQQKP GKAPKLLIYA ASSLDSGVPS  60
RFSGSGSGTD FTLTISSLQP EDFATYYCQQ SHNLPTFGGG TKVEIK                 106

SEQ ID NO: 67           moltype = AA  length = 7
FEATURE                 Location/Qualifiers
source                  1..7
                        mol_type = protein
                        organism = synthetic construct
SEQUENCE: 67
AASSLQE                                                            7

SEQ ID NO: 68           moltype = AA  length = 106
FEATURE                 Location/Qualifiers
source                  1..106
                        mol_type = protein
                        organism = synthetic construct
SEQUENCE: 68
DIQMTQSPSS LSASVGDRVT ITCRASQSIS SYLNWYQQKP GKAPKLLIYA ASSLQEGVPS  60
RFSGSGSGTD FTLTISSLQP EDFATYYCQQ SHNLPTFGGG TKVEIK                 106

SEQ ID NO: 69           moltype = AA  length = 8
FEATURE                 Location/Qualifiers
source                  1..8
                        mol_type = protein
                        organism = synthetic construct
SEQUENCE: 69
QQSHNLPS                                                           8

SEQ ID NO: 70           moltype = AA  length = 106
FEATURE                 Location/Qualifiers
source                  1..106
                        mol_type = protein
                        organism = synthetic construct
SEQUENCE: 70
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SHNLPSFGGG TKVEIK                 106

SEQ ID NO: 71           moltype = AA  length = 11
FEATURE                 Location/Qualifiers
source                  1..11
                        mol_type = protein
                        organism = synthetic construct
SEQUENCE: 71
GSISSSSNAW G                                                       11

SEQ ID NO: 72           moltype = AA  length = 121
FEATURE                 Location/Qualifiers
source                  1..121
                        mol_type = protein
                        organism = synthetic construct
SEQUENCE: 72
QLQLQESGPG LVKPSETLSL TCTVSGGSIS SSSNAWGWIR QPPGKRLEWI GSIYYTGSTY  60
YNPSLKSRVT ISVDTSKNQF SLKLSSVTAA DTAVYYCLRG HRRDYIAFDI WGQGTMVTVS  120
S                                                                  121

SEQ ID NO: 73           moltype = AA  length = 11
FEATURE                 Location/Qualifiers
source                  1..11
```

```
                      mol_type = protein
                      organism = synthetic construct
SEQUENCE: 73
RASQSILSYL N                                                     11

SEQ ID NO: 74         moltype = AA  length = 106
FEATURE               Location/Qualifiers
source                1..106
                      mol_type = protein
                      organism = synthetic construct
SEQUENCE: 74
DIQMTQSPSS LSASVGDRVT ITCRASQSIL SYLNWYQQKP GKAPKLLIYA ASSLQSGVPS  60
RFSGSGSGTD FTLTISSLQP EDFATYYCQQ SHNLPTFGGG TKVEIK                106

SEQ ID NO: 75         moltype = AA  length = 11
FEATURE               Location/Qualifiers
source                1..11
                      mol_type = protein
                      organism = synthetic construct
SEQUENCE: 75
GSISQSSYAW G                                                     11

SEQ ID NO: 76         moltype = AA  length = 121
FEATURE               Location/Qualifiers
source                1..121
                      mol_type = protein
                      organism = synthetic construct
SEQUENCE: 76
QLQLQESGPG LVKPSETLSL TCTVSGGSIS QSSYAWGWIR QPPGKRLEWI GSIYYTGSTY  60
YNPSLKSRVT ISVDTSKNQF SLKLSSVTAA DTAVYYCVRG HRRDYIAFDI WGQGTMVTVS  120
S                                                                121

SEQ ID NO: 77         moltype = AA  length = 11
FEATURE               Location/Qualifiers
source                1..11
                      mol_type = protein
                      organism = synthetic construct
SEQUENCE: 77
GSISSSSIAW G                                                     11

SEQ ID NO: 78         moltype = AA  length = 121
FEATURE               Location/Qualifiers
source                1..121
                      mol_type = protein
                      organism = synthetic construct
SEQUENCE: 78
QLQLQESGPG LVKPSETLSL TCTVSGGSIS SSSIAWGWIR QPPGKRLEWI GSIYYTGSTY  60
YNPSLKSRVT ISVDTSKNQF SLKLSSVTAA DTAVYYCVRG HRRDYIAFDI WAQGTMVTVS  120
S                                                                121

SEQ ID NO: 79         moltype = AA  length = 11
FEATURE               Location/Qualifiers
source                1..11
                      mol_type = protein
                      organism = synthetic construct
SEQUENCE: 79
GSISSSSYAW L                                                     11

SEQ ID NO: 80         moltype = AA  length = 121
FEATURE               Location/Qualifiers
source                1..121
                      mol_type = protein
                      organism = synthetic construct
SEQUENCE: 80
QLQLQESGPG LVKPSETLSL TCTVSGGSIS SSSYAWLWIR QPPGKRLEWI GSIYYTGSTY  60
YNPSLKSRVT ISVDTSKNQF SLKLSSVTAA DTAVYYCVRG HRRDYIAFDI WGQGTMVTVS  120
S                                                                121

SEQ ID NO: 81         moltype = AA  length = 11
FEATURE               Location/Qualifiers
source                1..11
                      mol_type = protein
                      organism = synthetic construct
SEQUENCE: 81
RADQSISSYL N                                                     11

SEQ ID NO: 82         moltype = AA  length = 106
FEATURE               Location/Qualifiers
source                1..106
```

```
                        mol_type = protein
                        organism = synthetic construct
SEQUENCE: 82
DIQMTQSPSS LSASVGDRVT ITCRADQSIS SYLNWYQQKP GKAPKLLIYA ASSLQSGVPS  60
RFSGSGSGTD FTLTISSLQP EDFATYYCQQ SHNLPTFGGG TKVEIK                106

SEQ ID NO: 83           moltype = AA  length = 106
FEATURE                 Location/Qualifiers
source                  1..106
                        mol_type = protein
                        organism = synthetic construct
SEQUENCE: 83
DIQMTQSPSS LSASVGDRVT ITCRASQSIS SLLNWYQQKP GKAPKLLIYA ASSLQSGVPS  60
RFSGSGSGTD FTLTISSLQP EDFATYYCQQ SHNLPTFGGG TKVEIK                106

SEQ ID NO: 84           moltype = AA  length = 7
FEATURE                 Location/Qualifiers
source                  1..7
                        mol_type = protein
                        organism = synthetic construct
SEQUENCE: 84
AASSLFS                                                           7

SEQ ID NO: 85           moltype = AA  length = 106
FEATURE                 Location/Qualifiers
source                  1..106
                        mol_type = protein
                        organism = synthetic construct
SEQUENCE: 85
DIQMTQSPSS LSASVGDRVT ITCRASQSIS SYLNWYQQKP GKAPKLLIYA ASSLFSGVPS  60
RFSGSGSGTD FTLTISSLQP EDFATYYCQQ SHNLPTFGGG TKVEIK                106

SEQ ID NO: 86           moltype = AA  length = 7
FEATURE                 Location/Qualifiers
source                  1..7
                        mol_type = protein
                        organism = synthetic construct
SEQUENCE: 86
AASSLYS                                                           7

SEQ ID NO: 87           moltype = AA  length = 106
FEATURE                 Location/Qualifiers
source                  1..106
                        mol_type = protein
                        organism = synthetic construct
SEQUENCE: 87
DIQMTQSPSS LSASVGDRVT ITCRASQSIS SYLNWYQQKP GKAPKLLIYA ASSLYSGVPS  60
RFSGSGSGTD FTLTISSLQP EDFATYYCQQ SHNLPTFGGG TKVEIK                106

SEQ ID NO: 88           moltype = AA  length = 9
FEATURE                 Location/Qualifiers
source                  1..9
                        mol_type = protein
                        organism = synthetic construct
SEQUENCE: 88
FQFNAYAMN                                                         9

SEQ ID NO: 89           moltype = AA  length = 19
FEATURE                 Location/Qualifiers
source                  1..19
                        mol_type = protein
                        organism = synthetic construct
SEQUENCE: 89
RIRSKSNNYA TYYADSVKP                                              19

SEQ ID NO: 90           moltype = AA  length = 14
FEATURE                 Location/Qualifiers
source                  1..14
                        mol_type = protein
                        organism = synthetic construct
SEQUENCE: 90
VRQSYGNSNY AMDH                                                   14

SEQ ID NO: 91           moltype = AA  length = 16
FEATURE                 Location/Qualifiers
source                  1..16
                        mol_type = protein
                        organism = synthetic construct
SEQUENCE: 91
```

-continued

```
RSSKRLLHSN GNTYLY                                                  16

SEQ ID NO: 92          moltype = AA  length = 7
FEATURE                Location/Qualifiers
source                 1..7
                       mol_type = protein
                       organism = synthetic construct
SEQUENCE: 92
RVSNLAS                                                            7

SEQ ID NO: 93          moltype = AA  length = 123
FEATURE                Location/Qualifiers
source                 1..123
                       mol_type = protein
                       organism = synthetic construct
SEQUENCE: 93
EVQLVESGGG LVQPGGSLRL SCAASGFQFN AYAMNWVRQA PGKGLEWVAR IRSKSNNYAT  60
YYADSVKPRF TISRDDSKNS LYLQMNSLKT EDTAVYYCVR QSYGNSNYAM DHWGQGTTVT  120
VSS                                                                123

SEQ ID NO: 94          moltype = AA  length = 112
FEATURE                Location/Qualifiers
source                 1..112
                       mol_type = protein
                       organism = synthetic construct
SEQUENCE: 94
DIVMTQSPLS LPVTPGEPAS ISCRSSKRLL HSNGNTYLYW YLQKPGQSPQ LLIYRVSNLA  60
SGVPDRFSGS GSGTDFTLKI SRVEAEDVGV YYCMQHLEYP FTFGGGTKVE IK          112

SEQ ID NO: 95          moltype = AA  length = 7
FEATURE                Location/Qualifiers
source                 1..7
                       mol_type = protein
                       organism = synthetic construct
SEQUENCE: 95
KMSNLAS                                                            7

SEQ ID NO: 96          moltype = AA  length = 9
FEATURE                Location/Qualifiers
source                 1..9
                       mol_type = protein
                       organism = synthetic construct
SEQUENCE: 96
MQHFEYPFT                                                          9

SEQ ID NO: 97          moltype = AA  length = 112
FEATURE                Location/Qualifiers
source                 1..112
                       mol_type = protein
                       organism = synthetic construct
SEQUENCE: 97
DIVMTQSPLS LPVTPGEPAS ISCRSSKRLL HSNGNTYLYW YLQKPGQSPQ LLIYKMSNLA  60
SGVPDRFSGS GSGTDFTLKI SRVEAEDVGV YYCMQHFEYP FTFGGGTKVE IK          112

SEQ ID NO: 98          moltype = AA  length = 123
FEATURE                Location/Qualifiers
source                 1..123
                       mol_type = protein
                       organism = synthetic construct
SEQUENCE: 98
EVQLVESGGG LVQPGGSLRL SCAASGFQFN AYAMNWVRQA PGKGLEWVAR IRSKSNNYAT  60
YYADSVKDRF TISRDDSKNS LYLQMNSLKT EDTAVYYCVR QSYGNSNYAM DYWGQGTTVT  120
VSS                                                                123

SEQ ID NO: 99          moltype = AA  length = 123
FEATURE                Location/Qualifiers
source                 1..123
                       mol_type = protein
                       organism = synthetic construct
SEQUENCE: 99
EVQLVESGGG LVQPGGSLRL SCAASGFQFN AYAMNWVRQA PGKGLEWVAR IRSKSNNYAT  60
YYADSVKDRF TISRDDSKNS LYLQMNSLKT EDTAVYYCVR QSYGNSNYAM DHWGQGTTVT  120
VSS                                                                123

SEQ ID NO: 100         moltype = AA  length = 112
FEATURE                Location/Qualifiers
source                 1..112
                       mol_type = protein
                       organism = synthetic construct
```

```
SEQUENCE: 100
DIVMTQSPLS LPVTPGEPAS ISCRSSKSLL HSNGNTYLYW YLQKPGQSPQ LLIYRVSNLA  60
SGVPDRFSGS GSGTDFTLKI SRVEAEDVGV YYCMQHFEYP FTFGGGTKVE IK          112

SEQ ID NO: 101         moltype = AA  length = 112
FEATURE                Location/Qualifiers
source                 1..112
                       mol_type = protein
                       organism = synthetic construct
SEQUENCE: 101
DIVMTQSPLS LPVTPGEPAS ISCRSSKSLL HSNGNTYLYW YLQKPGQSPQ LLIYKMSNLA  60
SGVPDRFSGS GSGTDFTLKI SRVEAEDVGV YYCMQHFEYP FTFGGGTKVE IK          112

SEQ ID NO: 102         moltype = AA  length = 16
FEATURE                Location/Qualifiers
source                 1..16
                       mol_type = protein
                       organism = synthetic construct
SEQUENCE: 102
RSSKSLQHSN GNTYLY                                                  16

SEQ ID NO: 103         moltype = AA  length = 112
FEATURE                Location/Qualifiers
source                 1..112
                       mol_type = protein
                       organism = synthetic construct
SEQUENCE: 103
DIVMTQSPLS LPVTPGEPAS ISCRSSKSLQ HSNGNTYLYW YLQKPGQSPQ LLIYRVSNLA  60
SGVPDRFSGS GSGTDFTLKI SRVEAEDVGV YYCMQHFEYP FTFGGGTKVE IK          112

SEQ ID NO: 104         moltype = AA  length = 19
FEATURE                Location/Qualifiers
source                 1..19
                       mol_type = protein
                       organism = synthetic construct
SEQUENCE: 104
RIRSKSNNYA TYYAGSVKD                                               19

SEQ ID NO: 105         moltype = AA  length = 7
FEATURE                Location/Qualifiers
source                 1..7
                       mol_type = protein
                       organism = synthetic construct
SEQUENCE: 105
KKSNLAS                                                            7

SEQ ID NO: 106         moltype = AA  length = 123
FEATURE                Location/Qualifiers
source                 1..123
                       mol_type = protein
                       organism = synthetic construct
SEQUENCE: 106
EVQLVESGGG LVQPGGSLRL SCAASGFQFN AYAMNWVRQA PGKGLEWVAR IRSKSNNYAT  60
YYAGSVKDRF TISRDDSKNS LYLQMNSLKT EDTAVYYCVR QSYGNSNYAM DYWGQGTTVT  120
VSS                                                                123

SEQ ID NO: 107         moltype = AA  length = 112
FEATURE                Location/Qualifiers
source                 1..112
                       mol_type = protein
                       organism = synthetic construct
SEQUENCE: 107
DIVMTQSPLS LPVTPGEPAS ISCRSSKSLL HSNGNTYLYW YLQKPGQSPQ LLIYKKSNLA  60
SGVPDRFSGS GSGTDFTLKI SRVEAEDVGV YYCMQHFEYP FTFGGGTKVE IK          112

SEQ ID NO: 108         moltype = AA  length = 112
FEATURE                Location/Qualifiers
source                 1..112
                       mol_type = protein
                       organism = synthetic construct
SEQUENCE: 108
DIVMTQSPLS LPVTPGEPAS ISCRSSKSLQ HSNGNTYLYW YLQKPGQSPQ LLIYRVSNLA  60
SGVPDRFSGS GSGTDFTLKI SRVEAEDVGV YYCMQHLEYP FTFGGGTKVE IK          112

SEQ ID NO: 109         moltype = AA  length = 9
FEATURE                Location/Qualifiers
source                 1..9
                       mol_type = protein
                       organism = synthetic construct
```

```
SEQUENCE: 109
FSFNAYAMN                                                  9

SEQ ID NO: 110          moltype = AA  length = 16
FEATURE                 Location/Qualifiers
source                  1..16
                        mol_type = protein
                        organism = synthetic construct
SEQUENCE: 110
RTSKSLLHSN GNTYLY                                          16

SEQ ID NO: 111          moltype = AA  length = 123
FEATURE                 Location/Qualifiers
source                  1..123
                        mol_type = protein
                        organism = synthetic construct
SEQUENCE: 111
EVQLVESGGG LVQPGGSLRL SCAASGFSFN AYAMNWVRQA PGKGLEWVAR IRSKSNNYAT  60
YYAGSVKDRF TISRDDSKNS LYLQMNSLKT EDTAVYYCVR QSYGNSNYAM DYWGQGTTVT  120
VSS                                                        123

SEQ ID NO: 112          moltype = AA  length = 112
FEATURE                 Location/Qualifiers
source                  1..112
                        mol_type = protein
                        organism = synthetic construct
SEQUENCE: 112
DIVMTQSPLS LPVTPGEPAS ISCRTSKSLL HSNGNTYLYW YLQKPGQSPQ LLIYRVSNLA  60
SGVPDRFSGS GSGTDFTLKI SRVEAEDVGV YYCMQHFEYP FTFGGGTKVE IK         112

SEQ ID NO: 113          moltype = AA  length = 19
FEATURE                 Location/Qualifiers
source                  1..19
                        mol_type = protein
                        organism = synthetic construct
SEQUENCE: 113
RIRSKSNNYA TYYAASVKP                                       19

SEQ ID NO: 114          moltype = AA  length = 123
FEATURE                 Location/Qualifiers
source                  1..123
                        mol_type = protein
                        organism = synthetic construct
SEQUENCE: 114
EVQLVESGGG LVQPGGSLRL SCAASGFTFN AYAMNWVRQA PGKGLEWVAR IRSKSNNYAT  60
YYAASVKPRF TISRDDSKNS LYLQMNSLKT EDTAVYYCVR QSYGNSNYAM DHWGQGTTVT  120
VSS                                                        123

SEQ ID NO: 115          moltype = AA  length = 9
FEATURE                 Location/Qualifiers
source                  1..9
                        mol_type = protein
                        organism = synthetic construct
VARIANT                 6
                        note = X is Y, H, W, or F
SEQUENCE: 115
FTFSSXGMH                                                  9

SEQ ID NO: 116          moltype = AA  length = 11
FEATURE                 Location/Qualifiers
source                  1..11
                        mol_type = protein
                        organism = synthetic construct
VARIANT                 7
                        note = X is N, V, Q, or A
SEQUENCE: 116
RASQSIXSYL N                                               11

SEQ ID NO: 117          moltype = AA  length = 7
FEATURE                 Location/Qualifiers
source                  1..7
                        mol_type = protein
                        organism = synthetic construct
VARIANT                 1
                        note = X is A, S, N, T, or V
VARIANT                 4
                        note = X is S, I, T, or L
SEQUENCE: 117
XASXLQS                                                    7
```

```
SEQ ID NO: 118          moltype = AA  length = 9
FEATURE                 Location/Qualifiers
source                  1..9
                        mol_type = protein
                        organism = synthetic construct
VARIANT                 9
                        note = X is T, F, S, W, or Y
SEQUENCE: 118
QESYSTPIX                                                         9

SEQ ID NO: 119          moltype = AA  length = 11
FEATURE                 Location/Qualifiers
source                  1..11
                        mol_type = protein
                        organism = synthetic construct
VARIANT                 6
                        note = X is I, P, or L
VARIANT                 9
                        note = X is F, L, I, W, or Y
VARIANT                 10
                        note = X is L, A, I, or V
SEQUENCE: 119
RASQSXSSXX N                                                      11

SEQ ID NO: 120          moltype = AA  length = 7
FEATURE                 Location/Qualifiers
source                  1..7
                        mol_type = protein
                        organism = synthetic construct
VARIANT                 2
                        note = X is A, I, L, or V
VARIANT                 3
                        note = X is S, E, T, or D
SEQUENCE: 120
AXXSLQS                                                           7

SEQ ID NO: 121          moltype = AA  length = 9
FEATURE                 Location/Qualifiers
source                  1..9
                        mol_type = protein
                        organism = synthetic construct
VARIANT                 4
                        note = X is H, I, or L
SEQUENCE: 121
QQGXSTPPT                                                         9

SEQ ID NO: 122          moltype = AA  length = 11
FEATURE                 Location/Qualifiers
source                  1..11
                        mol_type = protein
                        organism = synthetic construct
VARIANT                 5
                        note = X is S, Q, T, or N
VARIANT                 8
                        note = X is Y, N, I, L, W, F, or Q
VARIANT                 11
                        note = X is G, L, S, T, or I
SEQUENCE: 122
GSISXSSXAW X                                                      11

SEQ ID NO: 123          moltype = AA  length = 13
FEATURE                 Location/Qualifiers
source                  1..13
                        mol_type = protein
                        organism = synthetic construct
VARIANT                 1
                        note = X is L ,V, I, or A
SEQUENCE: 123
XRGHRRDYIA FDI                                                    13

SEQ ID NO: 124          moltype = AA  length = 11
FEATURE                 Location/Qualifiers
source                  1..11
                        mol_type = protein
                        organism = synthetic construct
VARIANT                 3
                        note = X is S, D, T, or E
VARIANT                 7
```

```
                        note = X is S, L, T, or I
VARIANT                 8
                        note = X is S, D, E, or T
VARIANT                 9
                        note = X is Y, L, I, W, or F
SEQUENCE: 124
RAXQSIXXXL N                                                    11

SEQ ID NO: 125          moltype = AA  length = 7
FEATURE                 Location/Qualifiers
source                  1..7
                        mol_type = protein
                        organism = synthetic construct
VARIANT                 1
                        note = X is A, D, E, or V
VARIANT                 6
                        note = X is Q, D, F, Y, W, N, or E
VARIANT                 7
                        note = X is S, E, T, or D
SEQUENCE: 125
XASSLXX                                                         7

SEQ ID NO: 126          moltype = AA  length = 8
FEATURE                 Location/Qualifiers
source                  1..8
                        mol_type = protein
                        organism = synthetic construct
VARIANT                 8
                        note = X is T or S
SEQUENCE: 126
QQSHNLPX                                                        8

SEQ ID NO: 127          moltype = AA  length = 9
FEATURE                 Location/Qualifiers
source                  1..9
                        mol_type = protein
                        organism = synthetic construct
VARIANT                 2
                        note = X is T, Q, S, or N
SEQUENCE: 127
FXFNAYAMN                                                       9

SEQ ID NO: 128          moltype = AA  length = 19
FEATURE                 Location/Qualifiers
source                  1..19
                        mol_type = protein
                        organism = synthetic construct
VARIANT                 15
                        note = X is D, A, G, E, or V
VARIANT                 19
                        note = X is D, P, or E
SEQUENCE: 128
RIRSKSNNYA TYYAXSVKX                                            19

SEQ ID NO: 129          moltype = AA  length = 14
FEATURE                 Location/Qualifiers
source                  1..14
                        mol_type = protein
                        organism = synthetic construct
VARIANT                 14
                        note = X is Y, H, W, or F
SEQUENCE: 129
VRQSYGNSNY AMDX                                                 14

SEQ ID NO: 130          moltype = AA  length = 16
FEATURE                 Location/Qualifiers
source                  1..16
                        mol_type = protein
                        organism = synthetic construct
VARIANT                 2
                        note = X is S or T
VARIANT                 5
                        note = X is S, R, T, or K
VARIANT                 7
                        note = X is L, Q, I, or N
SEQUENCE: 130
RXSKXLXHSN GNTYLY                                               16

SEQ ID NO: 131          moltype = AA  length = 7
```

```
FEATURE                Location/Qualifiers
source                 1..7
                       mol_type = protein
                       organism = synthetic construct
VARIANT                1
                       note = X is R or K
VARIANT                2
                       note = X is M, V, K, R, or A
SEQUENCE: 131
XXSNLAS                                                        7

SEQ ID NO: 132         moltype = AA  length = 9
FEATURE                Location/Qualifiers
source                 1..9
                       mol_type = protein
                       organism = synthetic construct
VARIANT                4
                       note = X is L, F, I, W, or Y
SEQUENCE: 132
MQHXEYPFT                                                      9

SEQ ID NO: 133         moltype = AA  length = 329
FEATURE                Location/Qualifiers
source                 1..329
                       mol_type = protein
                       organism = synthetic construct
SEQUENCE: 133
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                 329

SEQ ID NO: 134         moltype = AA  length = 329
FEATURE                Location/Qualifiers
source                 1..329
                       mol_type = protein
                       organism = synthetic construct
SEQUENCE: 134
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVCVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                 329

SEQ ID NO: 135         moltype = AA  length = 107
FEATURE                Location/Qualifiers
source                 1..107
                       mol_type = protein
                       organism = synthetic construct
SEQUENCE: 135
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC             107

SEQ ID NO: 136         moltype = AA  length = 355
FEATURE                Location/Qualifiers
source                 1..355
                       mol_type = protein
                       organism = Homo sapiens
SEQUENCE: 136
MDYTLDLSVT TVTDYYYPDI FSSPCDAELI QTNGKLLLAV FYCLLFVFSL LGNSLVILVL  60
VVCKKLRSIT DVYLLNLALS DLLFVFSFPF QTYYLLDQWV FGTVMCKVVS GFYYIGFYSS  120
MFFITLMSVD RYLAVVHAVY ALKVRTIRMG TTLCLAVWLT AIMATIPLLV FYQVASEDGV  180
LQCYSFYNQQ TLKWKIFTNF KMNILGLLIP FTIFMFCYIK ILHQLKRCQN HNKTKAIRLV  240
LIVVIASLLF WVPFNVVLFL TSLHSMHILD GCSISQQLTY ATHVTEIISF THCCVNPVIY  300
AFVGEKFKKH LSEIFQKSCS QIFNYLGRQM PRESCEKSSS CQQHSSRSSS VDYIL       355

SEQ ID NO: 137         moltype = AA  length = 355
FEATURE                Location/Qualifiers
source                 1..355
                       mol_type = protein
                       organism = Macaca fascicularis
SEQUENCE: 137
MDYTLDPSMT TMTDYYYPDS LSSPCDGELI QRNDKLLLAV FYCLLFVFSL LGNSLVILVL  60
VVCKKLRNIT DIYLLNLALS DLLFVFSFPF QTYYQLDQWV FGTVMCKVVS GFYYIGFYSS  120
MFFITLMSVD RYLAVVHAVY AIKVRTIRMG TTLSLVVWLT AIMATIPLLV FYQVASEDGV  180
LQCYSFYNQQ TLKWKIFTNF EMNILGLLIP FTIFMFCYIK ILHQLKRCQN HNKTKAIRLV  240
```

```
LIVVIASLLF WVPFNVVLFL TSLHSMHILD GCSISQQLNY ATHVTEIISF THCCVNPVIY  300
AFVGEKFKKH LSEIFQKSCS HIFIYLGRQM PRESCEKSSS CQQHSFRSSS IDYIL       355

SEQ ID NO: 138          moltype = AA  length = 356
FEATURE                 Location/Qualifiers
source                  1..356
                        mol_type = protein
                        organism = Macaca mulatta
SEQUENCE: 138
MDYTLDPSMT TMTDYYYPDS LSSPCDGELI QRNDKLLLAV FYCLLFVFSL LGNSLVILVL  60
VVCKKLRNIT DIYLLNLALS DLLFVFSFPF QTYYQLDQWV FGTVMCKVVS GFYYIGFYSS  120
MFFITLMSVD RYLAVVHAVY AIKVRTIRMG TTTLSLLVWL TAIMATIPLL VFYQVASEDG  180
VLQCYSFYNQ QTLKWKIFTN FEMNILGLLI PFTIFMFCYI KILHQLKRCQ NHNKTKAIRL  240
VLIVVIASLL FWVPFNVVLF LTSLHSMHIL DGCSISQQLN YATHVTEIIS FTHCCVNPVI  300
YAFVGEKFKK HLSEIFQKSC SHIFIYLGRQ MPRESCEKSS SCQQHSFRSS SIDYIL      356

SEQ ID NO: 139          moltype = AA  length = 19
FEATURE                 Location/Qualifiers
source                  1..19
                        mol_type = protein
                        organism = synthetic construct
VARIANT                 19
                        note = X is D or P
SEQUENCE: 139
RIRSKSNNYA TYYADSVKX                                             19

SEQ ID NO: 140          moltype = AA  length = 16
FEATURE                 Location/Qualifiers
source                  1..16
                        mol_type = protein
                        organism = synthetic construct
VARIANT                 7
                        note = X is L or Q
SEQUENCE: 140
RSSKSLXHSN GNTYLY                                                16

SEQ ID NO: 141          moltype = AA  length = 452
FEATURE                 Location/Qualifiers
source                  1..452
                        mol_type = protein
                        organism = synthetic construct
SEQUENCE: 141
EVQLVESGGG LVQPGGSLRL SCAASGFQFN AYAMNWVRQA PGKGLEWVAR IRSKSNNYAT  60
YYADSVKDRF TISRDDSKNS LYLQMNSLKT EDTAVYYCVR QSYGNSNYAM DHWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PG                              452

SEQ ID NO: 142          moltype = AA  length = 219
FEATURE                 Location/Qualifiers
source                  1..219
                        mol_type = protein
                        organism = synthetic construct
SEQUENCE: 142
DIVMTQSPLS LPVTPGEPAS ISCRSSKSLL HSNGNTYLYW YLQKPGQSPQ LLIYRVSNLA  60
SGVPDRFSGS GSGTDFTLKI SRVEAEDVGV YYCMQHFEYP FTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                       219

SEQ ID NO: 143          moltype = AA  length = 452
FEATURE                 Location/Qualifiers
source                  1..452
                        mol_type = protein
                        organism = synthetic construct
SEQUENCE: 143
EVQLVESGGG LVQPGGSLRL SCAASGFQFN AYAMNWVRQA PGKGLEWVAR IRSKSNNYAT  60
YYADSVKPRF TISRDDSKNS LYLQMNSLKT EDTAVYYCVR QSYGNSNYAM DHWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PG                              452

SEQ ID NO: 144          moltype = AA  length = 219
FEATURE                 Location/Qualifiers
```

-continued

```
source                  1..219
                        mol_type = protein
                        organism = synthetic construct
SEQUENCE: 144
DIVMTQSPLS LPVTPGEPAS ISCRSSKSLQ HSNGNTYLYW YLQKPGQSPQ LLIYRVSNLA  60
SGVPDRFSGS GSGTDFTLKI SRVEAEDVGV YYCMQHFEYP FTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 145          moltype = AA  length = 452
FEATURE                 Location/Qualifiers
source                  1..452
                        mol_type = protein
                        organism = synthetic construct
SEQUENCE: 145
EVQLVESGGG LVQPGGSLRL SCAASGFQFN AYAMNWVRQA PGKGLEWVAR IRSKSNNYAT  60
YYADSVKDRF TISRDDSKNS LYLQMNSLKT EDTAVYYCVR QSYGNSNYAM DHWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
AGAPSVFLFP PKPKDTLMIS RTPEVTCVVV CVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PG                                452

SEQ ID NO: 146          moltype = AA  length = 219
FEATURE                 Location/Qualifiers
source                  1..219
                        mol_type = protein
                        organism = synthetic construct
SEQUENCE: 146
DIVMTQSPLS LPVTPGEPAS ISCRSSKSLL HSNGNTYLYW YLQKPGQSPQ LLIYRVSNLA  60
SGVPDRFSGS GSGTDFTLKI SRVEAEDVGV YYCMQHFEYP FTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 147          moltype = AA  length = 452
FEATURE                 Location/Qualifiers
source                  1..452
                        mol_type = protein
                        organism = synthetic construct
SEQUENCE: 147
EVQLVESGGG LVQPGGSLRL SCAASGFQFN AYAMNWVRQA PGKGLEWVAR IRSKSNNYAT  60
YYADSVKPRF TISRDDSKNS LYLQMNSLKT EDTAVYYCVR QSYGNSNYAM DHWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
AGAPSVFLFP PKPKDTLMIS RTPEVTCVVV CVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PG                                452

SEQ ID NO: 148          moltype = AA  length = 219
FEATURE                 Location/Qualifiers
source                  1..219
                        mol_type = protein
                        organism = synthetic construct
SEQUENCE: 148
DIVMTQSPLS LPVTPGEPAS ISCRSSKSLQ HSNGNTYLYW YLQKPGQSPQ LLIYRVSNLA  60
SGVPDRFSGS GSGTDFTLKI SRVEAEDVGV YYCMQHFEYP FTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219
```